US009783836B2

(12) United States Patent
Rudenko et al.

(10) Patent No.: US 9,783,836 B2
(45) Date of Patent: Oct. 10, 2017

(54) THIOESTERASES AND CELLS FOR PRODUCTION OF TAILORED OILS

(71) Applicant: TerraVia Holdings, Inc., South San Francisco, CA (US)

(72) Inventors: George N. Rudenko, South San Francisco, CA (US); Jason Casolari, South San Francisco, CA (US); Scott Franklin, South San Francisco, CA (US)

(73) Assignee: TERRAVIA HOLDINGS, INC., South San Francisco, CA (US)

( * ) Notice: Subject to any disclaimer, the term of this patent is extended or adjusted under 35 U.S.C. 154(b) by 534 days.

(21) Appl. No.: 14/209,931

(22) Filed: Mar. 13, 2014

(65) Prior Publication Data

US 2014/0288320 A1 Sep. 25, 2014

Related U.S. Application Data

(63) Continuation-in-part of application No. 13/837,996, filed on Mar. 15, 2013, now Pat. No. 9,290,749.

(60) Provisional application No. 61/791,861, filed on Mar. 15, 2013, provisional application No. 61/917,217, filed on Dec. 17, 2013.

(51) Int. Cl.

| | |
|---|---|
| ***C12N 9/16*** | (2006.01) |
| ***C12N 1/12*** | (2006.01) |
| ***C12P 7/64*** | (2006.01) |

(52) U.S. Cl.

CPC .............. *C12P 7/6409* (2013.01); *C12N 1/12* (2013.01); *C12N 9/16* (2013.01); *C12P 7/6463* (2013.01)

(58) Field of Classification Search

None

See application file for complete search history.

(56) References Cited

U.S. PATENT DOCUMENTS

| | | | |
|---|---|---|---|
| 4,049,724 | A | 9/1977 | Sheng et al. |
| 4,288,378 | A | 9/1981 | Japikse et al. |
| 4,335,156 | A | 6/1982 | Kogan et al. |
| 4,584,139 | A | 4/1986 | Gray et al. |
| 4,603,188 | A | 7/1986 | Kusakawa et al. |
| 4,683,202 | A | 7/1987 | Mullis |
| 4,798,793 | A | 1/1989 | Eigtved |
| 4,940,835 | A | 7/1990 | Shah et al. |
| 4,940,845 | A | 7/1990 | Hirota et al. |
| 4,945,050 | A | 7/1990 | Sanford et al. |
| 4,992,189 | A | 2/1991 | Chen et al. |
| 5,080,848 | A | 1/1992 | Strauss et al. |
| 5,091,116 | A | 2/1992 | Krishnamurthy et al. |
| 5,156,963 | A | 10/1992 | Eigtved |
| 5,233,099 | A | 8/1993 | Tabata |
| 5,233,100 | A | 8/1993 | Tabata et al. |
| 5,258,197 | A | 11/1993 | Wheeler et al. |
| 5,268,192 | A | 12/1993 | Zook et al. |
| 5,298,421 | A | 3/1994 | Davies et al. |
| 5,298,637 | A | 3/1994 | Cooper |
| 5,304,481 | A | 4/1994 | Davies et al. |
| 5,304,664 | A | 4/1994 | Peppmoller et al. |
| 5,342,768 | A | 8/1994 | Pedersen et al. |
| 5,344,771 | A | 9/1994 | Davies et al. |
| 5,346,724 | A | 9/1994 | Ohgake et al. |
| 5,380,894 | A | 1/1995 | Burg et al. |
| 5,391,383 | A | 2/1995 | Sullivan et al. |
| 5,427,704 | A | 6/1995 | Lawate |
| 5,434,278 | A | 7/1995 | Pelloso et al. |
| 5,451,332 | A | 9/1995 | Lawate |
| 5,455,167 | A | 10/1995 | Voelker et al. |
| 5,458,795 | A | 10/1995 | Lawate |
| 5,475,160 | A | 12/1995 | Singleton et al. |
| 5,506,201 | A | 4/1996 | McDermott et al. |
| 5,512,482 | A | 4/1996 | Voelker et al. |
| 5,567,359 | A | 10/1996 | Cassidy et al. |
| 5,576,027 | A | 11/1996 | Friedman et al. |
| 5,639,790 | A | 6/1997 | Voelker et al. |
| 5,654,495 | A | 8/1997 | Voelker et al. |
| 5,667,997 | A | 9/1997 | Voelker et al. |
| 5,674,385 | A | 10/1997 | Ivaschenko et al. |
| 5,686,131 | A | 11/1997 | Sato et al. |
| 5,693,507 | A | 12/1997 | Daniell et al. |
| 5,723,761 | A | 3/1998 | Voelker et al. |
| 5,776,741 | A | 7/1998 | Pedersen et al. |
| 5,807,893 | A | 9/1998 | Voelker et al. |
| 5,833,999 | A | 11/1998 | Trinh et al. |
| 5,850,022 | A | 12/1998 | Dehesh et al. |

(Continued)

FOREIGN PATENT DOCUMENTS

| | | | |
|---|---|---|---|
| CN | 102 586 350 | A | 7/2012 |
| EP | 1 605 048 | A1 | 12/2005 |

(Continued)

OTHER PUBLICATIONS

Mittendorf et al 1999 (The Plant Journal 20: p. 45-55).*

U.S. Appl. No. 14/858,527, filed Sep. 18, 2015, Casolari et al.

U.S. Office Action, dated Jul. 16, 2015, issued in U.S. Appl. No. 13/797,733.

U.S. Final Office Action, dated Dec. 14, 2015, issued in U.S. Appl. No. 13/797,733.

U.S. Office Action, dated Jul. 22, 2015, issued in U.S. Appl. No. 13/837,996.

U.S. Notice of Allowance, dated Nov. 17, 2015, issued in U.S. Appl. No. 13/837,996.

PCT International Search Report and Written Opinion dated Jun. 24, 2014 issued in PCT/US2014/013676.

(Continued)

*Primary Examiner* — Matthew Keogh

(74) *Attorney, Agent, or Firm* — Weaver Austin Villeneuve & Sampson LLP

(57) ABSTRACT

The invention features plant acyl-ACP thioesterase genes of the FatB class and proteins encoded by these genes. The genes are useful for constructing recombinant host cells having altered fatty acid profiles. Oleaginous microalga host cells with the new genes or previously identified FatB genes are disclosed. The microalgae cells produce triglycerides with useful fatty acid profiles.

10 Claims, No Drawings

(56) References Cited

U.S. PATENT DOCUMENTS

| | | | |
|---|---|---|---|
| 5,885,440 | A | 3/1999 | Hoehn et al. |
| 5,888,947 | A | 3/1999 | Lambert et al. |
| 5,928,696 | A | 7/1999 | Best et al. |
| 5,942,479 | A | 8/1999 | Frankenbach et al. |
| 5,945,585 | A | 8/1999 | Hitz et al. |
| 6,020,509 | A | 2/2000 | Weerasooriya et al. |
| 6,022,577 | A | 2/2000 | Chrysam et al. |
| 6,027,900 | A | 2/2000 | Allnutt et al. |
| 6,051,539 | A | 4/2000 | Kodali et al. |
| 6,057,375 | A | 5/2000 | Wollenweber et al. |
| 6,080,853 | A | 6/2000 | Corrigan et al. |
| 6,086,903 | A | 7/2000 | Trinh et al. |
| 6,113,971 | A | 9/2000 | Elmaleh |
| 6,140,302 | A | 10/2000 | Lueder et al. |
| 6,150,512 | A | 11/2000 | Yuan |
| 6,217,746 | B1 | 4/2001 | Thakkar et al. |
| 6,268,517 | B1 | 7/2001 | Filler et al. |
| 6,278,006 | B1 | 8/2001 | Kodali et al. |
| 6,320,101 | B1 | 11/2001 | Kaplan et al. |
| 6,331,664 | B1 | 12/2001 | Rubin-Wilson et al. |
| 6,342,208 | B1 | 1/2002 | Hyldgaard et al. |
| 6,380,410 | B1 | 4/2002 | Oftring et al. |
| 6,391,815 | B1 | 5/2002 | Weston et al. |
| 6,395,965 | B1 | 5/2002 | Xia |
| 6,398,707 | B1 | 6/2002 | Wu et al. |
| 6,407,044 | B2 | 6/2002 | Dixon |
| 6,465,642 | B1 | 10/2002 | Kenneally et al. |
| 6,468,955 | B1 | 10/2002 | Smets et al. |
| 6,538,169 | B1 | 3/2003 | Pittman et al. |
| 6,590,113 | B1 | 7/2003 | Sleeter |
| 6,596,155 | B1 | 7/2003 | Gates et al. |
| 6,596,768 | B2 | 7/2003 | Block et al. |
| 6,630,066 | B2 | 10/2003 | Cash et al. |
| 6,680,426 | B2 | 1/2004 | Daniell et al. |
| 6,692,730 | B2 | 2/2004 | Perron et al. |
| 6,750,048 | B2 | 6/2004 | Ruecker et al. |
| 6,770,104 | B2 | 8/2004 | Murphy |
| 6,808,737 | B2 | 10/2004 | Ullanoormadam |
| 6,869,597 | B2 | 3/2005 | Arnaud |
| 6,881,873 | B2 | 4/2005 | Gillespie et al. |
| 6,924,333 | B2 | 8/2005 | Bloom et al. |
| 6,946,430 | B2 | 9/2005 | Sakai et al. |
| 6,977,322 | B2 | 12/2005 | Gillespie |
| 7,041,866 | B1 | 5/2006 | Gillespie |
| 7,053,267 | B2 | 5/2006 | Knauf et al. |
| 7,081,567 | B2 | 7/2006 | Xue et al. |
| 7,115,173 | B2 | 10/2006 | Caswell et al. |
| 7,115,760 | B2 | 10/2006 | Sparso et al. |
| 7,118,773 | B2 | 10/2006 | Floeter et al. |
| 7,135,290 | B2 | 11/2006 | Dillon |
| 7,135,620 | B2 | 11/2006 | Daniell et al. |
| 7,196,124 | B2 | 3/2007 | Parker et al. |
| 7,232,935 | B2 | 6/2007 | Jakkula et al. |
| 7,238,277 | B2 | 7/2007 | Dahlberg et al. |
| 7,262,158 | B1 | 8/2007 | Lukenbach et al. |
| 7,264,886 | B2 | 9/2007 | Cui et al. |
| 7,268,276 | B2 | 9/2007 | Ruezinsky et al. |
| 7,288,278 | B2 | 10/2007 | Mellerup et al. |
| 7,288,685 | B2 | 10/2007 | Marker |
| 7,588,931 | B2 | 9/2009 | Damude et al. |
| 7,622,570 | B2 | 11/2009 | Oswald et al. |
| 8,029,579 | B2 | 10/2011 | Knuth et al. |
| 8,530,207 | B2 | 9/2013 | Watts et al. |
| 9,290,749 | B2 | 3/2016 | Rudenko et al. |
| 9,567,615 | B2 | 2/2017 | Davis |
| 2002/0178467 | A1 | 11/2002 | Dehesh |
| 2003/0097686 | A1 | 5/2003 | Knauf et al. |
| 2003/0145350 | A1 | 7/2003 | Spener et al. |
| 2005/0005333 | A1 | 1/2005 | Ruezinsky et al. |
| 2005/0102716 | A1 | 5/2005 | Venkatramesh et al. |
| 2005/0262588 | A1 | 11/2005 | Dehesh et al. |
| 2007/0175091 | A1 | 8/2007 | Danzer et al. |
| 2007/0261138 | A1 | 11/2007 | Graham et al. |
| 2009/0176272 | A1 | 7/2009 | Champagne et al. |
| 2009/0317878 | A1 | 12/2009 | Champagne et al. |
| 2010/0058651 | A1 | 3/2010 | Knuth et al. |
| 2010/0105955 | A1 | 4/2010 | Alibhai et al. |
| 2010/0154293 | A1 | 6/2010 | Hom et al. |
| 2011/0072714 | A1 | 3/2011 | Gaertner et al. |
| 2011/0145944 | A1 | 6/2011 | Laga et al. |
| 2011/0250659 | A1 | 10/2011 | Roberts et al. |
| 2011/0293785 | A1* | 12/2011 | Franklin et al. ......... A23D 7/00 426/61 |
| 2012/0009636 | A1 | 1/2012 | Berry et al. |
| 2012/0283460 | A1 | 11/2012 | Franklin et al. |
| 2012/0288930 | A1 | 11/2012 | Trimbur et al. |
| 2013/0031678 | A1 | 1/2013 | Zheng et al. |
| 2013/0034887 | A1 | 2/2013 | Franklin et al. |
| 2014/0215654 | A1 | 7/2014 | Davis |
| 2014/0234920 | A1 | 8/2014 | Davis |
| 2014/0275586 | A1 | 9/2014 | Rudenko et al. |
| 2016/0032332 | A1 | 2/2016 | Davis et al. |
| 2016/0083758 | A1 | 3/2016 | Casolari et al. |
| 2016/0251685 | A1 | 9/2016 | Rudenko et al. |

FOREIGN PATENT DOCUMENTS

| | | | |
|---|---|---|---|
| EP | 1 640 437 | A1 | 3/2006 |
| EP | 1 681 337 | A1 | 7/2006 |
| EP | 1 741 767 | A1 | 1/2007 |
| EP | 1 741 768 | A1 | 1/2007 |
| EP | 1 795 576 | A1 | 6/2007 |
| EP | 1 682 466 | A1 | 11/2008 |
| WO | WO 89/01032 | A1 | 2/1989 |
| WO | WO 92/11373 | A1 | 7/1992 |
| WO | WO 92/20636 | A1 | 11/1992 |
| WO | WO 94/10288 | A2 | 5/1994 |
| WO | WO 95/13390 | A2 | 5/1995 |
| WO | WO 96/23892 | A2 | 8/1996 |
| WO | WO 98/55633 | A1 | 12/1998 |
| WO | WO 00/61740 | A1 | 10/2000 |
| WO | WO 00/66750 | A2 | 11/2000 |
| WO | WO 02/08403 | A2 | 1/2002 |
| WO | WO 2005/047216 | A1 | 5/2005 |
| WO | WO 2006/055322 | A2 | 5/2006 |
| WO | WO 2007/106903 | A2 | 9/2007 |
| WO | WO 2008/002643 | A2 | 1/2008 |
| WO | WO 2008/151149 | A2 | 12/2008 |
| WO | WO 2010/019813 | A2 | 2/2010 |
| WO | WO 2010/063031 | A2 | 6/2010 |
| WO | WO 2010/063032 | A2 | 6/2010 |
| WO | WO 2010/120939 | A2 | 10/2010 |
| WO | WO 2011/003034 | A2 | 1/2011 |
| WO | WO 2011/008565 | A1 | 1/2011 |
| WO | WO 2011/127069 | A1 | 10/2011 |
| WO | WO 2011/150410 | A2 | 12/2011 |
| WO | WO 2011/150411 | A1 | 12/2011 |
| WO | WO 2012/061647 | A2 | 5/2012 |
| WO | WO 2012/106560 | A1 | 8/2012 |
| WO | WO 2012/154626 | A1 | 11/2012 |
| WO | WO 2013/158938 | A1 | 10/2013 |
| WO | WO 2014/120829 | A1 | 8/2014 |
| WO | WO 2014/151904 | A1 | 9/2014 |
| WO | WO 2015/051319 | A2 | 4/2015 |
| WO | PCT/US2015/051042 | | 9/2015 |
| WO | WO 2016/014968 | A1 | 1/2016 |
| WO | WO 2016/044779 | A2 | 3/2016 |

OTHER PUBLICATIONS

PCT International Preliminary Report on Patentability and Written Opinion dated Aug. 13, 2015 issued in PCT/US2014/013676.

Database Geneseq [Online] (Jun. 6, 2000) "Bay C18:1 preferring acyl-ACP thioesterase protein from clone 3A-17.", retrieved from EBI accession No. GSP:AAY80558 Database accession No. AAY80558; and Database Geneseq [Online] (Jun. 6, 2000) "Bay C18:1 preferring acyl-ACP thioesterase protein.", retrieved from EBI accession No. GSP:AAY80559 Database accession No. AAY80559.

Database Geneseq [Online] (Nov. 2, 1995) "Camphor thioesterase.", retrieved from EBI accession No. GSP:AAR74148 Database accession No. AAR74148.

(56) References Cited

OTHER PUBLICATIONS

Database Geneseq [Online] (Oct. 26, 1996) "Cuphea C14:0-ACP thioesterase.", retrieved from EBI accession No. GSP:AAW02081 Database accession No. AAW02081.
Database Geneseq [Online] (Aug. 5, 2010) "U. californica fatty acyl-ACP thioesterase protein (without PTS), SEQ:139.", retrieved from EBI accession No. GSP:AYC84249 Database accession No. AYC84249.
Mexican Office Action [no tranlsation] dated Sep. 21, 2015 issued in MX/a/2015/009730.
PCT Invitation to Pay Additional Fees and, Where Applicable, Protest Fee dated Jun. 18, 2014 issued in PCT/US2014/026644.
PCT International Search Report and Written Opinion dated Aug. 29, 2014 issued in PCT/US2014/026644.
PCT International Preliminary Report on Patentability dated Sep. 24, 2015 issued in PCT/US2014/026644.
Genbank Accession No. U17097, Umbellularia californica UC FatB2 (FatB) mRNA, complete cds., Jun. 1, 1995, 2pp.
Genbank: Accession No. U39834.1, Cuphea hookeriana 8:0- and 10:0-ACP specific thioesterase (FatB2) mRNA, complete cds, May 21, 2014, 2pp.
Genbank Accession No. AAC49001, UC FatB2 (FatB) Umbellularica californica, May 30, 1995, 2pp.
PCT International Search Report and Written Opinion dated Dec. 22, 2015 issued in PCT/US2015/042044.
Database UniProt [Online] (Jul. 24, 2013) "SubName: Full =FatB type acyl-ACP thioesterase-3 {EC0:0000313:EMBL:AGG79285.1}," retrieved on Nov. 10, 2015 from EBI accession No. Uniprot:R4J2L6, Database accession No. R4J2L6 sequence, 1 page.
Database UniProt [Online] (Jul. 9, 2014) "SubName: Full=Uncharacterized protein {EC0:0000313:EMBL:KCW58039.1}," retrieved on Nov. 16, 2015 from EBI accession No. Uniprot:A0A059AWB4, Database accession No. A0A059AWB4 sequence, 1 page.
PCT Invitation to Pay Additional Fees and, Where Applicable, Protest Fee dated Jan. 13, 2016 issued in PCT/US2015/051042.
Apt et al., (1996) "Stable nuclear transformation of the diatom *Phaeodactylum tricornutum," Molecular and General Genetics*, 252:572-579.
Barnes et al., (2005) "Contribution of 5'- and 3'-untranslated regions of plastid mRNAs to the expression of *Chlamydomonas reinhardtii* chloroplast genes," *Mol Gen Genomics*274:625-636.
Blatti et al., (Sep. 2012) "Manipulating Fatty Acid Biosynthesis in Microalgae for Biofuel through Protein-Protein Interactions," *PLoS ONE* 7(9):e42949, 12pp.
Blowers et al., (Jan. 1989) "Studies on *Chlamydomonas* Chloroplast Transformation: Foreign DNA Can Be Stably Maintained in the Chromosome," *The Plant Cell*, 1:123-132.
Bonaventure et al., (Apr. 2003) "Disruption of the FATB Gene in Arabidopsis Dethonstrates an Essential Role of Saturated Fatty Acids in Plant Growth," *The Plant Cell* 15:1020-1033.
Boynton et al., (1988) "Chloroplast Transformation in *Chlamydomonas* with High Velocity Microprojectiles," *Science*, 240(4858):1534-1538.
Chasan, (Mar. 1995) "Engineering Fatty Acids—The Long and Short of It," *Plant Cell*, 7:235-237.
Chen et al.,(1988) "Recognition of prokaryotic transcription terminators by spinach chloroplast RNA polymerase," *Nucleic Acids Research*,16(17):8411-8431.
Chen et al., (2001) "Highly efficient expression of rabbit neutrophil peptide-1 gene in *Chlorella ellipsoidea* cells," *Current Genetics*, 39(5):365-370.
Chow et al., (1999) "Electrotransformation of *Chlorella vulgaris," Plant Cell Reports*, 18:778-780.
Cobley et al., (Sep. 1993) "Construction of Shuttle Plasmids Which Can Be Efficiently Mobilzed from *Escherichia coli* into the Chromatically Adapting Cyanobacterium, *Fremyella diplosiphon," Plasmid*,30(2): 90-105.
Cobley et al., (2002) "CpeR is an activator required for expression of the phycoerythrin operon (*cpeBA*) in the cyanobacterium Fremyella diplosiphon and is encoded in the phycoerythrin linker-polypeptide operon (*cpeCDESTR*)," *Molecular Microbiololgy*,44(6): 1517-1531.
Comai et al., (Oct. 15, 1988) "Chloroplast Transport of a Ribulose Bisphosphate Carboxylase Small Subunit-5-Enolpyruvyl 3-Phosphoshikimate Synthase Chimeric Protein Requires Part of the Mature Small Subunit in Addition to the Transit Peptide," *The Journal of Biological Chemistry*, 263(29): 15104-15109.
Courchesne, Noémie Manuelle Dorval el al., (2009) "Enhancement of lipid production using biochemical, genetic and transcription factor engineering approaches," *Journal of Biotechnology*, 141(1):31-41.
Davies et al., (1992) "Expression of the arylsulfatase gene from the $\beta_2$-tubulin promoter in *Chlamydomonas reinhardtii," Nucleic Acids Res.*, 20(12):2959-2965.
Dawson et al.,(1997) "Stable Transformation of *Chlorella*: Rescue of Nitrate Reductase-Deficient Mutants with the Nitrate Reductase Gene," *Current Microbiol.*, 35(6):356-362.
Debuchy et al.,(1989) "The argininosuccinate lyase gene of *Chlamydomonas reinhardtii*: an important tool for nuclear transformation and for correlating the genetic and molecular maps of the ARG7 locus," *EMBO Journal*, 8(10):2803-2809.
Dehesh et al. (1996) "Production of high levels of 8:0 and 10:0 fatty acids in transgenic canola by overexpression of *Ch FatB2*, a thioesterase cDNA from *Cuphea hookeriana," The Plant Journal*, 9(2):167-172.
Dehesh et al., (1998) "KAS IV: a 3-ketoacyl-ACP synthase from *Cuphea* sp. is a medium chain specific condensing enzyme," *The Plant Journal*, 15:383-390.
Deshnium et al., (1995) "Transformation of *Synechococcus* with a gene for choline oxidase enhances tolerance to salt stress," *Plant Mol. Biol.*,29(5):897-907.
Dörmann et al., (Jan. 1995) "Cloning and Expression in *Escherichia coli* of a Novel Thioesterase from *Arabidopsis thaliana* Specific for Long-Chain Acyl-Acyl Carrier Proteins," *Archives of Biochemistry and Biophysics*, 316(1):612-618.
Eccleston et al., (1996) "Medium-chain fatty Acid biosynthesis and utilization in *Brassica napus* plants expressing lauroyl-acyl carrier protein thioesterase," *Planta*, 198:46-53.
El-Sheekh et al., (1999) "Stable transformation of the intact cells of *Chlorella kessleri* with high velocity microprojectiles," *Biologia Plantarium*, 42:(2):209-216.
Facciotti et al., (1998) "Molecular dissection of the plant acyl-acyl carrier protein thioesterases," *Fett/Lipid*, 100(4-5, S.):167-172.
Facciotti et al., (Jun. 1, 1999) "Improved stearate phenotype in transgenic canola expressing a modified acyl-acyl carrier protein thioesterase," *Nat Biotechnol.*, 17(6):593-597.
Falciatore et al., (May 1999) "Transformation of Nonselectable Reporter Genes in Marine Diatoms," *Mar. Biotechnol.*, 1(3):239-251.
Frenz et al., (1989) "Hydrocarbon recovery by extraction with a biocompatible solvent from free and immobilized cultures of *Botryococcus braunii," Enzyme Microb. Technol.*, 11:717-724.
Fromm et al., (Sep. 1985) "Expression of genes transferred into monocot and dicot plant cells by electroporation," *Proc. Natl. Acad. Sci. USA*, 82:5824 5828.
Ginalski et al., (2003) "Detection of reliable and unexpected protein fold predictions using 3D-Jury," *Nucleic Acids Research*, 31(13): 3291-3292.
Giuffrida et al., (2004) "Formation and Hydrolysis of Triacylglycerol and Sterol Epdxides: Role of Unsaturated Triacylglycerol Peroxyl Radicals," *Free Radical Biology and & Medicine*, 37(1):104-114.
Gruber et al., (1991) "*Escherichia coli-Anacystis nidulans* Plasmid Shuttle Vectors Containing the $P_L$ Promoter from Bacteriophage Lambda," *Current Micro*. 22:15-19.
Gruber et al., (1996) "Expression of the *Volvox* gene encoding nitrate reductase: Mutation-dependent activation of cryptic splice sites and intron-enhanced gene expression from a cDNA," *Plant Molecular Biology*, 31(1):1-12.
Guo et al. (Jun. 22, 2004) "Protein tolerance to random amino acid change," *Proc. Natl. Acad. Sci. USA*, 101(25):9205-9210.

(56) References Cited

OTHER PUBLICATIONS

Hall et al., (1993) "Expression of a foreign gene in *Chlamydomonas reinhardtii*," *Gene*, 124:75-81.
Hallmann et al., (Nov. 1994) "Reporter genes and highly regulated promoters as tools for transformation experiments in *Volvox carteri*," *Proc. Natl. Acad. Sci. USA*, 91:11562-11566.
Hanley-Bowdoin et al., (Feb. 1987) "Chloroplast promoters," *TIBS*, 12:67-70.
Hawkins et al., (1999) "Expression of Human Growth Hormone by the Eukaryotic Alga, *Chlorella*," *Current Microbiology*, 38:335-341.
Heise et al., (1994) "Factors Controlling Medium-Chain Fatty Acid Synthesis in Plastids From *Cuphea* Embryos," *Prog. Lipid Res.*, 33(1/2):87-95.
Hejazi et al., (Apr. 2004) "Milking of microalgae," *TRENDS in Biotechnology*, 22(4):189-194.
Hill et al., (1998) "Functional Analysis of Conserved Histidines in ADP-Glucose Pyrophosphorylase from *Escherichia coli*," *Biochem. Biophys. Res. Comm.*, 244(2):573-577.
Hillen et al., (1982) "Hydrocracking of the Oils of *Botryococcus braunii* to Transport Fuels," *Biotechnology and Bioengineering*, XXIV:193-205.
Hitz et al., (1994) "Cloning of a Higher-Plant Plastid ω-6 Fatty Acid Desaturase cDNA and Its Expression in a Cyanobacterium," *Plant Physiol.*,105(2):635-641.
Huang et al. (2006) "Expression of mercuric reductase from *Bacillus megaterium* MB1 in eukaryotic microalga *Chlorella* sp. DT: an approach for mercury phytoremediation," *Appl. Microbiol. Biotechnol.* 72:197-205.
Inoue et al., (1994) "Analysis of Oil Derived From Liquefaction of *Botryococcus braunii*," *Biomass Bioenergy*, 6(4):269-274).
Isbell et al., (Feb. 1994) "Acid-Catalyzed Condensation of Oleic Acid into Estolides and Polyestolides," *JAOCS*, 71(2):169-174.
Jakobiak et al. (Dec. 2004) "The Bacterial Paromomycin Resistance Gene, *aphH*, as a Dominant Selectable Marker in *Volvox carteri*," *Protist*, 155(4):381-393.
Jarvis et al. (1991) "Transient expression of firefly luciferase in protoplasts of the green alga *Chlorella ellipsoidea*," *Current Genetics*, 19:317-321.
Jha et al., (2006) "Cloning and functional expression of an acyl-ACP thioesterase FatB type from *Diploknema* (*Madhuca*) *butyracea seeds* in *Escherichia coli*," *Plant Physiology and Biochemistry*, 44:645-655.
Jiang et al., (Apr. 2005) "The Actin Gene Promoter-driven bar as a Dominant Selectable Marker for Nuclear Transformation of Dunaliella salina," *Acta Genetica Sinica*, 32(4):424-433.
Jones et al., (Mar. 1995) "Palmitoyl-Acyl Carrier Protein (ACP) Thioesterase and the Evolutionary Origin of Plant Acyl-ACP Thioesterases," *The Plant Cell*, 7:359-371.
Kalscheuer et al., (1999) "Establishment of a gene transfer system for *Rhodococcus opacus* PD630 based on electroporation and its application for recombinant biosynthesis of poly(3-hydroxyalkanoic acids)," *Applied and Environmental Microbiology*, 52:508-515.
Kang et al., (Jul. 2000) "The Regulation Activity of Chlorella Virus Gene 5' Upstream Sequence in *Escherichia coli* and Eucaryotic Algae," [English Abstract] *Chinese Journal of Biotechnology*, 16(4):6 pages.
Kang et al., (2004) "Genetic diversity in chlorella viruses flanking *kcv*, a gene that encodes a potassium ion channel protein," *Virology*, 326(1):150-159.
Kawasaki et al.,(2004) "Immediate early genes expressed in chlorovirus infections," *Virology*, 318(1):214-223.
Kim et al., (2002) Stable Integration and Functional Expression of Flounder Growth Hormone Gene in Transformed Microalga, *Chlorella ellipsoidea, Mar. Biotechnol.*, 4(1):63-73.
Kindle, (Feb. 1990) "High-frequency nuclear transformation of *Chlamydomonas reinhardtii*," *Proc. Natl. Acad. Sci. USA*, 87(3): 1228-1232.
Klein et al., (1987) "High-velocity microprojectiles for delivering nucleic acids into living cells," *Nature* London 327(7):70-73.
Knauf, (Feb. 1987) "The application of genetic engineering to oilseed crops," *TIBTECH*, 5:40-47.
Knutzon et al., (Jul. 1999) "Lysophosphatidic Acid Acyltransferase from Coconut Endosperm Mediates the Insertion of Laurate at the sn-2 Position of Triacylglycerols in Lauric Rapeseed Oil and Can Increase Total Laurate Levels," *Plant Physiology*, 120:739-746.
Kojima et al., (1999) "Growth and Hydrocarbon Production of Microalga *Botryococcus braunii* in Bubble Column Photobioreactors," *Journal of Bioscience and Bioengineering*, 87(6): 811-815.
Koksharova et al., (Feb. 2002) "Genetic tools for cyanobacteria," *Appl Microbiol Biotechnol* 58(2): 123-137.
Krebbers et al., (1982) "The maize chloroplast genes for the β and ε subunits of the photosynthetic coupling factor $CF_1$ are fused," *Nucleic Acids Research*, 10(16):4985-5002.
La Scala et al., (Jan. 2002) "The Effect of Fatty Acid Composition on the Acrylation Kinetics of Epoxidized Triacylglycerols", *Journal of the American Oil Chemists' Society*, 79(1):59-63.
Lapidot et al., (May 2002) "Stable Chloroplast Transformation of the Unicellular Red Alga *Porphyridium* Species," *Plant Physiol.*, 129(1):7-12.
Larson et al., (2002) "Acyl CoA profilesof transgenic plants that accumulate medium-chain fatty acids indicate inefficient storage lipid synthesis in developing oilseeds," *The Plant Journal*, 32(4):519-527.
Lumbreras et al., (1998) "Efficient foreign gene expression in *Chlamydomonas reinhardtii* mediated by an endogenous intron," *Plant Journal*, 14(4):441-447.
Manuell et al., (2007) "Robust expression of a bioactive mammalian protein in *Chlamydomonas* chloroplast," *Plant Biotechnol Journal*, 5:402-412.
Mayer et al., (Feb. 4, 2005) "A Structural Model of the Plant Acyl-Acyl Carrier Protein Thioesterase FatB Comprises Two Helix/4-Stranded Sheet Domains, the N-terminal Domain Containing Residues That Affect Specificity and the C-terminal Domain Containing Catalytic Residues," *The Journal of Biological Chemistry*, 280(5):3621-3627.
Mayer et al., (Jan. 3, 2007) "Identification of amino acid residues involved in substrate specificity of plant acyl-ACP thioesterases using a bioinformatics-guided approach," *BMC Plant Biology*, 7(1):1-11 pages.
Mayfield et al., (Jan. 21, 2003) "Expression and assembly of a fully active antibody in algae," *Proc. Natl. Acad. Sci. USA*, 100(2):438-442.
Mekhedov et al., (Feb. 2000) "Toward a Functional Catalog of the Plant Genome. A Survey of Genes for Lipid Biosynthesis," *Plant Physiology*, 122:389-401.
Mendes et al. (2003) "Supercritical carbon dioxide extraction of compounds with pharmaceutical importance from microalgae," *Inorganica Chimica Acta*, 356:328-334.
Metzger et al., (Jun. 2003) "Lycopanerols I-L, Four New Tetraterpenoid Ethers from *Botryococcus braunii*," *J Nat. Prod.* 66(6):772-778.
Metzger et al., (2005) "*Botryococcus braunii*: a rich source for hydrocarbons and related ether lipids," *Appl Microbiol Biotechnol* 66:486-496.
Miao et al., (2004) "High yield bio-oil production from fast pyrolysis by metabolic controlling of *Chlorella protothecoides*," *Journal of Biotechnology*, 110:85-93.
Miao et al., (2006) "Biodiesel production from heterotrophic microalgal oil," *Biosource Technology*, 97:841-846.
Minowa et al., (1995) "Oil production from algal cells of *Dunaliella tertiolecta* by direct thermochemical liquefaction," *Fuel*, 74(12):1735-1738.
Mitra et al., (Oct. 14, 1994) "A Chlorella Virus Gene Promoter Functions as a Strong Promoter Both in Plants and Bacteria," *Biochemical Biophysical Research Communication*, 204(1): 187-194.
Mitra et al., (Oct. 1994) "The *Chlorella* virus adenine methyltransferase gene promoter is a strong promoter in plants," *Plant Mol. Biol.*, 26(1):85-93.

(56) References Cited

OTHER PUBLICATIONS

Moreno-Pérez et al., (2012) "Reduced expression of FatA thioesterases in Arabidopsis affects the oil content and fatty acid composition of the seeds," *Planta*, 235:629-639.
Mullet et al., (1985) "Multiple transcripts for higher plant rbcL and atpB genes and localization of the transcription initiation site of the rbcL gene," *Plant Molecular Biology*, 4:39-54.
Oda et al., (2000) "Degradation of Polylactide by Commercial Proteases," *Journal of Polymers and the Environment*, 8(1):29-32.
Onai et al., (2004) "Natural transformation of the thermophilic cyanobacterium *Thermosynechococcus elongatus* BP-1: a simple and efficient method for gene transfer," *Mol Genet Genomics*, 271(1):50-59.
Park et al., (2005) "Isolation and Characterization of Chlorella Virus from Fresh Water in Korea and Application in Chlorella Transformation System," *The Plant Patholology Journal*, 21(1): 13-20.
Pröschold et al., (Aug. 2005) "Portrait of a species: *Chlamydomonas reinhardtii*," *Genetics*, 170: 1601-1610.
Radakovits et al., (Apr. 2010) "Genetic Engineering of Algae for Enhanced Biofuel Production," *Eukaryotic Cell*, 9(4):486-501.
Rao et al., (2006) "Antioxidant Activity of *Botryococcus braunii* Extract Elucidated in Vitro Models," *J. Agric. Food Chem.*, 54(13):4593-4599.
Rehm et al., (2001)"Heterologous expression of the acyl-acyl carrier protein thioesterase gene from the plant *Umbellularia californica* mediates polyhydroxyalkanoate biosynthesis in recombinant *Escherichia coli*," *Appl Microbiol Biotechnol*, 55:205-209.
Rismani-Yazdi et al., (2011) "Transcriptome sequencing and annotation of the microalgae *Dunaliella tertiolecta*: Pathway description and gene discovery for production of next-generation biofuels," *BMC Genomics*, 12:148, 17 pages; doi: 10.1186/1471-2164-12-148.
Rosenberg, Julian N. et al., (2008) "A green light for engineered algae: redirecting metabolism to fuel a biotechnology revolution," *Current Opinion in Biotechnology*, 19(5):430-436.
Salas et al., (Jul. 1, 2002) "Characterization of substrate specificity of plant FatA and FatB acyl-ACP thioesterases," *Archives of Biochemistry and Biophysics*, 403(1):25-34.
Sanford, (Dec. 1988) "The biolistic process," *Trends in Biotech.* 6:299-302.
Sawayama et al. (1999) Possibility of renewable energy production and $CO_2$ mitigation by thermochemical liquefaction of microalgae *Biomass and Bioenergy*, 17:33-39.
Schreier et al., (1985) "The use of nuclear-encoded sequences to direct the light-regulated synthesis and transport of a foreign protein into plant chloroplasts," *EMBO J.* 4(1):25-32.
Schultz et al., (Apr. 2005) "A common core of secondary structure of the internal transcribed spacer 2 (ITS2) throughout the Eukaryota," *RNA*, 11(4):361-364.
Schütt et al., (1998) "The role of acyl carrier protein isoforms from *Cuphea lanceolata* seeds in the de-novo biosynthesis of medium-chain fatty acids," *Publication, Planta*, 205:263-268.
Shao et al., (2002) "Cloning and expression of metallothionein mutant α-KKS-α in *Anabaena* sp. PCC 7120," *Marine Pollution Bulletin*,45(1-12):163-167.
Sheehan, John; Dunahay, Terri; Benemann, John; Roessler, Paul; (Jul. 1998) "A Look Back at the U.S. Department of Energy's Aquatic Species Program: Biodiesel from Algae," Prepared for U.S. Department of Energy's Office of Fuels Development, Prepared by *National Renewable Energy Laboratory*, NREL/TP-580-24190, 328 pages.
Stemmer et al., (1995) "Single-step assembly of a gene and entire plasmid from large numbers of oligodeoxyribonucleotides," *Gene*, 164(1):49-53.
Tan et al., (Aug. 2005) "Establishment of a Micro-Particle Bombardment Transformation System for *Dunaliella salina*," *The Journal of Microbiology*, 43(4):361-365.
Tang et al., (Aug. 1995) "Insertion Mutagenesis of *Chlamydomonas reinhardtii* by Electroporation and Heterologous DNA," *Biochemistry and Molecular Biology International*, 36(5): 1025-1035.
Tjellström et al. (Feb. 20, 2013) "Disruption of plastid acyl:acyl carrier protein synthetases increases medium chain fatty acid accumulation in seeds of transgenic Arabidopsis," *FEBS Letters*, 587(7):936-942.
Tyystjärvi et al., (2005) "Mathematical modelling of the light response curve of photoinhibition of Photosystem II," *Photosynthesis Research*, 84(1-3):21-27.
Vázquez-Bermúdez et al., (Jan. 2000) "Uptake of 2-Oxoglutarate in *Synechococcus* Strains Transformed with the *Escherichia coli kgtP* Gene," *Journal of Bacteriology*, 182(1):211-215.
Vázquez-Bermúdez et al., (2003) "Carbon supply and 2-oxoglutarate ejects on expression of nitrate reductase and nitrogen-regulated genes in *Synechococcus* sp. strain PCC 7942," *FEMS Microbiology Letters*, 221(2):155-159.
Voelker, (1996) "Plant Acyl-Acp Thioesterases: Chain-Length Determining Enzymes in Plant Fatty Acid Biosynthesis," *Genetic Engineering*, Edited by: Setlow JK. Plenum Pres, New York, 18:111-133.
Voelker et al., (Dec. 1994) "Alteration of the Specificity and Regulation of Fatty Acid Synthesis of *Escherichia coli* by Expression of a Plant Medium Chain Acyl-Acyl Carrier Protein Thioesterase," *Journal of Bacteriology*, 176(23):7320-7327.
Voelker et al., (1997) "Broad-Range and Binary-Range Acyl-Acyl-Carrier-Protein Thioesterases Suggest an Alternative Mechanism for Medium-Chain Production in Seeds," *Plant Physiol.*, 114:669-677.
Voetz et al., (1994) "Three Different cDNAs Encoding Acyl Carrier Proteins from *Cuphea lanceolata*," *Plant Physiol.*, 106:785-786.
Walker et al., (2005) "Characterisation of the *Dunaliella tertiolecta RbcS* genes and their promoter activity in *Chlamydomonas reinhardtii*," *Plant Cell Rep.* 23(10-11): 727-735.
Westphal et al., (Mar. 27, 2001) "*Vippl* deletion mutant of *Synechocystis*: A connection between bacterial phage shock and thylakoid biogenesis?" *Proc. Natl. Acad. Sci. USA*, 98(7):4243-4248.
Wiberg et al., (2000) "The distribution of caprylate, caprate and laurate in lipids from developing and mature seeds of transgenic *Brassica napus* L.," *Planta*, 212:33-40.
Wirth et al., (1989) "Transformation of various species of gram-negative bacteria belonging to 11 different genera by electroporation," *Mol Gen Genet.* 216(1):175-177.
Wolk et al., (Mar. 1984) "Construction of shuttle vectors capable of conjugative transfer from *Escherichia coli* to nitrogen-fixing filamentous cyanobacteria," *Proc. Natl. Acad. Sci. USA*, 81(5): 1561-1565.
Wong et al., (1992) "*Arabidopsis thaliana* small subunit leader and transit peptide enhance the expression of *Bacillus thuringiensis* proteins in transgenic plants," *Plant Molecular Biology*, 20:81-93.
Wu et al., (2001) "Identification of *Chlorella* spp. isolates using ribosomal DNA sequences," *Bot. Bull. Acad. Sin.*42:115-121.
Yu et al., (2011) "Modifications of the metabolic pathways of lipid and triacylglycerol production in microalgae,"*Microbial Cell Factories*, 10:91 [Retrieved from the Internet Jul. 24, 2012: <URL:http://www.microbialcellfactories.com/content/10/1/91>], 11 pages.
Yuan et al., (Nov. 1995) "Modification of the substrate specificity of an acyl-acyl carrier protein thioesterase by protein engineering," *Proc. Natl. Acad. Sci. USA*, 92:10639-10643.
Yuan et al., (Feb. 16, 1996) "The Catalytic Cysteine and Histidine in the Plant Acyl-Acyl Carrier Protein Thioesterases," *The Journal of Biological Chemistry*, 271(7):3417-3419.
Zurawski et al., (1981) "The structure of the gene for the large subunit of ribulose 1,5-bisphosphate carboxylase from spinach chloroplast DNA," *Nucleic Acids Res.* 9(14):3251-3270.
Zurawski et al., (Dec. 1982) "Nucleotide sequence of the gene for the $M_r$ 32,000 thylakoid membrane protein from *Spinacia oleracea* and *Nicotiana debneyi* predicts a totally conserved primary translation product of $M_r$ 38,950," *Proc. Natl. Acad. Sci. USA*, 79:7699-7703.
U.S. Office Action, dated Jul. 26, 2016, issued in U.S. Appl. No. 13/797,733.
U.S. Notice of Allowance, dated Sep. 21, 2016, issued in U.S. Appl. No. 13/797,733.

(56) References Cited

OTHER PUBLICATIONS

U.S. Office Action (Requirement for Restriction/Election), dated Jul. 12, 2016, issued in U.S. Appl. No. 14/167,908.
U.S. Office Action, dated Apr. 3, 2017, issued in U.S. Appl. No. 14/167,908.
U.S. Office Action, dated Jan. 19, 2017, issued in U.S. Appl. No. 14/808,361.
U.S. Notice of Allowance, dated Apr. 28, 2017, issued in U.S. Appl. No. 14/808,361.
European Examination Report dated Oct. 25, 2016 issued in EP 14 706 996.7.
European Partial Supplementary Search Report (Communication pursuant to Rule 164(1)EPC) dated Jul. 6, 2016 issued in EP 14 76 9502.7.
European Extended Search Report dated Oct. 13, 2016 issued in EP 14 76 9502.7.
PCT International Preliminary Report on Patentability dated Feb. 2, 2017 issued in PCT/US2015/042044.
PCT International Search Report and Written Opinion dated Mar. 31, 2016 issued in PCT/US2015/051042.
Dubois et al., (2007) "Fatty acid profiles of 80 vegetable oils with regard to their nutritional potential," *Eur. J. Lipid Sci. Technol.*, 109:710-732.

* cited by examiner

THIOESTERASES AND CELLS FOR PRODUCTION OF TAILORED OILS

CROSS REFERENCE TO RELATED APPLICATIONS

This application is a Continuation-in-part of U.S. patent application Ser. No. 13/837,996, filed Mar. 15, 2013, and claims the benefit of U.S. Provisional Patent Application Ser. No. 61/791,861, filed Mar. 15, 2013, and U.S. Provisional Patent Application Ser. No. 61/917,217, filed Dec. 17, 2013, each of which is hereby incorporated by reference herein in its entirety.

SEQUENCE LISTING

The instant application contains a Sequence Listing which has been submitted electronically in ASCII format and is hereby incorporated by reference in its entirety. Said ASCII copy, created on Jun. 5, 2014, is named SOLAP019AUS_SL.txt and is 579,821 bytes in size.

BACKGROUND

Certain organisms including plants and some microalgae use a type II fatty acid biosynthetic pathway, characterized by the use of discrete, monofunctional enzymes for fatty acid synthesis. In contrast, mammals and fungi use a single, large, multifunctional protein.

Type II fatty acid biosynthesis typically involves extension of a growing acyl-ACP (acyl-carrier protein) chain by two carbon units followed by cleavage by an acyl-ACP thioesterase. In plants, two main classes of acyl-ACP thioesterases have been identified: (i) those encoded by genes of the FatA class, which tend to hydrolyze oleoyl-ACP into oleate (an 18:1 fatty acid) and ACP, and (ii) those encoded by genes of the FatB class, which liberate C8-C16 fatty acids from corresponding acyl-ACP molecules.

Different FatB genes from various plants have specificities for different acyl chain lengths. As a result, different gene products will produce different fatty acid profiles in plant seeds. See, U.S. Pat. Nos. 5,850,022; 5,723,761; 5,639,790; 5,807,893; 5,455,167; 5,654,495; 5,512,482; 5,298,421; 5,667,997; and 5,344,771; 5,304,481. Recently, FatB genes have been cloned into oleaginous microalgae to produce triglycerides with altered fatty acid profiles. See, WO2010/063032, WO2011/150411, WO2012/106560, and WO2013/158938.

SUMMARY

In various aspects, the invention(s) contemplated herein may include, but need not be limited to, any one or more of the following embodiments:

Embodiment 1

A nucleic acid construct including a regulatory element and a FatB gene expressing an active acyl-ACP thioesterase operable to produce an altered fatty acid profile in an oil produced by a cell expressing the nucleic acid construct, wherein the FatB gene expresses a protein having an amino acid sequence falling within Glade 5 of Table 1a, the sequence having at least 94.6% sequence identity with each of SEQ ID NOs: 88, 82, 85, and 103, and optionally wherein the fatty acid of the oil is enriched in C8 and C10 fatty acids.

Embodiment 2

A nucleic acid construct including a regulatory element and a FatB gene expressing an active acyl-ACP thioesterase operable to produce an altered fatty acid profile in an oil produced by a cell expressing the nucleic acid construct, wherein the FatB gene expresses a protein having an amino acid sequence falling within one of clades 1-12 of Table 1a.

Embodiment 3

The nucleic acid construct of embodiment 2, wherein the FatB gene expresses a protein having an amino acid sequence falling within Glade 1 of Table 1a, the sequence having at least 85.9% sequence identity with each of SEQ ID NOs: 19, 161, 22, and 160, and optionally wherein the fatty acid of the oil is enriched in C14 and C16 fatty acids.

Embodiment 4

The nucleic acid construct of embodiment 2, wherein the FatB gene expresses a protein having an amino acid sequence falling within Glade 2 of Table 1a, the sequence having at least 89.5% sequence identity with each of SEQ ID NOs: 134-136, 132, 133, 137, 124, 122, 123, 125, and optionally wherein the fatty acid of the oil is enriched in C12 and C14 fatty acids.

Embodiment 5

The nucleic acid construct of embodiment 2, wherein the FatB gene expresses a protein having an amino acid sequence falling within Glade 3 of Table 1a, the sequence having at least 92.5% sequence identity with each of SEQ ID NOs: 126 and 127, and optionally wherein the fatty acid of the oil is enriched in C12 and C14 fatty acids.

Embodiment 6

The nucleic acid construct of embodiment 2, wherein the FatB gene expresses a protein having an amino acid sequence falling within Glade 4 of Table 1a, the sequence having at least 83.8% sequence identity with SEQ ID NO: 79, and optionally wherein the fatty acid of the oil is enriched in C12 and C14 fatty acids.

Embodiment 7

The nucleic acid construct of embodiment 2, wherein the FatB gene expresses a protein having an amino acid sequence falling within Glade 6 of Table 1a, the sequence having at least 99.9% sequence identity with each of SEQ ID NOs: 111 and 110, and optionally wherein the fatty acid of the oil is enriched in C10 fatty acids.

Embodiment 8

The nucleic acid construct of embodiment 2, wherein the FatB gene expresses a protein having an amino acid sequence falling within Glade 7 of Table 1a, the sequence having at least 89.5% sequence identity with each of SEQ ID NOs: 73, 106, 185, 172, 171, 173, 174, and optionally wherein the fatty acid of the oil is enriched in C10 and C12 fatty acids.

Embodiment 9

The nucleic acid construct of embodiment 2, wherein the FatB gene expresses a protein having an amino acid sequence falling within Glade 8 of Table 1a, the sequence having at least 85.9% sequence identity with each of SEQ ID NOs: 112, 113, 142, 145, 143, 144, 139, 140, 138, 141, and optionally wherein the fatty acid of the oil is enriched in C12 and C14 fatty acids.

Embodiment 10

The nucleic acid construct of embodiment 2, wherein the FatB gene expresses a protein having an amino acid sequence falling within Glade 9 of Table 1a, the sequence having at least 83.8% sequence identity with each of SEQ ID NOs: 187-189, and optionally wherein the fatty acid of the oil is enriched in C12 and C14 fatty acids.

Embodiment 11

The nucleic acid construct of embodiment 2, wherein the FatB gene expresses a protein having an amino acid sequence falling within Glade 10 of Table 1a, the sequence having at least 95.9% sequence identity with each of SEQ ID NOs: 147, 149, 146, 150, 152, 151, 148, 154, 156, 155, 157, 108, 75, 190, 191, and 192, and optionally wherein the fatty acid of the oil is enriched in C14 and C16 fatty acids.

Embodiment 12

The nucleic acid construct of embodiment 2, wherein the FatB gene expresses a protein having an amino acid sequence falling within Glade 11 of Table 1a, the sequence having at least 88.7% sequence identity with SEQ ID NO: 121, and optionally wherein the fatty acid of the oil is enriched in C14 and C16 fatty acids.

Embodiment 13

The nucleic acid construct of embodiment 2, wherein the FatB gene expresses a protein having an amino acid sequence falling within Glade 12 of Table 1a, the sequence having at least 72.8% sequence identity with each of SEQ ID NOs: 129 and 186, and optionally wherein the fatty acid of the oil is enriched in C16 fatty acids.

Embodiment 14

An isolated nucleic acid or recombinant DNA construct including a nucleic acid, wherein the nucleic acid has at least 80% sequence identity to any of SEQ ID NOS: 2, 3, 5, 6, 8, 9, 11, 12, 14, 15, 17, 18, 20, 21, 23, 24, 26, 27, 29, 30, 32, 33, 35, 36, 38, 39, 41, 42, 44, 45, 47, 48, 50, 51, 53, 54, 56, 57, 59, 60, 62, 63, 65, 66, 68, 69, 71, 72, 74, 76, 78, 80, 81, 83, 84, 86, 87, 89, 90, 92, 93, 95, 96, 98, 99, 101, 102, 104, 105, 107, 109 or any equivalent sequences by virtue of the degeneracy of the genetic code.

Embodiment 15

An isolated nucleic acid sequence encoding a protein or a host cell expressing a protein having at least 80% sequence identity to any of SEQ ID NOS: 1, 4, 7, 10, 13, 16, 19, 22, 25, 28, 31, 34, 37, 40, 43, 46, 49, 52, 55, 58, 61, 64, 67, 70, 73, 75, 77, 79, 82, 85, 88, 91, 94, 97, 100, 103, 106, 108, 110-192 or a fragment thereof having acyl-ACP thioesterase activity.

Embodiment 16

The isolated nucleic acid of embodiment 15, wherein, the protein has acyl-ACP thioesterase activity operable to alter the fatty acid profile of an oil produced by a recombinant cell including that sequence.

Embodiment 17

A method of producing a recombinant cell that produces an altered fatty acid profile, the method including transforming the cell with a nucleic acid according to any of embodiments 1-3.

Embodiment 18

A host cell produced by the method of embodiment 17.

Embodiment 19

The host cell of embodiment 18, wherein the host cell is selected from a plant cell, a microbial cell, and a microalgal cell.

Embodiment 20

A method for producing an oil or oil-derived product, the method including cultivating a host cell of embodiment 5 or 6, and extracting oil produced thereby, optionally wherein the cultivation is heterotrophic growth on sugar.

Embodiment 21

The method of embodiment 20, further including producing a fatty acid, fuel, chemical, or other oil-derived product from the oil.

Embodiment 22

An oil produced by the method of embodiment 20, optionally having a fatty acid profile including at least 20% C8, C10, C12, C14 or C16 fatty acids.

Embodiment 23

An oil-derived product produced by the method of embodiment 21.

Embodiment 24

The oil of embodiment 23, wherein the oil is produced by a microalgae and optionally, lacks C24-alpha sterols.

DESCRIPTION OF ILLUSTRATIVE EMBODIMENTS OF THE INVENTION

Definitions

As used with respect to nucleic acids, the term "isolated" refers to a nucleic acid that is free of at least one other component that is typically present with the naturally occurring nucleic acid. Thus, a naturally occurring nucleic acid is isolated if it has been purified away from at least one other component that occurs naturally with the nucleic acid.

A "natural oil" or "natural fat" shall mean a predominantly triglyceride oil obtained from an organism, where the oil has not undergone blending with another natural or synthetic oil, or fractionation so as to substantially alter the fatty acid profile of the triglyceride. In connection with an oil comprising triglycerides of a particular regiospecificity, the natural oil or natural fat has not been subjected to interesterification or other synthetic process to obtain that regiospecific triglyceride profile, rather the regiospecificity is produced naturally, by a cell or population of cells. In connection with a natural oil or natural fat, and as used generally throughout the present disclosure, the terms oil and fat are used interchangeably, except where otherwise noted. Thus, an "oil" or a "fat" can be liquid, solid, or partially solid at room temperature, depending on the makeup of the substance and other conditions. Here, the term "fractionation" means removing material from the oil in a way that changes its fatty acid profile relative to the profile produced by the organism, however accomplished. The terms "natural oil" and "natural fat" encompass such oils obtained from an organism, where the oil has undergone minimal processing, including refining, bleaching and/or degumming, which does not substantially change its triglyceride profile. A natural oil can also be a "noninteresterified natural oil", which means that the natural oil has not undergone a process in which fatty acids have been redistributed in their acyl linkages to glycerol and remain essentially in the same configuration as when recovered from the organism.

"Exogenous gene" shall mean a nucleic acid that codes for the expression of an RNA and/or protein that has been introduced into a cell (e.g. by transformation/transfection), and is also referred to as a "transgene". A cell comprising an exogenous gene may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell, for example, as an insertion into the genome (nuclear or plastid) or as an episomal molecule.

"Fatty acids" shall mean free fatty acids, fatty acid salts, or fatty acyl moieties in a glycerolipid. It will be understood that fatty acyl groups of glycerolipids can be described in terms of the carboxylic acid or anion of a carboxylic acid that is produced when the triglyceride is hydrolyzed or saponified.

"Microalgae" are microbial organisms that contain a chloroplast or other plastid, and optionally that are capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as *Chlamydomonas*, as well as microbes such as, for example, Volvox, which is a simple multicellular photosynthetic microbe of two distinct cell types. Microalgae include cells such as *Chlorella, Dunaliella*, and *Prototheca*. Microalgae also include other microbial photosynthetic organisms that exhibit cell-cell adhesion, such as *Agmenellum, Anabaena*, and *Pyrobotrys*. Microalgae also include obligate heterotrophic microorganisms that have lost the ability to perform photosynthesis, such as certain dinoflagellate algae species and species of the genus *Prototheca.*

An "oleaginous" cell is a cell capable of producing at least 20% lipid by dry cell weight, naturally or through recombinant or classical strain improvement. An "oleaginous microbe" or "oleaginous microorganism" is a microbe, including a microalga that is oleaginous.

The term "percent sequence identity," in the context of two or more amino acid or nucleic acid sequences, refers to two or more sequences or subsequences that are the same or have a specified percentage of amino acid residues or nucleotides that are the same, when compared and aligned for maximum correspondence, as measured using a sequence comparison algorithm or by visual inspection. For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted using the NCBI BLAST software (ncbi.nlm.nih.gov/BLAST/) set to default parameters. For example, to compare two nucleic acid sequences, one may use blastn with the "BLAST 2 Sequences" tool Version 2.0.12 (Apr. 21, 2000) set at the following default parameters: Matrix: BLOSUM62; Reward for match: 1; Penalty for mismatch: −2; Open Gap: 5 and Extension Gap: 2 penalties; Gap x drop-off: 50; Expect: 10; Word Size: 11; Filter: on. For a pairwise comparison of two amino acid sequences, one may use the "BLAST 2 Sequences" tool Version 2.0.12 (Apr. 21, 2000) with blastp set, for example, at the following default parameters: Matrix: BLOSUM62; Open Gap: 11 and Extension Gap: 1 penalties; Gap x drop-off 50; Expect: 10; Word Size: 3; Filter: on.

In connection with a natural oil, a "profile" is the distribution of particular species or triglycerides or fatty acyl groups within the oil. A "fatty acid profile" is the distribution of fatty acyl groups in the triglycerides of the oil without reference to attachment to a glycerol backbone. Fatty acid profiles are typically determined by conversion to a fatty acid methyl ester (FAME), followed by gas chromatography (GC) analysis with flame ionization detection (FID). The fatty acid profile can be expressed as one or more percent of a fatty acid in the total fatty acid signal determined from the area under the curve for that fatty acid. FAME-GC-FID measurement approximate weight percentages of the fatty acids.

As used herein, an oil is said to be "enriched" in one or more particular fatty acids if there is at least a 10% increase in the mass of that fatty acid in the oil relative to the non-enriched oil. For example, in the case of a cell expressing a heterologous FatB gene described herein, the oil produced by the cell is said to be enriched in, e.g., C8 and C16 fatty acids if the mass of these fatty acids in the oil is at least 10% greater than in oil produced by a cell of the same type that does not express the heterologous FatB gene (e.g., wild type oil).

"Recombinant" is a cell, nucleic acid, protein or vector that has been modified due to the introduction of an exogenous nucleic acid or the alteration of a native nucleic acid. Thus, e.g., recombinant (host) cells can express genes that are not found within the native (non-recombinant) form of the cell or express native genes differently than those genes are expressed by a non-recombinant cell. Recombinant cells can, without limitation, include recombinant nucleic acids that encode a gene product or suppression elements such as mutations, knockouts, antisense, interfering RNA (RNAi) or dsRNA that reduce the levels of active gene product in a cell. A "recombinant nucleic acid" is a nucleic acid originally formed in vitro, in general, by the manipulation of nucleic acid, e.g., using polymerases, ligases, exonucleases, and endonucleases, using chemical synthesis, or otherwise is in a form not normally found in nature. Recombinant nucleic acids may be produced, for example, to place two or more nucleic acids in operable linkage. Thus, an isolated nucleic acid or an expression vector formed in vitro by nucleic by ligating DNA molecules that are not normally joined in nature, are both considered recombinant for the purposes of this invention. Recombinant nucleic acids can also be produced in other ways; e.g., using chemical DNA synthesis. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

Embodiments of the present invention relate to the use of FatB genes isolated from plants, which can be expressed in a host cell in order to alter the fatty acid profile of an oil produced by the recombinant cell. Although the microalga, *Prototheca moriformis*, was used to screen the genes for ability to the alter fatty acid profile, the genes are useful in a wide variety of host cells. For example, the genes can be expressed in bacteria, other microalgae, or higher plants. The genes can be expressed in higher plants according to the methods of U.S. Pat. Nos. 5,850,022; 5,723,761; 5,639,790; 5,807,893; 5,455,167; 5,654,495; 5,512,482; 5,298,421; 5,667,997; 5,344,771; and 5,304,481. The fatty acids can be further converted to triglycerides, fatty aldehydes, fatty alcohols and other oleochemicals either synthetically or biosynthetically.

In specific embodiments, triglycerides are produced by a host cell expressing a novel FatB gene. A triglyceride-containing natural oil can be recovered from the host cell. The natural oil can be refined, degummed, bleached and/or deodorized. The oil, in its natural or processed form, can be used for foods, chemicals, fuels, cosmetics, plastics, and other uses. In other embodiments, the FatB gene may not be novel, but the expression of the gene in a microalga is novel.

The genes can be used in a variety of genetic constructs including plasmids or other vectors for expression or recombination in a host cell. The genes can be codon optimized for expression in a target host cell. The proteins produced by the genes can be used in vivo or in purified form.

For example, the gene can be prepared in an expression vector comprising an operably linked promoter and 5'UTR. Where a plastidic cell is used as the host, a suitably active plastid targeting peptide can be fused to the FATB gene, as in the examples below. Generally, for the newly identified FATB genes, there are roughly 50 amino acids at the N-terminal that constitute a plastid transit peptide, which are responsible for transporting the enzyme to the chloroplast. In the examples below, this transit peptide is replaced with a 38 amino acid sequence that is effective in the *Prototheca moriformis* host cell for transporting the enzyme to the plastids of those cells. Thus, the invention contemplates deletions and fusion proteins in order to optimize enzyme activity in a given host cell. For example, a transit peptide from the host or related species may be used instead of that of the newly discovered plant genes described here.

A selectable marker gene may be included in the vector to assist in isolating a transformed cell. Examples of selectable markers useful in microlagae include sucrose invertase and antibiotic resistance genes.

The gene sequences disclosed can also be used to prepare antisense, or inhibitory RNA (e.g., RNAi or hairpin RNA) to inhibit complementary genes in a plant or other organism.

FatB genes found to be useful in producing desired fatty acid profiles in a cell are summarized below in Table 1. Nucleic acids or proteins having the sequence of SEQ ID NOS: 1-109 can be used to alter the fatty acid profile of a recombinant cell. Variant nucleic acids can also be used; e.g., variants having at least 70, 80, 85, 90, 95, 96, 97, 98, or 99% sequence identity to SEQ ID NOS: 2, 3, 5, 6, 8, 9, 11, 12, 14, 15, 17, 18, 20, 21, 23, 24, 26, 27, 29, 30, 32, 33, 35, 36, 38, 39, 41, 42, 44, 45, 47, 48, 50, 51, 53, 54, 56, 57, 59, 60, 62, 63, 65, 66, 68, 69, 71, 72, 74, 76, 78, 80, 81, 83, 84, 86, 87, 89, 90, 92, 93, 95, 96, 98, 99, 101, 102, 104, 105, 107 or 109. Codon optimization of the genes for a variety of host organisms is contemplated, as is the use of gene fragments. Preferred codons for *Prototheca* strains and for *Chlorella protothecoides* are shown below in Tables 2 and 3, respectively. Codon usage for *Cuphea wrightii* is shown in Table 3a. Codon usage for *Arabidopsis* is shown in Table 3b; for example, the most preferred of codon for each amino acid can be selected. Codon tables for other organisms including microalgae and higher plants are known in the art. In some embodiments, the first and/or second most preferred *Prototheca* codons are employed for codon optimization. In specific embodiments, the novel amino acid sequences contained in the sequence listings below are converted into nucleic acid sequences according to the most preferred codon usage in *Prototheca, Chlorella, Cuphea wrightii*, or *Arabidopsis* as set forth in tables 2 through 3b or nucleic acid sequences having at least 70, 80, 85, 90, 95, 96, 97, 98, or 99% sequence identity to these derived nucleic acid sequences.

In embodiments of the invention, there is protein or a nucleic acid encoding a protein having any of SEQ ID NOS: 1, 4, 7, 10, 13, 16, 19, 22, 25, 28, 31, 34, 37, 40, 43, 46, 49, 52, 55, 58, 61, 64, 67, 70, 73, 75, 77, 79, 82, 85, 88, 91, 94, 97, 100, 103, 106, 108, or 110-192. In an embodiment, there is protein or a nucleic acid encoding a protein having at least 70, 75, 80, 85, 90, 91, 92, 93, 94, 95, 96, 97, 98, 99, or 100% sequence identity with any of SEQ ID NOS: 1, 4, 7, 10, 13, 16, 19, 22, 25, 28, 31, 34, 37, 40, 43, 46, 49, 52, 55, 58, 61, 64, 67, 70, 73, 75, 77, 79, 82, 85, 88, 91, 94, 97, 100, 103, 106, 108, or 110-192. In certain embodiments, the invention encompasses a fragment any of the above-described proteins or nucleic acids (including fragments of protein or nucleic acid variants), wherein the protein fragment has acyl-ACP thioesterase activity or the nucleic acid fragment encodes such a protein fragment. In other embodiments, the fragment includes a domain of an acyl-ACP thioesterase that mediates a particular function, e.g., a specificity-determining domain. Illustrative fragments can be produced by C-terminal and/or N-terminal truncations and include at least 50%, 55%, 60%, 65%, 70%, 75%, 80%, 85%, 90%, 95%, 96%, 97%, 98%, or 99% of the full-length sequences disclosed herein.

In certain embodiments, percent sequence identity for variants of the nucleic acids or proteins discussed above can be calculated by using the full-length nucleic acid sequence (e.g., one of SEQ ID NOS: 2, 3, 5, 6, 8, 9, 11, 12, 14, 15, 17, 18, 20, 21, 23, 24, 26, 27, 29, 30, 32, 33, 35, 36, 38, 39, 41, 42, 44, 45, 47, 48, 50, 51, 53, 54, 56, 57, 59, 60, 62, 63, 65, 66, 68, 69, 71, 72, 74, 76, 78, 80, 81, 83, 84, 86, 87, 89, 90, 92, 93, 95, 96, 98, 99, 101, 102, 104, 105, 107 or 109) or full-length amino acid sequence (e.g., one of SEQ ID NOS: 1, 4, 7, 10, 13, 16, 19, 22, 25, 28, 31, 34, 37, 40, 43, 46, 49, 52, 55, 58, 61, 64, 67, 70, 73, 75, 77, 79, 82, 85, 88, 91, 94, 97, 100, 103, 106, 108, or 110-192) as the reference sequence and comparing the full-length test sequence to this reference sequence. In some embodiments relating to fragments, percent sequence identity for variants of nucleic acid or protein fragments can be calculated over the entire length of the fragment.

The nucleic acids can be in isolated form, or part of a vector or other construct, chromosome or host cell. It has been found that is many cases the full length gene (and protein) is not needed; for example, deletion of some or all of the N-terminal hydrophobic domain (typically an 18 amino acid domain starting with LPDW) yields a still-functional gene. In addition, fusions of the specificity determining regions of the genes in Table 1 with catalytic domains of other acyl-ACP thioesterases can yield functional genes. Thus, in certain embodiments, the invention encompasses functional fragments (e.g., specificity determining regions) of the disclosed nucleic acid or amino acids fused to heterologous acyl-ACP thioesterase nucleic acid or amino acid sequences, respectively.

TABLE 1

FatB genes according to embodiments of the present invention

| Species | Gene Name | Sequence Variant (relative to dominant transcript identified) | Amino Acid Sequence of CDS (no additional tags) | Native CDS nucleotide sequence (not codon-optimized, no additional cloning sites) | *Prototheca moriformis* codon-optimized nucleotide sequence of CDS |
|---|---|---|---|---|---|
| *Cinnamomum camphora* | CcFATB1b | M25L, M322R, ΔT367-D368 | SEQ ID NO: 1 | SEQ ID NO: 2 | SEQ ID NO: 3 |
| *Cinnamomum camphora* | CcFATB4 | “wild-type” | SEQ ID NO: 4 | SEQ ID NO: 5 | SEQ ID NO: 6 |
| *Cinnamomum camphora* | CcFATB3 | “wild-type” | SEQ ID NO: 7 | SEQ ID NO: 8 | SEQ ID NO: 9 |
| *Cuphea hyssopifolia* | ChsFATB1 | “wild-type” | SEQ ID NO: 10 | SEQ ID NO: 11 | SEQ ID NO: 12 |
| *Cuphea hyssopifolia* | ChsFATB2 | “wild-type” | SEQ ID NO: 13 | SEQ ID NO: 14 | SEQ ID NO: 15 |
| *Cuphea hyssopifolia* | ChsFATB2b | +a.a.248-259 | SEQ ID NO: 16 | SEQ ID NO: 17 | SEQ ID NO: 18 |
| *Cuphea hyssopifolia* | ChsFATB3 | “wild-type” | SEQ ID NO: 19 | SEQ ID NO: 20 | SEQ ID NO: 21 |
| *Cuphea hyssopifolia* | ChsFATB3b | V204I, C239F, E243D, M251V | SEQ ID NO: 22 | SEQ ID NO: 23 | SEQ ID NO: 24 |
| *Cuphea* PSR23 | CuPSR23FATB3 | “wild-type” | SEQ ID NO: 25 | SEQ ID NO: 26 | SEQ ID NO: 27 |
| *Cuphea wrightii* | CwFATB3 | “wild-type” | SEQ ID NO: 28 | SEQ ID NO: 29 | SEQ ID NO: 30 |
| *Cuphea wrightii* | CwFATB4a | “wild-type” | SEQ ID NO: 31 | SEQ ID NO: 32 | SEQ ID NO: 33 |
| *Cuphea wrightii* | CwFATB4b | “wild-type” | SEQ ID NO: 34 | SEQ ID NO: 35 | SEQ ID NO: 36 |
| *Cuphea wrightii* | CwFATB5 | “wild-type” | SEQ ID NO: 37 | SEQ ID NO: 38 | SEQ ID NO: 39 |
| *Cuphea heterophylla* | ChtFATB1a | “wild-type” | SEQ ID NO: 40 | SEQ ID NO: 41 | SEQ ID NO: 42 |
| *Cuphea heterophylla* | ChtFATB1b | P16S, T20P, G94S, G105W, S293F, L305F | SEQ ID NO: 43 | SEQ ID NO: 44 | SEQ ID NO: 45 |
| *Cuphea heterophylla* | ChtFATB2b | “wild-type” | SEQ ID NO: 46 | SEQ ID NO: 47 | SEQ ID NO: 48 |
| *Cuphea heterophylla* | ChtFATB2a | S17P, P21S, T28N, L30P, S33L, G76D, S78P, G137W | SEQ IDO NO: 49 | SEQ ID NO: 50 | SEQ ID NO: 51 |
| *Cuphea heterophylla* | ChtFATB2c | G76D, S78P | SEQ ID NO: 52 | SEQ ID NO: 53 | SEQ ID NO: 54 |
| *Cuphea heterophylla* | ChtFATB2d | S21P, T28N, L30P, S33L, G76D, R97L, H124L, W127L, I132S, K258N, C303R, E309G, K334T, T386A | SEQ ID NO: 55 | SEQ ID NO: 56 | SEQ ID NO: 57 |
| *Cuphea heterophylla* | ChtFATB2e | G76D, R97L, H124L, I132S, G152S, H165L, T211N, K258N, C303R, E309G, K334T, T386A | SEQ ID NO: 58 | SEQ ID NO: 59 | SEQ ID NO: 60 |

TABLE 1-continued

FatB genes according to embodiments of the present invention

| Species | Gene Name | Sequence Variant (relative to dominant transcript identified) | Amino Acid Sequence of CDS (no additional tags) | Native CDS nucleotide sequence (not codon-optimized, no additional cloning sites) | *Prototheca moriformis* codon-optimized nucleotide sequence of CDS |
|---|---|---|---|---|---|
| *Cuphea heterophylla* | ChtFATB2f | R97L, H124L, I132S, G152S, H165L, T211N | SEQ ID NO: 61 | SEQ ID NO: 62 | SEQ ID NO: 63 |
| *Cuphea heterophylla* | ChtFATB2g | A6T, A16V, S17P, G76D, R97L, H124L, I132S, S143I, G152S, A157T, H165L, T211N, G414A | SEQ ID NO: 64 | SEQ ID NO: 65 | SEQ ID NO: 66 |
| *Cuphea heterophylla* | ChtFATB3a | “wild-type” | SEQ ID NO: 67 | SEQ ID NO: 68 | SEQ ID NO: 69 |
| *Cuphea heterophylla* | ChtFATB3b | C67G, H72Q, L128F, N179I | SEQ ID NO: 70 | SEQ ID NO: 71 | SEQ ID NO: 72 |
| *Cuphea viscosissima* | CvisFATB1 | published | SEQ ID NO: 73 | N/A | SEQ ID NO: 74 |
| *Cuphea viscosissima* | CvisFATB2 | published | SEQ ID NO: 75 | N/A | SEQ ID NO: 76 |
| *Cuphea viscosissima* | CvisFATB3 | published | SEQ ID NO: 77 | N/A | SEQ ID NO: 78 |
| *Cuphea calcarata* | CcalcFATB1 | “wild-type” | SEQ ID NO: 79 | SEQ ID 80 | SEQ ID 81 |
| *Cuphea painteri* | CpaiFATB1 | “wild-type” | SEQ ID NO: 82 | SEQ ID 83 | SEQ ID 84 |
| *Cuphea hookeriana* | ChookFATB4 | “wild-type” | SEQ ID NO: 85 | SEQ ID 86 | SEQ ID 87 |
| *Cuphea avigera* var. *pulcherrima* | CaFATB1 | “wild-type” | SEQ ID NO: 88 | SEQ ID 89 | SEQ ID 90 |
| *Cuphea paucipetala* | CPauFATB1 | “wild-type” | SEQ ID NO: 91 | SEQ ID 92 | SEQ ID 93 |
| *Cuphea procumbens* | CprocFATB1 | “wild-type” | SEQ ID NO: 94 | SEQ ID 95 | SEQ ID 96 |
| *Cuphea procumbens* | CprocFATB2 | “wild-type” | SEQ ID NO: 97 | SEQ ID 98 | SEQ ID 99 |
| *Cuphea procumbens* | CprocFATB3 | “wild-type” | SEQ ID NO: 100 | SEQ ID 101 | SEQ ID 102 |
| *Cuphea ignea* | CigneaFATB1 | “wildtype”; partial (missing N-terminal portion of native transit peptide, fused to CpSAD1tp_trimmed transit peptide) | SEQ ID NO: 103 | SEQ ID 104 | SEQ ID 105 |
| Consensus | JcFATB1 | Consensus sequence | SEQ ID NO: 106 | None, can be codon optimized for a given host | SEQ ID NO: 107 |
| Consensus | JcFATB2 | Consensus sequence | SEQ ID NO: 108 | None, can be codon optimized for a given host | SEQ ID NO: 109 |

In certain embodiments, a host cell (e.g. plant or microalgal cell) is transformed to produce a recombinant FATB protein falling into one of clades 1-12 of Table 1a. These clades were determined by sequence alignment and observation of changes in fatty acid profile when expressed in *Prototheca*. See Example 5. The FATB amino acid sequence can fall within x % amino acid sequence identity of each sequence in that Glade listed in Table 1a, where x is a first second or third cutoff value, also listed in Table 1a.

TABLE 1a

Groupings of Novel FatB genes into clades.

| Clade No. | Amino Acid SEQ ID Nos. in Clade | Example Function (see Table 6) | First Cutoff Value (minimum % amino acid identity to members of clade) | Second Cutoff Value | Third Cutoff Value |
|---|---|---|---|---|---|
| 1 | ChsFATB3 (SEQ ID NO: 19)<br>ChsFATB3d (SEQ ID NO: 161)<br>ChsFATB3b (SEQ ID NO: 22)<br>ChsFATB3c (SEQ ID NO: 160) | Increase C14/C16 fatty acids | 85.9 | 97.4 | 98 |
| 2 | ChtFATB1a.2 (SEQ ID NO: 134)<br>ChtFATB1a.3 (SEQ ID NO: 135)<br>ChtFATB1a.4 (SEQ ID NO: 136)<br>ChtFATB1a (SEQ ID NO: 132)_<br>ChtFATB1a.1 (SEQ ID NO: 133)<br>ChtFATB1b (SEQ ID NO: 137)<br>CwFATB5b (SEQ ID NO: 124)<br>CwFATB5 (SEQ ID NO: 122)<br>CwFATB5a (SEQ ID NO: 123)<br>CwFATB5c (SEQ ID NO: 125) | Increase C12/C14 fatty acids | 89.5 | 95 | 98 |
| 3 | CwFATB5.1 (SEQ ID NO: 126)<br>CwFATB5.1a (SEQ ID NO: 127) | Increase C12/C14 fatty acids | 92.5 | 95 | 98 |
| 4 | CcalcFATB1 (SEQ ID NO: 79) | Increase C12/C14 fatty acids | 83.8 | 93 | 95 |
| 5 | CaFATB1 (SEQ ID NO: 88)<br>CpaiFATB1 (SEQ ID NO: 82)<br>ChookFATB4 (SEQ ID NO: 85)<br>CigneaFATB1 (SEQ ID NO: 103) | Increase C8/C10 fatty acids | 94.6 | 96 | 98 |
| 6 | CuPSR23FATB3b (SEQ ID NO: 111)<br>CuPSR23FATB3 (SEQ ID NO: 110) | Increase C10 fatty acids | 99.9 | | |
| 7 | CvisFATB1 (SEQ ID NO: 73)<br>JcFATB1/SzFATB1 (SEQ ID NO: 106)<br>CgFATB1b (SEQ ID NO: 185)<br>CprocFATB1 (SEQ ID NO: 172)<br>CpauFATB1 (SEQ ID NO: 171)<br>CprocFATB2 (SEQ ID NO: 173)<br>CprocFATB3 (SEQ ID NO: 174) | Increase C10/C12 fatty acids | 89.5 | 93 | 96 |
| 8 | CwFATB3 (SEQ ID NO: 112)<br>CwFATB3a (SEQ ID NO: 113)<br>ChtFATB2e (SEQ ID NO: 142)<br>ChtFATB2h (SEQ ID NO: 145)<br>ChtFATB2f (SEQ ID NO: 143)<br>ChtFATB2g (SEQ ID NO: 144)<br>ChtFATB2a (SEQ ID NO: 139)<br>ChtFATB2c (SEQ ID NO: 140)<br>ChtFATB2b (SEQ ID NO: 138)<br>ChtFATB2d (SEQ ID NO: 141) | Increase C12/C14 fatty acids | 85.9 | 98.9 | 99.5 |
| 9 | CcrFATB2c (SEQ ID NO: 187)<br>CcrFATB2 (SEQ ID NO: 188)<br>CcrFATB2b (SEQ ID NO: 189) | Increase C12/C14 fatty acids | 83.8 | 90 | 95 |
| 10 | ChtFATB3b (SEQ ID NO: 147)<br>ChtFATB3d (SEQ ID NO: 149)<br>ChtFATB3a (SEQ ID NO: 146)<br>ChtFATB3e (SEQ ID NO: 150)<br>ChtFATB3g (SEQ ID NO: 152)<br>ChtFATB3f (SEQ ID NO: 151)<br>ChtFATB3c (SEQ ID NO: 148)<br>ChsFATB2 (SEQ ID NO: 154)<br>ChsFATB2c (SEQ ID NO: 156)<br>ChsFATB2b (SEQ ID NO: 155)<br>ChsFATB2d (SEQ ID NO: 157)<br>JcFATB2/SzFATB2 (SEQ ID NO: 108)<br>CvisFATB2 (SEQ ID NO: 75)<br>CcrFATB1 (SEQ ID NO: 190)<br>CcrFATB1b (SEQ ID NO: 191)<br>CcrFATB1c (SEQ ID NO: 192) | Increase C14/C16 fatty acids | 95.9 | 98 | 99 |

TABLE 1a-continued

| Groupings of Novel FatB genes into clades. | | | | | |
|---|---|---|---|---|---|
| Clade No. | Amino Acid SEQ ID Nos. in Clade | Example Function (see Table 6) | First Cutoff Value (minimum % amino acid identity to members of clade) | Second Cutoff Value | Third Cutoff Value |
| 11 | CwFATB4b.1 (SEQ ID NO: 121) | Increase C14/C16 fatty acids | 88.7 | 94.5 | 97 |
| 12 | CcFATB3 (SEQ ID NO: 129) UcFATB3 (SEQ ID NO: 186) (predicted) | Increase C16 fatty acids | 72.8 | 85 | 90 |

TABLE 2

Preferred codon usage in *Prototheca* strains

| | | | | | |
|---|---|---|---|---|---|
| Ala | GCG | 345 (0.36) | Asn | AAT | 8 (0.04) |
| | GCA | 66 (0.07) | | AAC | 201 (0.96) |
| | GCT | 101 (0.11) | | | |
| | GCC | 442 (0.46) | Pro | CCG | 161 (0.29) |
| | | | | CCA | 49 (0.09) |
| Cys | TGT | 12 (0.10) | | CCT | 71 (0.13) |
| | TGC | 105 (0.90) | | CCC | 267 (0.49) |
| Asp | GAT | 43 (0.12) | Gln | CAG | 226 (0.82) |
| | GAC | 316 (0.88) | | CAA | 48 (0.18) |
| Glu | GAG | 377 (0.96) | Arg | AGG | 33 (0.06) |
| | GAA | 14 (0.04) | | AGA | 14 (0.02) |
| | | | | CGG | 102 (0.18) |
| Phe | TTT | 89 (0.29) | | CGA | 49 (0.08) |
| | TTC | 216 (0.71) | | CGT | 51 (0.09) |
| | | | | CGC | 331 (0.57) |
| Gly | GGG | 92 (0.12) | | | |
| | GGA | 56 (0.07) | Ser | AGT | 16 (0.03) |
| | GGT | 76 (0.10) | | AGC | 123 (0.22) |
| | GGC | 559 (0.71) | | TCG | 152 (0.28) |
| | | | | TCA | 31 (0.06) |
| His | CAT | 42 (0.21) | | TCT | 55 (0.10) |
| | CAC | 154 (0.79) | | TCC | 173 (0.31) |
| Ile | ATA | 4 (0.01) | Thr | ACG | 184 (0.38) |
| | ATT | 30 (0.08) | | ACA | 24 (0.05) |
| | ATC | 338 (0.91) | | ACT | 21 (0.05) |
| | | | | ACC | 249 (0.52) |
| Lys | AAG | 284 (0.98) | | | |
| | AAA | 7 (0.02) | Val | GTG | 308 (0.50) |
| | | | | GTA | 9 (0.01) |
| Leu | TTG | 26 (0.04) | | GTT | 35 (0.06) |
| | TTA | 3 (0.00) | | GTC | 262 (0.43) |
| | CTG | 447 (0.61) | | | |
| | CTA | 20 (0.03) | Trp | TGG | 107 (1.00) |
| | CTT | 45 (0.06) | | | |
| | CTC | 190 (0.26) | Tyr | TAT | 10 (0.05) |
| | | | | TAC | 180 (0.95) |
| Met | ATG | 191 (1.00) | | | |
| | | | Stop | TGA/TAG/TAA | |

TABLE 3

Preferred codon usage in *Chlorella protothecoides*

| | | | |
|---|---|---|---|
| TTC (Phe) | TAC (Tyr) | TGC (Cys) | TGA (Stop) |
| TGG (Trp) | CCC (Pro) | CAC (His) | CGC (Arg) |
| CTG (Leu) | CAG (Gln) | ATC (Ile) | ACC (Thr) |
| GAC (Asp) | TCC (Ser) | ATG (Met) | AAG (Lys) |
| GCC (Ala) | AAC (Asn) | GGC (Gly) | GTG (Val) |
| GAG (Glu) | | | |

TABLE 3a

Codon usage for *Cuphea wrightii*

| | | | |
|---|---|---|---|
| UUU F 0.48 19.5 (52) | UCU S 0.21 19.5 (52) | UAU Y 0.45 6.4 (17) | UGU C 0.41 10.5 (28) |
| UUC F 0.52 21.3 (57) | UCC S 0.26 23.6 (63) | UAC Y 0.55 7.9 (21) | UGC C 0.59 15.0 (40) |
| UUA L 0.07 5.2 (14) | UCA S 0.18 16.8 (45) | UAA * 0.33 0.7 (2) | UGA * 0.33 0.7 (2) |
| UUG L 0.19 14.6 (39) | UCG S 0.11 9.7 (26) | UAG * 0.33 0.7 (2) | UGG W 1.00 15.4 (41) |
| CUU L 0.27 21.0 (56) | CCU P 0.48 21.7 (58) | CAU H 0.60 11.2 (30) | CGU R 0.09 5.6 (15) |
| CUC L 0.22 17.2 (46) | CCC P 0.16 7.1 (19) | CAC H 0.40 7.5 (20) | CGC R 0.13 7.9 (21) |
| CUA L 0.13 10.1 (27) | CCA P 0.21 9.7 (26) | CAA Q 0.31 8.6 (23) | CGA R 0.11 6.7 (18) |
| CUG L 0.12 9.7 (26) | CCG P 0.16 7.1 (19) | CAG Q 0.69 19.5 (52) | CGG R 0.16 9.4 (25) |
| AUU I 0.44 22.8 (61) | ACU T 0.33 16.8 (45) | AAU N 0.66 31.4 (84) | AGU S 0.18 16.1 (43) |
| AUC I 0.29 15.4 (41) | ACC T 0.27 13.9 (37) | AAC N 0.34 16.5 (44) | AGC S 0.07 6.0 (16) |
| AUA I 0.27 13.9 (37) | ACA T 0.26 13.5 (36) | AAA K 0.42 21.0 (56) | AGA R 0.24 14.2 (38) |
| AUG M 1.00 28.1 (75) | ACG T 0.14 7.1 (19) | AAG K 0.58 29.2 (78) | AGG R 0.27 16.1 (43) |
| GUU V 0.28 19.8 (53) | GCU A 0.35 31.4 (84) | GAU D 0.63 35.9 (96) | GGU G 0.29 26.6 (71) |
| GUC V 0.21 15.0 (40) | GCC A 0.20 18.0 (48) | GAC D 0.37 21.0 (56) | GGC G 0.20 18.0 (48) |
| GUA V 0.14 10.1 (27) | GCA A 0.33 29.6 (79) | GAA E 0.41 18.3 (49) | GGA G 0.35 31.4 (84) |
| GUG V 0.36 25.1 (67) | GCG A 0.11 9.7 (26) | GAG E 0.59 26.2 (70) | GGG G 0.16 14.2 (38) |

TABLE 3B

| Codon usage for *Arabidopsis* | | | |
|---|---|---|---|
| UUU F 0.51 21.8 (678320) | UCU S 0.28 25.2 (782818) | UAU Y 0.52 14.6 (455089) | UGU C 0.60 10.5 (327640) |
| UUC F 0.49 20.7 (642407) | UCC S 0.13 11.2 (348173) | UAC Y 0.48 13.7 (427132) | UGC C 0.40 7.2 (222769) |
| UUA L 0.14 12.7 (394867) | UCA S 0.20 18.3 (568570) | UAA * 0.36 0.9 ( 29405) | UGA * 0.44 1.2 (36260) |
| UUG L 0.22 20.9 (649150) | UCG S 0.10 9.3 (290158) | UAG * 0.20 0.5 (16417) | UGG W 1.00 12.5 (388049) |
| CUU L 0.26 24.1 (750114) | CCU P 0.38 18.7 (580962) | CAU H 0.61 13.8 (428694) | CGU R 0.17 9.0 (280392) |
| CUC L 0.17 16.1 (500524) | CCC P 0.11 5.3 (165252) | CAC H 0.39 8.7 (271155) | CGC R 0.07 3.8 (117543) |
| CUA L 0.11 9.9 (307000) | CCA P 0.33 16.1 (502101) | CAA Q 0.56 19.4 (604800) | CGA R 0.12 6.3 (195736) |
| CUG L 0.11 9.8 (305822) | CCG P 0.18 8.6 (268115) | CAG Q 0.44 15.2 (473809) | CGG R 0.09 4.9 (151572) |
| AUU I 0.41 21.5 (668227) | ACU T 0.34 17.5 (544807) | AAU N 0.52 22.3 (693344) | AGU S 0.16 14.0 (435738) |
| AUC I 0.35 18.5 (576287) | ACC T 0.20 10.3 (321640) | AAC N 0.48 20.9 (650826) | AGC S 0.13 11.3 (352568) |
| AUA I 0.24 12.6 (391867) | ACA T 0.31 15.7 (487161) | AAA K 0.49 30.8 (957374) | AGA R 0.35 19.0 (589788) |
| AUG M 1.00 24.5 (762852) | ACG T 0.15 7.7 (240652) | AAG K 0.51 32.7 (1016176) | AGG R 0.20 11.0 (340922) |
| GUU V 0.40 27.2 (847061) | GCU A 0.43 28.3 (880808) | GAU D 0.68 36.6 (1139637) | GGU G 0.34 22.2 (689891) |
| GUC V 0.19 12.8 (397008) | GCC A 0.16 10.3 (321500) | GAC D 0.32 17.2 (535668) | GGC G 0.14 9.2 (284681) |
| GUA V 0.15 9.9 (308605) | GCA A 0.27 17.5 (543180) | GAA E 0.52 34.3 (1068012) | GGA G 0.37 24.2 (751489) |
| GUG V 0.26 17.4 (539873) | GCG A 0.14 9.0 (280804) | GAG E 0.48 32.2 (1002594) | GGG G 0.16 10.2 (316620) |

Host Cells

The host cell can be a single cell (e.g., microalga, bacteria, yeast) or part of a multicellular organism such as a plant or fungus. Methods for expressing Fatb genes in a plant are given in U.S. Pat. Nos. 5,850,022; 5,723,761; 5,639,790; 5,807,893; 5,455,167; 5,654,495; 5,512,482; 5,298,421; 5,667,997; and 5,344,771; 5,304,481, or can be accomplished using other techniques generally known in plant biotechnology. Engineering of oleaginous microbes including those of Chlorophyta is disclosed in WO2010/063032, WO2011,150411, and WO2012/106560 and in the examples below.

Examples of oleaginous host cells include plant cells and microbial cells having a type II fatty acid biosynthetic pathway, including plastidic oleaginous cells such as those of oleaginous algae. Specific examples of microalgal cells include heterotrophic or obligate heterotrophic microalgae of the phylum Chlorophyta, the class Trebouxiophytae, the order Chlorellales, or the family Chlorellacae. Examples of oleaginous microalgae are provided in Published PCT Patent Applications WO2008/151149, WO2010/06032, WO2011/150410, and WO2011/150411, including species of *Chlorella* and *Prototheca*, a genus comprising obligate heterotrophs. The oleaginous cells can be, for example, capable of producing 25, 30, 40, 50, 60, 70, 80, 85, or about 90% oil by cell weight, ±5%. Optionally, the oils produced can be low in DHA or EPA fatty acids. For example, the oils can comprise less than 5%, 2%, or 1% DHA and/or EPA. The above-mentioned publications also disclose methods for cultivating such cells and extracting oil, especially from microalgal cells; such methods are applicable to the cells disclosed herein and incorporated by reference for these teachings. When microalgal cells are used they can be cultivated autotrophically (unless an obligate heterotroph) or in the dark using a sugar (e.g., glucose, fructose and/or sucrose). In any of the embodiments described herein, the cells can be heterotrophic cells comprising an exogenous invertase gene so as to allow the cells to produce oil from a sucrose feedstock. Alternately, or in addition, the cells can metabolize xylose from cellulosic feedstocks. For example, the cells can be genetically engineered to express one or more xylose metabolism genes such as those encoding an active xylose transporter, a xylulose-5-phosphate transporter, a xylose isomerase, a xylulokinase, a xylitol dehydrogenase and a xylose reductase. See WO2012/154626, "GENETICALLY ENGINEERED MICROORGANISMS THAT METABOLIZE XYLOSE", published Nov. 15, 2012.

Oils and Related Products

The oleaginous cells express one or more exogenous genes encoding fatty acid biosynthesis enzymes. As a result, some embodiments feature natural oils that were not obtainable from a non-plant or non-seed oil, or not obtainable at all.

The oleaginous cells produce a storage oil, which is primarily triacylglyceride and may be stored in storage bodies of the cell. A raw oil may be obtained from the cells by disrupting the cells and isolating the oil. WO2008/151149, WO2010/06032, WO2011/150410, and WO2011/1504 disclose heterotrophic cultivation and oil isolation techniques. For example, oil may be obtained by cultivating, drying and pressing the cells. The oils produced may be refined, bleached and deodorized (RBD) as known in the art or as described in WO2010/120939. The raw or RBD oils may be used in a variety of food, chemical, and industrial products or processes. After recovery of the oil, a valuable residual biomass remains. Uses for the residual biomass include the production of paper, plastics, absorbents, adsorbents, as animal feed, for human nutrition, or for fertilizer.

Where a fatty acid profile of a triglyceride (also referred to as a "triacylglyceride" or "TAG") cell oil is given here, it will be understood that this refers to a nonfractionated sample of the storage oil extracted from the cell analyzed under conditions in which phospholipids have been removed or with an analysis method that is substantially insensitive to the fatty acids of the phospholipids (e.g. using chromatography and mass spectrometry). The oil may be subjected to an RBD process to remove phospholipids, free fatty acids and odors yet have only minor or negligible changes to the fatty acid profile of the triglycerides in the oil. Because the cells are oleaginous, in some cases the storage oil will constitute the bulk of all the TAGs in the cell.

The stable carbon isotope value δ13C is an expression of the ratio of 13C/12C relative to a standard (e.g. PDB, carbonite of fossil skeleton of *Belemnite americana* from Peedee formation of South Carolina). The stable carbon isotope value δ13C (0/00) of the oils can be related to the δ13C value of the feedstock used. In some embodiments, the oils are derived from oleaginous organisms heterotrophically grown on sugar derived from a C4 plant such as corn or sugarcane. In some embodiments the δ13C (0/00) of the oil is from −10 to −17 0/00 or from −13 to −16 0/00.

The oils produced according to the above methods in some cases are made using a microalgal host cell. As described above, the microalga can be, without limitation, fall in the classification of Chlorophyta, Trebouxiophyceae, Chlorellales, Chlorellaceae, or Chlorophyceae. It has been found that microalgae of Trebouxiophyceae can be distinguished from vegetable oils based on their sterol profiles. Oil produced by *Chlorella protothecoides* was found to produce sterols that appeared to be brassicasterol, ergosterol, campesterol, stigmasterol, and β-sitosterol, when detected by GC-MS. However, it is believed that all sterols produced by *Chlorella* have C24β stereochemistry. Thus, it is believed that the molecules detected as campesterol, stigmasterol, and β-sitosterol, are actually 22,23-dihydrobrassicasterol, proferasterol and clionasterol, respectively. Thus, the oils produced by the microalgae described above can be distinguished from plant oils by the presence of sterols with C24β stereochemistry and the absence of C24α stereochemistry in the sterols present. For example, the oils produced may contain 22,23-dihydrobrassicasterol while lacking campesterol; contain clionasterol, while lacking in β-sitosterol, and/or contain poriferasterol while lacking stigmasterol. Alternately, or in addition, the oils may contain significant amounts of $\Delta^7$-poriferasterol.

In one embodiment, the oils provided herein are not vegetable oils. Vegetable oils are oils extracted from plants and plant seeds. Vegetable oils can be distinguished from the non-plant oils provided herein on the basis of their oil content. A variety of methods for analyzing the oil content can be employed to determine the source of the oil or whether adulteration of an oil provided herein with an oil of a different (e.g. plant) origin has occurred. The determination can be made on the basis of one or a combination of the analytical methods. These tests include but are not limited to analysis of one or more of free fatty acids, fatty acid profile, total triacylglycerol content, diacylglycerol content, peroxide values, spectroscopic properties (e.g. UV absorption), sterol profile, sterol degradation products, antioxidants (e.g. tocopherols), pigments (e.g. chlorophyll), d13C values and sensory analysis (e.g. taste, odor, and mouth feel). Many such tests have been standardized for commercial oils such as the Codex Alimentarius standards for edible fats and oils.

Sterol profile analysis is a particularly well-known method for determining the biological source of organic matter. Campesterol, b-sitosterol, and stigamsterol are common plant sterols, with b-sitosterol being a principle plant sterol. For example, b-sitosterol was found to be in greatest abundance in an analysis of certain seed oils, approximately 64% in corn, 29% in rapeseed, 64% in sunflower, 74% in cottonseed, 26% in soybean, and 79% in olive oil (Gul et al. J. Cell and Molecular Biology 5:71-79, 2006).

Oil isolated from *Prototheca moriformis* strain UTEX1435 were separately clarified (CL), refined and bleached (RB), or refined, bleached and deodorized (RBD) and were tested for sterol content according to the procedure described in JAOCS vol. 60, no. 8, August 1983. Results of the analysis are shown below (units in mg/100 g):

| | Sterol | Crude | Clarified | Refined & bleached | Refined, bleached, & deodorized |
|---|---|---|---|---|---|
| 1 | Ergosterol | 384 (56%) | 398 (55%) | 293 (50%) | 302 (50%) |
| 2 | 5,22-cholestadien-24-methyl-3-ol (Brassicasterol) | 14.6 (2.1%) | 18.8 (2.6%) | 14 (2.4%) | 15.2 (2.5%) |
| 3 | 24-methylcholest-5-en-3-ol (Campesterol or 22,23-dihydro-brassicasterol) | 10.7 (1.6%) | 11.9 (1.6%) | 10.9 (1.8%) | 10.8 (1.8%) |
| 4 | 5,22-cholestadien-24-ethyl-3-ol (Stigmasterol or poriferasterol) | 57.7 (8.4%) | 59.2 (8.2%) | 46.8 (7.9%) | 49.9 (8.3%) |
| 5 | 24-ethylcholest-5-en-3-ol (β-Sitosterol or clionasterol) | 9.64 (1.4%) | 9.92 (1.4%) | 9.26 (1.6%) | 10.2 (1.7%) |
| 6 | Other sterols | 209 | 221 | 216 | 213 |
| | Total sterols | 685.64 | 718.82 | 589.96 | 601.1 |

These results show three striking features. First, ergosterol was found to be the most abundant of all the sterols, accounting for about 50% or more of the total sterols. The amount of ergosterol is greater than that of campesterol, β-sitosterol, and stigmasterol combined. Ergosterol is steroid commonly found in fungus and not commonly found in plants, and its presence particularly in significant amounts serves as a useful marker for non-plant oils. Secondly, the oil was found to contain brassicasterol. With the exception of rapeseed oil, brassicasterol is not commonly found in plant based oils. Thirdly, less than 2% β-sitosterol was found to be present. β-sitosterol is a prominent plant sterol not commonly found in microalgae, and its presence particularly in significant amounts serves as a useful marker for oils of plant origin. In summary, *Prototheca moriformis* strain UTEX1435 has been found to contain both significant amounts of ergosterol and only trace amounts of β-sitosterol as a percentage of total sterol content. Accordingly, the ratio of ergosterol:β-sitosterol or in combination with the presence of brassicasterol can be used to distinguish this oil from plant oils.

In some embodiments, the oil content of an oil provided herein contains, as a percentage of total sterols, less than 20%, 15%, 10%, 5%, 4%, 3%, 2%, or 1% β-sitosterol. In other embodiments the oil is free from β-sitosterol.

In some embodiments, the oil is free from one or more of β-sitosterol, campesterol, or stigmasterol. In some embodiments the oil is free from β-sitosterol, campesterol, and stigmasterol. In some embodiments the oil is free from campesterol. In some embodiments the oil is free from stigmasterol.

In some embodiments, the oil content of an oil provided herein comprises, as a percentage of total sterols, less than 20%, 15%, 10%, 5%, 4%, 3%, 2%, or 1% 24-ethylcholest-5-en-3-ol. In some embodiments, the 24-ethylcholest-5-en-3-ol is clionasterol. In some embodiments, the oil content of an oil provided herein comprises, as a percentage of total sterols, at least 1%, 2%, 3%, 4%, 5%, 6%, 7%, 8%, 9%, or 10% clionasterol.

In some embodiments, the oil content of an oil provided herein contains, as a percentage of total sterols, less than 20%, 15%, 10%, 5%, 4%, 3%, 2%, or 1% 24-methylcholest-5-en-3-ol. In some embodiments, the 24-methylcholest-5-en-3-ol is 22,23-dihydrobrassicasterol. In some embodiments, the oil content of an oil provided herein comprises, as a percentage of total sterols, at least 1%, 2%, 3%, 4%, 5%, 6%, 7%, 8%, 9%, or 10% 22,23-dihydrobrassicasterol.

In some embodiments, the oil content of an oil provided herein contains, as a percentage of total sterols, less than 20%, 15%, 10%, 5%, 4%, 3%, 2%, or 1% 5,22-cholestadien-24-ethyl-3-ol. In some embodiments, the 5,22-cholestadien-24-ethyl-3-ol is poriferasterol. In some embodiments, the oil content of an oil provided herein comprises, as a percentage of total sterols, at least 1%, 2%, 3%, 4%, 5%, 6%, 7%, 8%, 9%, or 10% poriferasterol.

In some embodiments, the oil content of an oil provided herein contains ergosterol or brassicasterol or a combination of the two. In some embodiments, the oil content contains, as a percentage of total sterols, at least 5%, 10%, 20%, 25%, 35%, 40%, 45%, 50%, 55%, 60%, or 65% ergosterol. In some embodiments, the oil content contains, as a percentage of total sterols, at least 25% ergosterol. In some embodiments, the oil content contains, as a percentage of total sterols, at least 40% ergosterol. In some embodiments, the oil content contains, as a percentage of total sterols, at least 5%, 10%, 20%, 25%, 35%, 40%, 45%, 50%, 55%, 60%, or 65% of a combination of ergosterol and brassicasterol.

In some embodiments, the oil content contains, as a percentage of total sterols, at least 1%, 2%, 3%, 4% or 5% brassicasterol. In some embodiments, the oil content contains, as a percentage of total sterols less than 10%, 9%, 8%, 7%, 6%, or 5% brassicasterol.

In some embodiments the ratio of ergosterol to brassicasterol is at least 5:1, 10:1, 15:1, or 20:1.

In some embodiments, the oil content contains, as a percentage of total sterols, at least 5%, 10%, 20%, 25%, 35%, 40%, 45%, 50%, 55%, 60%, or 65% ergosterol and less than 20%, 15%, 10%, 5%, 4%, 3%, 2%, or 1% β-sitosterol. In some embodiments, the oil content contains, as a percentage of total sterols, at least 25% ergosterol and less than 5% β-sitosterol. In some embodiments, the oil content further comprises brassicasterol.

Sterols contain from 27 to 29 carbon atoms (C27 to C29) and are found in all eukaryotes. Animals exclusively make C27 sterols as they lack the ability to further modify the C27 sterols to produce C28 and C29 sterols. Plants however are able to synthesize C28 and C29 sterols, and C28/C29 plant sterols are often referred to as phytosterols. The sterol profile of a given plant is high in C29 sterols, and the primary sterols in plants are typically the C29 sterols b-sitosterol and stigmasterol. In contrast, the sterol profile of non-plant organisms contain greater percentages of C27 and C28 sterols. For example the sterols in fungi and in many microalgae are principally C28 sterols. The sterol profile and particularly the striking predominance of C29 sterols over C28 sterols in plants has been exploited for determining the proportion of plant and marine matter in soil samples (Huang, Wen-Yen, Meinschein W. G., "Sterols as ecological indicators"; Geochimica et Cosmochimia Acta. Vol 43. pp 739-745).

In some embodiments the primary sterols in the microalgal oils provided herein are sterols other than b-sitosterol and stigmasterol. In some embodiments of the microalgal oils, C29 sterols make up less than 50%, 40%, 30%, 20%, 10%, or 5% by weight of the total sterol content.

In some embodiments the microalgal oils provided herein contain C28 sterols in excess of C29 sterols. In some embodiments of the microalgal oils, C28 sterols make up greater than 50%, 60%, 70%, 80%, 90%, or 95% by weight of the total sterol content. In some embodiments the C28 sterol is ergosterol. In some embodiments the C28 sterol is brassicasterol.

In embodiments of the present invention, oleaginous cells expressing one or more of the genes of Table 1 can produce an oil with at least 20, 40, 60 or 70% of C8, C10, C12, C14 or C16 fatty acids. In a specific embodiment, the level of myristate (C14:0) in the oil is greater than 30%.

Thus, in embodiments of the invention, there is a process for producing an oil, triglyceride, fatty acid, or derivative of any of these, comprising transforming a cell with any of the nucleic acids discussed herein. In another embodiment, the transformed cell is cultivated to produce an oil and, optionally, the oil is extracted. Oil extracted in this way can be used to produce food, oleochemicals or other products.

The oils discussed above alone or in combination are useful in the production of foods, fuels and chemicals (including plastics, foams, films, etc). The oils, triglycerides, fatty acids from the oils may be subjected to C—H activation, hydroamino methylation, methoxy-carbonation, ozonolysis, enzymatic transformations, epoxidation, methylation, dimerization, thiolation, metathesis, hydro-alkylation, lactonization, or other chemical processes.

After extracting the oil, a residual biomass may be left, which may have use as a fuel, as an animal feed, or as an ingredient in paper, plastic, or other product. For example, residual biomass from heterotrophic algae can be used in such products.

Example 1. Discovery of Novel Fatb Sequences

Sequences of novel plant acyl-ACP thioesterases involved in seed-specific mid-chain (C8-C16) fatty acid biosynthesis in higher plants were isolated. Seed-specific lipid production genes were isolated through direct interrogation of RNA pools accumulating in oilseeds. Based on phylogenetic analysis, novel enzymes can be classified as members of FatB family of acyl-ACP thioesterases.

Seeds of oleaginous plants were obtained from local grocery stores or requested through USDA ARS National Plant Germplasm System (NPGS) from North Central Regional Plant Introduction Station (NCRIS) or USDA ARS North Central Soil Conservation Research Laboratory (Morris, Mich.). Dry seeds were homogenized in liquid nitrogen to powder, resuspended in cold extraction buffer containing 6-8M Urea and 3M LiCl and left on ice for a few hours to overnight at 4° C. The seed homogenate was passed through NucleoSpin Filters (Macherey-Nagel) by centrifugation at 20,000 g for 20 minutes in the refrigerated microcentrifuge (4° C.). The resulting RNA pellets were resuspended in the buffer containing 20 mM Tris HCl, pH7.5, 0.5% SDS, 100 mM NaCl, 25 mM EDTA, 2% PVPP) and RNA was subsequently extracted once with Phenol-Chloroform-Isoamyl Alcohol (25:24:1, v/v) and once with chloroform. RNA was finally precipitated with isopropyl alcohol (0.7 Vol.) in the presence of 150 mM of Na Acetate, pH5.2, washed with 80% ethanol by centrifugation, and dried. RNA samples were treated with Turbo DNAse (Lifetech) and purified further using RNeasy kits (Qiagen) following manufacturers' protocols. The resulting purified RNA samples were converted to pair-end cDNA libraries and subjected to next-generation sequencing (2×100 bp) using Illumina Hiseq 2000 platform. RNA sequence reads were assembled into corresponding seed transcriptomes using Trinity or Oases packages. Putative thioesterase-containing cDNA contigs were identified by mining transcriptomes for sequences with homology to known thioesterases. These in silico identified putative thioesterase cDNAs have been further verified by direct reverse transcription PCR analysis using seed RNA and primer pairs targeting full-length thioesterase cDNAs. The resulting amplified products were cloned and sequenced de novo to confirm authenticity of identified thioesterase genes.

To interrogate evolutionary and functional relationship between novel acyl-ACP thioesterases and the members of two existing thioesterase classes (FatA and FatB), we performed a phylogenetic analysis using published full-length (Mayer and Shanklin, 2007) and truncated (THYME database) amino acid thioesterase sequences. Novel proteins appear to group with known acyl-ACP FatB thioesterases involved in biosynthesis of C8-C16 fatty acids. Moreover, novel thioesterases appear to cluster into 3 predominant out-groups suggesting distinct functional similarity and evolutionary relatedness among members of each cluster.

The amino acid sequences of the FatB genes follow are shown in Table 4.

TABLE 4

| Amino acid sequences of FatB genes: | |
|---|---|
| CuPSR23 FATB3 | SEQ ID NO: 110 |
| CuPSR23 FATB3b | SEQ ID NO: 111 |
| CwFATB3 | SEQ ID NO: 112 |
| CwFATB3a | SEQ ID NO: 113 |
| CwFATB3b | SEQ ID NO: 114 |
| CwFATB3c | SEQ ID NO: 115 |
| CwFATB4a | SEQ ID NO: 116 |
| CwFATB4a.1 | SEQ ID NO: 117 |
| CwFATB4a.2 | SEQ ID NO: 118 |
| CwFATB4a.3 | SEQ ID NO: 119 |
| CwFATB4b | SEQ ID NO: 120 |
| CwFATB4b.1 | SEQ ID NO: 121 |
| CwFATB5 | SEQ ID NO: 122 |
| CwFATB5a | SEQ ID NO: 123 |
| CwFATB5b | SEQ ID NO: 124 |
| CwFATB5c | SEQ ID NO: 125 |
| CwFATB5.1 | SEQ ID NO: 126 |
| CwFATB5.1a | SEQ ID NO: 127 |
| CcFATB2b | SEQ ID NO: 128 |
| CcFATB3 | SEQ ID NO: 129 |
| CcFATB3b | SEQ ID NO: 130 |
| CcFATB3c | SEQ ID NO: 131 |
| ChtFATB1a | SEQ ID NO: 132 |
| ChtFATB1a.1 | SEQ ID NO: 133 |
| ChtFATB1a.2 | SEQ ID NO: 134 |
| ChtFATB1a.3 | SEQ ID NO: 135 |
| ChtFATB1a.4 | SEQ ID NO: 136 |
| ChtFATB1b | SEQ ID NO: 137 |
| ChtFATB2b | SEQ ID NO: 138 |
| ChtFATB2a | SEQ ID NO: 139 |
| ChtFATB2c | SEQ ID NO: 140 |
| ChtFATB2d | SEQ ID NO: 141 |
| ChtFATB2e | SEQ ID NO: 142 |
| ChtFATB2f | SEQ ID NO: 143 |
| ChtFATB2g | SEQ ID NO: 144 |
| ChtFATB2h | SEQ ID NO: 145 |
| ChtFATB3a | SEQ ID NO: 146 |
| ChtFATB3b | SEQ ID NO: 147 |
| ChtFATB3c | SEQ ID NO: 148 |
| ChtFATB3d | SEQ ID NO: 149 |
| ChtFATB3e | SEQ ID NO: 150 |
| ChtFATB3f | SEQ ID NO: 151 |
| ChtFATB3g | SEQ ID NO: 152 |
| ChsFATB1 | SEQ ID NO: 153 |
| ChsFATB2 | SEQ ID NO: 154 |
| ChsFatB2b | SEQ ID NO: 155 |
| ChsFatB2c | SEQ ID NO: 156 |
| ChsFatB2d | SEQ ID NO: 157 |
| Chs FATB3 | SEQ ID NO: 158 |
| ChsFatb3b | SEQ ID NO: 159 |
| ChsFatB3c | SEQ ID NO: 160 |
| ChsFATB3d | SEQ ID NO: 161 |
| ChsFATB3e | SEQ ID NO: 162 |
| ChsFATB3f | SEQ ID NO: 163 |
| ChsFATB3g | SEQ ID NO: 164 |
| ChsFATB3h | SEQ ID NO: 165 |
| ChsFATB3i | SEQ ID NO: 166 |
| ChsFATB3j | SEQ ID NO: 167 |

```
ChsFATB3j:
MVAAEASSALFSVRTPGTSPKPGKFGNWPTSLSVPFKSKSNHNGGFQVKA

NASARPKANGSAVSLKSGSLDTQEDTSSSSSPPRTFINQLPDWSMLLSAI

TTVFVAAEKQWTMLDRKSKRPDMLMDPFGVDRVVQDGAVFRQSFSIRSYE

IGADRTASIETLMNIFQETSLNHCKSIGLLNDGFGRTPEMCKRDLIWVVT

KMHIEVNRYPTWGDTIEVNTWVSESGKTGMGRDWLISDFHTGDILIRATS

VCAMMNQKTRRFSKFPYEVRQELAPHFVDSAPVIEDYQKLHKLDVKTGDS

ICNGLTPRWNDLDVNQHVNNVKYIGWILESVPTEVFETQELCGLTLEYRQ

ECGRDSVLESVTAMDPSKEGDRSLYQHLLRLEDGTDIAKGRTKWRPKNAG

KTSNGNSIS
```

Example 2. Cloning and Fatty Acid Analysis of Cells Transformed with Novel Fatb Genes In the example below, we detail the effect of expressing plant oilseed transcriptome-derived, heterologous thioesterases in the UTEX1435 (web.biosci.utexas.edu/utex/) strain, Strain A.

As in Example 1, RNA was extracted from dried plant seeds and submitted for paired-end sequencing using the Illumina Hiseq 2000 platform. RNA sequence reads were assembled into corresponding seed transcriptomes using Trinity or Oases packages and putative thioesterase-containing cDNA contigs were identified by mining transcriptomes for sequences with homology to known thioesterases. These in silico identified putative thioesterase cDNAs were verified by direct reverse transcription PCR analysis using seed RNA and primer pairs targeting full-length thioesterase cDNAs. The resulting amplified products were cloned and sequenced de novo to confirm authenticity of identified thioesterase genes and to identify sequence variants arising from expression of different gene alleles or diversity of sequences within a population of seeds. The resulting amino acid sequences were subjected to phylogenetic analysis using published full-length (Mayer and Shanklin, 2007) and truncated (THYME database) FatB sequences. The thioesterases that clustered with acyl-ACP FatB thioesterases, which are involved in biosynthesis of C8-C16 fatty acids, were pursued.

Construction of Transforming Vectors Expressing Acyl-ACP FatB Thioesterases 27 putative acyl-ACP FatB thioesterases from the species *Cinnamomum camphora, Cuphea hyssopifolia, Cuphea* PSR23, *Cuphea wrightii, Cuphea heterophylla*, and *Cuphea viscosissima* were synthesized in a codon-optimized form to reflect *Prototheca moriformis* (UTEX 1435) codon usage. Of the 27 genes synthesized, 24 were identified by our transcriptome sequencing efforts and the 3 genes from *Cuphea viscosissima*, were from published sequences in GenBank.

Transgenic strains were generated via transformation of the base strain Strain A (*Prototheca moriformis*, derived from UTEX 1435 by classical mutation and screening for high oil production) with a construct encoding 1 of the 27 FatB thioesterases. The construct pSZ2760 encoding *Cinnamomum camphora* (Cc) FATB1b is shown as an example, but identical methods were used to generate each of the remaining 26 constructs encoding the different respective thioesterases. Construct pSZ2760 can be written as 6S::CrTUB2:ScSUC2:CvNR::PmAMT3:CcFATB1b:CvNR::6S. The sequence of the transforming DNA is provided in Table 5 (pSZ2760). The relevant restriction sites in the construct from 5'-3', BspQ1, KpnI, AscI, MfeI, EcoRI, SpeI, XhoI, SacI, BspQ1, respectively, are indicated in lowercase, bold, and underlined. BspQ1 sites delimit the 5' and 3' ends of the transforming DNA. Bold, lowercase sequences at the 5' and 3' end of the construct represent genomic DNA from UTEX 1435 that target integration to the 6S locus via homologous recombination. Proceeding in the 5' to 3' direction, the selection cassette has the *C. reinhardtii* β-tubulin promoter driving expression of the *S. cerevisiae* gene SUC2 (conferring the ability to grow on sucrose) and the *Chlorella vulgaris* Nitrate Reductase (NR) gene 3' UTR. The promoter is indicated by lowercase, boxed text. The initiator ATG and terminator TGA for ScSUC2 are indicated by bold, uppercase italics, while the coding region is indicated with lowercase italics. The 3' UTR is indicated by lowercase underlined text. The spacer region between the two cassettes is indicated by upper case text. The second cassette containing the codon optimized CcFATB1b gene (Table 5; pSZ2760) from *Cinnamomum camphora* is driven by the *Prototheca moriformis* endogenous AMT3 promoter, and has the *Chlorella vulgaris* Nitrate Reductase (NR) gene 3' UTR. In this cassette, the AMT3 promoter is indicated by lowercase, boxed text. The initiator ATG and terminator TGA for the CcFATB1b gene are indicated in bold, uppercase italics, while the coding region is indicated by lowercase italics and the spacer region is indicated by upper case text. The 3' UTR is indicated by lowercase underlined text. The final construct was sequenced to ensure correct reading frame and targeting sequences.

TABLE 5

| pSZ2760 Transforming construct |
|---|
| gctcttcgccgccgccactcctgctcgagcgcgcccgcgcgtgcgccgccagcgccttggccttttcgccgcgctcgtgcgcgtcgctgatgtccatcaccag |
| gtccatgaggtctgccttgcgccggctgagccactgcttcgtccgggcggccaagaggagcatgagggaggactcctggtccagggtcctgacgtggtcgcgg |
| ctctgggagcgggccagcatcatctggctctgccgcaccgaggccgcctccaactggtcctccagcagccgcagtcgccgccgaccctggcagaggaagacag |
| gtgagggggtatgaattgtacagaacaaccacgagccttgtctaggcagaatccctaccagtcatggctttacctggatgacggcctgcgaacagctgtcca |
| gcgaccctcgctgccgccgcttctcccgcacgcttctttccagcaccgtgatggcgcgagccagcgccgcacgctggcgctgcgcttcgccgatctgaggaca |
| gtcggggaactctgatcagtctaaacccccttgcgcgttagtgttgccatcctttgcagaccggtgagagccgacttgttgtgcgccacccccacaccacct |
| cctcccagaccaattctgtcaccttttggcgaaggcatcggcctcggcctgcagagaggacagcagtgcccagccgctgggggttggcggatgcacgctcag |
| gtaccctttcttgcgctatgacacttccagcaaaaggtagggcgggctgcgagacggcttcccggcgctgcatgcaacaccgatgatgcttcgacccccgaa |
| gctccttcggggctgcatgggcgctccgatgccgctccagggcgagcgctgtttaaatagccaggcccccgattgcaaagacattatagcgagctaccaaagc |
| catattcaaacacctagatcactaccacttctacacaggccactcgagcttgtgatcgcactccgctaagggggcgcctcttcctcttcgtttcagtcacaac |
| ccgcaaacggcgcgcc*ATGctgctgcaggccttcctgttcctgctggccggcttcgccgccaagatcagcgcctccatgacgaacgagacgtccgaccgcccc* |
| *ctggtgcacttcacccccaacaagggctggatgaacgaccccaacggcctgtggtacgacgagaaggacgccaagtggcacctgtacttccagtacaacccga* |
| *acgacaccgtctgggggacgcccttgttctggggccacgccacgtccgacgacctgaccaactgggaggaccagcccatcgccatcgccccgaagcgcaacga* |
| *ctccggcgccttctccggctccatggtggtggactacaacaacacctccggcttcttcaacgacaccatcgacccgcgccagcgctgcgtggccatctggacc* |
| *tacaacaccccggagtccgaggagcagtacatctcctacagcctggacggcggctacaccttcaccgagtaccagaagaaccccgtgctggccgccaactcca* |
| *cccagttccgcgacccgaaggtcttctggtacgagccctcccagaagtggatcatgaccgcggccaagtcccaggactacaagatcgagatctactcctccga* |
| *cgacctgaagtcctggaagctggagtccgcgttcgccaacgagggcttcctcggctaccagtacgagtgccccggcctgatcgaggtccccaccgagcaggac* |
| *cccagcaagtcctactgggtgatgttcatctccatcaaccccggcgccccggccggcggctccttcaaccagtacttcgtcggcagcttcaacggcacccact* |
| *tcgaggccttcgacaaccagtcccgcgtggtggacttcggcaaggactactacgccctgcagaccttcttcaacaccgacccgacctacgggagcgccctggg* |
| *catcgcgtgggcctccaactgggagtactccgccttcgtgcccaccaacccctggcgctcctccatgtccctcgtgcgcaagttctccctcaacaccgagtac* |
| *caggccaacccggagacggagctgatcaacctgaaggccgagccgatcctgaacatcagcaacgccggcccctggagccggttcgccaccaacaccacgttga* |
| *cgaaggccaacagctacaacgtcgacctgtccaacagcaccggcaccctggagttcgagctggtgtacgccgtcaacaccacccagacgatctccaagtccgt* |

TABLE 5-continued

| pSZ2760 Transforming construct |
| --- |
| gttcgcggacctctccctctggttcaagggcctggaggaccccgaggagtacctccgcatgggcttcgaggtgtccgcgtcctccttcttcctggaccgcggg |
| aacagcaaggtgaagttcgtgaaggagaacccctacttcaccaaccgcatgagcgtgaacaaccagcccttcaagagcgagaacgacctgtcctactacaagg |
| tgtacggcttgctggaccagaacatcctggagctgtacttcaacgacggcgacgtcgtgtccaccaacacctacttcatgaccaccgggaacgccctgggctc |
| cgtgaacatgacgacgggggtggacaacctgttctacatcgacaagttccaggtgcgcgaggtcaagTGAcaattggcagcagcagctcggatagtatcgaca |
| cactctggacgctggtcgtgtgatggactgttgccgccacacttgctgccttgacctgtgaatatccctgccgcttttatcaaacagcctcagtgtgtttgat |
| cttgtgtgtacgcgcttttgcgagttgctagctgcttgtgctatttgcgaataccacccccagcatccccttccctcgtttcatatcgcttgcatcccaaccg |
| caacttatctacgctgtcctgctatccctcagcgctgctcctgctcctgctcactgcccctcgcacagccttggtttgggctccgcctgtattctcctggtac |
| tgcaacctgtaaaccagcactgcaatgctgatgcacgggaagtagtgggatgggaacacaaatggaAAGCTGTATAGGGATAAgaattcggccgacaggacgc |
| gcgtcaaaggtgctggtcgtgtatgccctggccggcaggtcgttgctgctgctggttagtgattccgcaaccctgattttggcgtcttattttggcgtggcaa |
| acgctggcgcccgcgagccgggccggcggcgatgcggtgccccacggctgccggaatccaagggaggcaagagcgcccgggtcagttgaagggctttacgcgc |
| aaggtacagccgctcctgcaaggctgcgtggtggaattggacgtgcaggtcctgctgaagttcctccaccgcctcaccagcggacaaagcaccggtgtatcag |
| gtccgtgtcatccactctaaagaactcgactacgacctactgatggccctagattcttcatcaaaaacgcctgagacacttgcccaggattgaaactccctga |
| agggaccaccaggggccctgagttgttccttccccccgtggcgagctgccagccaggctgtacctgtgatcgaggctggcgggaaaataggcttcgtgtgctc |
| aggtcatgggaggtgcaggacagctcatgaaacgccaacaatcgcacaattcatgtcaagctaatcagctatttcctcttcacgagctgtaattgtcccaaaa |
| ttctggtctaccgggggtgatccttcgtgtacgggcccttccctcaaccctaggtatgcgcgcatgcggtcgccgcgcaactcgcgcgagggccgagggtttg |
| ggacgggccgtcccgaaatgcagttgcacccggatgcgtggcaccttttttgcgataatttatgcaatggactgctctgcaaaattctggctctgtcgccaac |
| cctaggatcagcggcgtaggatttcgtaatcattcgtcctgatggggagctaccgactaccctaatatcagcccgactgcctgacgccagcgtccacttttgt |
| gcacacattccattcgtgcccaagacatttcattgtggtgcgaagcgtccccagttacgctcacctgtttcccgacctccttactgttctgtcgacagagcgg |
| gcccacaggccggtcgcagccactagtATGgccaccacctccctggcctccgccttctgctccatgaaggccgtgatgctggcccgcgacggccgcggcctga |
| agccccgctcctccgacctgcagctgcgcgccggcaacgcccagacctccctgaagatgatcaacggcaccaagttctcctacaccgagtccctgaagaagct |
| gcccgactggtccatgctgttcgccgtgatcaccaccatcttctccgccgccgagaagcagtggaccaacctggagtggaagcccaagcccaacccccccag |
| ctgctggacgaccacttcggccccacggcctggtgttccgccgcaccttcgccatccgctcctacgaggtgggccccgaccgctccacctccatcgtggccg |
| tgatgaaccacctgcaggaggccgccctgaaccacgccaagtccgtgggcatcctgggcgacggcttcggcaccaccctggagatgtccaagcgcgacctgat |
| ctgggtggtgaagcgcacccacgtggccgtggagcgctaccccgcctggggcgacaccgtggaggtggagtgctgggtgggcgcctccggcaacaacggccgc |
| cgccacgacttcctggtgcgcgactgcaagaccggcgagatcctgacccgctgcacctccctgtccgtgatgatgaacacccgcacccgccgcctgtccaaga |
| tccccgaggaggtgcgcggcgagatcggccccgccttcatcgacaacgtggccgtgaaggacgaggagatcaagaagccccagaagctgaacgactccaccgc |
| cgactacatccagggcggcctgacccccgctggaacgacctggacatcaaccagcacgtgaacaacatcaagtacgtggactggatcctggagaccgtgccc |
| gactccatcttcgagtcccaccacatctcctccttcaccatcgagtaccgccgcgagtgcacccgcgactccgtgctgcagtccctgaccaccgtgtccggcg |
| gctcctccgaggccggcctggtgtgcgagcacctgctgcagctggagggcggctccgaggtgctgcgcgccaagaccgagtggcgccccaagctgtccttccg |
| cggcatctccgtgatccccgccgagtcctccgtgatggactacaaggaccacgacggcgactacaaggaccacgacatcgactacaaggacgacgacgacaag |
| TGActcgaggcagcagcagctcggatagtatcgacacactctggacgctggtcgtgtgatggactgttgccgccacacttgctgccttgacctgtgaatatcc |
| ctgccgcttttatcaaacagcctcagtgtgtttgatcttgtgtgtacgcgcttttgcgagttgctagctgcttgtgctatttgcgaataccacccccagcatc |
| cccttccctcgtttcatatcgcttgcatcccaaccgcaacttatctacgctgtcctgctatccctcagcgctgctcctgctcctgctcactgcccctcgcaca |
| gccttggtttgggctccgcctgtattctcctggtactgcaacctgtaaaccagcactgcaatgctgatgcacgggaagtagtgggatgggaacacaaatggaA |
| AGCTGTATAGGGATAACAGGGTAATgagctcttgttttccagaaggagttgctccttgagcctttcattctcagcctcgataacctccaaagccgctctaatt |
| gtggagggggttcgaatttaaaagcttggaatgttggttcgtgcgtctggaacaagcccagacttgttgctcactgggaaaggaccatcagctccaaaaaac |
| ttgccgctcaaaccgcgtacctctgctttcgcgcaatctgccctgttgaaatcgccaccacattcatattgtgacgcttgagcagtctgtaattgcctcagaa |
| tgtggaatcatctgcccccctgtgcgagcccatgccaggcatgtcgcgggcgaggacacccgccactcgtacagcagaccattatgctacctcacaatagttca |

TABLE 5-continued

| pSZ2760 Transforming construct |
|---|
| taacagtgaccatatttctcgaagctccccaacgagcacctccatgctctgagtggccacccccggccctggtgcttgcggagggcaggtcaaccggcatgg |
| ggctaccgaaatccccgaccggatcccaccacccccgcgatgggaagaatctctccccgggatgtgggcccaccaccagcacaacctgctggcccaggcgagc |
| gtcaaaccataccacacaaatatccttggcatcggccctgaattccttctgccgctctgctacccggtgcttctgtccgaagcaggggttgctagggatcgct |
| ccgagtccgcaaacccttgtcgcgtggcggggcttgttcgagcttgaagagc |

Constructs encoding the identified heterologous FatB genes, such as CcFATB1b from pSZ2760 in Table 6, were transformed into Strain A, and selected for the ability to grow on sucrose. Transformations, cell culture, lipid production and fatty acid analysis were all carried out as previously described. After cultivating on sucrose under low nitrogen conditions to accumulate oil, fatty acid profiles were determined by FAME-GC. The top performer from each transformation, as judged by the ability to produce the highest level of midchain fatty acids, is shown in Table 4.

TABLE 6

Alteration of Fatty Acid Profiles in S3150 upon Expression of Heterologous FatB Thioesterases

| | | | FA profile of top performer from each transformation (%; primary lipid in Strain A background) | | | | | | | | | |
|---|---|---|---|---|---|---|---|---|---|---|---|---|
| Species | Gene Name | SZ Plasmid | Strain | C8:0 | C10:0 | C12:0 | C14:0 | C16:0 | C18:0 | C18:1 | C18:2 | C18:3α |
| *Cinnamomum camphora* | CcFATB1b | pSZ2760 | A; T526; D1670-13 | 0 | 0 | 1 | 15 | 26 | 2 | 46 | 9 | 1 |
| *Cinnamomum camphora* | CcFATB4 | pSZ2756 | A; T525; D1666-31 | 0 | 1 | 33 | 4 | 7 | 2 | 41 | 10 | 1 |
| *Cinnamomum camphora* | CcFATB3 | pSZ2755 | A; T525; D1665-4 | 0 | 0 | 0 | 3 | 44 | 3 | 41 | 8 | 0 |
| *Cuphea hyssopifolia* | ChsFATB1 | pSZ2778 | A; T535; D1689-30 | 0 | 0 | 0 | 2 | 22 | 4 | 63 | 8 | 1 |
| *Cuphea hyssopifolia* | ChsFATB2 | pSZ2796 | A; T537; D1700-46 | 0 | 0 | 0 | 6 | 53 | 3 | 32 | 6 | 0 |
| *Cuphea hyssopifolia* | ChsFATB2b | pSZ2792 | A; T537; D1696-9 | 0 | 0 | 0 | 5 | 26 | 2 | 56 | 9 | 1 |
| *Cuphea hyssopifolia* | ChsFATB3 | pSZ2797 | A; T537; D1701-48 | 0 | 0 | 8 | 34 | 27 | 2 | 24 | 5 | 1 |
| *Cuphea hyssopifolia* | ChsFATB3b | pSZ2795 | A; T537; D1699-1 | 0 | 0 | 7 | 29 | 27 | 1 | 28 | 6 | 1 |
| *Cuphea* PSR23 | CuPSR23FATB3 | pSZ2793 | A; T537; D1697-13 | 0 | 1 | 0 | 2 | 24 | 3 | 61 | 8 | 1 |
| *Cuphea wrightii* | CwFATB3 | pSZ2751 | A; T525; D1661-22 | 0 | 2 | 17 | 9 | 19 | 2 | 41 | 8 | 1 |
| *Cuphea wrightii* | CwFATB4a | pSZ2752 | A; T525; D1662-30 | 0 | 0 | 0 | 4 | 48 | 3 | 36 | 7 | 1 |
| *Cuphea wrightii* | CwFATB4b | pSZ2753 | A; T525; D1663-29 | 0 | 0 | 0 | 5 | 52 | 3 | 32 | 6 | 1 |
| *Cuphea wrightii* | CwFATB5 | pSZ2754 | A; T525; D1664-39 | 0 | 0 | 0 | 3 | 27 | 3 | 57 | 7 | 1 |
| *Cuphea heterophylla* | ChtFATB1a | pSZ2757 | A; T525; D1667-19 | 0 | 0 | 5 | 18 | 27 | 2 | 39 | 7 | 1 |
| *Cuphea heterophylla* | ChtFATB1b | pSZ2773 | A; T535; D1685-29 | 0 | 0 | 2 | 7 | 27 | 3 | 53 | 8 | 1 |
| *Cuphea heterophylla* | ChtFATB2b | pSZ2780 | A; T535; D1691-8 | 0 | 0 | 0 | 2 | 25 | 3 | 61 | 8 | 1 |
| *Cuphea heterophylla* | ChtFATB2a | pSZ2774 | A; T537; D1702-24 | 0 | 0 | 0 | 2 | 27 | 3 | 59 | 6 | 0 |
| *Cuphea heterophylla* | ChtFATB2c | pSZ2758 | A; T525; D1668-22 | 0 | 0 | 3 | 2 | 23 | 3 | 58 | 7 | 1 |
| *Cuphea heterophylla* | ChtFATB2d | pSZ2759 | A; T526; D1669-19 | 0 | 0 | 4 | 4 | 23 | 3 | 54 | 9 | 1 |
| *Cuphea heterophylla* | ChtFATB2e | pSZ2775 | A; T535; D1686-23 | 0 | 1 | 2 | 3 | 24 | 3 | 57 | 8 | 1 |
| *Cuphea heterophylla* | ChtFATB2f | pSZ2777 | A; T535; D1688-33 | 0 | 0 | 0 | 2 | 28 | 3 | 57 | 8 | 1 |
| *Cuphea heterophylla* | ChtFATB2g | pSZ2794 | A; T537; D1698-19 | 0 | 0 | 0 | 2 | 22 | 3 | 62 | 9 | 1 |
| *Cuphea heterophylla* | ChtFATB3a | pSZ2776 | A; T535; D1687-23 | 0 | 0 | 0 | 5 | 47 | 4 | 37 | 7 | 1 |
| *Cuphea heterophylla* | ChtFATB3b | pSZ2779 | A; T535; D1690-31 | 0 | 0 | 0 | 6 | 49 | 5 | 32 | 7 | 0 |
| *Cuphea viscosissima* | CvisFATB1 | pSZ2810 | A; T540; D1711-30 | 0 | 1 | 0 | 2 | 24 | 3 | 60 | 8 | 0 |
| *Cuphea viscosissima* | CvisFATB2 | pSZ2817 | A; T547; D1718-1 | 0 | 0 | 0 | 4 | 51 | 2 | 36 | 6 | 0 |

TABLE 6-continued

Alteration of Fatty Acid Profiles in S3150 upon Expression of Heterologous FatB Thioesterases

| Species | Gene Name | SZ Plasmid | FA profile of top performer from each transformation (%; primary lipid in Strain A background) | | | | | | | | | |
|---|---|---|---|---|---|---|---|---|---|---|---|---|
| | | | Strain | C8:0 | C10:0 | C12:0 | C14:0 | C16:0 | C18:0 | C18:1 | C18:2 | C18:3α |
| *Cuphea viscosissima* | CvisFATB3 | pSZ2791 | A; T537; D1695-1 | 0 | 0 | 0 | 8 | 28 | 2 | 52 | 8 | 1 |
| | | | A (parent strain): | 0 | 0 | 0 | 2 | 28 | 3 | 58 | 7 | 0 |

Many of the acyl-ACP FatB thioesterases were found to exhibit midchain activity when expressed in *Prototheca moriformis*. For example, expression of CcFATB1b causes an increase in myristate levels from 2% of total fatty acids in the parent, Strain A, to ~15% in the D1670-13 primary transformant. Other examples include CcFATB4, which exhibits an increase in laurate levels from 0% in Strain A to ~33%, and ChsFATB3, which exhibits an increase in myristate levels to ~34%. Although some of the acyl-ACP thioesterases did not exhibit dramatic effects on midchain levels in the current incarnation, efforts will likely develop to optimize some of these constructs.

Sequences of the Heterologous Acyl-ACP Thioesterases Identified and Transformed into *P. moriformis* (UTEX 1435)

A complete listing of relevant sequences for the transforming constructs, such as the deduced amino acid sequence of the encoded acyl-ACP thioesterase, the native CDS coding sequence, the *Prototheca moriformis* codon-optimized coding sequence, and the nature of the sequence variants examined, is provided as SEQ ID NOS: 1-78.

Example 3. Discovery and Cloning of Additional Fatb Genes

Additional FATB genes were obtained from seeds as described above. The species and number of FatB genes identified were:

| Species | Accession Number | Novel FatB Thioesterase Genes |
|---|---|---|
| *Cuphea calcarata* | 534665 | 1 |
| *Cuphea painteri* | 288248 | 1 |
| *Cuphea hookeriana* | 534896 | 1 |

-continued

| Species | Accession Number | Novel FatB Thioesterase Genes |
|---|---|---|
| *Cuphea avigera* var. *pulcherrima* | Ames 17868 | 1 |
| *Cuphea paucipetala* | 534877 | 1 |
| *Cuphea procumbens* | 534881 | 3 |
| *Cuphea ignea* | 534773 | 1 |

The thioesterases that clustered with acyl-ACP FatB thioesterases, which are involved in biosynthesis of C8-C16 fatty acids, were pursued. The native, putative plastid-targeting transit peptide sequence is indicated by underlining.

Construction of Transforming Vectors Expressing Acyl-ACP FatB Thioesterases. The nine putative Acyl-ACP FatB Thioesterases from the species *Cuphea calcarata, Cuphea painter, Cuphea hookeriana, Cuphea avigera* var. *pulcherrima, Cuphea paucipetala, Cuphea procumbens*, and *Cuphea ignea* were synthesized in a codon-optimized form to reflect UTEX 1435 codon usage. In contrast to the previous example, the new Acyl-ACP FatB thioesterases were synthesized with a modified transit peptide from *Chlorella protothecoides* (Cp) in place of the native transit peptide. The modified transit peptide derived from the CpSAD1 gene, "CpSAD1tp_trimmed", was synthesized as an in-frame, N-terminal fusion to the FatB acyl-ACP thioesterases in place of the native transit peptide; the resulting sequences are listed below. The novel FatB genes were cloned into *Prototheca moriformis* as described above. Constructs encoding heterologous FatB genes were transformed into strain S6165 (a descendant of S3150/Strain A) and selected for the ability to grow on sucrose. Transformations, cell culture, lipid production and fatty acid analysis were all carried out as previously described. The results for the nine novel FatB acyl-ACP thioesterases are displayed in the table immediately below.

| Species | Gene Name | SZ Plasmid | FA profile of top performer from each transformation (%; primary lipid) | | | | | | | | | |
|---|---|---|---|---|---|---|---|---|---|---|---|---|
| | | | Strain | C8:0 | C10:0 | C12:0 | C14:0 | C16:0 | C18:0 | C18:1 | C18:2 | C18:3α |
| *Cuphea calcarata* | CcalcFATB1 | pSZ3764 | S6165; T778; D2508-26 | 0 | 1 | 12 | 18 | 29 | 2 | 29 | 5 | 1 |
| *Cuphea painteri* | CpaiFATB1 | pSZ3838 | S6165; T841; D2796-22 | 8 | 17 | 1 | 2 | 18 | 2 | 43 | 6 | 1 |
| *Cuphea hookeriana* | ChookFATB4 | pSZ3837 | S6165; T788; D2552-18 | 0 | 0 | 0 | 2 | 32 | 2 | 54 | 7 | 1 |
| *Cuphea avigera* var. | CaFATB1 | pSZ4084 | S6165; T841; | 22 | 9 | 0 | 2 | 32 | 2 | 54 | 7 | 1 |

-continued

| Species | Gene Name | SZ Plasmid | FA profile of top performer from each transformation (%; primary lipid) Strain | C8:0 | C10:0 | C12:0 | C14:0 | C16:0 | C18:0 | C18:1 | C18:2 | C18:3α |
|---|---|---|---|---|---|---|---|---|---|---|---|---|
| *pulcherrima* | | | D2800-7 | | | | | | | | | |
| *Cuphea paucipetala* | CpauFATB1 | pSZ3762 | S6165; T778; D2506-46 | 0 | 9 | 1 | 3 | 28 | 2 | 47 | 7 | 1 |
| *Cuphea procumbens* | CprocFATB1 | pSZ3929 | S6165; T814; D2675-3 | 0 | 5 | 1 | 3 | 30 | 2 | 50 | 7 | 1 |
| *Cuphea procumbens* | CprocFATB2 | pSZ3839 | S6165; T788; D2553-2 | 0 | 0 | 0 | 2 | 32 | 3 | 55 | 6 | 1 |
| *Cupheo procumbens* | CprocFATB3 | pSZ3763 | S6165; T778; D2507-29 | 0 | 3 | 1 | 2 | 28 | 3 | 54 | 6 | 1 |
| *Cuphea ignea* | CigneaFATB1 | pSZ3930 | S6165; T814; D2676-34 | 0 | 8 | 1 | 4 | 24 | 2 | 51 | 8 | 1 |
| | | | S6165: (parent strain) | 0 | 0 | 0 | 2 | 29 | 3 | 58 | 6 | 1 |

Of particular note are: CpaiFATB1, which exhibits 17% C10:0 and 8% C8:0 fatty acid levels; CpauFATB1, which exhibits 9% C10:0 and 1% C12:0 fatty acid levels; CigneaFATB1, which exhibits 8% C10:0 and 1% C12:0 fatty acid levels; CcalcFATB1, which exhibits 18% C14:0 and 12% C12:0 levels; and CaFATB1, which exhibits 22% C8:0 and 9% C10:0 fatty acid levels.

CaFATB1, which exhibits high C8:0 and C10:0 levels, is of particular interest. CaFATB1 arose from two separate contigs that were assembled from the *Cupha avigera* var. *pulcherrima* transcriptome, S17_Cavig_trinity_7406 and S17_Cavig_trinity_7407. Although the two partial contigs exhibit only 17 nucleotides of overlap, we were able to assemble a putative full length transcript encoding CaFATB1 from the two contigs and then subsequently confirm the existence of the full-length transcript by direct reverse transcription PCR analysis using seed RNA and primer pairs targeting the full-length CaFATB1 thioesterase cDNA. Tjellstrom et al. (2013) discloses the expression of a newly identified fatty acyl-ACP thioesterase from *Cuphea pulcherrima* that they named "CpuFATB3" (Genbank accession number KC675178). The coding sequence of CpuFATB3 is 100% identical to the CaFATB1 gene we identified and contains one nucleotide difference in the RNA sequence outside the predicted coding region. Tjellstrom et al. (2013) showed that CpuFATB3 produces an average of 4.8% C8:0 when expressed in *Arabidopsis*, and further requires deletion of two acyl-ACP synthetases, AAE15/16, to produce an average of 9.2% C8:0 with a maximum level of ~12% C8.0. The CaFATB1 gene we identified was codon-optimized for expression in UTEX1435 and generated as a CpSAD1tp-trimmed transit peptide fusion before introduction into S6165. The CpSAD1tp_trimmed:CaFATB1 gene produces an average C8:0 level of 14% and a maximum level of 22% C8:0 without requiring the deletion of endogenous acyl-ACP synthetases.

TABLE 7

Amino Acid Sequences of Additional Novel FatB Acyl-ACP Thioesterases. In the appended sequence listings, the native, putative plastid-targeting transit peptide sequence is underlined:

| FatB | Sequence ID NO: |
|---|---|
| CcalcFATB1 (*Cuphea calcarata* FATB1) | SEQ ID NO: 168 |
| ChookFATB4 (*Cuphea hookeriana* FATB4) | SEQ ID NO: 169 |
| CaFATB1 (*Cuphea avigera* var. *pulcherrima* FATB1) | SEQ ID NO: 170 |
| CpauFATB1 (*Cuphea paucipetala* FATB1) | SEQ ID NO: 171 |
| CprocFATB1 (*Cuphea procumbens* FATB1) | SEQ ID NO: 172 |
| CprocFATB2 (*Cuphea procumbens* FATB2) | SEQ ID NO: 173 |
| CprocFATB3 (*Cuphea procumbens* FATB3) | SEQ ID NO: 174 |

TABLE 7-continued

Amino Acid Sequences of Additional Novel FatB Acyl-ACP Thioesterases. In the appended sequence listings, the native, putative plastid-targeting transit peptide sequence is underlined:

| FatB | Sequence ID NO: |
|---|---|
| CigneaFATB1 (*Cuphea ignea* FATB1) | SEQ ID NO: 175 |
| CcalcFATB1 (*Cuphea calcarata* FATB1) | SEQ ID NO: 176 |
| ChookFATB4 (*Cuphea hookeriana* FATB4) | SEQ ID NO: 177 |
| CaFATB1 (*Cuphea avigera* var. *pulcherrima FATB1*) | SEQ ID NO: 178 |
| CpauFATB1 (*Cuphea paucipetala* FATB1) | SEQ ID NO: 179 |
| CprocFATB1 (*Cuphea procumbens* FATB1) | SEQ ID NO: 180 |
| CprocFATB2 (*Cuphea procumbens* FATB2) | SEQ ID NO: 181 |
| CprocFATB3 (*Cuphea procumbens* FATB3) | SEQ ID NO: 182 |
| CigneaFATB1 (*Cuphea ignea* FATB1) | SEQ ID NO: 183 |

Example 4. Fatb Consensus Sequences: Discovery, Cloning and Fatty Acid Profiles In the course of testing several new putative midchain FatB thioesterases in UTEX1435, 53150 (Strain A above), we identified several thioesterases with increased C10:0 and C16:0 activity above the background midchain levels found in the strain. We reasoned that a consensus sequence could be obtained for an idealized C10:0 thioesterase and C16:0 thioesterase from aligning the best-performing C10:0 and C16:0 thioesterases. A consensus C10:0 specific thioesterase sequence was generated using the *C. palustris* FatB1 (CpFATB1), C. PSR23FatB3 (CuPSR23FATB3), *C. viscosissima* FatB1 (CvisFATB1), *C. glossostoma* FatB1 (CgFATB1), and *C. carthagenensis* FatB2 (CcrFATB2) sequences as inputs resulting in a C10:0 specific consensus sequence termed JcFATB1/SzFATB1. A consensus C16:0 specific thioesterase sequence was generated using the *C. heterophylla* FatB3a (ChtFATB3a), *C. carthagenensis* FatB1 (CcrFATB1), *C. viscosissima* FatB2 (CvisFATB2), *C. hookeriana* FatB1 (ChFATB1; AAC48990), *C. hyssopifolia* FatB2 (ChsFATB2), *C. calophylla* FatB2 (CcalFATB2; ABB71581), *C. hookeriana* FatB1-1 (ChFATB1-1; AAC72882), *C. lanceolata* FatB1 (C1FATB1; CAC19933), and *C. wrightii* FatB4a (CwFATB4a) sequences as inputs resulting in a C16:0 specific consensus sequence termed JcFATB2/SzFATB2. The resulting consensus sequences were synthesized, cloned into a vector identical to that used to test other FatB thioesterases, and introduced into S3150 as described above. The consensus amino acid sequences are given as SEQ ID NOs. 106 and 107; the nucleic acid sequences were based on these amino acid sequences using codon optimization for *Prototheca moriformis*. The transformants were selected, cultivated and the oil was extracted and analyzed by FAME-GC-FID. The fatty acid profiles obtained are given in the table below.

| Species | Gene Name | SZ Plasmid | Strain | FA profile of top performer from each transformation (%; primary lipid) | | | | | | | | |
|---|---|---|---|---|---|---|---|---|---|---|---|---|
| | | | | C8:0 | C10:0 | C12:0 | C14:0 | C16:0 | C18:0 | C18:1 | C18:2 | C18:3α |
| Consensus Sequence 1 | JcFATB1 | pSZ3187 | S3150; T617; D1930-18 | 0 | 2 | 0 | 2 | 26 | 3 | 57 | 8 | 1 |
| Consensus Sequence 2 | JcFATB2 | pSZ3100 | S3150; T600; D1872-17 | 0 | 0 | 0 | 6 | 54 | 3 | 29 | 6 | 0 |
| | | | S3150 (parent strain): | 0 | 0 | 0 | 2 | 28 | 3 | 58 | 7 | 0 |

Example 5. Clade Analysis

Various novel FATB thioesterases were clustered according to a neighbor joining algorithm. These were found to form twelve clades as listed in Table 1a. Putative function was assigned based on expression in *Prototheca* as described above.

The described embodiments of the invention are intended to be merely exemplary and numerous variations and modifications will be apparent to those skilled in the art. All such variations and modifications are intended to be within the scope of the present invention.

What is claimed is:

1. A recombinant nucleic acid encoding an acyl-ACP thioesterase having at least 97% sequence identity to any of SEQ ID NOs: 92 or 93 or any equivalent sequences by virtue of the degeneracy of the genetic code, or a C-terminal and/or N-terminal truncated fragment comprising at least 90% of the full-length sequences thereof.

2. A recombinant nucleic acid encoding an acyl-ACP thioesterase having at least 97% sequence identity to SEQ ID NOs: 91, 171 or 179, or a C-terminal and/or N-terminal truncated fragment comprising at least 90% of the full-length sequences thereof, wherein the recombinant nucleic acid also comprises a heterologous nucleic acid.

3. A method of producing a recombinant acyl-ACP thioesterase, the method comprising transforming a cell with a nucleic acid according to any of claim 1 or 2.

4. A vector comprising the recombinant nucleic acid of claim 1 or 2.

5. A host cell comprising a recombinant nucleic acid encoding an acyl-ACP thioesterase having at least 97% sequence identity to SEQ ID NO:91, 171 or 179, wherein the recombinant nucleic acid comprises an exogenous nucleic acid, and wherein the host cell has an altered fatty acid profile.

6. The host cell of claim 5, wherein the host cell is selected from a plant cell, a microbial cell, and a microalgal cell.

7. The host cell of claim 6, wherein the microalgal cell is a *Prototheca* cell.

8. The host cell of claim 6, wherein the microalgal cell is a *Prototheca moriformis* cell.

9. A method for producing an oil or oil-derived product, the method comprising cultivating a host cell of claim 5, and extracting oil produced thereby, optionally wherein the cultivation is heterotrophic growth on sugar.

10. The method of claim 9, further comprising producing a fatty acid, fuel, chemical, or other oil-derived product from the oil.

* * * * *

SEQUENCE LISTING

```
<160> NUMBER OF SEQ ID NOS: 193

<210> SEQ ID NO 1
<211> LENGTH: 380
<212> TYPE: PRT
<213> ORGANISM: Cinnamomum camphora
<220> FEATURE:
<223> OTHER INFORMATION: Cinnamomum camphora (Cc) FATB1b variant M25L,
      M322R, deltaT367-D368 amino acid sequence

<400> SEQUENCE: 1

Met Ala Thr Thr Ser Leu Ala Ser Ala Phe Cys Ser Met Lys Ala Val
1               5                   10                  15

Met Leu Ala Arg Asp Gly Arg Gly Leu Lys Pro Arg Ser Ser Asp Leu
            20                  25                  30

Gln Leu Arg Ala Gly Asn Ala Gln Thr Ser Leu Lys Met Ile Asn Gly
        35                  40                  45

Thr Lys Phe Ser Tyr Thr Glu Ser Leu Lys Lys Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Asn Pro Pro Gln Leu Leu
                85                  90                  95

Asp Asp His Phe Gly Pro His Gly Leu Val Phe Arg Arg Thr Phe Ala
            100                 105                 110

Ile Arg Ser Tyr Glu Val Gly Pro Asp Arg Ser Thr Ser Ile Val Ala
        115                 120                 125

Val Met Asn His Leu Gln Glu Ala Ala Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Ile Trp Val Val Lys Arg Thr His Val Ala Val Glu Arg Tyr
                165                 170                 175

Pro Ala Trp Gly Asp Thr Val Glu Val Glu Cys Trp Val Gly Ala Ser
            180                 185                 190

Gly Asn Asn Gly Arg Arg His Asp Phe Leu Val Arg Asp Cys Lys Thr
        195                 200                 205
```

-continued

```
Gly Glu Ile Leu Thr Arg Cys Thr Ser Leu Ser Val Met Met Asn Thr
    210                 215                 220

Arg Thr Arg Arg Leu Ser Lys Ile Pro Glu Glu Val Arg Gly Glu Ile
225                 230                 235                 240

Gly Pro Ala Phe Ile Asp Asn Val Ala Val Lys Asp Glu Glu Ile Lys
                245                 250                 255

Lys Pro Gln Lys Leu Asn Asp Ser Thr Ala Asp Tyr Ile Gln Gly Gly
            260                 265                 270

Leu Thr Pro Arg Trp Asn Asp Leu Asp Ile Asn Gln His Val Asn Asn
        275                 280                 285

Ile Lys Tyr Val Asp Trp Ile Leu Glu Thr Val Pro Asp Ser Ile Phe
    290                 295                 300

Glu Ser His His Ile Ser Ser Phe Thr Ile Glu Tyr Arg Arg Glu Cys
305                 310                 315                 320

Thr Arg Asp Ser Val Leu Gln Ser Leu Thr Thr Val Ser Gly Gly Ser
                325                 330                 335

Ser Glu Ala Gly Leu Val Cys Glu His Leu Leu Gln Leu Glu Gly Gly
            340                 345                 350

Ser Glu Val Leu Arg Ala Lys Thr Glu Trp Arg Pro Lys Leu Ser Phe
        355                 360                 365

Arg Gly Ile Ser Val Ile Pro Ala Glu Ser Ser Val
    370                 375                 380
```

<210> SEQ ID NO 2
<211> LENGTH: 1128
<212> TYPE: DNA
<213> ORGANISM: Cinnamomum camphora
<220> FEATURE:
<223> OTHER INFORMATION: Cinnamomum camphora (Cc) FATB1b variant M25L, M322R, deltaT367-D368 coding DNA sequence

<400> SEQUENCE: 2

```
ttagcttctg ctttctgctc gatgaaagct gtaatgttgg ctcgtgatgg caggggcttg     60

aaacccagga gcagtgattt gcagctgagg gcgggaaatg cacaaacctc tttgaagatg    120

atcaatggga ccaagttcag ttacacagag agcttgaaaa agttgcctga ctggagcatg    180

ctctttgcag tgatcacgac catcttttcg gctgctgaga agcagtggac caatctagag    240

tggaagccga agccgaatcc accccagttg cttgatgacc attttgggcc gcatgggtta    300

gttttcaggc gcacctttgc catcagatcg tatgaggtgg gacctgaccg ctccacatct    360

atagtggctg ttatgaatca cttgcaggag gctgcactta atcatgcgaa gagtgtggga    420

attctaggag atggattcgg tacgacgcta gagatgagta agagagatct gatatgggtt    480

gtgaaacgca cgcatgttgc tgtggaacgg taccctgctt ggggtgatac tgttgaagta    540

gagtgctggg ttggtgcatc gggaaataat ggcaggcgcc atgatttcct tgtccgggac    600

tgcaaaacag gcgaaattct tacaagatgt accagtcttt cggtgatgat gaatacaagg    660

acaaggaggt tgtccaaaat ccctgaagaa gttagagggg agatagggcc tgcattcatt    720

gataatgtgg ctgtcaagga cgaggaaatt aagaaaccac agaagctcaa tgacagcact    780

gcagattaca tccaaggagg attgactcct cgatggaatg atttggatat caatcagcac    840

gttaacaaca tcaaatacgt tgactggatt cttgagactg tcccagactc aatctttgag    900

agtcatcata tttccagctt cactattgaa tacaggagag agtgcacgag ggatagcgtg    960

ctgcagtccc tgaccactgt ctccggtggc tcgtcggaag ctgggttagt gtgcgagcac   1020
```

```
ttgctccagc ttgaaggtgg gtctgaggta ttgagggcaa aaacagagtg gaggcctaag   1080

cttagtttca gagggattag tgtgataccc gcagaatcga gtgtctaa                1128
```

<210> SEQ ID NO 3
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cinnamomum camphora (Cc) FATB1b variant M25L, M322R, deltaT367-D368 coding DNA sequence codon optimized for Prototheca moriformis

<400> SEQUENCE: 3

```
ttagcttctg ctttctgctc gatgaaagct gtaatgttgg ctcgtgatgg caggggcttg     60

aaacccagga gcagtgattt gcagctgagg gcgggaaatg cacaaacctc tttgaagatg    120

atcaatggga ccaagttcag ttacacagag agcttgaaaa agttgcctga ctggagcatg    180

ctctttgcag tgatcacgac catcttttcg gctgctgaga agcagtggac caatctagag    240

tggaagccga agccgaatcc accccagttg cttgatgacc attttgggcc gcatgggtta    300

gttttcaggc gcacctttgc catcagatcg tatgaggtgg gacctgaccg ctccacatct    360

atagtggctg ttatgaatca cttgcaggag gctgcactta atcatgcgaa gagtgtggga    420

attctaggag atggattcgg tacgacgcta gagatgagta agagagatct gatatgggtt    480

gtgaaacgca cgcatgttgc tgtggaacgg taccctgctt ggggtgatac tgttgaagta    540

gagtgctggg ttggtgcatc gggaaataat ggcaggcgcc atgatttcct tgtccgggac    600

tgcaaaacag gcgaaattct tacaagatgt accagtcttt cggtgatgat gaatacaagg    660

acaaggaggt tgtccaaaat ccctgaagaa gttagagggg agatagggcc tgcattcatt    720

gataatgtgg ctgtcaagga cgaggaaatt aagaaaccac agaagctcaa tgacagcact    780

gcagattaca tccaaggagg attgactcct cgatggaatg atttggatat caatcagcac    840

gttaacaaca tcaaatacgt tgactggatt cttgagactg tcccagactc aatctttgag    900

agtcatcata tttccagctt cactattgaa tacaggagag agtgcacgag ggatagcgtg    960

ctgcagtccc tgaccactgt ctccggtggc tcgtcggaag ctgggttagt gtgcgagcac   1020

ttgctccagc ttgaaggtgg gtctgaggta ttgagggcaa aaacagagtg gaggcctaag   1080

cttagtttca gagggattag tgtgataccc gcagaatcga gtgtctaa                1128
```

<210> SEQ ID NO 4
<211> LENGTH: 357
<212> TYPE: PRT
<213> ORGANISM: Cinnamomum camphora
<220> FEATURE:
<223> OTHER INFORMATION: Cinnamomum camphora (Cc) FATB4 amino acid sequence

<400> SEQUENCE: 4

```
Met Val Thr Thr Ser Leu Ala Ser Ala Tyr Phe Ser Met Lys Ala Val
1               5                   10                  15

Met Leu Ala Pro Asp Gly Arg Gly Ile Lys Pro Arg Ser Ser Gly Leu
            20                  25                  30

Gln Val Arg Ala Gly Asn Glu Arg Asn Ser Cys Lys Val Ile Asn Gly
        35                  40                  45

Thr Lys Val Lys Asp Thr Glu Gly Leu Lys Gly Cys Ser Thr Leu Gln
    50                  55                  60
```

```
Gly Gln Ser Met Leu Asp Asp His Phe Gly Leu His Gly Leu Val Phe
65                  70                  75                  80

Arg Arg Thr Phe Ala Ile Arg Cys Tyr Glu Val Gly Pro Asp Arg Ser
                85                  90                  95

Thr Ser Ile Met Ala Val Met Asn His Leu Gln Glu Ala Ala Arg Asn
            100                 105                 110

His Ala Glu Ser Leu Gly Leu Leu Gly Asp Gly Phe Gly Glu Thr Leu
        115                 120                 125

Glu Met Ser Lys Arg Asp Leu Ile Trp Val Val Arg Arg Thr His Val
    130                 135                 140

Ala Val Glu Arg Tyr Pro Ala Trp Gly Asp Thr Val Glu Val Glu Ala
145                 150                 155                 160

Trp Val Gly Ala Ser Gly Asn Thr Gly Met Arg Arg Asp Phe Leu Val
                165                 170                 175

Arg Asp Cys Lys Thr Gly His Ile Leu Thr Arg Cys Thr Ser Val Ser
            180                 185                 190

Val Met Met Asn Met Arg Thr Arg Arg Leu Ser Lys Ile Pro Gln Glu
        195                 200                 205

Val Arg Ala Glu Ile Asp Pro Leu Phe Ile Glu Lys Val Ala Val Lys
    210                 215                 220

Glu Gly Glu Ile Lys Lys Leu Gln Lys Leu Asn Asp Ser Thr Ala Asp
225                 230                 235                 240

Tyr Ile Gln Gly Gly Trp Thr Pro Arg Trp Asn Asp Leu Asp Val Asn
                245                 250                 255

Gln His Val Asn Asn Ile Ile Tyr Val Gly Trp Ile Phe Lys Ser Val
            260                 265                 270

Pro Asp Ser Ile Ser Glu Asn His His Leu Ser Ser Ile Thr Leu Glu
        275                 280                 285

Tyr Arg Arg Glu Cys Thr Arg Gly Asn Lys Leu Gln Ser Leu Thr Thr
    290                 295                 300

Val Cys Gly Gly Ser Ser Glu Ala Gly Ile Ile Cys Glu His Leu Leu
305                 310                 315                 320

Gln Leu Glu Asp Gly Ser Glu Val Leu Arg Ala Arg Thr Glu Trp Arg
                325                 330                 335

Pro Lys His Thr Asp Ser Phe Gln Gly Ile Ser Glu Arg Phe Pro Gln
            340                 345                 350

Gln Glu Pro His Lys
        355
```

<210> SEQ ID NO 5
<211> LENGTH: 1074
<212> TYPE: DNA
<213> ORGANISM: Cinnamomum camphora
<220> FEATURE:
<223> OTHER INFORMATION: Cinnamomum camphora (Cc) FATB4 coding DNA sequence

<400> SEQUENCE: 5

```
atggtcacca cctctttagc ttccgcttac ttctcgatga aagctgtaat gttggctcct      60

gacggcaggg gcataaagcc caggagcagt ggtttgcagg tgagggcggg aaatgaacga     120

aactcttgca aggtgatcaa tgggaccaag gtcaaagaca cggagggctt gaaagggtgc     180

agcacgttgc aaggccagag catgcttgat gaccattttg gtctgcatgg gctagttttc     240

aggcgcacct ttgcaatcag atgctatgag gttggacctg accgctccac atccataatg     300
```

-continued gctgttatga atcacttgca ggaagctgca cgtaatcatg cggagagtct gggacttcta 360
ggagatggat tcggtgagac actggagatg agtaagagag atctgatatg ggttgtgaga 420
cgcacgcatg ttgctgtgga acggtaccct gcttggggcg atactgttga agtcgaggcc 480
tgggtgggtg catcaggtaa cactggcatg cgccgcgatt tccttgtccg cgactgcaaa 540
actggccaca ttcttacaag atgtaccagt gtttcagtga tgatgaatat gaggacaagg 600
agattgtcca aaattcccca agaagttaga gcggagattg accctctttt cattgaaaag 660
gttgctgtca aggaagggga aattaaaaaa ttacagaagt tgaatgatag cactgcagat 720
tacattcaag gggttggac tcctcgatgg aatgatttgg atgtcaatca gcacgtgaac 780
aatatcatat acgttggctg gatttttaag agcgtcccag actctatctc tgagaatcat 840
catctttcta gcatcactct cgaatacagg agagagtgca caaggggcaa caagctgcag 900
tccctgacca ctgtttgtgg tggctcgtcg gaagctggga tcatatgtga gcacctactc 960
cagcttgagg atgggtctga ggttttgagg gcaagaacag agtggaggcc caagcacacc 1020
gatagtttcc aaggcattag tgagagattc ccgcagcaag aaccgcataa gtaa 1074

<210> SEQ ID NO 6
<211> LENGTH: 1074
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cinnamomum camphora (Cc) FATB4 coding DNA sequence codon optimized for Prototheca moriformis

<400> SEQUENCE: 6
atggtgacca cctccctggc ctccgcctac ttctccatga aggccgtgat gctggccccc 60
gacggccgcg gcatcaagcc ccgctcctcc ggcctgcagg tgcgcgccgg caacgagcgc 120
aactcctgca aggtgatcaa cggcaccaag gtgaaggaca ccgagggcct gaagggctgc 180
tccaccctgc agggccagtc catgctggac gaccacttcg gcctgcacgg cctggtgttc 240
cgccgcacct tcgccatccg ctgctacgag gtgggccccg accgctccac ctccatcatg 300
gccgtgatga accacctgca ggaggccgcc cgcaaccacg ccgagtccct gggcctgctg 360
ggcgacggct tcggcgagac cctggagatg tccaagcgcg acctgatctg ggtggtgcgc 420
cgcacccacg tggccgtgga gcgctacccc gcctggggcg acaccgtgga ggtggaggcc 480
tgggtgggcg cctccggcaa caccggcatg cgccgcgact tcctggtgcg cgactgcaag 540
accggccaca tcctgacccg ctgcacctcc gtgtccgtga tgatgaacat gcgcacccgc 600
cgcctgtcca agatccccca ggaggtgcgc gccgagatcg acccccctgtt catcgagaag 660 gtggccgtga aggagggcga gatcaagaag ctgcagaagc tgaacgactc caccgccgac 720
tacatccagg gcggctggac cccccgctgg aacgacctgg acgtgaacca gcacgtgaac 780
aacatcatct acgtgggctg gatcttcaag tccgtgcccg actccatctc cgagaaccac 840
cacctgtcct ccatcaccct ggagtaccgc cgcgagtgca cccgcggcaa caagctgcag 900
tccctgacca ccgtgtgcgg cggctcctcc gaggccggca tcatctgcga gcacctgctg 960
cagctggagg acggctccga ggtgctgcgc gcccgcaccg agtggcgccc caagcacacc 1020
gactccttcc agggcatctc cgagcgcttc ccccagcagg agccccacaa gtga 1074

<210> SEQ ID NO 7
<211> LENGTH: 419

```
<212> TYPE: PRT
<213> ORGANISM: Cinnamomum camphora
<220> FEATURE:
<223> OTHER INFORMATION: Cinnamomum camphora (Cc) FATB3 amino acid
      sequence

<400> SEQUENCE: 7

Met Val Ala Thr Ala Ala Ala Ser Ala Phe Phe Pro Val Gly Ala Pro
1               5                   10                  15

Ala Thr Ser Ser Ala Thr Ser Ala Lys Ala Ser Met Met Pro Asp Asn
            20                  25                  30

Leu Asp Ala Arg Gly Ile Lys Pro Lys Pro Ala Ser Ser Ser Gly Leu
        35                  40                  45

Gln Val Lys Ala Asn Ala His Ala Ser Pro Lys Ile Asn Gly Ser Lys
    50                  55                  60

Val Ser Thr Asp Thr Leu Lys Gly Glu Asp Thr Leu Thr Ser Ser Pro
65                  70                  75                  80

Ala Pro Arg Thr Phe Ile Asn Gln Leu Pro Asp Trp Ser Met Phe Leu
                85                  90                  95

Ala Ala Ile Thr Thr Ile Phe Leu Ala Ala Glu Lys Gln Trp Thr Asn
            100                 105                 110

Leu Asp Trp Lys Pro Arg Arg Pro Asp Met Leu Ala Asp Pro Phe Gly
        115                 120                 125

Ile Gly Arg Phe Met Gln Asp Gly Leu Ile Phe Arg Gln His Phe Ala
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ala Leu Asn His Val Arg Ser Ala
                165                 170                 175

Gly Leu Leu Gly Asp Gly Phe Gly Ala Thr Pro Glu Met Ser Arg Arg
            180                 185                 190

Asp Leu Ile Trp Val Val Thr Arg Met Gln Val Leu Val Asp Arg Tyr
        195                 200                 205

Pro Ala Trp Gly Asp Ile Val Glu Val Glu Thr Trp Val Gly Ala Ser
    210                 215                 220

Gly Lys Asn Gly Met Arg Arg Asp Trp Leu Val Arg Asp Ser Gln Thr
225                 230                 235                 240

Gly Glu Ile Leu Thr Arg Ala Thr Ser Val Trp Val Met Met Asn Lys
                245                 250                 255

Arg Thr Arg Arg Leu Ser Lys Leu Pro Glu Glu Val Arg Gly Glu Ile
            260                 265                 270

Gly Pro Tyr Phe Ile Glu Asp Val Ala Ile Ile Glu Glu Asp Asn Arg
        275                 280                 285

Lys Leu Gln Lys Leu Asn Glu Asn Thr Ala Asp Asn Val Arg Arg Gly
    290                 295                 300

Leu Thr Pro Arg Trp Ser Asp Leu Asp Val Asn Gln His Val Asn Asn
305                 310                 315                 320

Val Lys Tyr Ile Gly Trp Ile Leu Glu Ser Ala Pro Gly Ser Ile Leu
                325                 330                 335

Glu Ser His Glu Leu Ser Cys Met Thr Leu Glu Tyr Arg Arg Glu Cys
            340                 345                 350

Gly Lys Asp Ser Val Leu Gln Ser Met Thr Ala Val Ser Gly Gly Gly
        355                 360                 365

Ser Ala Ala Gly Gly Ser Pro Glu Ser Ser Val Glu Cys Asp His Leu
    370                 375                 380
```

-continued

Leu Gln Leu Glu Ser Gly Pro Glu Val Val Arg Gly Arg Thr Glu Trp
385 390 395 400

Arg Pro Lys Ser Ala Asn Asn Ser Arg Ser Ile Leu Glu Met Pro Ala
405 410 415

Glu Ser Leu

<210> SEQ ID NO 8
<211> LENGTH: 1254
<212> TYPE: DNA
<213> ORGANISM: Cinnamomum camphora
<220> FEATURE:
<223> OTHER INFORMATION: Cinnamomum camphora (Cc) FATB3 coding DNA sequence

<400> SEQUENCE: 8

```
atggttgcca ccgctgctgc ttctgctttc ttcccggtcg gtgctccggc tacgtcatct     60
gcaacttcag ccaaagcgtc gatgatgcct gataatttgg atgccagagg catcaaaccg    120
aagccggctt cgtccagcgg cttgcaggtt aaggcaaatg cccatgcctc tcccaagatt    180
aatggttcca aggtgagcac ggataccttg aagggggaag acaccttaac ttcctcgccc    240
gccccacgga cctttatcaa ccaattgcct gactggagca tgttccttgc tgccatcaca    300
actattttct tggctgccga gaagcagtgg acgaatctcg actggaagcc cagaagaccc    360
gacatgcttg ctgacccgtt tggcatcggg aggtttatgc aggatgggct gattttcagg    420
cagcactttg caatcagatc ttatgagatt ggggctgata gaacggcgtc tatagagact    480
ttaatgaatc acttgcagga gactgcactt aatcatgtga ggagtgctgg actcctaggt    540
gatggatttg gtgcgacacc tgagatgagt agaagagatc tgatatgggt tgtaacacgt    600
atgcaggttc ttgtggaccg ctaccctgct tggggtgata ttgttgaagt agagacctgg    660
gttggtgcat ctggaaaaaa tggtatgcgc cgtgattggc ttgttcggga cagccaaact    720
ggtgaaattc tcacacgagc taccagtgtt tgggtgatga tgaataaacg gacaaggcga    780
ttgtccaaac ttcctgaaga agttagaggg gaaatagggc cttattttat agaagatgtt    840
gctatcatag aggaggacaa caggaaacta cagaagctca atgaaaacac tgctgataat    900
gttcgaaggg gtttgactcc tcgctggagt gatctggatg ttaatcagca tgtgaacaat    960
gtcaaataca ttggttggat tcttgagagt gcaccaggat ccatcttgga gagtcatgag   1020
ctttcctgca tgacccttga atacaggaga gaatgtggga aggacagtgt gctgcagtca   1080
atgactgctg tctctggtgg aggcagtgca gcaggtggct caccagaatc tagcgttgag   1140
tgtgaccact tgctccagct agagagtggg cctgaagttg tgaggggaag aaccgagtgg   1200
aggcccaaga gtgctaataa ctcgaggagc atcctggaga tgccggccga gagc         1254
```

<210> SEQ ID NO 9
<211> LENGTH: 1260
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cinnamomum camphora (Cc) FATB4 coding DNA sequence codon optimized for Prototheca moriformis

<400> SEQUENCE: 9

```
atggtggcca ccgccgccgc ctccgccttc ttccccgtgg gcgcccccgc cacctcctcc     60
gccacctccg ccaaggcctc catgatgccc gacaacctgg acgcccgcgg catcaagccc    120
```

```
aagcccgcct cctcctccgg cctgcaggtg aaggccaacg cccacgcctc ccccaagatc    180

aacggctcca aggtgtccac cgacaccctg aagggcgagg acaccctgac ctcctccccc    240

gccccccgca ccttcatcaa ccagctgccc gactggtcca tgttcctggc cgccatcacc    300

accatcttcc tggccgccga gaagcagtgg accaacctgg actggaagcc ccgccgcccc    360

gacatgctgg ccgacccctt cggcatcggc cgcttcatgc aggacggcct gatcttccgc    420

cagcacttcg ccatccgctc ctacgagatc ggcgccgacc gcaccgcctc catcgagacc    480

ctgatgaacc acctgcagga gaccgccctg aaccacgtgc gctccgccgg cctgctgggc    540

gacggcttcg gcgccacccc cgagatgtcc cgccgcgacc tgatctgggt ggtgacccgc    600

atgcaggtgc tggtggaccg ctaccccgcc tggggcgaca tcgtggaggt ggagacctgg    660

gtgggcgcct ccggcaagaa cggcatgcgc cgcgactggc tggtgcgcga ctcccagacc    720

ggcgagatcc tgacccgcgc cacctccgtg tgggtgatga tgaacaagcg cacccgccgc    780

ctgtccaagc tgcccgagga ggtgcgcggc gagatcggcc cctacttcat cgaggacgtg    840

gccatcatcg aggaggacaa ccgcaagctg cagaagctga acgagaacac cgccgacaac    900

gtgcgccgcg gcctgacccc ccgctggtcc gacctggacg tgaaccagca cgtgaacaac    960

gtgaagtaca tcggctggat cctggagtcc gcccccggct ccatcctgga gtcccacgag   1020

ctgtcctgca tgaccctgga gtaccgccgc gagtgcggca aggactccgt gctgcagtcc   1080

atgaccgccg tgtccggcgg cggctccgcc gccggcggct cccccgagtc ctccgtggag   1140

tgcgaccacc tgctgcagct ggagtccggc cccgaggtgg tgcgcggccg caccgagtgg   1200

cgccccaagt ccgccaacaa ctcccgctcc atcctggaga tgcccgccga gtccctgtga   1260
```

```
<210> SEQ ID NO 10
<211> LENGTH: 361
<212> TYPE: PRT
<213> ORGANISM: Cuphea hyssopifolia
<220> FEATURE:
<223> OTHER INFORMATION: Cuphea hyssopifolia (Chs) FATB1 amino acid
      sequence

<400> SEQUENCE: 10

Met Val Ala Thr Asn Ala Ala Ala Phe Ser Ala Tyr Thr Phe Phe Leu
1               5                   10                  15

Thr Ser Pro Thr His Gly Tyr Ser Ser Lys Arg Leu Ala Asp Thr Gln
            20                  25                  30

Asn Gly Tyr Pro Gly Thr Ser Leu Lys Ser Lys Ser Thr Pro Pro Pro
        35                  40                  45

Ala Ala Ala Ala Ala Arg Asn Gly Ala Leu Pro Leu Leu Ala Ser Ile
    50                  55                  60

Cys Lys Cys Pro Lys Lys Ala Asp Gly Ser Met Gln Leu Asp Ser Ser
65                  70                  75                  80

Leu Val Phe Gly Phe Gln Phe Tyr Ile Arg Ser Tyr Glu Val Gly Ala
                85                  90                  95

Asp Gln Thr Val Ser Ile Gln Thr Val Leu Asn Tyr Leu Gln Glu Ala
            100                 105                 110

Ala Ile Asn His Val Gln Ser Ala Gly Tyr Phe Gly Asp Ser Phe Gly
        115                 120                 125

Ala Thr Pro Glu Met Thr Lys Arg Asn Leu Ile Trp Val Ile Thr Lys
    130                 135                 140

Met Gln Val Leu Val Asp Arg Tyr Pro Ala Trp Gly Asp Val Val Gln
145                 150                 155                 160
```

```
Val Asp Thr Trp Thr Cys Ser Ser Gly Lys Asn Ser Met Gln Arg Asp
                165                 170                 175

Trp Phe Val Arg Asp Leu Lys Thr Gly Asp Ile Ile Thr Arg Ala Ser
            180                 185                 190

Ser Val Trp Val Leu Met Asn Arg Leu Thr Arg Lys Leu Ser Lys Ile
        195                 200                 205

Pro Glu Ala Val Leu Glu Glu Ala Lys Leu Phe Val Met Asn Thr Ala
    210                 215                 220

Pro Thr Val Asp Asp Asn Arg Lys Leu Pro Lys Leu Asp Gly Ser Ser
225                 230                 235                 240

Ala Asp Tyr Val Leu Ser Gly Leu Thr Pro Arg Trp Ser Asp Leu Asp
                245                 250                 255

Met Asn Gln His Val Asn Asn Val Lys Tyr Ile Ala Trp Ile Leu Glu
            260                 265                 270

Ser Val Pro Gln Ser Ile Pro Glu Thr His Lys Leu Ser Ala Ile Thr
        275                 280                 285

Val Glu Tyr Arg Arg Glu Cys Gly Lys Asn Ser Val Leu Gln Ser Leu
    290                 295                 300

Thr Asn Val Ser Gly Asp Gly Ile Thr Cys Gly Asn Ser Ile Ile Glu
305                 310                 315                 320

Cys His His Leu Leu Gln Leu Glu Thr Gly Pro Glu Ile Leu Leu Ala
                325                 330                 335

Arg Thr Glu Trp Ile Ser Lys Glu Pro Gly Phe Arg Gly Ala Pro Ile
            340                 345                 350

Gln Ala Glu Lys Val Tyr Asn Asn Lys
        355                 360
```

<210> SEQ ID NO 11
<211> LENGTH: 1086
<212> TYPE: DNA
<213> ORGANISM: Cuphea hyssopifolia
<220> FEATURE:
<223> OTHER INFORMATION: Cuphea hyssopifolia (Chs) FATB1 coding DNA sequence

<400> SEQUENCE: 11

```
atggttgcca ctaatgctgc tgccttttct gcttatactt tcttccttac ttcaccaact     60

catggttact cttccaaacg tctcgccgat actcaaaatg gttatccggg tacctccttg    120

aaatcgaaat ccactcctcc accagctgct gctgctgctc gtaacggtgc attgccactg    180

ctggcctcca tctgcaaatg ccccaaaaag gctgatggga gtatgcaact agacagctcc    240

ttggtcttcg ggtttcaatt ttacattaga tcatatgaag tgggtgcgga tcaaaccgtg    300

tcaatacaga cagtactcaa ttacttacag gaggcagcca tcaatcatgt tcagagtgct    360

ggctattttg gtgatagttt tggcgccacc ccggaaatga ccaagaggaa cctcatctgg    420

gttatcacta agatgcaggt tttggtggat cgctatcccg cttggggcga tgttgttcaa    480

gttgatacat ggacctgtag ttctggtaaa aacagcatgc agcgtgattg gttcgtacgg    540

gatctcaaaa ctggagatat tataacaaga gcctcgagcg tgtgggtgct gatgaataga    600

ctcaccagaa aattatcaaa aattcctgaa gcagttctgg aagaagcaaa actttttgtg    660

atgaacactg cccccaccgt agatgacaac aggaagctac caaagctgga tggcagcagt    720

gctgattatg tcctctctgg cttaactcct agatggagcg acttagatat gaaccagcat    780

gtcaacaatg tgaagtacat agcctggatc cttgagagtg tccctcagag cataccggag    840
```

-continued

```
acacacaagc tgtcagcgat aaccgtggag tacaggagag aatgtggcaa gaacagcgtc    900

ctccagtctc tgaccaacgt ctccggggat ggaatcacat gtggaaacag tattatcgag    960

tgccaccatt tgcttcaact tgagactggc ccagagattc tactagcgcg gacggagtgg   1020

atatccaagg aacctgggtt caggggagct ccaatccagg cagagaaagt ctacaacaac   1080

aaataa                                                              1086


<210> SEQ ID NO 12
<211> LENGTH: 1086
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cuphea hyssopifolia (Chs) FATB1 coding DNA
      sequence codon optimized for Prototheca moriformis

<400> SEQUENCE: 12

atggtggcca ccaacgccgc cgccttctcc gcctacacct tcttcctgac ctcccccacc     60

cacggctact cctccaagcg cctggccgac acccagaacg gctaccccgg cacctccctg    120

aagtccaagt ccaccccccc ccccgccgcc gccgccgccc gcaacggcgc cctgcccctg    180

ctggcctcca tctgcaagtg ccccaagaag gccgacggct ccatgcagct ggactcctcc    240

ctggtgttcg gcttccagtt ctacatccgc tcctacgagg tgggcgccga ccagaccgtg    300

tccatccaga ccgtgctgaa ctacctgcag gaggccgcca tcaaccacgt gcagtccgcc    360

ggctacttcg gcgactcctt cggcgccacc cccgagatga ccaagcgcaa cctgatctgg    420

gtgatcacca agatgcaggt gctggtggac cgctaccccg cctggggcga cgtggtgcag    480

gtggacacct ggacctgctc ctccggcaag aactccatgc agcgcgactg gttcgtgcgc    540

gacctgaaga ccggcgacat catcacccgc gcctcctccg tgtgggtgct gatgaaccgc    600

ctgacccgca agctgtccaa gatccccgag gccgtgctgg aggaggccaa gctgttcgtg    660

atgaacaccg cccccaccgt ggacgacaac cgcaagctgc ccaagctgga cggctcctcc    720

gccgactacg tgctgtccgg cctgaccccc cgctggtccg acctggacat gaaccagcac    780

gtgaacaacg tgaagtacat cgcctggatc ctggagtccg tgccccagtc catccccgag    840

acccacaagc tgtccgccat caccgtggag taccgccgcg agtgcggcaa gaactccgtg    900

ctgcagtccc tgaccaacgt gtccggcgac ggcatcacct gcggcaactc catcatcgag    960

tgccaccacc tgctgcagct ggagaccggc cccgagatcc tgctggcccg caccgagtgg   1020

atctccaagg agcccggctt ccgcggcgcc cccatccagg ccgagaaggt gtacaacaac   1080

aagtga                                                              1086


<210> SEQ ID NO 13
<211> LENGTH: 415
<212> TYPE: PRT
<213> ORGANISM: Cuphea hyssopifolia
<220> FEATURE:
<223> OTHER INFORMATION: Cuphea hyssopifolia (Chs) FATB2 amino acid
      sequence

<400> SEQUENCE: 13

Met Val Ala Thr Ala Ala Ser Ser Ala Phe Phe Pro Val Pro Ser Pro
1               5                   10                  15

Asp Ala Ser Ser Arg Pro Gly Lys Leu Gly Asn Gly Ser Ser Ser Leu
            20                  25                  30
```

-continued

```
Ser Pro Leu Lys Pro Lys Leu Met Ala Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Asp Gly Phe Gly Arg Thr Leu Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Arg Leu Ser Lys Ile Pro Asp Glu Val Arg His Glu Ile Glu
            260                 265                 270

Pro His Phe Val Asp Ser Ala Pro Val Ile Glu Asp Asp Asp Arg Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Ser Gly Ser Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Pro Ile Ala Ser Gly Glu Thr Ser Pro Gly Asp Ser Ser
                405                 410                 415
```

<210> SEQ ID NO 14
<211> LENGTH: 1248
<212> TYPE: DNA
<213> ORGANISM: Cuphea hyssopifolia
<220> FEATURE:
<223> OTHER INFORMATION: Cuphea hyssopifolia (Chs) FATB2 coding DNA sequence

<400> SEQUENCE: 14

```
atggtggcta ccgctgcaag ttcagcattc ttccctgtgc cgtcccccga cgcctcctct     60
agacctggaa agctcggcaa tgggtcatcg agcttgagcc ccctcaagcc caaattgatg    120
gccaatggcg ggttgcaggt taaggcaaac gccagtgccc ctcctaagat caatggttct    180
tcggtcggtc taaagtccgg cagtctcaag actcaggaag acactccttc ggcgcctcct    240
ccccggactt ttattaacca gctgcctgat tggagtatgc ttcttgctgc aatcactact    300
gtcttcttgg cagcagagaa gcagtggatg atgcttgatt ggaaacccaa gaggcctgac    360
atgcttgtgg acccgttcgg attgggaagg attgttcaag atgggcttgt gttcaggcag    420
aatttttcga ttaggtccta tgaaataggc gctgatcgca ctgcgtctat agagacggtg    480
atgaaccact tgcaggaaac agctctcaat catgttaaga gtgctgggct tcttaatgac    540
ggctttggtc gtactcttga gatgtataaa agggacctta tttgggttgt tgcaaaaatg    600
caggtcatgg ttaaccgcta tcctacttgg ggcgacacgg ttgaagtgaa tacttgggtt    660
gccaagtcag ggaaaaatgg tatgcgtcgt gattggctca taagtgattg caatacagga    720
gaaattctta ctagagcatc aagtgtgtgg gtcatgatga atcaaaagac aagaagattg    780
tcaaaaattc cagatgaggt tcgacatgag atagagcctc atttcgtgga ctctgctccc    840
gtcattgaag atgatgaccg gaaacttccc aagctggatg agaagactgc tgactccatc    900
cgcaagggtc taactccgaa gtggaatgac ttggatgtca atcagcacgt caacaacgtg    960
aagtacattg ggtggattct tgagagtact ccaccagaag ttctggagac ccaggagtta   1020
tgttccctta ccctggaata taggcgggaa tgcggaaggg agagcgtgct ggagtccctc   1080
actgctgtgg acccctctgg aaagggctct gggtctcagt tccagcacct tctgcggctt   1140
gaggatggag gtgagattgt gaaggggaga actgagtggc gacccaagac tgcaggaatc   1200
aatgggccaa tagcatccgg ggagacctca cctggagact cttcttag                1248
```

<210> SEQ ID NO 15
<211> LENGTH: 1248
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea hyssopifolia (Chs) FATB2 coding DNA sequence codon optimized for Prototheca moriformis

<400> SEQUENCE: 15

```
atggtggcca ccgccgcctc ctccgccttc ttccccgtgc cctcccccga cgcctcctcc     60
cgccccggca agctgggcaa cggctcctcc tccctgtccc ccctgaagcc caagctgatg    120
gccaacggcg gcctgcaggt gaaggccaac gcctccgccc cccccaagat caacggctcc    180
tccgtgggcc tgaagtccgg ctccctgaag acccaggagg acacccccctc cgcccccccc    240
ccccgcacct tcatcaacca gctgcccgac tggtccatgc tgctggccgc catcaccacc    300
gtgttcctgg ccgccgagaa gcagtggatg atgctggact ggaagcccaa gcgccccgac    360
atgctggtgg accccttcgg cctgggccgc atcgtgcagg acggcctggt gttccgccag    420
aacttctcca tccgctccta cgagatcggc gccgaccgca ccgcctccat cgagaccgtg    480
atgaaccacc tgcaggagac cgccctgaac cacgtgaagt ccgccggcct gctgaacgac    540
ggcttcggcc gcaccctgga gatgtacaag cgcgacctga tctgggtggt ggccaagatg    600
```

```
caggtgatgg tgaaccgcta ccccacctgg ggcgacaccg tggaggtgaa cacctgggtg    660

gccaagtccg gcaagaacgg catgcgccgc gactggctga tctccgactg caacaccggc    720

gagatcctga cccgcgcctc ctccgtgtgg gtgatgatga accagaagac ccgccgcctg    780

tccaagatcc ccgacgaggt gcgccacgag atcgagcccc acttcgtgga ctccgccccc    840

gtgatcgagg acgacgaccg caagctgccc aagctggacg agaagaccgc cgactccatc    900

cgcaagggcc tgacccccaa gtggaacgac ctggacgtga accagcacgt gaacaacgtg    960

aagtacatcg gctggatcct ggagtccacc ccccccgagg tgctggagac ccaggagctg   1020

tgctccctga ccctggagta ccgccgcgag tgcggccgcg agtccgtgct ggagtccctg   1080

accgccgtgg acccctccgg caagggctcc ggctcccagt tccagcacct gctgcgcctg   1140

gaggacggcg gcgagatcgt gaagggccgc accgagtggc gccccaagac cgccggcatc   1200

aacggcccca tcgcctccgg cgagacctcc cccggcgact cctcctga                1248


<210> SEQ ID NO 16
<211> LENGTH: 427
<212> TYPE: PRT
<213> ORGANISM: Cuphea hyssopifolia
<220> FEATURE:
<223> OTHER INFORMATION: Cuphea hyssopifolia (Chs) FATB2b +a.a.248-259
      variant amino acid sequence

<400> SEQUENCE: 16

Met Val Ala Thr Ala Ala Ser Ser Ala Phe Phe Pro Val Pro Ser Pro
1               5                   10                  15

Asp Ala Ser Ser Arg Pro Gly Lys Leu Gly Asn Gly Ser Ser Ser Leu
            20                  25                  30

Ser Pro Leu Lys Pro Lys Leu Met Ala Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Asp Gly Phe Gly Arg Thr Leu Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240
```

-continued

```
Glu Ile Leu Thr Arg Ala Ser Ser Lys Ser Gln Ile Met Leu Pro Leu
                245                 250                 255

His Tyr Cys Ser Val Trp Val Met Met Asn Gln Lys Thr Arg Arg Leu
            260                 265                 270

Ser Lys Ile Pro Asp Glu Val Arg His Glu Ile Glu Pro His Phe Val
        275                 280                 285

Asp Ser Ala Pro Val Ile Glu Asp Asp Asp Arg Lys Leu Pro Lys Leu
    290                 295                 300

Asp Glu Lys Thr Ala Asp Ser Ile Arg Lys Gly Leu Thr Pro Lys Trp
305                 310                 315                 320

Asn Asp Leu Asp Val Asn Gln His Val Asn Asn Val Lys Tyr Ile Gly
                325                 330                 335

Trp Ile Leu Glu Ser Thr Pro Pro Glu Val Leu Glu Thr Gln Glu Leu
            340                 345                 350

Cys Ser Leu Thr Leu Glu Tyr Arg Arg Glu Cys Gly Arg Glu Ser Val
        355                 360                 365

Leu Glu Ser Leu Thr Ala Val Asp Pro Ser Gly Lys Gly Ser Gly Ser
    370                 375                 380

Gln Phe Gln His Leu Leu Arg Leu Glu Asp Gly Gly Glu Ile Val Lys
385                 390                 395                 400

Gly Arg Thr Glu Trp Arg Pro Lys Thr Ala Gly Ile Asn Gly Pro Ile
                405                 410                 415

Ala Ser Gly Glu Thr Ser Pro Gly Asp Ser Ser
            420                 425
```

<210> SEQ ID NO 17
<211> LENGTH: 1284
<212> TYPE: DNA
<213> ORGANISM: Cuphea hyssopifolia
<220> FEATURE:
<223> OTHER INFORMATION: Cuphea hyssopifolia (Chs) FATB2b+a.a.248-259
variant coding DNA sequence

<400> SEQUENCE: 17

```
atggtggcta ccgctgcaag ttcagcattc ttccctgtgc cgtcccccga cgcctcctct     60

agacctggaa agctcggcaa tgggtcatcg agcttgagcc ccctcaagcc caaattgatg    120

gccaatggcg ggttgcaggt taaggcaaac gccagtgccc ctcctaagat caatggttct    180

tcggtcggtc taaagtccgg cagtctcaag actcaggaag acactccttc ggcgcctcct    240

ccccggactt ttattaacca gctgcctgat tggagtatgc ttcttgctgc aatcactact    300

gtcttcttgg cagcagagaa gcagtggatg atgcttgatt ggaaacccaa gaggcctgac    360

atgcttgtgg acccgttcgg attgggaagg attgttcaag atgggcttgt gttcaggcag    420

aatttttcga ttaggtccta tgaaataggc gctgatcgca ctgcgtctat agagacggtg    480

atgaaccact tgcaggaaac agctctcaat catgttaaga gtgctgggct tcttaatgac    540

ggctttggtc gtactcttga gatgtataaa agggacctta tttgggttgt tgcaaaaatg    600

caggtcatgg ttaaccgcta tcctacttgg ggcgacacgg ttgaagtgaa tacttgggtt    660

gccaagtcag ggaaaaatgg tatgcgtcgt gattggctca taagtgattg caatacagga    720

gaaattctta ctagagcatc aagtaaaagc caaattatgt taccctcaca ttattgcagt    780

gtgtgggtca tgatgaatca aaagacaaga agattgtcaa aaattccaga tgaggttcga    840

catgagatag agcctcattt cgtggactct gctcccgtca ttgaagatga tgaccggaaa    900

cttcccaagc tggatgagaa gactgctgac tccatccgca agggtctaac tccgaagtgg    960
```

```
aatgacttgg atgtcaatca gcacgtcaac aacgtgaagt acattgggtg gattcttgag   1020

agtactccac cagaagttct ggagacccag gagttatgtt cccttaccct ggaatatagg   1080

cgggaatgcg gaagggagag cgtgctggag tccctcactg ctgtggaccc ctctggaaag   1140

ggctctgggt ctcagttcca gcaccttctg cggcttgagg atggaggtga gattgtgaag   1200

gggagaactg agtggcgacc caagactgca ggaatcaatg ggccaatagc atccggggag   1260

acctcacctg gagactcttc ttag                                          1284


<210> SEQ ID NO 18
<211> LENGTH: 1284
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cuphea hyssopifolia (Chs) FATB2b +a.a.248-259
      variant coding DNA sequence codon optimized for Prototheca
      moriformis

<400> SEQUENCE: 18

atggtggcca ccgccgcctc ctccgccttc ttccccgtgc cctcccccga cgcctcctcc     60

cgccccggca agctgggcaa cggctcctcc tccctgtccc ccctgaagcc caagctgatg    120

gccaacggcg gcctgcaggt gaaggccaac gcctccgccc cccccaagat caacggctcc    180

tccgtgggcc tgaagtccgg ctccctgaag acccaggagg acacccccto cgcccccccc    240

ccccgcacct tcatcaacca gctgcccgac tggtccatgc tgctggccgc catcaccacc    300

gtgttcctgg ccgccgagaa gcagtggatg atgctggact ggaagcccaa gcgccccgac    360

atgctggtgg accccttcgg cctgggccgc atcgtgcagg acggcctggt gttccgccag    420

aacttctcca tccgctccta cgagatcggc gccgaccgca ccgcctccat cgagaccgtg    480

atgaaccacc tgcaggagac cgccctgaac cacgtgaagt ccgccggcct gctgaacgac    540

ggcttcggcc gcaccctgga gatgtacaag cgcgacctga tctgggtggt ggccaagatg    600

caggtgatgg tgaaccgcta ccccacctgg ggcgacaccg tggaggtgaa cacctgggtg    660

gccaagtccg gcaagaacgg catgcgccgc gactggctga tctccgactg caacaccggc    720

gagatcctga cccgcgcctc ctccaagtcc cagatcatgc tgcccctgca ctactgctcc    780

gtgtgggtga tgatgaacca gaagacccgc cgcctgtcca agatccccga cgaggtgcgc    840

cacgagatcg agccccactt cgtggactcc gcccccgtga tcgaggacga cgaccgcaag    900

ctgcccaagc tggacgagaa gaccgccgac tccatccgca agggcctgac ccccaagtgg    960

aacgacctgg acgtgaacca gcacgtgaac aacgtgaagt acatcggctg gatcctggag   1020

tccacccccc ccgaggtgct ggagacccag gagctgtgct ccctgaccct ggagtaccgc   1080

cgcgagtgcg gccgcgagtc cgtgctggag tccctgaccg ccgtggaccc ctccggcaag   1140

ggctccggct cccagttcca gcacctgctg cgcctggagg acggcggcga gatcgtgaag   1200

ggccgcaccg agtggcgccc caagaccgcc ggcatcaacg gccccatcgc ctccggcgag   1260

acctcccccg gcgactcctc ctga                                          1284


<210> SEQ ID NO 19
<211> LENGTH: 417
<212> TYPE: PRT
<213> ORGANISM: Cuphea hyssopifolia
<220> FEATURE:
<223> OTHER INFORMATION: Cuphea hyssopifolia (Chs) FATB3 amino acid
      sequence
```

<400> SEQUENCE: 19

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Thr Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Thr Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Pro Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Val Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Cys His
225                 230                 235                 240

Thr Gly Glu Ile Leu Ile Arg Ala Thr Ser Met Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Arg Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Ala Asp Ile Ala Lys Gly Arg Thr Lys Trp Arg Pro Lys Asn Ala Gly
385                 390                 395                 400

Thr Asn Gly Ala Ile Ser Thr Gly Lys Thr Ser Asn Gly Asn Ser Ile 405 410 415

Ser

<210> SEQ ID NO 20
<211> LENGTH: 1254
<212> TYPE: DNA
<213> ORGANISM: Cuphea hyssopifolia
<220> FEATURE:
<223> OTHER INFORMATION: Cuphea hyssopifolia (Chs) FATB3 coding DNA sequence

<400> SEQUENCE: 20

```
atggtggctg ccgaagcaag ttctgcactc ttctccgttc gaaccccggg aacctcccct     60
aaacccggga agttcgggaa ttggccaacg agcttgagcg tccccttcaa gtccaaatca    120
aaccacaatg gcggctttca ggttaaggca aacgccagtg cccgtcctaa ggctaacggt    180
tctgcagtaa gtctaaagtc tggcagcctc gacactcagg aggacacttc atcgtcgtcc    240
tctcctcctc ggactttcat taaccagttg cccgactgga gtatgctgct gtccgcgatc    300
acgaccgtct tcgtggcggc tgagaagcag tggacgatgc ttgatcggaa atctaagagg    360
cccgacatgc tcatggaccc gtttggggtt gacagggttg ttcaggatgg ggctgtgttc    420
agacagagtt tttcgattag gtcttacgaa ataggcgctg atcgaacagc ctctatagag    480
acgctgatga acatcttcca ggaaacatct ctcaatcatt gtaagagtat cggtcttctc    540
aatgacggct ttggtcgtac tcctgagatg tgtaagaggg acctcatttg ggtggttaca    600
aaaatgcacg tcgaggttaa tcgctatcct acttggggtg atactatcga ggtcaatact    660
tgggtctccg agtcggggaa aaccggtatg ggtcgtgatt ggctgataag tgattgtcat    720
acaggagaaa ttctaataag agcaacgagc atgtgtgcta tgatgaatca aaagacgaga    780
agattctcaa aatttccata tgaggttcga caggagttgg cgcctcattt tgtggactct    840
gctcctgtca ttgaagacta tcaaaaattg cacaagcttg atgtgaagac gggtgattcc    900
atttgcaatg gcctaactcc aaggtggaat gacttggatg tcaatcagca cgttaacaat    960
gtgaagtaca ttgggtggat tctcgagagt gttccaacgg aagttttcga gacccaggag   1020
ctatgtggcc tcacccttga gtataggcgg gaatgcggaa gggacagtgt gctggagtcc   1080
gtgaccgcta tggatccatc aaaagaggga gacagatctc tgtaccagca ccttcttcgg   1140
cttgaggatg gggctgatat cgcgaagggc agaaccaagt ggcggccgaa gaatgcagga   1200
accaatgggg caatatcaac aggaaagact tcaaatggaa actcgatctc ttag         1254
```

<210> SEQ ID NO 21
<211> LENGTH: 1254
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea hyssopifolia (Chs) FATB3 coding DNA sequence codon optimized for Prototheca moriformis

<400> SEQUENCE: 21

```
atggtggccg ccgaggcctc ctccgccctg ttctccgtgc gcacccccgg cacctccccc     60
aagcccggca agttcggcaa ctggcccacc tccctgtccg tgcccttcaa gtccaagtcc    120
aaccacaacg gcggcttcca ggtgaaggcc aacgcctccg cccgccccaa ggccaacggc    180
tccgccgtgt ccctgaagtc cggctccctg gacacccagg aggacacctc ctcctcctcc    240
```

-continued

```
tcccccccc gcaccttcat caaccagctg cccgactggt ccatgctgct gtccgccatc    300

accaccgtgt tcgtggccgc cgagaagcag tggaccatgc tggaccgcaa gtccaagcgc    360

cccgacatgc tgatggaccc cttcggcgtg gaccgcgtgg tgcaggacgg cgccgtgttc    420

cgccagtcct tctccatccg ctcctacgag atcggcgccg accgcaccgc ctccatcgag    480

accctgatga acatcttcca ggagacctcc ctgaaccact gcaagtccat cggcctgctg    540

aacgacggct tcggccgcac ccccgagatg tgcaagcgcg acctgatctg ggtggtgacc    600

aagatgcacg tggaggtgaa ccgctacccc acctggggcg acaccatcga ggtgaacacc    660

tgggtgtccg agtccggcaa gaccggcatg ggccgcgact ggctgatctc cgactgccac    720

accggcgaga tcctgatccg cgccacctcc atgtgcgcca tgatgaacca gaagacccgc    780

cgcttctcca agttccccta cgaggtgcgc caggagctgg cccccactt cgtggactcc    840

gcccccgtga tcgaggacta ccagaagctg cacaagctgg acgtgaagac cggcgactcc    900

atctgcaacg gcctgacccc ccgctggaac gacctggacg tgaaccagca cgtgaacaac    960

gtgaagtaca tcggctggat cctggagtcc gtgcccaccg aggtgttcga gacccaggag   1020

ctgtgcggcc tgaccctgga gtaccgccgc gagtgcggcc gcgactccgt gctggagtcc   1080

gtgaccgcca tggacccctc caaggagggc gaccgctccc tgtaccagca cctgctgcgc   1140

ctggaggacg gcgccgacat cgccaagggc cgcaccaagt ggcgccccaa gaacgccggc   1200

accaacggcg ccatctccac cggcaagacc tccaacggca actccatctc ctga         1254


<210> SEQ ID NO 22
<211> LENGTH: 417
<212> TYPE: PRT
<213> ORGANISM: Cuphea hyssopifolia
<220> FEATURE:
<223> OTHER INFORMATION: Cuphea hyssopifolia (Chs) FATB3b (V204I,C239F,
      E243D, M251V variant) amino acid sequence

<400> SEQUENCE: 22

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Thr Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Thr Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Pro Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
```

-continued

```
            180                 185                 190

Arg Asp Leu Ile Trp Val Val Thr Lys Met His Ile Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Phe His
225                 230                 235                 240

Thr Gly Asp Ile Leu Ile Arg Ala Thr Ser Val Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Arg Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Ala Asp Ile Ala Lys Gly Arg Thr Lys Trp Arg Pro Lys Asn Ala Gly
385                 390                 395                 400

Thr Asn Gly Ala Ile Ser Thr Gly Lys Thr Ser Asn Gly Asn Ser Ile
                405                 410                 415

Ser


<210> SEQ ID NO 23
<211> LENGTH: 1254
<212> TYPE: DNA
<213> ORGANISM: Cuphea hyssopifolia
<220> FEATURE:
<223> OTHER INFORMATION: Cuphea hyssopifolia (Chs) FATB3b (V204I,C239F,
      E243D, M251V variant) coding DNA sequence

<400> SEQUENCE: 23

atggtggctg ccgaagcaag ttctgcactc ttctccgttc gaaccccggg aacctcccct     60

aaacccggga agttcgggaa ttggccaacg agcttgagcg tccccttcaa gtccaaatca    120

aaccacaatg gcggctttca ggttaaggca aacgccagtg cccgtcctaa ggctaacggt    180

tctgcagtaa gtctaaagtc tggcagcctc gacactcagg aggacacttc atcgtcgtcc    240

tctcctcctc ggactttcat taaccagttg cccgactgga gtatgctgct gtccgcgatc    300

acgaccgtct tcgtggcggc tgagaagcag tggacgatgc ttgatcggaa atctaagagg    360

cccgacatgc tcatggaccc gtttggggtt gacagggttg ttcaggatgg ggctgtgttc    420

agacagagtt tttcgattag gtcttacgaa ataggcgctg atcgaacagc ctctatagag    480

acgctgatga acatcttcca ggaaacatct ctcaatcatt gtaagagtat cggtcttctc    540

aatgacggct ttggtcgtac tcctgagatg tgtaagaggg acctcatttg ggtggttaca    600

aaaatgcaca tcgaggttaa tcgctatcct acttggggtg atactatcga ggtcaatact    660
```

-continued

```
tgggtctccg agtcggggaa aaccggtatg ggtcgtgatt ggctgataag tgattttcat    720

acaggagaca ttctaataag agcaacgagc gtgtgtgcta tgatgaatca aaagacgaga    780

agattctcaa aatttccata tgaggttcga caggagttag cgcctcattt tgtggactct    840

gctccagtca ttgaagacta tcaaaaattg cacaagcttg atgtgaagac gggtgattcc    900

atttgcaatg gcctaactcc aaggtggaat gacttggatg tcaatcagca cgttaacaat    960

gtgaagtaca ttgggtggat tctcgagagt gttccaacgg aagttttcga gacccaggag   1020

ctatgtggcc tcacccttga gtataggcgg gaatgcggaa gggacagtgt gctggagtcc   1080

gtgaccgcta tggatccctc aaaagaggga gacagatctc tgtaccagca ccttcttcgg   1140

cttgaggatg gggctgatat cgcgaagggc agaaccaagt ggcggccgaa gaatgcagga   1200

accaatgggg caatatcaac aggaaagact tcaaatggaa actcgatctc ttag         1254
```

```
<210> SEQ ID NO 24
<211> LENGTH: 1254
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cuphea hyssopifolia (Chs) FATB3b (V204I,C239F,
      E243D, M251V variant) coding DNA sequence codon optimized
      for Prototheca moriformis

<400> SEQUENCE: 24

atggtggccg ccgaggcctc ctccgccctg ttctccgtgc gcacccccgg cacctccccc     60

aagcccggca agttcggcaa ctggcccacc tccctgtccg tgcccttcaa gtccaagtcc    120

aaccacaacg gcggcttcca ggtgaaggcc aacgcctccg cccgccccaa ggccaacggc    180

tccgccgtgt ccctgaagtc cggctccctg gacacccagg aggacacctc ctcctcctcc    240

tcccccccccc gcaccttcat caaccagctg cccgactggt ccatgctgct gtccgccatc    300

accaccgtgt tcgtggccgc cgagaagcag tggaccatgc tggaccgcaa gtccaagcgc    360

cccgacatgc tgatggaccc cttcggcgtg gaccgcgtgg tgcaggacgg cgccgtgttc    420

cgccagtcct tctccatccg ctcctacgag atcggcgccg accgcaccgc ctccatcgag    480

accctgatga acatcttcca ggagacctcc ctgaaccact gcaagtccat cggcctgctg    540

aacgacggct tcggccgcac ccccgagatg tgcaagcgcg acctgatctg ggtggtgacc    600

aagatgcaca tcgaggtgaa ccgctacccc acctggggcg acaccatcga ggtgaacacc    660

tgggtgtccg agtccggcaa gaccggcatg ggccgcgact ggctgatctc cgacttccac    720

accggcgaca tcctgatccg cgccacctcc gtgtgcgcca tgatgaacca gaagacccgc    780

cgcttctcca agttccccta cgaggtgcgc caggagctgg ccccccactt cgtggactcc    840

gcccccgtga tcgaggacta ccagaagctg cacaagctgg acgtgaagac cggcgactcc    900

atctgcaacg gcctgacccc ccgctggaac gacctggacg tgaaccagca cgtgaacaac    960

gtgaagtaca tcggctggat cctggagtcc gtgcccaccg aggtgttcga gacccaggag   1020

ctgtgcggcc tgaccctgga gtaccgccgc gagtgcggcc gcgactccgt gctggagtcc   1080

gtgaccgcca tggacccctc caaggagggc gaccgctccc tgtaccagca cctgctgcgc   1140

ctggaggacg gcgccgacat cgccaagggc cgcaccaagt ggcgccccaa gaacgccggc   1200

accaacggcg ccatctccac cggcaagacc tccaacggca actccatctc ctga         1254

<210> SEQ ID NO 25
```

<211> LENGTH: 419
<212> TYPE: PRT
<213> ORGANISM: Cuphea sp.
<220> FEATURE:
<223> OTHER INFORMATION: Cuphea PSR23 (Cu) FATB3 amino acid sequence

<400> SEQUENCE: 25

```
Met Val Val Ala Ala Ala Thr Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Thr Phe Lys Pro Lys Ser Ile Pro Asn Ala Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Cys Ile Val Arg Asp Gly Leu Val Ser Arg Gln Ser Phe Leu
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Ile Asn Thr Trp Phe Ser Gln Ser
    210                 215                 220

Gly Lys Ile Gly Met Ala Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Gln
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Val Asp Pro Ser Glu
        355                 360                 365

Asn Gly Gly Arg Ser Gln Tyr Lys His Leu Leu Arg Leu Glu Asp Gly
    370                 375                 380
```

Thr Asp Ile Val Lys Ser Arg Thr Glu Trp Arg Pro Lys Asn Ala Gly
385 390 395 400

Thr Asn Gly Ala Ile Ser Thr Ser Thr Ala Lys Thr Ser Asn Gly Asn
405 410 415

Ser Val Ser

<210> SEQ ID NO 26
<211> LENGTH: 1260
<212> TYPE: DNA
<213> ORGANISM: Cuphea sp.
<220> FEATURE:
<223> OTHER INFORMATION: Cuphea PSR23 (Cu) FATB3 coding DNA sequence

<400> SEQUENCE: 26
atggtggtgg ctgcagcaac ttctgcattc ttccccgttc cagccccggg aacctcccct 60
aaacccggga agtccggcaa ctggccatcg agcttgagcc ctaccttcaa gcccaagtca 120
atccccaatg ccggatttca ggttaaggca aatgccagtg cccatcctaa ggctaacggt 180
tctgcagtaa atctaaagtc tggcagcctc aacactcagg aggacacttc gtcgtcccct 240
cctccccggg ctttccttaa ccagttgcct gattggagta tgcttctgac tgcaatcacg 300
accgtcttcg tggcggcaga gaagcagtgg actatgcttg ataggaaatc taagaggcct 360
gacatgctcg tggactcggt tgggttgaag tgtattgttc gggatgggct cgtgtccaga 420
cagagttttt tgattagatc ttatgaaata ggcgctgatc gaacagcctc tatagagacg 480
ctgatgaacc acttgcagga aacatctatc aatcattgta agagtttggg tcttctcaat 540
gacggctttg gtcgtactcc tgggatgtgt aaaaacgacc tcatttgggt gcttacaaaa 600
atgcagatca tggtgaatcg ctacccaact tggggcgata ctgttgagat caatacctgg 660
ttctctcagt cggggaaaat cggtatggct agcgattggc taataagtga ttgcaacaca 720
ggagaaattc ttataagagc aacgagcgtg tgggctatga tgaatcaaaa gacgagaaga 780
ttctcaagac ttccatacga ggttcgccag gagttaacgc ctcattttgt ggactctcct 840
catgtcattg aagacaatga tcagaaattg cataagtttg atgtgaagac tggtgattcc 900
attcgcaagg gtctaactcc gaggtggaac gacttggatg tgaatcagca cgtaagcaac 960
gtgaagtaca ttgggtggat tctcgagagt atgccaatag aagttttgga gacacaggag 1020
ctatgctctc tcaccgtaga atataggcgg gaatgcggaa tggacagtgt gctggagtcc 1080
gtgactgctg tggatccctc agaaaatgga ggccggtctc agtacaagca ccttctgcgg 1140
cttgaggatg ggactgatat cgtgaagagc agaactgagt ggcgaccgaa gaatgcagga 1200
actaacgggg cgatatcaac atcaacagca aagacttcaa atggaaactc ggtctcttag 1260

<210> SEQ ID NO 27
<211> LENGTH: 1260
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea PSR23 (Cu) FATB3 coding DNA sequence codon optimized for Prototheca moriformis

<400> SEQUENCE: 27
atggtggtgg ccgccgccac ctccgccttc ttccccgtgc ccgcccccgg cacctccccc 60
aagcccggca agtccggcaa ctggccctcc tccctgtccc ccaccttcaa gcccaagtcc 120

```
atccccaacg ccggcttcca ggtgaaggcc aacgcctccg cccaccccaa ggccaacggc    180

tccgccgtga acctgaagtc cggctccctg aacacccagg aggacacctc ctcctccccc    240

cccccccgcg ccttcctgaa ccagctgccc gactggtcca tgctgctgac cgccatcacc    300

accgtgttcg tggccgccga gaagcagtgg accatgctgg accgcaagtc caagcgcccc    360

gacatgctgg tggactccgt gggcctgaag tgcatcgtgc gcgacggcct ggtgtcccgc    420

cagtccttcc tgatccgctc ctacgagatc ggcgccgacc gcaccgcctc catcgagacc    480

ctgatgaacc acctgcagga gacctccatc aaccactgca agtccctggg cctgctgaac    540

gacggcttcg gccgcacccc cggcatgtgc aagaacgacc tgatctgggt gctgaccaag    600

atgcagatca tggtgaaccg ctaccccacc tggggcgaca ccgtggagat caacacctgg    660

ttctcccagt ccggcaagat cggcatggcc tccgactggc tgatctccga ctgcaacacc    720

ggcgagatcc tgatccgcgc cacctccgtg tgggccatga tgaaccagaa gacccgccgc    780

ttctcccgcc tgccctacga ggtgcgccag gagctgaccc cccacttcgt ggactccccc    840

cacgtgatcg aggacaacga ccagaagctg cacaagttcg acgtgaagac cggcgactcc    900

atccgcaagg gcctgacccc ccgctggaac gacctggacg tgaaccagca cgtgtccaac    960

gtgaagtaca tcggctggat cctggagtcc atgcccatcg aggtgctgga gacccaggag   1020

ctgtgctccc tgaccgtgga gtaccgccgc gagtgcggca tggactccgt gctggagtcc   1080

gtgaccgccg tggacccctc cgagaacggc ggccgctccc agtacaagca cctgctgcgc   1140

ctggaggacg gcaccgacat cgtgaagtcc cgcaccgagt ggcgccccaa gaacgccggc   1200

accaacggcg ccatctccac ctccaccgcc aagacctcca acggcaactc cgtgtcctga   1260


<210> SEQ ID NO 28
<211> LENGTH: 408
<212> TYPE: PRT
<213> ORGANISM: Cuphea wrightii
<220> FEATURE:
<223> OTHER INFORMATION: Cuphea wrightii (Cw) FATB3 amino acid sequence

<400> SEQUENCE: 28

Met Val Val Ala Ala Ala Ala Ser Ser Ala Phe Phe Pro Val Pro Ala
1               5                   10                  15

Pro Arg Thr Thr Pro Lys Pro Gly Lys Phe Gly Asn Trp Pro Ser Ser
            20                  25                  30

Leu Ser Pro Pro Phe Lys Pro Lys Ser Asn Pro Asn Gly Arg Phe Gln
        35                  40                  45

Val Lys Ala Asn Val Ser Pro His Pro Lys Ala Asn Gly Ser Ala Val
    50                  55                  60

Ser Leu Lys Ser Gly Ser Leu Asn Thr Leu Glu Asp Pro Pro Ser Ser
65                  70                  75                  80

Pro Pro Pro Arg Thr Phe Leu Asn Gln Leu Pro Asp Trp Ser Arg Leu
                85                  90                  95

Arg Thr Ala Ile Thr Thr Val Phe Val Ala Ala Glu Lys Gln Phe Thr
            100                 105                 110

Arg Leu Asp Arg Lys Ser Lys Arg Pro Asp Met Leu Val Asp Trp Phe
        115                 120                 125

Gly Ser Glu Thr Ile Val Gln Asp Gly Leu Val Phe Arg Glu Arg Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
```

-continued

```
                165                 170                 175

Val Gly Leu Leu Asn Asp Gly Phe Gly Arg Thr Ser Glu Met Cys Thr
            180                 185                 190

Arg Asp Leu Ile Trp Val Leu Thr Lys Met Gln Ile Val Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asp Trp Leu Ile Ser Asp Cys Asn
225                 230                 235                 240

Thr Gly Glu Ile Leu Val Arg Ala Thr Ser Ala Trp Ala Met Met Asn
                245                 250                 255

Gln Lys Thr Arg Arg Phe Ser Lys Leu Pro Cys Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Gly Trp Asn Asp Leu Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Glu Ser Val Val Glu Ser Val Thr Ser Met Asn Pro Ser
        355                 360                 365

Lys Val Gly Asp Arg Ser Gln Tyr Gln His Leu Leu Arg Leu Glu Asp
    370                 375                 380

Gly Ala Asp Ile Met Lys Gly Arg Thr Glu Trp Arg Pro Lys Asn Ala
385                 390                 395                 400

Gly Thr Asn Arg Ala Ile Ser Thr
                405
```

<210> SEQ ID NO 29
<211> LENGTH: 1227
<212> TYPE: DNA
<213> ORGANISM: Cuphea wrightii
<220> FEATURE:
<223> OTHER INFORMATION: Cuphea wrightii (Cw) FATB3 coding DNA sequence

<400> SEQUENCE: 29

```
atggtggtgg ctgctgcagc aagttctgca ttcttccctg ttccagcacc tagaaccacg     60

cctaaacccg ggaagttcgg caattggcca tcgagcttga gcccgccctt caagcccaag    120

tcaaacccca atggtagatt tcaggttaag gcaaatgtca gtcctcatcc taaggctaac    180

ggttctgcag taagtctaaa gtctggcagc ctcaacactc tggaggaccc tccgtcgtcc    240

cctcctcctc ggactttcct taaccagttg cctgattgga gtaggcttcg gactgcaatc    300

acgaccgtct tcgtggcggc agagaagcag ttcactaggc tcgatcgaaa atctaagagg    360

cctgacatgc tagtggactg gtttgggtca gagactattg ttcaggatgg gctcgtgttc    420

agagagagat tttcgatcag gtcttacgaa ataggcgctg atcgaacagc ctctatagag    480

acgctgatga accacttgca ggacacatct ctgaatcatt gtaagagtgt gggtcttctc    540

aatgacggct ttggtcgtac ctcggagatg tgtacaagag acctcatttg ggtgcttaca    600

aaaatgcaga tcgtggtgaa tcgctatcca acttggggcg atactgtcga gatcaatagc    660
```

-continued

```
tggttctccc agtcggggaa aatcggtatg ggtcgcgatt ggctaataag tgattgcaac    720

acaggagaaa ttcttgtaag agcaacgagc gcttgggcca tgatgaatca aaagacgaga    780

agattctcaa aacttccatg cgaggttcgc caggagatag cgcctcattt tgtggacgct    840

cctcctgtca ttgaagacaa tgatcggaaa ttgcataagt ttgatgtgaa gactggtgat    900

tccatttgca agggtctaac tccggggtgg aatgacttgg atgtcaatca gcacgtaagc    960

aacgtgaagt acattgggtg gattctcgag agtatgccta cagaagtttt ggagacccag   1020

gagctatgct ctctcaccct tgaatatagg cgggaatgtg gaagggaaag tgtggtagag   1080

tccgtgacct ctatgaatcc ctcaaaagtt ggagaccggt ctcagtacca acaccttctg   1140

cggcttgagg atggggctga tatcatgaag ggcagaactg agtggagacc aaagaatgca   1200

ggaaccaacc gggcgatatc aacatga                                       1227
```

<210> SEQ ID NO 30
<211> LENGTH: 1227
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea wrightii (Cw) FATB3 coding DNA sequence codon optimized for Prototheca moriformis

<400> SEQUENCE: 30

```
atggtggtgg ccgccgccgc ctcctccgcc ttcttccccg tgcccgcccc ccgcaccacc     60

cccaagcccg gcaagttcgg caactggccc tcctccctgt cccccccctt caagcccaag    120

tccaacccca acggccgctt ccaggtgaag gccaacgtgt ccccccaccc caaggccaac    180

ggctccgccg tgtccctgaa gtccggctcc ctgaacaccc tggaggaccc cccctcctcc    240

cccccccccc gcaccttcct gaaccagctg cccgactggt cccgcctgcg caccgccatc    300

accaccgtgt tcgtggccgc cgagaagcag ttcacccgcc tggaccgcaa gtccaagcgc    360

cccgacatgc tggtggactg gttcggctcc gagaccatcg tgcaggacgg cctggtgttc    420

cgcgagcgct tctccatccg ctcctacgag atcggcgccg accgcaccgc ctccatcgag    480

accctgatga accacctgca ggacacctcc ctgaaccact gcaagtccgt gggcctgctg    540

aacgacggct tcggccgcac ctccgagatg tgcacccgcg acctgatctg ggtgctgacc    600

aagatgcaga tcgtggtgaa ccgctacccc acctggggcg acaccgtgga gatcaactcc    660

tggttctccc agtccggcaa gatcggcatg ggccgcgact ggctgatctc cgactgcaac    720

accggcgaga tcctggtgcg cgccacctcc gcctgggcca tgatgaacca gaagacccgc    780

cgcttctcca agctgccctg cgaggtgcgc caggagatcg ccccccactt cgtggacgcc    840

ccccccgtga tcgaggacaa cgaccgcaag ctgcacaagt tcgacgtgaa gaccggcgac    900

tccatctgca agggcctgac ccccggctgg aacgacctgg acgtgaacca gcacgtgtcc    960

aacgtgaagt acatcggctg gatcctggag tccatgccca ccgaggtgct ggagacccag   1020

gagctgtgct ccctgaccct ggagtaccgc cgcgagtgcg gccgcgagtc cgtggtggag   1080

tccgtgacct ccatgaaccc ctccaaggtg ggcgaccgct cccagtacca gcacctgctg   1140

cgcctggagg acggcgccga catcatgaag ggccgcaccg agtggcgccc caagaacgcc   1200

ggcaccaacc gcgccatctc cacctga                                       1227
```

<210> SEQ ID NO 31
<211> LENGTH: 416

-continued

```
<212> TYPE: PRT
<213> ORGANISM: Cuphea wrightii
<220> FEATURE:
<223> OTHER INFORMATION: Cuphea wrightii (Cw) FATB4a amino acid sequence

<400> SEQUENCE: 31

Met Val Ala Thr Ala Ala Ser Ser Ala Phe Phe Pro Val Pro Ser Ala
1               5                   10                  15

Asp Thr Ser Ser Ser Arg Pro Gly Lys Leu Gly Ser Gly Pro Ser Ser
            20                  25                  30

Leu Ser Pro Leu Lys Pro Lys Ser Ile Pro Asn Gly Gly Leu Gln Val
        35                  40                  45

Lys Ala Asn Ala Ser Ala Pro Pro Lys Ile Asn Gly Ser Ser Val Gly
    50                  55                  60

Leu Lys Ser Gly Gly Phe Lys Thr Gln Glu Asp Ser Pro Ser Ala Pro
65                  70                  75                  80

Pro Pro Arg Thr Phe Ile Asn Gln Leu Pro Asp Trp Ser Met Leu Leu
                85                  90                  95

Ala Ala Ile Thr Thr Val Phe Leu Ala Ala Glu Lys Gln Trp Met Met
            100                 105                 110

Leu Asp Trp Lys Pro Lys Arg Pro Asp Met Leu Val Asp Pro Phe Gly
        115                 120                 125

Leu Gly Ser Ile Val Gln Asp Gly Leu Val Phe Arg Gln Asn Phe Ser
    130                 135                 140

Ile Arg Ser Tyr Glu Ile Gly Ala Asp Arg Thr Ala Ser Ile Glu Thr
145                 150                 155                 160

Val Met Asn His Leu Gln Glu Thr Ala Leu Asn His Val Lys Ile Ala
                165                 170                 175

Gly Leu Ser Asn Asp Gly Phe Gly Arg Thr Pro Glu Met Tyr Lys Arg
            180                 185                 190

Asp Leu Ile Trp Val Val Ala Lys Met Gln Val Met Val Asn Arg Tyr
        195                 200                 205

Pro Thr Trp Gly Asp Thr Val Glu Val Asn Thr Trp Val Ala Lys Ser
    210                 215                 220

Gly Lys Asn Gly Met Arg Arg Asp Trp Leu Ile Ser Asp Cys Asn Thr
225                 230                 235                 240

Gly Glu Ile Leu Thr Arg Ala Ser Ser Val Trp Val Met Met Asn Gln
                245                 250                 255

Lys Thr Arg Arg Leu Ser Lys Ile Pro Asp Glu Val Arg Asn Glu Ile
            260                 265                 270

Glu Pro His Phe Val Asp Ser Ala Pro Val Val Glu Asp Asp Asp Arg
        275                 280                 285

Lys Leu Pro Lys Leu Asp Glu Asn Thr Ala Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Pro Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Ala
        355                 360                 365

Glu Gly Tyr Ala Ser Arg Phe Gln His Leu Leu Arg Leu Glu Asp Gly
    370                 375                 380
```

-continued

```
Gly Glu Ile Val Lys Ala Arg Thr Glu Trp Arg Pro Lys Asn Ala Gly
385                 390                 395                 400

Ile Asn Gly Val Val Pro Ser Glu Glu Ser Ser Pro Gly Asp Phe Phe
                405                 410                 415


<210> SEQ ID NO 32
<211> LENGTH: 1251
<212> TYPE: DNA
<213> ORGANISM: Cuphea wrightii
<220> FEATURE:
<223> OTHER INFORMATION: Cuphea wrightii (Cw) FATB4a coding DNA sequence

<400> SEQUENCE: 32

ttggtggcta ccgctgcaag ttctgcattt ttccccgtgc catccgccga cacctcctcc     60

tcgagacccg gaaagctcgg cagtggacca tcgagcttga gccccctcaa gcccaaatcg    120

atccccaatg gcggcttgca ggttaaggca aacgccagtg cccctcctaa gatcaatggt    180

tcctcggtcg gtctaaagtc gggcggtttc aagactcagg aagactctcc ttcggcccct    240

cctccgcgga cttttatcaa ccagttgcct gattggagta tgcttcttgc tgcaatcact    300

actgtcttct tggctgcaga gaagcagtgg atgatgcttg attggaaacc taagaggcct    360

gacatgctcg tggacccgtt cggattggga agtattgttc aggatgggct tgtgttcagg    420

cagaattttt caattaggtc ctacgaaata ggcgccgatc gaactgcgtc tatagagacg    480

gtgatgaacc atttgcagga aacagctctc aatcatgtca agattgctgg gctttctaat    540

gacggctttg gtcgtactcc tgagatgtat aaaagagacc ttatttgggt tgttgcaaaa    600

atgcaggtca tggttaaccg ctatcctact tggggtgaca cggttgaagt gaatacttgg    660

gttgccaagt cagggaaaaa tggtatgcgt cgtgactggc tcataagtga ttgcaatact    720

ggagagattc ttacaagagc atcaagcgtg tgggtcatga tgaatcaaaa gacaagaaga    780

ttgtcaaaaa ttccagatga ggttcgaaat gagatagagc ctcattttgt ggactctgct    840

cccgtcgttg aagatgatga tcggaaactt cccaagctgg atgagaacac tgctgactcc    900

atccgcaagg gtctaactcc gaggtggaat gacttggatg tcaatcagca cgtcaacaac    960

gtgaagtaca tcggatggat tcttgagagt actccaccag aagttctgga gacccaggag   1020

ttatgctccc tgaccctgga atacaggcgg gaatgtggaa gggagagcgt gctggagtcc   1080

ctcactgctg tcgacccgtc tgcagagggc tatgcgtccc ggtttcagca ccttctgcgg   1140

cttgaggatg gaggtgagat cgtgaaggcg agaactgagt ggcgacccaa gaatgctgga   1200

atcaatgggg tggtaccatc cgaggagtcc tcacctggag acttctttta g            1251


<210> SEQ ID NO 33
<211> LENGTH: 1251
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cuphea wrightii (Cw) FATB4a coding DNA sequence
      codon optimized for Prototheca moriformis

<400> SEQUENCE: 33

atggtggcca ccgccgcctc ctccgccttc ttccccgtgc cctccgccga cacctcctcc     60

tcccgccccg gcaagctggg ctccggcccc tcctccctgt ccccccctgaa gcccaagtcc    120

atccccaacg gcggcctgca ggtgaaggcc aacgcctccg cccccccccaa gatcaacggc    180

tcctccgtgg gcctgaagtc cggcggcttc aagacccagg aggactcccc ctccgccccc    240
```

```
ccccccgca ccttcatcaa ccagctgccc gactggtcca tgctgctggc cgccatcacc    300

accgtgttcc tggccgccga gaagcagtgg atgatgctgg actggaagcc caagcgcccc    360

gacatgctgg tggacccctt cggcctgggc tccatcgtgc aggacggcct ggtgttccgc    420

cagaacttct ccatccgctc ctacgagatc ggcgccgacc gcaccgcctc catcgagacc    480

gtgatgaacc acctgcagga gaccgccctg aaccacgtga agatcgccgg cctgtccaac    540

gacggcttcg gccgcacccc cgagatgtac aagcgcgacc tgatctgggt ggtggccaag    600

atgcaggtga tggtgaaccg ctaccccacc tggggcgaca ccgtggaggt gaacacctgg    660

gtggccaagt ccggcaagaa cggcatgcgc cgcgactggc tgatctccga ctgcaacacc    720

ggcgagatcc tgacccgcgc ctcctccgtg tgggtgatga tgaaccagaa gacccgccgc    780

ctgtccaaga tccccgacga ggtgcgcaac gagatcgagc cccacttcgt ggactccgcc    840

cccgtggtgg aggacgacga ccgcaagctg cccaagctgg acgagaacac cgccgactcc    900

atccgcaagg gcctgacccc ccgctggaac gacctggacg tgaaccagca cgtgaacaac    960

gtgaagtaca tcggctggat cctggagtcc accccccccg aggtgctgga gacccaggag   1020

ctgtgctccc tgaccctgga gtaccgccgc gagtgcggcc gcgagtccgt gctggagtcc   1080

ctgaccgccg tggacccctc cgccgagggc tacgcctccc gcttccagca cctgctgcgc   1140

ctggaggacg gcggcgagat cgtgaaggcc cgcaccgagt ggcgccccaa gaacgccggc   1200

atcaacggcg tggtgccctc cgaggagtcc tcccccggcg acttcttctg a            1251
```

```
<210> SEQ ID NO 34
<211> LENGTH: 417
<212> TYPE: PRT
<213> ORGANISM: Cuphea wrightii
<220> FEATURE:
<223> OTHER INFORMATION: Cuphea wrightii (Cw) FATB4b amino acid sequence

<400> SEQUENCE: 34

Met Val Ala Thr Ala Ala Ser Ser Ala Phe Phe Pro Val Pro Ser Ala
1               5                   10                  15

Asp Thr Ser Ser Ser Arg Pro Gly Lys Leu Gly Asn Gly Pro Ser Ser
            20                  25                  30

Leu Ser Pro Leu Lys Pro Lys Ser Ile Pro Asn Gly Gly Leu Gln Val
        35                  40                  45

Lys Ala Asn Ala Ser Ala Pro Pro Lys Ile Asn Gly Ser Ser Val Gly
    50                  55                  60

Leu Lys Ser Gly Ser Phe Lys Thr Gln Glu Asp Ala Pro Ser Ala Pro
65                  70                  75                  80

Pro Pro Arg Thr Phe Ile Asn Gln Leu Pro Asp Trp Ser Met Leu Leu
                85                  90                  95

Ala Ala Ile Thr Thr Val Phe Leu Ala Ala Glu Lys Gln Trp Met Met
            100                 105                 110

Leu Asp Trp Lys Pro Lys Arg Pro Asp Met Leu Val Asp Pro Phe Gly
        115                 120                 125

Leu Gly Ser Ile Val Gln Asp Gly Leu Val Phe Arg Gln Asn Phe Ser
    130                 135                 140

Ile Arg Ser Tyr Glu Ile Gly Ala Asp Arg Thr Ala Ser Ile Glu Thr
145                 150                 155                 160

Val Met Asn His Leu Gln Glu Thr Ala Leu Asn His Val Lys Ile Ala
                165                 170                 175

Gly Leu Ser Ser Asp Gly Phe Gly Arg Thr Pro Ala Met Ser Lys Arg
```

```
            180                 185                 190

Asp Leu Ile Trp Val Val Ala Lys Met Gln Val Met Val Asn Arg Tyr
        195                 200                 205

Pro Ala Trp Gly Asp Thr Val Glu Val Asn Thr Trp Val Ala Lys Ser
    210                 215                 220

Gly Lys Asn Gly Met Arg Arg Asp Trp Leu Ile Ser Asp Cys Asn Thr
225                 230                 235                 240

Gly Glu Ile Leu Thr Arg Ala Ser Ser Val Trp Val Met Met Asn Gln
                245                 250                 255

Lys Thr Arg Arg Leu Ser Lys Ile Pro Asp Glu Val Arg Asn Glu Ile
            260                 265                 270

Glu Pro His Phe Val Asp Ser Ala Pro Val Val Glu Asp Asp Asp Arg
        275                 280                 285

Lys Leu Pro Lys Leu Asp Glu Asn Thr Ala Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Ala Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Gly
        355                 360                 365

Glu Gly Asp Gly Ser Lys Phe Gln His Leu Leu Arg Leu Glu Asp Gly
    370                 375                 380

Gly Glu Ile Val Lys Ala Arg Thr Glu Trp Arg Pro Lys Asn Ala Gly
385                 390                 395                 400

Ile Asn Gly Val Val Pro Ser Glu Glu Ser Ser Pro Gly Gly Asp Phe
                405                 410                 415

Phe


<210> SEQ ID NO 35
<211> LENGTH: 1254
<212> TYPE: DNA
<213> ORGANISM: Cuphea wrightii
<220> FEATURE:
<223> OTHER INFORMATION: Cuphea wrightii (Cw) FATB4b coding DNA sequence

<400> SEQUENCE: 35

ttggtggcta ccgctgcaag ttctgcattt ttccccgtac catccgccga cacctcctca     60

tcgagacccg gaaagctcgg caatgggcca tcgagcttga gccccctcaa gccgaaatcg    120

atccccaatg gcgggttgca ggttaaggca aacgccagtg cccctcctaa gatcaatggt    180

tcctcggtcg gtctgaagtc gggcagtttc aagactcagg aagacgctcc ttcggcccct    240

cctcctcgga cttttatcaa ccagttgcct gattggagta tgcttcttgc tgcaatcact    300

actgtcttct tggctgcaga gaagcagtgg atgatgcttg attggaaacc taagaggcct    360

gacatgcttg tcgacccgtt cggattggga agtattgttc aggatgggct tgttttcagg    420

cagaatttct cgattaggtc ctacgaaata ggcgctgatc gcactgcgtc tatagagacg    480

gtgatgaacc atttgcagga aacagctctc aatcatgtta agattgctgg gctttctagt    540

gatggctttg gtcgtactcc tgcgatgtct aaacgggacc tcatttgggt tgttgcgaaa    600

atgcaggtca tggttaaccg ctaccctgct tggggtgaca cggttgaagt gaatacttgg    660

gttgccaagt cagggaaaaa tggtatgcgt cgtgactggc tcataagtga ttgcaacact    720
```

ggagagattc ttacaagagc atcaagcgtg tgggtcatga tgaatcaaaa gacaagaaga 780
ttgtcaaaaa ttccagatga ggttcgaaat gagatagagc ctcattttgt ggactctgcg 840
cccgtcgttg aagacgatga ccggaaactt cccaagctgg atgagaacac tgctgactcc 900
atccgcaagg gtctaactcc gaggtggaat gacttggatg tcaatcagca cgtcaacaac 960
gtgaagtaca ttgggtggat tcttgagagt actccagcag aagttctgga gacccaggaa 1020
ttatgttccc tgaccctgga atacaggcgg gaatgtggaa gggagagcgt gctggagtcc 1080
ctcactgctg tagatccgtc tggagagggc gatgggtcca agttccagca ccttctgcgg 1140
cttgaggatg gaggtgagat cgtgaaggcg agaactgagt ggcgaccaaa gaatgctgga 1200
atcaatgggg tggtaccatc cgaggagtcc tcacctggtg gagacttctt ttaa 1254

<210> SEQ ID NO 36
<211> LENGTH: 1254
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cuphea wrightii (Cw) FATB4b coding DNA sequence
      codon optimized for Prototheca moriformis

<400> SEQUENCE: 36
atggtggcca ccgccgcctc ctccgccttc ttccccgtgc cctccgccga cacctcctcc 60
tcccgccccg gcaagctggg caacggcccc tcctccctgt ccccccctgaa gcccaagtcc 120 atccccaacg gcggcctgca ggtgaaggcc aacgcctccg cccccccccaa gatcaacggc 180 tcctccgtgg gcctgaagtc cggctccttc aagacccagg aggacgcccc ctccgccccc 240 ccccccgca ccttcatcaa ccagctgccc gactggtcca tgctgctggc cgccatcacc 300
accgtgttcc tggccgccga gaagcagtgg atgatgctgg actggaagcc caagcgcccc 360
gacatgctgg tggacccctt cggcctgggc tccatcgtgc aggacggcct ggtgttccgc 420
cagaacttct ccatccgctc ctacgagatc ggcgccgacc gcaccgcctc catcgagacc 480
gtgatgaacc acctgcagga gaccgccctg aaccacgtga agatcgccgg cctgtcctcc 540
gacggcttcg gccgcacccc cgccatgtcc aagcgcgacc tgatctgggt ggtggccaag 600
atgcaggtga tggtgaaccg ctaccccgcc tggggcgaca ccgtggaggt gaacacctgg 660
gtggccaagt ccggcaagaa cggcatgcgc cgcgactggc tgatctccga ctgcaacacc 720
ggcgagatcc tgacccgcgc ctcctccgtg tgggtgatga tgaaccagaa gacccgccgc 780
ctgtccaaga tccccgacga ggtgcgcaac gagatcgagc cccacttcgt ggactccgcc 840
cccgtggtgg aggacgacga ccgcaagctg cccaagctgg acgagaacac cgccgactcc 900
atccgcaagg gcctgacccc ccgctggaac gacctggacg tgaaccagca cgtgaacaac 960
gtgaagtaca tcggctggat cctggagtcc acccccgccg aggtgctgga gacccaggag 1020
ctgtgctccc tgaccctgga gtaccgccgc gagtgcggcc gcgagtccgt gctggagtcc 1080
ctgaccgccg tggacccctc cggcgagggc gacggctcca agttccagca cctgctgcgc 1140
ctggaggacg gcggcgagat cgtgaaggcc cgcaccgagt ggcgccccaa gaacgccggc 1200
atcaacggcg tggtgccctc cgaggagtcc tcccccggcg gcgacttctt ctga 1254

<210> SEQ ID NO 37
<211> LENGTH: 413
<212> TYPE: PRT

```
<213> ORGANISM: Cuphea wrightii
<220> FEATURE:
<223> OTHER INFORMATION: Cuphea wrightii (Cw) FATB5 amino acid sequence

<400> SEQUENCE: 37

Met Val Ala Ala Ala Ala Ser Ser Ala Phe Phe Ser Val Pro Thr Pro
1               5                   10                  15

Gly Thr Pro Pro Lys Pro Gly Lys Phe Gly Asn Trp Pro Ser Ser Leu
            20                  25                  30

Ser Val Pro Phe Lys Pro Asp Asn Gly Gly Phe His Val Lys Ala Asn
        35                  40                  45

Ala Ser Ala His Pro Lys Ala Asn Gly Ser Ala Val Asn Leu Lys Ser
    50                  55                  60

Gly Ser Leu Glu Thr Pro Pro Arg Ser Phe Ile Asn Gln Leu Pro Asp
65                  70                  75                  80

Leu Ser Val Leu Leu Ser Lys Ile Thr Thr Val Phe Gly Ala Ala Glu
                85                  90                  95

Lys Gln Trp Lys Arg Pro Gly Met Leu Val Glu Pro Phe Gly Val Asp
            100                 105                 110

Arg Ile Phe Gln Asp Gly Val Phe Phe Arg Gln Ser Phe Ser Ile Arg
        115                 120                 125

Ser Tyr Glu Ile Gly Val Asp Arg Thr Ala Ser Ile Glu Thr Leu Met
    130                 135                 140

Asn Ile Phe Gln Glu Thr Ser Leu Asn His Cys Lys Ser Ile Gly Leu
145                 150                 155                 160

Leu Asn Asp Gly Phe Gly Arg Thr Pro Glu Met Cys Lys Arg Asp Leu
                165                 170                 175

Ile Trp Val Val Thr Lys Ile Gln Val Glu Val Asn Arg Tyr Pro Thr
            180                 185                 190

Trp Gly Asp Thr Ile Glu Val Asn Thr Trp Val Ser Glu Ser Gly Lys
        195                 200                 205

Asn Gly Met Gly Arg Asp Trp Leu Ile Ser Asp Cys Arg Thr Gly Glu
    210                 215                 220

Ile Leu Ile Arg Ala Thr Ser Val Trp Ala Met Met Asn Gln Asn Thr
225                 230                 235                 240

Arg Arg Leu Ser Lys Phe Pro Tyr Glu Val Arg Gln Glu Ile Ala Pro
                245                 250                 255

His Phe Val Asp Ser Ala Pro Val Ile Glu Asp Asp Gln Lys Leu Gln
            260                 265                 270

Lys Leu Asp Val Lys Thr Gly Asp Ser Ile Arg Asp Gly Leu Thr Pro
        275                 280                 285

Arg Trp Asn Asp Leu Asp Val Asn Gln His Val Asn Asn Val Lys Tyr
    290                 295                 300

Ile Gly Trp Ile Leu Lys Ser Val Pro Ile Glu Val Phe Glu Thr Gln
305                 310                 315                 320

Glu Leu Cys Gly Val Thr Leu Glu Tyr Arg Arg Glu Cys Gly Arg Asp
                325                 330                 335

Ser Val Leu Glu Ser Val Thr Ala Met Asp Pro Ala Lys Glu Gly Asp
            340                 345                 350

Arg Cys Val Tyr Gln His Leu Leu Arg Leu Glu Asp Gly Ala Asp Ile
        355                 360                 365

Thr Ile Gly Arg Thr Glu Trp Arg Pro Lys Asn Ala Gly Ala Asn Gly
    370                 375                 380

Ala Met Ser Ser Gly Lys Thr Ser Asn Gly Asn Cys Leu Ile Glu Gly
```

385 390 395 400

Arg Gly Trp Gln Pro Phe Arg Val Val Arg Leu Ile Phe
405 410

<210> SEQ ID NO 38
<211> LENGTH: 1242
<212> TYPE: DNA
<213> ORGANISM: Cuphea wrightii
<220> FEATURE:
<223> OTHER INFORMATION: Cuphea wrightii (Cw) FATB5 coding DNA sequence

<400> SEQUENCE: 38
atggtggctg ccgcagcaag ttctgcattc ttctctgttc caaccccggg aacgccccct 60
aaacccggga agttcggtaa ctggccatcg agcttgagcg tccccttcaa gcccgacaat 120
ggtggctttc atgtcaaggc aaacgccagt gcccatccta aggctaatgg ttctgcggta 180
aatctaaagt ctggcagcct cgagactcct cctcggagtt tcattaacca gctgccggac 240
ttgagtgtgc ttctgtccaa aatcacgact gtcttcgggg cggctgagaa gcagtggaag 300
aggcccggca tgctcgtgga accgtttggg gttgacagga tttttcagga tggtgttttt 360
ttcagacaga gtttttctat caggtcttac gaaataggcg ttgatcgaac agcctcgata 420
gagacactga tgaacatctt ccaggaaaca tctttgaatc attgcaagag tatcggtctt 480
ctcaacgatg gctttggtcg tactcctgag atgtgtaaga gggacctcat ttgggtggtt 540
acgaaaattc aggtcgaggt gaatcgctat cctacttggg gtgacactat cgaagtcaat 600
acttgggtct cggagtcggg gaaaaacggt atgggtcggg attggctgat aagtgattgc 660
cgtactggag agattcttat aagagcaacg agcgtgtggg cgatgatgaa tcaaaacacg 720
agaagattgt caaaatttcc atatgaggtt cgacaggaga tagcgcctca ttttgtggac 780
tctgctcctg tcattgaaga cgatcaaaag ttgcagaagc ttgatgtgaa gacaggtgat 840
tccattcgcg atggtctaac tccgagatgg aatgacttgg atgtcaatca acacgttaac 900
aatgtgaagt acattggatg gattctcaag agtgttccaa tagaagtttt cgagacacag 960
gagctatgcg gcgtcacact tgaatatagg cgggaatgcg gaagggacag tgtgctggag 1020
tcagtgaccg ctatggatcc agcaaaagag ggagaccggt gtgtgtacca gcaccttctt 1080
cggcttgagg atggagctga tatcactata ggcagaaccg agtggcggcc gaagaatgca 1140
ggagccaatg gtgcaatgtc atcaggaaag acttcaaatg gaaactgtct catagaagga 1200
aggggttggc aacctttccg agttgtgcgt ttaattttct ga 1242

<210> SEQ ID NO 39
<211> LENGTH: 1242
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea wrightii (Cw) FATB5 coding DNA sequence codon optimized for Prototheca moriformis

<400> SEQUENCE: 39
atggtggccg ccgccgcctc ctccgccttc ttctccgtgc ccacccccgg cacccccccc 60
aagcccggca agttcggcaa ctggccctcc tccctgtccg tgcccttcaa gcccgacaac 120
ggcggcttcc acgtgaaggc caacgcctcc gcccacccca aggccaacgg ctccgccgtg 180
aacctgaagt ccggctccct ggagaccccc ccccgctcct tcatcaacca gctgcccgac 240

```
ctgtccgtgc tgctgtccaa gatcaccacc gtgttcggcg ccgccgagaa gcagtggaag    300

cgccccggca tgctggtgga gcccttcggc gtggaccgca tcttccagga cggcgtgttc    360

ttccgccagt ccttctccat ccgctcctac gagatcggcg tggaccgcac cgcctccatc    420

gagaccctga tgaacatctt ccaggagacc tccctgaacc actgcaagtc catcggcctg    480

ctgaacgacg gcttcggccg cacccccgag atgtgcaagc gcgacctgat ctgggtggtg    540

accaagatcc aggtggaggt gaaccgctac cccacctggg gcgacaccat cgaggtgaac    600

acctgggtgt ccgagtccgg caagaacggc atgggccgcg actggctgat ctccgactgc    660

cgcaccggcg agatcctgat ccgcgccacc tccgtgtggg ccatgatgaa ccagaacacc    720

cgccgcctgt ccaagttccc ctacgaggtg cgccaggaga tcgcccccca cttcgtggac    780

tccgcccccg tgatcgagga cgaccagaag ctgcagaagc tggacgtgaa gaccggcgac    840

tccatccgcg acggcctgac cccccgctgg aacgacctgg acgtgaacca gcacgtgaac    900

aacgtgaagt acatcggctg gatcctgaag tccgtgccca tcgaggtgtt cgagacccag    960

gagctgtgcg gcgtgaccct ggagtaccgc cgcgagtgcg gccgcgactc cgtgctggag   1020

tccgtgaccg ccatggaccc cgccaaggag ggcgaccgct gcgtgtacca gcacctgctg   1080

cgcctggagg acggcgccga catcaccatc ggccgcaccg agtggcgccc caagaacgcc   1140

ggcgccaacg gcgccatgtc ctccggcaag acctccaacg gcaactgcct gatcgagggc   1200

cgcggctggc agcccttccg cgtggtgcgc ctgatcttct ga                      1242


<210> SEQ ID NO 40
<211> LENGTH: 410
<212> TYPE: PRT
<213> ORGANISM: Cuphea heterophylla
<220> FEATURE:
<223> OTHER INFORMATION: Cuphea heterophylla (Cht) FATB1a amino acid
      sequence

<400> SEQUENCE: 40

Met Val Ala Ala Ala Ala Ser Ser Ala Phe Phe Ser Val Pro Thr Pro
1               5                   10                  15

Gly Thr Ser Thr Lys Pro Gly Asn Phe Gly Asn Trp Pro Ser Ser Leu
            20                  25                  30

Ser Val Pro Phe Lys Pro Glu Ser Asn His Asn Gly Gly Phe Arg Val
        35                  40                  45

Lys Ala Asn Ala Ser Ala His Pro Lys Ala Asn Gly Ser Ala Val Asn
    50                  55                  60

Leu Lys Ser Gly Ser Leu Glu Thr Gln Glu Asp Thr Ser Ser Ser Ser
65                  70                  75                  80

Pro Pro Pro Arg Thr Phe Ile Lys Gln Leu Pro Asp Trp Gly Met Leu
                85                  90                  95

Leu Ser Lys Ile Thr Thr Val Phe Gly Ala Ala Glu Arg Gln Trp Lys
            100                 105                 110

Arg Pro Gly Met Leu Val Glu Pro Phe Gly Val Asp Arg Ile Phe Gln
        115                 120                 125

Asp Gly Val Phe Phe Arg Gln Ser Phe Ser Ile Arg Ser Tyr Glu Ile
    130                 135                 140

Gly Ala Asp Arg Thr Ala Ser Ile Glu Thr Leu Met Asn Ile Phe Gln
145                 150                 155                 160

Glu Thr Ser Leu Asn His Cys Lys Ser Ile Gly Leu Leu Asn Asp Gly
                165                 170                 175

Phe Gly Arg Thr Pro Glu Met Cys Lys Arg Asp Leu Ile Trp Val Val
```

-continued

```
            180                 185                 190

Thr Lys Ile Gln Val Glu Val Asn Arg Tyr Pro Thr Trp Gly Asp Thr
        195                 200                 205

Ile Glu Val Asn Thr Trp Val Ser Glu Ser Gly Lys Asn Gly Met Gly
    210                 215                 220

Arg Asp Trp Leu Ile Ser Asp Cys Arg Thr Gly Glu Ile Leu Ile Arg
225                 230                 235                 240

Ala Thr Ser Val Trp Ala Met Met Asn Arg Lys Thr Arg Arg Leu Ser
                245                 250                 255

Lys Phe Pro Tyr Glu Val Arg Gln Glu Ile Ala Pro His Phe Val Asp
            260                 265                 270

Ser Ala Pro Val Ile Glu Asp Asp Lys Lys Leu His Lys Leu Asp Val
        275                 280                 285

Lys Thr Gly Asp Ser Ile Arg Lys Gly Leu Thr Pro Arg Trp Asn Asp
    290                 295                 300

Leu Asp Val Asn Gln His Val Asn Asn Val Lys Tyr Ile Gly Trp Ile
305                 310                 315                 320

Leu Lys Ser Val Pro Ala Glu Val Phe Glu Thr Gln Glu Leu Cys Gly
                325                 330                 335

Val Thr Leu Glu Tyr Arg Arg Glu Cys Gly Arg Asp Ser Val Leu Glu
            340                 345                 350

Ser Val Thr Ala Met Asp Thr Ala Lys Glu Gly Asp Arg Ser Leu Tyr
        355                 360                 365

Gln His Leu Leu Arg Leu Glu Asp Gly Ala Asp Ile Thr Ile Gly Arg
    370                 375                 380

Thr Glu Trp Arg Pro Lys Asn Ala Gly Ala Asn Gly Ala Ile Ser Thr
385                 390                 395                 400

Gly Lys Thr Ser Asn Glu Asn Ser Val Ser
                405                 410


<210> SEQ ID NO 41
<211> LENGTH: 1233
<212> TYPE: DNA
<213> ORGANISM: Cuphea heterophylla
<220> FEATURE:
<223> OTHER INFORMATION: Cuphea heterophylla (Cht) FATB1a coding DNA
      sequence

<400> SEQUENCE: 41

atggtggctg ccgcagcaag ttctgcattc ttctccgttc caaccccggg aacctccact     60

aaacccggga acttcggcaa ttggccatcg agcttgagcg tccccttcaa gcccgaatca    120

aaccacaatg gtggctttcg ggtcaaggca aacgccagtg ctcatcctaa ggctaacggt    180

tctgcagtaa atctaaagtc tggcagcctc gagactcagg aggacacttc atcgtcgtcc    240

cctcctcctc ggacttttat taagcagttg cccgactggg gtatgcttct gtccaaaatc    300

acgactgtct tcggggcggc tgagaggcag tggaagaggc ccggcatgct tgtggaaccg    360

tttggggttg acaggatttt tcaggatggg gtttttttca gacagagttt ttcgatcagg    420

tcttacgaaa taggcgctga tcgaacagcc tcaatagaga cgctgatgaa catcttccag    480

gaaacatctc tgaatcattg taagagtatc ggtcttctca atgacggctt tggtcgtact    540

cctgagatgt gtaagaggga cctcatttgg gtggttacga aaattcaggt cgaggtgaat    600

cgctatccta cttggggtga tactattgag gtcaatactt gggtctcaga gtcggggaaa    660

aacggtatgg gtcgtgattg gctgataagc gattgccgta ccggagaaat tcttataaga    720
```

gcaacgagcg tgtgggctat gatgaatcga aagacgagaa gattgtcaaa atttccatat 780
gaggttcgac aggagatagc gcctcatttt gtggactctg ctcctgtcat tgaagacgat 840
aaaaaattgc acaagcttga tgttaagacg ggtgattcca ttcgcaaggg tctaactcca 900
aggtggaatg acttggatgt caatcagcac gttaacaatg tgaagtacat tgggtggatt 960
ctcaagagtg ttccagcaga agttttcgag acccaggagc tatgcggagt cacccttgag 1020
tacaggcggg aatgtggaag ggacagtgtg ctggagtccg tgaccgctat ggataccgca 1080
aaagagggag accggtctct gtaccagcac cttcttcggc ttgaggatgg ggctgatatc 1140
accataggca gaaccgagtg gcggccgaag aatgcaggag ccaatggggc aatatcaaca 1200
ggaaagactt caaatgaaaa ctctgtctct tag 1233

<210> SEQ ID NO 42
<211> LENGTH: 1233
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea heterophylla (Cht) FATB1a coding DNA sequence codon optimized for Prototheca moriformis

<400> SEQUENCE: 42
atggtggccg ccgccgcctc ctccgccttc ttctccgtgc ccacccccgg cacctccacc 60
aagcccggca acttcggcaa ctggccctcc tccctgtccg tgcccttcaa gcccgagtcc 120
aaccacaacg gcggcttccg cgtgaaggcc aacgcctccg cccaccccaa ggccaacggc 180
tccgccgtga acctgaagtc cggctccctg gagacccagg aggacacctc ctcctcctcc 240
cccccccccc gcaccttcat caagcagctg cccgactggg gcatgctgct gtccaagatc 300
accaccgtgt tcggcgccgc cgagcgccag tggaagcgcc ccggcatgct ggtggagccc 360
ttcggcgtgg accgcatctt ccaggacggc gtgttcttcc gccagtcctt ctccatccgc 420
tcctacgaga tcggcgccga ccgcaccgcc tccatcgaga ccctgatgaa catcttccag 480
gagacctccc tgaaccactg caagtccatc ggcctgctga acgacggctt cggccgcacc 540
cccgagatgt gcaagcgcga cctgatctgg gtggtgacca agatccaggt ggaggtgaac 600
cgctacccca cctggggcga caccatcgag gtgaacacct gggtgtccga gtccggcaag 660
aacggcatgg gccgcgactg gctgatctcc gactgccgca ccggcgagat cctgatccgc 720
gccacctccg tgtgggccat gatgaaccgc aagacccgcc gcctgtccaa gttcccctac 780
gaggtgcgcc aggagatcgc cccccacttc gtggactccg cccccgtgat cgaggacgac 840
aagaagctgc acaagctgga cgtgaagacc ggcgactcca tccgcaaggg cctgaccccc 900
cgctggaacg acctggacgt gaaccagcac gtgaacaacg tgaagtacat cggctggatc 960
ctgaagtccg tgcccgccga ggtgttcgag acccaggagc tgtgcggcgt gaccctggag 1020
taccgccgcg agtgcggccg cgactccgtg ctggagtccg tgaccgccat ggacaccgcc 1080
aaggagggcg accgctccct gtaccagcac ctgctgcgcc tggaggacgg cgccgacatc 1140
accatcggcc gcaccgagtg gcgccccaag aacgccggcg ccaacggcgc catctccacc 1200
ggcaagacct ccaacgagaa ctccgtgtcc tga 1233

<210> SEQ ID NO 43
<211> LENGTH: 410
<212> TYPE: PRT
<213> ORGANISM: Cuphea heterophylla
<220> FEATURE:
<223> OTHER INFORMATION: Cuphea heterophylla (Cht) FATB1b (P16S, T20P,
      G94S, G105W, S293F, L305F variant) amino acid sequence

<400> SEQUENCE: 43

```
Met Val Ala Ala Ala Ala Ser Ser Ala Phe Phe Ser Val Pro Thr Ser
1               5                   10                  15

Gly Thr Ser Pro Lys Pro Gly Asn Phe Gly Asn Trp Pro Ser Ser Leu
            20                  25                  30

Ser Val Pro Phe Lys Pro Glu Ser Ser His Asn Gly Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Glu Thr Gln Glu Asp Thr Ser Ser Ser Ser
65                  70                  75                  80

Pro Pro Pro Arg Thr Phe Ile Lys Gln Leu Pro Asp Trp Ser Met Leu
                85                  90                  95

Leu Ser Lys Ile Thr Thr Val Phe Trp Ala Ala Glu Arg Gln Trp Lys
            100                 105                 110

Arg Pro Gly Met Leu Val Glu Pro Phe Gly Val Asp Arg Ile Phe Gln
        115                 120                 125

Asp Gly Val Phe Phe Arg Gln Ser Phe Ser Ile Arg Ser Tyr Glu Ile
    130                 135                 140

Gly Ala Asp Arg Thr Ala Ser Ile Glu Thr Leu Met Asn Ile Phe Gln
145                 150                 155                 160

Glu Thr Ser Leu Asn His Cys Lys Ser Ile Gly Leu Leu Asn Asp Gly
                165                 170                 175

Phe Gly Arg Thr Pro Glu Met Cys Lys Arg Asp Leu Ile Trp Val Val
            180                 185                 190

Thr Lys Ile Gln Val Glu Val Asn Arg Tyr Pro Thr Trp Gly Asp Thr
        195                 200                 205

Ile Glu Val Asn Thr Trp Val Ser Glu Ser Gly Lys Asn Gly Met Gly
    210                 215                 220

Arg Asp Trp Leu Ile Ser Asp Cys Arg Thr Gly Glu Ile Leu Ile Arg
225                 230                 235                 240

Ala Thr Ser Val Trp Ala Met Met Asn Arg Lys Thr Arg Arg Leu Ser
                245                 250                 255

Lys Phe Pro Tyr Glu Val Arg Gln Glu Ile Ala Pro His Phe Val Asp
            260                 265                 270

Ser Ala Pro Val Ile Glu Asp Asp Lys Lys Leu His Lys Leu Asp Val
        275                 280                 285

Lys Thr Gly Asp Phe Ile Arg Lys Gly Leu Thr Pro Arg Trp Asn Asp
    290                 295                 300

Phe Asp Val Asn Gln His Val Asn Asn Val Lys Tyr Ile Gly Trp Ile
305                 310                 315                 320

Leu Lys Ser Val Pro Ala Glu Val Phe Glu Thr Gln Glu Leu Cys Gly
                325                 330                 335

Val Thr Leu Glu Tyr Arg Arg Glu Cys Gly Arg Asp Ser Val Leu Glu
            340                 345                 350

Ser Val Thr Ala Met Asp Thr Ala Lys Glu Gly Asp Arg Ser Leu Tyr
        355                 360                 365

Gln His Leu Leu Arg Leu Glu Asp Gly Ala Asp Ile Thr Ile Gly Arg
    370                 375                 380

Thr Glu Trp Arg Pro Lys Asn Ala Gly Ala Asn Gly Ala Ile Ser Thr
```

-continued 385 390 395 400

Gly Lys Thr Ser Asn Glu Asn Ser Val Ser
405 410

<210> SEQ ID NO 44
<211> LENGTH: 1233
<212> TYPE: DNA
<213> ORGANISM: Cuphea heterophylla
<220> FEATURE:
<223> OTHER INFORMATION: Cuphea heterophylla (Cht) FATB1b(P16S, T20P, G94S, G105W, S293F, L305F variant) coding DNA sequence

<400> SEQUENCE: 44
atggtggctg ccgcagcaag ttctgcattc ttctccgttc caacctcggg aacctcccct 60
aaacccggga acttcggcaa ttggccatcg agcttgagcg tccccttcaa gcccgaatca 120
agccacaatg gtggctttca ggtcaaggca aacgccagtg cccatcctaa ggctaacggt 180
tctgcagtaa atctaaagtc tggcagcctc gagactcagg aggacacttc atcgtcgtcc 240
cctcctcctc ggacttttat taagcagttg cccgactgga gtatgcttct gtccaaaatc 300
acgactgtct tctgggcggc tgagaggcag tggaagaggc ccggcatgct tgtggaaccg 360
tttggggttg acaggatttt tcaggatggg gttttttca gacagagttt ttcgatcagg 420
tcttacgaaa taggcgctga tcgaacagcc tcaatagaga cgctgatgaa catcttccag 480
gaaacatctc tgaatcattg taagagtatc ggtcttctca atgacggctt tggtcgtact 540
cctgagatgt gtaagaggga cctcatttgg gtggttacga aaattcaggt cgaggtgaat 600
cgctatccta cttggggtga tactattgag gtcaatactt gggtctcaga gtcggggaaa 660
aacggtatgg gtcgtgattg gctgataagc gattgccgta ccggagaaat tcttataaga 720
gcaacgagcg tgtgggctat gatgaatcga aagacgagaa gattgtcaaa atttccatat 780
gaggttcgac aggagatagc gcctcatttt gtggactctg ctcctgtcat tgaagacgat 840
aaaaaattgc acaagcttga tgttaagacg ggtgatttca ttcgcaaggg tctaactcca 900
aggtggaatg actttgatgt caatcagcac gttaacaatg tgaagtacat tgggtggatt 960
ctcaagagtg ttccagcaga agttttcgag acccaggagc tatgcggagt caccccttgag 1020 tataggcggg aatgtggaag ggacagtgtg ctggagtccg tgaccgctat ggataccgca 1080
aaagagggag accggtctct gtaccagcac cttcttcggc ttgaggatgg ggctgatatc 1140
accataggca gaaccgagtg gcggccgaag aatgcaggag ccaatggggc aatatcaaca 1200
ggaaagactt caaatgaaaa ctctgtctct tag 1233

<210> SEQ ID NO 45
<211> LENGTH: 1233
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea heterophylla (Cht) FATB1b (P16S, T20P, G94S, G105W, S293F, L305F variant) coding DNA sequence codon optimized for Prototheca moriformis

<400> SEQUENCE: 45
atggtggccg ccgccgcctc ctccgccttc ttctccgtgc ccacctccgg cacctccccc 60
aagcccggca acttcggcaa ctggccctcc tccctgtccg tgcccttcaa gcccgagtcc 120
tcccacaacg gcggcttcca ggtgaaggcc aacgcctccg cccaccccaa ggccaacggc 180

-continued

```
tccgccgtga acctgaagtc cggctccctg gagacccagg aggacacctc ctcctcctcc    240

cccccccccc gcaccttcat caagcagctg cccgactggt ccatgctgct gtccaagatc    300

accaccgtgt tctgggccgc cgagcgccag tggaagcgcc ccggcatgct ggtggagccc    360

ttcggcgtgg accgcatctt ccaggacggc gtgttcttcc gccagtcctt ctccatccgc    420

tcctacgaga tcggcgccga ccgcaccgcc tccatcgaga ccctgatgaa catcttccag    480

gagacctccc tgaaccactg caagtccatc ggcctgctga acgacggctt cggccgcacc    540

cccgagatgt gcaagcgcga cctgatctgg gtggtgacca agatccaggt ggaggtgaac    600

cgctacccca cctggggcga caccatcgag gtgaacacct gggtgtccga gtccggcaag    660

aacggcatgg gccgcgactg gctgatctcc gactgccgca ccggcgagat cctgatccgc    720

gccacctccg tgtgggccat gatgaaccgc aagacccgcc gcctgtccaa gttcccctac    780

gaggtgcgcc aggagatcgc cccccacttc gtggactccg cccccgtgat cgaggacgac    840

aagaagctgc acaagctgga cgtgaagacc ggcgacttca tccgcaaggg cctgaccccc    900

cgctggaacg acttcgacgt gaaccagcac gtgaacaacg tgaagtacat cggctggatc    960

ctgaagtccg tgcccgccga ggtgttcgag acccaggagc tgtgcggcgt gaccctggag   1020

taccgccgcg agtgcggccg cgactccgtg ctggagtccg tgaccgccat ggacaccgcc   1080

aaggagggcg accgctccct gtaccagcac ctgctgcgcc tggaggacgg cgccgacatc   1140

accatcggcc gcaccgagtg gcgccccaag aacgccggcg ccaacggcgc catctccacc   1200

ggcaagacct ccaacgagaa ctccgtgtcc tga                                 1233
```

```
<210> SEQ ID NO 46
<211> LENGTH: 418
<212> TYPE: PRT
<213> ORGANISM: Cuphea heterophylla
<220> FEATURE:
<223> OTHER INFORMATION: Cuphea heterophylla (Cht) FATB2b amino acid
      sequence

<400> SEQUENCE: 46

Met Val Val Ala Ala Ala Ala Ser Ser Ala Phe Phe Pro Val Pro Ala
1               5                   10                  15

Ser Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Gln Glu Gly Thr Ser Ser Ser
65                  70                  75                  80

Pro Pro Pro Arg Thr Phe Leu Asn Gln Leu Pro Asp Trp Ser Arg Leu
                85                  90                  95

Arg Thr Ala Ile Thr Thr Val Phe Val Ala Ala Glu Lys Gln Leu Thr
            100                 105                 110

Met Leu Asp Arg Lys Ser Lys Lys Pro Asp Met His Val Asp Trp Phe
        115                 120                 125

Gly Leu Glu Ile Ile Val Gln Asp Gly Leu Val Phe Arg Glu Ser Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175
```

```
Val Gly Leu Leu Asn Asp Gly Phe Gly Arg Thr Pro Glu Met Cys Lys
            180                 185                 190

Arg Asp Leu Ile Trp Val Leu Thr Lys Met Gln Ile Met Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Lys Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
305                 310                 315                 320

Asn Val Lys Tyr Ile Gly Trp Ile Leu Glu Ser Met Pro Lys Glu Val
                325                 330                 335

Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser


<210> SEQ ID NO 47
<211> LENGTH: 1257
<212> TYPE: DNA
<213> ORGANISM: Cuphea heterophylla
<220> FEATURE:
<223> OTHER INFORMATION: Cuphea heterophylla (Cht) FATB2b coding DNA
      sequence

<400> SEQUENCE: 47

atggtggtgg ctgctgcagc aagctctgca ttcttccctg ttccggcatc tggaacctcc     60

cctaaacccg ggaagttcgg gacttggcta tcgagctcga gcccttccta caagcccaag    120

tcaaacccca gtggtggatt tcaggttaag gcaaatgcca gtgctcatcc taaggctaac    180

ggttccgcag taagtctaaa gtctggcagc ctcaacactc aggagggcac ttcgtcgtcc    240

cctcctcctc ggactttcct taaccagttg cctgattgga gtaggcttcg gactgcaatc    300

acgaccgtct tcgtggcggc agagaagcag ttgactatgc tcgatcgaaa gtctaagaag    360

cctgacatgc acgtggactg gtttgggttg gagattattg ttcaggatgg gctcgtgttc    420

agagagagtt tttcgatcag gtcttacgaa ataggcgctg atcgaacagc ctctatagaa    480

acgttgatga accatttgca ggacacatct ttgaaccatt gtaagagtgt gggtcttctc    540

aatgacggct ttggtcgtac cccggagatg tgtaaaaggg acctcatttg ggtgcttaca    600
```

-continued

```
aaaatgcaga tcatggtgaa tcgctatcca acttggggcg atactgtcga gatcaatagc    660

tggttctccc agtccgggaa aatcggtatg ggtcgcaatt ggctaataag tgattgcaac    720

acaggagaaa ttcttataag agcaacgagc atttgggcca tgatgaatca aaagacgaga    780

agattctcaa aacttccaaa cgaggttcgc caggagatag cgcctcattt tgtggacgcc    840

cctcctgtca ttgaagacaa tgatcgaaaa ttgcataagt ttgatgtgaa gactggtgat    900

tccatttgca agggtctaac accggagtgg aatgacttgg atgtcaatca gcacgtaagc    960

aacgtgaagt acattgggtg gattctcgag agtatgccaa aagaagtttt ggacacccag   1020

gagctatgct ctctcaccct tgaatatagg cgggaatgcg gaagggatag tgtgctggag   1080

tctgtgaccg ctatggatcc ctcaaaagtt ggagaccgat ctcagtacca gcaccttctg   1140

cggcttgaag atgggactga tatcatgaag ggcagaactg agtggcgacc aaagaatgca   1200

ggaaccaacg gggctatatc aacaggaaag acttcaaatg gaaactcggt ctcttag      1257
```

```
<210> SEQ ID NO 48
<211> LENGTH: 1257
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cuphea heterophylla (Cht) FATB2b coding DNA
      sequence codon optimized for Prototheca moriformis

<400> SEQUENCE: 48

atggtggtgg ccgccgccgc ctcctccgcc ttcttccccg tgcccgcctc cggcacctcc     60

cccaagcccg gcaagttcgg cacctggctg tcctcctcct ccccctccta caagcccaag    120

tccaacccct ccggcggctt ccaggtgaag gccaacgcct ccgcccaccc caaggccaac    180

ggctccgccg tgtccctgaa gtccggctcc ctgaacaccc aggagggcac ctcctcctcc    240

cccccccccc gcaccttcct gaaccagctg cccgactggt cccgcctgcg caccgccatc    300

accaccgtgt tcgtggccgc cgagaagcag ctgaccatgc tggaccgcaa gtccaagaag    360

cccgacatgc acgtggactg gttcggcctg gagatcatcg tgcaggacgg cctggtgttc    420

cgcgagtcct tctccatccg ctcctacgag atcggcgccg accgcaccgc ctccatcgag    480

accctgatga accacctgca ggacacctcc ctgaaccact gcaagtccgt gggcctgctg    540

aacgacggct tcggccgcac ccccgagatg tgcaagcgcg acctgatctg ggtgctgacc    600

aagatgcaga tcatggtgaa ccgctacccc acctggggcg acaccgtgga gatcaactcc    660

tggttctccc agtccggcaa gatcggcatg ggccgcaact ggctgatctc cgactgcaac    720

accggcgaga tcctgatccg cgccacctcc atctgggcca tgatgaacca gaagacccgc    780

cgcttctcca agctgcccaa cgaggtgcgc caggagatcg ccccccactt cgtggacgcc    840

ccccccgtga tcgaggacaa cgaccgcaag ctgcacaagt tcgacgtgaa gaccggcgac    900

tccatctgca agggcctgac ccccgagtgg aacgacctgg acgtgaacca gcacgtgtcc    960

aacgtgaagt acatcggctg gatcctggag tccatgccca aggaggtgct ggacacccag   1020

gagctgtgct ccctgaccct ggagtaccgc cgcgagtgcg gccgcgactc cgtgctggag   1080

tccgtgaccg ccatggaccc ctccaaggtg ggcgaccgct cccagtacca gcacctgctg   1140

cgcctggagg acggcaccga catcatgaag ggccgcaccg agtggcgccc caagaacgcc   1200

ggcaccaacg gcgccatctc caccggcaag acctccaacg gcaactccgt gtcctga      1257
```

-continued

<210> SEQ ID NO 49
<211> LENGTH: 418
<212> TYPE: PRT
<213> ORGANISM: Cuphea heterophylla
<220> FEATURE:
<223> OTHER INFORMATION: Cuphea heterophylla (Cht) FATB2a (S17P, P21S, T28N, L30P, S33L, G76D, S78P, G137W variant) amino acid sequence

<400> SEQUENCE: 49

```
Met Val Val Ala Ala Ala Ala Ser Ser Ala Phe Phe Pro Val Pro Ala
1               5                   10                  15

Pro Gly Thr Thr Ser Lys Pro Gly Lys Phe Gly Asn Trp Pro Ser Ser
            20                  25                  30

Leu Ser Pro Ser Phe Lys Pro Lys Ser Asn Pro Asn Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Lys Glu Asp Thr Pro Ser Ser
65                  70                  75                  80

Pro Pro Pro Arg Thr Phe Leu Asn Gln Leu Pro Asp Trp Ser Arg Leu
                85                  90                  95

Arg Thr Ala Ile Thr Thr Val Phe Val Ala Ala Glu Lys Gln Leu Thr
            100                 105                 110

Met Leu Asp Arg Lys Ser Lys Lys Pro Asp Met His Val Asp Trp Phe
        115                 120                 125

Gly Leu Glu Ile Ile Val Gln Asp Trp Leu Val Phe Arg Glu Ser Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Pro Glu Met Cys Lys
            180                 185                 190

Arg Asp Leu Ile Trp Val Leu Thr Lys Met Gln Ile Met Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Lys Thr Arg Arg Phe Ser Lys Leu Pro Asn Glu Val Arg Gln Glu
            260                 265                 270

Ile Ala Pro His Phe Val Asp Ala Pro Pro Leu Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
305                 310                 315                 320

Asn Val Lys Tyr Ile Gly Trp Ile Leu Glu Ser Met Pro Lys Glu Val
                325                 330                 335

Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365
```

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser

<210> SEQ ID NO 50
<211> LENGTH: 1257
<212> TYPE: DNA
<213> ORGANISM: Cuphea heterophylla
<220> FEATURE:
<223> OTHER INFORMATION: Cuphea heterophylla (Cht) FATB2a (S17P, P21S, T28N, L30P, S33L, G76D, S78P, G137W variant) coding DNA sequence

<400> SEQUENCE: 50
atggtggtgg ctgctgcagc aagttctgca ttcttccctg ttccagcacc tggaaccacg 60
tctaaacccg ggaagttcgg caattggcca tcgagcttga gcccttcctt caagcccaag 120
tcaaacccca atggtggatt tcaggttaag gcaaatgcca gcgctcatcc taaggctaac 180
gggtctgcag taagtctaaa gtctggcagc ctcaacacta aggaggacac tccgtcgtcc 240
cctcctcctc ggactttcct taaccagttg cctgattgga gtaggcttcg gactgcaatc 300
acgaccgtct tcgtggcggc agagaagcag ttgactatgc tcgatcgaaa gtctaagaag 360
cctgacatgc acgtggactg gtttgggttg gagattattg ttcaggattg gctcgtgttc 420
agagagagtt tttcgatcag gtcttacgaa ataggcgctg atcgaacagc ctctatagaa 480
acgttgatga accatttgca ggacacatct ttgaaccatt gtaagagtgt gggtcttctc 540
aatgacggct ttggtcgtac ccccggagatg tgtaaaaggg acctcatttg ggtgcttaca 600
aaaatgcaga tcatggtgaa tcgctatcca acttggggcg atactgtcga gatcaatagc 660
tggttctccc agtccgggaa aatcggtatg ggtcgcaatt ggctaataag tgattgcaac 720
acaggagaaa ttcttataag agcaacgagc atttgggcca tgatgaatca aaagacgaga 780
agattctcaa aacttccaaa cgaggttcgc caggagatag ctcctcattt tgtggacgcc 840
cctcctctca ttgaagacaa tgatcgaaaa ttgcataagt ttgatgtgaa gactggtgat 900
tccatttgca agggtctaac accggagtgg aatgacttgg atgtcaatca gcacgtaagc 960
aacgtgaagt acattgggtg gattctcgag agtatgccaa aagaagtttt ggacacccag 1020
gagctatgct ctctcaccct tgaatatagg cgggaatgcg gaagggacag tgtgctggag 1080
tctgtgaccg ctatggatcc ctcaaaagtt ggagaccgat ctcagtacca gcaccttctg 1140
cggcttgaag atgggactga tatcatgaag ggcagaactg agtggcgacc aaagaatgca 1200
ggaaccaacg gggcgatatc aacaggaaag acttcaaatg gaaactcggt ctcttag 1257

<210> SEQ ID NO 51
<211> LENGTH: 1257
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea heterophylla (Cht) FATB2a (S17P, P21S, T28N, L30P, S33L, G76D, S78P, G137W variant) coding DNA sequence codon optimized for Prototheca moriformis

<400> SEQUENCE: 51

```
atggtggtgg ccgccgccgc ctcctccgcc ttcttccccg tgcccgcccc cggcaccacc     60

tccaagcccg gcaagttcgg caactggccc tcctccctgt cccccctcctt caagcccaag    120

tccaacccca acggcggctt ccaggtgaag gccaacgcct ccgcccaccc caaggccaac    180

ggctccgccg tgtccctgaa gtccggctcc ctgaacacca aggaggacac cccctcctcc    240

cccccccccc gcaccttcct gaaccagctg cccgactggt cccgcctgcg caccgccatc    300

accaccgtgt tcgtggccgc cgagaagcag ctgaccatgc tggaccgcaa gtccaagaag    360

cccgacatgc acgtggactg gttcggcctg gagatcatcg tgcaggactg gctggtgttc    420

cgcgagtcct tctccatccg ctcctacgag atcggcgccg accgcaccgc ctccatcgag    480

accctgatga accacctgca ggacacctcc ctgaaccact gcaagtccgt gggcctgctg    540

aacgacggct tcggccgcac ccccgagatg tgcaagcgcg acctgatctg ggtgctgacc    600

aagatgcaga tcatggtgaa ccgctacccc acctggggcg acaccgtgga gatcaactcc    660

tggttctccc agtccggcaa gatcggcatg ggccgcaact ggctgatctc cgactgcaac    720

accggcgaga tcctgatccg cgccacctcc atctgggcca tgatgaacca gaagacccgc    780

cgcttctcca agctgcccaa cgaggtgcgc caggagatcg ccccccactt cgtggacgcc    840

ccccccctga tcgaggacaa cgaccgcaag ctgcacaagt tcgacgtgaa gaccggcgac    900

tccatctgca agggcctgac ccccgagtgg aacgacctgg acgtgaacca gcacgtgtcc    960

aacgtgaagt acatcggctg gatcctggag tccatgccca aggaggtgct ggacacccag   1020

gagctgtgct ccctgaccct ggagtaccgc cgcgagtgcg gccgcgactc cgtgctggag   1080

tccgtgaccg ccatggaccc ctccaaggtg ggcgaccgct cccagtacca gcacctgctg   1140

cgcctggagg acggcaccga catcatgaag ggccgcaccg agtggcgccc caagaacgcc   1200

ggcaccaacg gcgccatctc caccggcaag acctccaacg gcaactccgt gtcctga      1257
```

```
<210> SEQ ID NO 52
<211> LENGTH: 418
<212> TYPE: PRT
<213> ORGANISM: Cuphea heterophylla
<220> FEATURE:
<223> OTHER INFORMATION: Cuphea heterophylla (Cht) FATB2c (G76D, S78P
      variant) amino acid sequence

<400> SEQUENCE: 52

Met Val Val Ala Ala Ala Ala Ser Ser Ala Phe Phe Pro Val Pro Ala
1               5                   10                  15

Ser Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Lys Glu Asp Thr Pro Ser Ser
65                  70                  75                  80

Pro Pro Pro Arg Thr Phe Leu Asn Gln Leu Pro Asp Trp Asn Arg Leu
                85                  90                  95

Arg Thr Ala Ile Thr Thr Val Phe Val Ala Ala Glu Lys Gln Leu Thr
            100                 105                 110

Met Leu Asp Arg Lys Ser Lys Lys Pro Asp Met His Val Asp Trp Phe
        115                 120                 125

Gly Leu Glu Ile Ile Val Gln Asp Gly Leu Val Phe Arg Glu Ser Phe
    130                 135                 140
```

```
Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Pro Glu Met Cys Lys
            180                 185                 190

Arg Asp Leu Ile Trp Val Leu Thr Lys Met Gln Ile Met Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Lys Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
305                 310                 315                 320

Asn Val Lys Tyr Ile Gly Trp Ile Leu Glu Ser Met Pro Lys Glu Val
                325                 330                 335

Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser
```

<210> SEQ ID NO 53
<211> LENGTH: 1257
<212> TYPE: DNA
<213> ORGANISM: Cuphea heterophylla
<220> FEATURE:
<223> OTHER INFORMATION: Cuphea heterophylla (Cht) FATB2c (G76D, S78P variant) coding DNA sequence

<400> SEQUENCE: 53

```
atggtggtgg ctgctgcagc aagctctgca ttcttccctg ttccggcatc tggaacctcc      60

cctaaacccg ggaagttcgg gacttggcta tcgagctcga gcccttccta caagcccaag     120

tcaaacccca gtggtggatt tcaggttaag gcaaatgcca gtgctcatcc taaggctaac     180

ggttccgcag taagtctaaa gtctggcagc ctcaacacta aggaggacac tccgtcgtcc     240

cctcctcctc ggactttcct taaccagttg cctgattgga ataggcttcg gactgcaatc     300

acgaccgtct tcgtggcggc agagaagcag ttgactatgc tcgatcgaaa gtctaagaag     360

cctgacatgc acgtggactg gtttgggttg gagattattg ttcaggatgg gctcgtgttc     420
```

```
agagagagtt tttcgatcag gtcttacgaa ataggcgctg atcgaacagc ctctatagaa    480
acgttgatga accatttgca ggacacatct ttgaaccatt gtaagagtgt gggtcttctc    540
aatgacggct ttggtcgtac cccggagatg tgtaaaaggg acctcatttg ggtgcttaca    600
aaaatgcaga tcatggtgaa tcgctatcca acttggggcg atactgtcga gatcaatagc    660
tggttctccc agtccgggaa aatcggtatg ggtcgcaatt ggctaataag tgattgcaac    720
acaggagaaa ttcttataag agcaacgagc atttgggcca tgatgaatca aaagacgaga    780
agattctcaa aacttccaaa cgaggttcgc caggagatag cgcctcattt tgtggacgcc    840
cctcctgtca ttgaagacaa tgatcgaaaa ttgcataagt ttgatgtgaa gactggtgat    900
tccatttgca agggtctaac accggagtgg aatgacttgg atgtcaatca gcacgtaagc    960
aacgtgaagt acattgggtg gattctcgag agtatgccaa aagaagtttt ggacacccag   1020
gagctatgct ctctcaccct tgaatatagg cgggaatgcg gaagggacag tgtgctggag   1080
tctgtgaccg ctatggatcc ctcaaaagtt ggggaccgat ctcagtacca gcaccttctg   1140
cggcttgaag atgggactga tatcatgaag ggcagaactg agtggcgacc aaagaatgca   1200
ggaaccaacg ggctatatc aacaggaaag acttcaaatg gaaactcggt ctcttag       1257
```

<210> SEQ ID NO 54
<211> LENGTH: 1257
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea heterophylla (Cht) FATB2c (G76D, S78P variant) coding DNA sequence codon optimized for Prototheca moriformis

<400> SEQUENCE: 54

```
atggtggtgg ccgccgccgc ctcctccgcc ttcttccccg tgcccgcctc cggcacctcc     60
cccaagcccg gcaagttcgg cacctggctg tcctcctcct ccccctccta caagcccaag    120
tccaacccct ccggcggctt ccaggtgaag gccaacgcct ccgcccaccc caaggccaac    180
ggctccgccg tgtccctgaa gtccggctcc ctgaacacca aggaggacac cccctcctcc    240
cccccccccc gcaccttcct gaaccagctg cccgactgga accgcctgcg caccgccatc    300
accaccgtgt tcgtggccgc cgagaagcag ctgaccatgc tggaccgcaa gtccaagaag    360
cccgacatgc acgtggactg gttcggcctg gagatcatcg tgcaggacgg cctggtgttc    420
cgcgagtcct tctccatccg ctcctacgag atcggcgccg accgcaccgc ctccatcgag    480
accctgatga accacctgca ggacacctcc ctgaaccact gcaagtccgt gggcctgctg    540
aacgacggct tcggccgcac ccccgagatg tgcaagcgcg acctgatctg ggtgctgacc    600
aagatgcaga tcatggtgaa ccgctacccc acctggggcg acaccgtgga gatcaactcc    660
tggttctccc agtccggcaa gatcggcatg ggccgcaact ggctgatctc cgactgcaac    720
accggcgaga tcctgatccg cgccacctcc atctgggcca tgatgaacca gaagacccgc    780
cgcttctcca agctgcccaa cgaggtgcgc caggagatcg ccccccactt cgtggacgcc    840
ccccccgtga tcgaggacaa cgaccgcaag ctgcacaagt tcgacgtgaa gaccggcgac    900
tccatctgca agggcctgac ccccgagtgg aacgacctgg acgtgaacca gcacgtgtcc    960
aacgtgaagt acatcggctg gatcctggag tccatgccca aggaggtgct ggacacccag   1020
gagctgtgct ccctgaccct ggagtaccgc cgcgagtgcg gccgcgactc cgtgctggag   1080
```

-continued tccgtgaccg ccatggaccc ctccaaggtg ggcgaccgct cccagtacca gcacctgctg 1140
cgcctggagg acggcaccga catcatgaag ggccgcaccg agtggcgccc caagaacgcc 1200
ggcaccaacg gcgccatctc caccggcaag acctccaacg gcaactccgt gtcctga 1257

<210> SEQ ID NO 55
<211> LENGTH: 418
<212> TYPE: PRT
<213> ORGANISM: Cuphea heterophylla
<220> FEATURE:
<223> OTHER INFORMATION: Cuphea heterophylla (Cht) FATB2d (S21P, T28N, L30P, S33L, G76D, R97L, H124L, W127L, I132S, K258N, C303R, E309G, K334T, T386A variant) amino acid sequence

<400> SEQUENCE: 55

Met Val Val Ala Ala Ala Ala Ser Ser Ala Phe Phe Pro Val Pro Ala
1 5 10 15

Pro Gly Thr Thr Ser Lys Pro Gly Lys Phe Gly Asn Trp Pro Ser Ser
20 25 30

Leu Ser Pro Ser Phe Lys Pro Lys Ser Asn Pro Asn Gly Gly Phe Gln
35 40 45

Val Lys Ala Asn Ala Ser Ala His Pro Lys Ala Asn Gly Ser Ala Val
50 55 60

Ser Leu Lys Ser Gly Ser Leu Asn Thr Gln Glu Asp Thr Ser Ser Ser
65 70 75 80

Pro Pro Pro Arg Thr Phe Leu Asn Gln Leu Pro Asp Trp Ser Arg Leu
85 90 95

Leu Thr Ala Ile Ser Thr Val Phe Val Ala Ala Glu Lys Gln Leu Thr
100 105 110

Met Leu Asp Arg Lys Ser Lys Arg Pro Asp Met Leu Val Asp Leu Phe
115 120 125

Gly Leu Glu Ser Ile Val Gln Asp Gly Leu Val Phe Arg Glu Ser Tyr
130 135 140

Ser Ile Arg Ser Tyr Glu Ile Gly Ala Asp Arg Thr Ala Ser Ile Glu
145 150 155 160

Thr Leu Met Asn His Leu Gln Asp Thr Ser Leu Asn His Cys Lys Ser
165 170 175

Val Gly Leu Leu Asn Asp Gly Phe Gly Arg Thr Pro Glu Met Cys Lys
180 185 190

Arg Asp Leu Ile Trp Val Leu Thr Lys Met Gln Ile Met Val Asn Arg
195 200 205

Tyr Pro Thr Trp Gly Asp Thr Val Glu Ile Asn Ser Trp Phe Ser Gln
210 215 220

Ser Gly Lys Ile Gly Met Gly Arg Asn Trp Leu Ile Ser Asp Cys Asn
225 230 235 240

Thr Gly Glu Ile Leu Ile Arg Ala Thr Ser Ile Trp Ala Met Met Asn
245 250 255

Gln Asn Thr Arg Arg Phe Ser Lys Leu Pro Asn Glu Val Arg Gln Glu
260 265 270

Ile Ala Pro His Phe Val Asp Ala Pro Pro Val Ile Glu Asp Asn Asp
275 280 285

Arg Lys Leu His Lys Phe Asp Val Lys Thr Gly Asp Ser Ile Arg Lys
290 295 300

Gly Leu Thr Pro Gly Trp Asn Asp Leu Asp Val Asn Gln His Val Ser
305 310 315 320

Asn Val Lys Tyr Ile Gly Trp Ile Leu Glu Ser Met Pro Thr Glu Val

```
                325                 330                 335

Leu Glu Thr Gln Glu Leu Cys Ser Leu Thr Leu Glu Tyr Arg Arg Glu
            340                 345                 350

Cys Gly Arg Glu Ser Val Leu Glu Ser Val Thr Ala Met Asn Pro Ser
        355                 360                 365

Lys Val Gly Asp Arg Ser Gln Tyr Gln His Leu Leu Arg Leu Glu Asp
    370                 375                 380

Gly Ala Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser
```

<210> SEQ ID NO 56
<211> LENGTH: 1257
<212> TYPE: DNA
<213> ORGANISM: Cuphea heterophylla
<220> FEATURE:
<223> OTHER INFORMATION: Cuphea heterophylla (Cht) FATB2d (S21P, T28N, L30P, S33L, G76D, R97L, H124L, W127L, I132S, K258N, C303R, E309G, K334T, T386A variant) coding DNA sequence

<400> SEQUENCE: 56

```
atggtggtgg ctgctgcagc aagttctgca ttcttccctg ttccagcacc tggaaccacg     60

tctaaacccg ggaagttcgg caattggcca tcgagcttga gcccttcctt caagcccaag    120

tcaaacccca atggtggatt tcaggttaag gcaaatgcca gtgctcatcc taaggctaac    180

ggttctgcgg taagtctaaa gtctggcagc ctcaacactc aggaggacac ttcgtcgtcc    240

cctcctcctc ggacattcct taaccagttg cctgattgga gtaggcttct gactgcaatc    300

tcgaccgtct tcgtggcggc agagaagcag ttgactatgc tcgatcgaaa atctaagagg    360

cctgacatgc tcgtggactt gtttgggttg gagagtattg ttcaggatgg gctcgtgttc    420

agagagagtt attcgatcag gtcttacgaa ataggcgctg atcgaacagc ctctatagaa    480

acgttgatga accatttgca ggacacatct ttgaaccatt gtaagagtgt gggtcttctc    540

aatgacggct ttggtcgtac cccggagatg tgtaaaaggg acctcatttg ggtgcttaca    600

aaaatgcaga tcatggtgaa tcgctatcca acttggggcg atactgtcga gatcaatagc    660

tggttctccc agtccgggaa aatcggtatg ggtcgcaatt ggctaataag tgattgcaac    720

acaggagaaa ttcttataag agcaacgagc atttgggcca tgatgaatca aaatacgaga    780

agattctcaa aacttccaaa cgaggttcgc caggagatag cgcctcattt tgttgacgct    840

cctcctgtca ttgaagacaa tgatcgaaaa ttgcataagt ttgatgtgaa gactggtgat    900

tccattcgca agggtctaac tccggggtgg aatgacttgg atgtcaatca gcacgtaagc    960

aacgtgaagt acattgggtg gattctcgag agtatgccaa cagaagtttt ggagacccag   1020

gagctatgct ctctcaccct tgaatatagg cgggaatgcg gaagggaaag tgtgctggag   1080

tccgtgaccg ctatgaatcc ctcaaaagtt ggagaccggt ctcagtacca gcaccttcta   1140

cggcttgagg atggggctga tatcatgaag ggcagaactg agtggcgacc aaagaatgca   1200

ggaaccaacg gggcgatatc aacaggaaag acttcaaatg gaaactcggt ctcttag      1257
```

<210> SEQ ID NO 57
<211> LENGTH: 1257
<212> TYPE: DNA
<213> ORGANISM: Artificial Sequence
<220> FEATURE:

<223> OTHER INFORMATION: Description of Artificial Sequence: Synthetic polynucleotide
<220> FEATURE:
<223> OTHER INFORMATION: Cuphea heterophylla (Cht) FATB2d (S21P, T28N, L30P, S33L, G76D, R97L, H124L, W127L, I132S, K258N, C303R, E309G, K334T, T386A variant) coding DNA sequence codon optimized for Prototheca moriformis

<400> SEQUENCE: 57

```
atggtggtgg ccgccgccgc ctcctccgcc ttcttccccg tgcccgcccc cggcaccacc     60

tccaagcccg gcaagttcgg caactggccc tcctccctgt ccccctcctt caagcccaag    120

tccaacccca acggcggctt ccaggtgaag gccaacgcct ccgcccaccc caaggccaac    180

ggctccgccg tgtccctgaa gtccggctcc ctgaacaccc aggaggacac ctcctcctcc    240

cccccccccc gcaccttcct gaaccagctg cccgactggt cccgcctgct gaccgccatc    300

tccaccgtgt tcgtggccgc cgagaagcag ctgaccatgc tggaccgcaa gtccaagcgc    360

cccgacatgc tggtggacct gttcggcctg gagtccatcg tgcaggacgg cctggtgttc    420

cgcgagtcct actccatccg ctcctacgag atcggcgccg accgcaccgc ctccatcgag    480

accctgatga accacctgca ggacacctcc ctgaaccact gcaagtccgt gggcctgctg    540

aacgacggct tcggccgcac ccccgagatg tgcaagcgcg acctgatctg ggtgctgacc    600

aagatgcaga tcatggtgaa ccgctacccc acctggggcg acaccgtgga gatcaactcc    660

tggttctccc agtccggcaa gatcggcatg ggccgcaact ggctgatctc cgactgcaac    720

accggcgaga tcctgatccg cgccacctcc atctgggcca tgatgaacca gaacacccgc    780

cgcttctcca agctgcccaa cgaggtgcgc caggagatcg ccccccactt cgtggacgcc    840

ccccccgtga tcgaggacaa cgaccgcaag ctgcacaagt tcgacgtgaa gaccggcgac    900

tccatccgca agggcctgac ccccggctgg aacgacctgg acgtgaacca gcacgtgtcc    960

aacgtgaagt acatcggctg gatcctggag tccatgccca ccgaggtgct ggagacccag   1020

gagctgtgct ccctgaccct ggagtaccgc cgcgagtgcg gccgcgagtc cgtgctggag   1080

tccgtgaccg ccatgaaccc ctccaaggtg ggcgaccgct cccagtacca gcacctgctg   1140

cgcctggagg acggcgccga catcatgaag ggccgcaccg agtggcgccc caagaacgcc   1200

ggcaccaacg gcgccatctc caccggcaag acctccaacg gcaactccgt gtcctga      1257
```

<210> SEQ ID NO 58
<211> LENGTH: 418
<212> TYPE: PRT
<213> ORGANISM: Cuphea heterophylla
<220> FEATURE:
<223> OTHER INFORMATION: Cuphea heterophylla (Cht) FATB2e (G76D, R97L, H124L, I132S, G152S, H165L, T211N, K258N, C303R, E309G, K334T, T386A variant) amino acid sequence

<400> SEQUENCE: 58

```
Met Val Val Ala Ala Ala Ala Ser Ser Ala Phe Phe Pro Val Pro Ala
1               5                   10                  15

Ser Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Gln Glu Asp Thr Ser Ser Ser
65                  70                  75                  80
```

-continued

```
Pro Pro Pro Gln Thr Phe Leu Asn Gln Leu Pro Asp Trp Ser Arg Leu
                85                  90                  95

Leu Thr Ala Ile Ser Thr Val Phe Val Ala Ala Glu Lys Gln Leu Thr
            100                 105                 110

Met Leu Asp Arg Lys Ser Lys Arg Pro Asp Met Leu Val Asp Trp Phe
        115                 120                 125

Gly Leu Glu Ser Ile Val Gln Asp Gly Leu Val Phe Arg Glu Ser Tyr
    130                 135                 140

Ser Ile Arg Ser Tyr Glu Ile Ser Ala Asp Arg Thr Ala Ser Ile Glu
145                 150                 155                 160

Thr Val Met Asn Leu Leu Gln Glu Thr Ser Leu Asn His Cys Lys Ser
                165                 170                 175

Met Gly Ile Leu Asn Asp Gly Phe Gly Arg Thr Pro Glu Met Cys Lys
            180                 185                 190

Arg Asp Leu Ile Trp Val Leu Thr Lys Met Gln Ile Leu Val Asn Arg
        195                 200                 205

Tyr Pro Asn Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Asn Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Arg Lys
    290                 295                 300

Gly Leu Thr Pro Gly Trp Asn Asp Leu Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asn Pro Ser
        355                 360                 365

Lys Val Gly Asp Arg Ser Gln Tyr Gln His Leu Leu Arg Leu Glu Asp
    370                 375                 380

Gly Ala Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser
```

<210> SEQ ID NO 59
<211> LENGTH: 1257
<212> TYPE: DNA
<213> ORGANISM: Cuphea heterophylla
<220> FEATURE:
<223> OTHER INFORMATION: Cuphea heterophylla (Cht) FATB2e (G76D, R97L, H124L, I132S, G152S, H165L, T211N, K258N, C303R, E309G, K334T, T386A variant) coding DNA sequence

<400> SEQUENCE: 59

```
atggtggtgg ctgctgcagc aagctctgca ttcttccctg ttccggcatc tggaacctcc      60
```

```
cctaaacccg ggaagttcgg gacttggcta tcgagctcga gcccttccta caagcccaag    120
tcaaacccca gtggtggatt tcaggttaag gcaaatgcca gtgctcatcc taaggctaac    180
ggttctgcag taagtctaaa gtctggcagc ctcaacactc aggaggacac ttcgtcgtcc    240
cctcctcctc agacattcct taaccagttg cctgattgga gtaggcttct gacagcaatc    300
tcgaccgtct tcgtggcggc agagaagcag ttgactatgc tcgatcgaaa atctaaaagg    360
cctgacatgc tcgtggactg gtttgggttg gagagtattg ttcaggatgg gctcgtgttc    420
agagagagtt attcgatcag gtcttacgaa ataagcgctg atcgaacagc ctctatagag    480
acggtgatga acctcttgca ggaaacatct ctcaatcatt gtaagagtat gggtattctc    540
aatgacggct ttggtcgtac cccggagatg tgcaaaaggg acctcatttg ggtgcttaca    600
aaaatgcaga tcttggtgaa tcgctatcca aattggggtg atactgtcga gatcaatagc    660
tggttctccc agtccgggaa aatcggtatg ggtcgcaatt ggctaataag tgattgcaac    720
acaggagaaa ttcttataag agcaacgagc atttgggcca tgatgaatca aaatacgaga    780
agattctcaa aacttccaaa cgaggttcgc caggagatag cgcctcattt tgttgacgct    840
cctcctgtca ttgaagacaa tgatcgaaaa ttgcataagt ttgatgtgaa gactggtgat    900
tccattcgca agggtctaac tccggggtgg aatgacttgg atgtcaatca gcacgtaagc    960
aacgtgaagt acattgggtg gattctcgag agtatgccaa cagaagtttt ggagacccag   1020
gagctatgct ctctcaccct tgaatatagg cgggaatgcg gaagggacag tgtgctggag   1080
tccgtgaccg ctatgaatcc ctcaaaagtt ggagaccggt ctcagtacca gcaccttcta   1140
cggcttgagg atggggctga tatcatgaag ggcagaactg agtggcgacc aaagaatgca   1200
ggaaccaacg gggcgatatc aacaggaaag acttcaaatg gaaactcggt ctcttag      1257
```

<210> SEQ ID NO 60
<211> LENGTH: 1257
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea heterophylla (Cht) FATB2e (G76D, R97L, H124L, I132S, G152S, H165L, T211N, K258N, C303R, E309G, K334T, T386A variant) coding DNA sequence codon optimized for Prototheca moriformis

<400> SEQUENCE: 60

```
atggtggtgg ccgccgccgc ctcctccgcc ttcttccccg tgcccgcctc cggcacctcc     60
cccaagcccg gcaagttcgg cacctggctg tcctcctcct ccccctccta caagcccaag    120
tccaacccct ccggcggctt ccaggtgaag gccaacgcct ccgcccaccc caaggccaac    180
ggctccgccg tgtccctgaa gtccggctcc ctgaacaccc aggaggacac ctcctcctcc    240
cccccccccc agaccttcct gaaccagctg cccgactggt cccgcctgct gaccgccatc    300
tccaccgtgt tcgtggccgc cgagaagcag ctgaccatgc tggaccgcaa gtccaagcgc    360
cccgacatgc tggtggactg gttcggcctg gagtccatcg tgcaggacgg cctggtgttc    420
cgcgagtcct actccatccg ctcctacgag atctccgccg accgcaccgc ctccatcgag    480
accgtgatga acctgctgca ggagacctcc ctgaaccact gcaagtccat gggcatcctg    540
aacgacggct tcggccgcac ccccgagatg tgcaagcgcg acctgatctg ggtgctgacc    600
aagatgcaga tcctggtgaa ccgctacccc aactggggcg acaccgtgga gatcaactcc    660
tggttctccc agtccggcaa gatcggcatg ggccgcaact ggctgatctc cgactgcaac    720
```

accggcgaga tcctgatccg cgccacctcc atctgggcca tgatgaacca gaacacccgc 780
cgcttctcca agctgcccaa cgaggtgcgc caggagatcg ccccccactt cgtggacgcc 840
ccccccgtga tcgaggacaa cgaccgcaag ctgcacaagt tcgacgtgaa gaccggcgac 900
tccatccgca agggcctgac cccccggctgg aacgacctgg acgtgaacca gcacgtgtcc 960
aacgtgaagt acatcggctg gatcctggag tccatgccca ccgaggtgct ggagacccag 1020
gagctgtgct ccctgaccct ggagtaccgc cgcgagtgcg gccgcgactc cgtgctggag 1080
tccgtgaccg ccatgaaccc ctccaaggtg ggcgaccgct cccagtacca gcacctgctg 1140
cgcctggagg acggcgccga catcatgaag ggccgcaccg agtggcgccc caagaacgcc 1200
ggcaccaacg gcgccatctc caccggcaag acctccaacg gcaactccgt gtcctga 1257

<210> SEQ ID NO 61
<211> LENGTH: 418
<212> TYPE: PRT
<213> ORGANISM: Cuphea heterophylla
<220> FEATURE:
<223> OTHER INFORMATION: Cuphea heterophylla (Cht) FATB2f (R97L, H124L, I132S, G152S, H165L, T211N variant) amino acid sequence

<400> SEQUENCE: 61

Met Val Val Ala Ala Ala Ala Ser Ser Ala Phe Phe Pro Val Pro Ala
1 5 10 15

Ser Gly Thr Ser Pro Lys Pro Gly Lys Phe Gly Thr Trp Leu Ser Ser
20 25 30

Ser Ser Pro Ser Tyr Lys Pro Lys Ser Asn Pro Ser Gly Gly Phe Gln
35 40 45

Val Lys Ala Asn Ala Ser Ala His Pro Lys Ala Asn Gly Ser Ala Val
50 55 60

Ser Leu Lys Ser Gly Ser Leu Asn Thr Gln Glu Gly Thr Ser Ser Ser
65 70 75 80

Pro Pro Pro Arg Thr Phe Leu Asn Gln Leu Pro Asp Trp Ser Arg Leu
85 90 95

Leu Thr Ala Ile Ser Thr Val Phe Val Ala Ala Glu Lys Gln Leu Thr
100 105 110

Met Leu Asp Arg Lys Ser Lys Arg Pro Asp Met Leu Val Asp Trp Phe
115 120 125

Gly Leu Glu Ser Ile Val Gln Asp Gly Leu Val Phe Arg Glu Ser Tyr
130 135 140

Ser Ile Arg Ser Tyr Glu Ile Ser Ala Asp Arg Thr Ala Ser Ile Glu
145 150 155 160

Thr Val Met Asn Leu Leu Gln Glu Thr Ser Leu Asn His Cys Lys Ser
165 170 175

Met Gly Ile Leu Asn Asp Gly Phe Gly Arg Thr Pro Glu Met Cys Lys
180 185 190

Arg Asp Leu Ile Trp Val Leu Thr Lys Met Gln Ile Leu Val Asn Arg
195 200 205

Tyr Pro Asn Trp Gly Asp Thr Val Glu Ile Asn Ser Trp Phe Ser Gln
210 215 220

Ser Gly Lys Ile Gly Met Gly Arg Asn Trp Leu Ile Ser Asp Cys Asn
225 230 235 240

Thr Gly Glu Ile Leu Ile Arg Ala Thr Ser Ile Trp Ala Met Met Asn
245 250 255

Gln Lys Thr Arg Arg Phe Ser Lys Leu Pro Asn Glu Val Arg Gln Glu

-continued

```
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
305                 310                 315                 320

Asn Val Lys Tyr Ile Gly Trp Ile Leu Glu Ser Met Pro Lys Glu Val
                325                 330                 335

Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser


<210> SEQ ID NO 62
<211> LENGTH: 1257
<212> TYPE: DNA
<213> ORGANISM: Cuphea heterophylla
<220> FEATURE:
<223> OTHER INFORMATION: Cuphea heterophylla (Cht) FATB2f (R97L, H124L,
      I132S, G152S, H165L, T211N variant) coding DNA sequence

<400> SEQUENCE: 62

atggtggtgg ctgctgcagc aagctctgca ttcttccctg ttccggcatc tggaacctcc      60

cctaaacccg ggaagttcgg gacttggcta tcgagctcga gcccttccta caagcccaag     120

tcaaacccca gtggtggatt tcaggttaaa gcaaatgcca gtgctcatcc taaggctaac     180

ggttccgcag taagtctaaa gtctggcagc ctcaacactc aggagggcac ttcgtcgtcc     240

cctcctcctc ggacattcct taaccagttg cctgattgga gtaggcttct gactgcaatc     300

tcgaccgtct tcgtggcggc agagaagcag ttgactatgc tcgatcgaaa atctaagagg     360

cctgacatgc tcgtggactg gtttgggttg gagagtattg ttcaggatgg gctcgtgttc     420

agagagagtt attcgatcag gtcttacgaa ataagcgctg atcgaacagc ctctatagag     480

acggtgatga acctcttgca ggaaacatct ctcaatcatt gtaagagtat gggtattctc     540

aatgacggct ttggtcgtac ccccggagatg tgcaaaaggg acctcatttg ggtgcttaca     600

aaaatgcaga tcttggtgaa tcgctatcca aattggggtg atactgtcga gatcaatagc     660

tggttctccc agtccgggaa aatcggtatg ggtcgcaatt ggctaataag tgattgcaac     720

acaggagaaa ttcttataag agcaacgagc atttgggcca tgatgaatca aaagacgaga     780

agattctcaa aacttccaaa tgaggttcgc caggagatag cgcctcattt tgtggacgcc     840

cctcctgtca ttgaagacaa tgatcgaaaa ttgcataagt ttgatgtgaa gactggtgat     900

tccatttgca agggtctaac accggagtgg aacgacttgg atgtcaatca gcacgtaagc     960

aacgtgaagt acattgggtg gattctcgag agtatgccaa aagaagtttt ggacacccag    1020

gagctatgct ctctcaccct tgaatatagg cgggaatgcg gaagggacag tgtgctggag    1080

tctgtgaccg ctatggatcc ctcaaaagtt ggagaccgat ctcagtacca gcaccttctg    1140
```

cggcttgaag atgggactga tatcatgaag ggcagaactg agtggcgacc aaagaatgca 1200
ggaaccaacg gggcgatatc aacaggaaag acttcaaatg gaaactcggt ctcttag 1257

<210> SEQ ID NO 63
<211> LENGTH: 1257
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea heterophylla (Cht) FATB2f (R97L, H124L, I132S, G152S, H165L, T211N variant) coding DNA sequence codon optimized for Prototheca moriformis

<400> SEQUENCE: 63
atggtggtgg ccgccgccgc ctcctccgcc ttcttccccg tgcccgcctc cggcacctcc 60
cccaagcccg gcaagttcgg cacctggctg tcctcctcct ccccctccta caagcccaag 120
tccaacccct ccggcggctt ccaggtgaag gccaacgcct ccgcccaccc caaggccaac 180
ggctccgccg tgtccctgaa gtccggctcc ctgaacaccc aggagggcac ctcctcctcc 240
cccccccccc gcaccttcct gaaccagctg cccgactggt cccgcctgct gaccgccatc 300
tccaccgtgt tcgtggccgc cgagaagcag ctgaccatgc tggaccgcaa gtccaagcgc 360
cccgacatgc tggtggactg gttcggcctg gagtccatcg tgcaggacgg cctggtgttc 420
cgcgagtcct actccatccg ctcctacgag atctccgccg accgcaccgc ctccatcgag 480
accgtgatga acctgctgca ggagacctcc ctgaaccact gcaagtccat gggcatcctg 540
aacgacggct tcggccgcac ccccgagatg tgcaagcgcg acctgatctg ggtgctgacc 600
aagatgcaga tcctggtgaa ccgctacccc aactggggcg acaccgtgga gatcaactcc 660
tggttctccc agtccggcaa gatcggcatg ggccgcaact ggctgatctc cgactgcaac 720
accggcgaga tcctgatccg cgccacctcc atctgggcca tgatgaacca gaagacccgc 780
cgcttctcca agctgcccaa cgaggtgcgc caggagatcg ccccccactt cgtggacgcc 840
ccccccgtga tcgaggacaa cgaccgcaag ctgcacaagt tcgacgtgaa gaccggcgac 900
tccatctgca agggcctgac ccccgagtgg aacgacctgg acgtgaacca gcacgtgtcc 960
aacgtgaagt acatcggctg gatcctggag tccatgccca aggaggtgct ggacacccag 1020
gagctgtgct ccctgaccct ggagtaccgc cgcgagtgcg gccgcgactc cgtgctggag 1080
tccgtgaccg ccatggaccc ctccaaggtg ggcgaccgct cccagtacca gcacctgctg 1140
cgcctggagg acggcaccga catcatgaag ggccgcaccg agtggcgccc caagaacgcc 1200
ggcaccaacg gcgccatctc caccggcaag acctccaacg gcaactccgt gtcctga 1257

<210> SEQ ID NO 64
<211> LENGTH: 418
<212> TYPE: PRT
<213> ORGANISM: Cuphea heterophylla
<220> FEATURE:
<223> OTHER INFORMATION: Cuphea heterophylla (Cht) FATB2g (A6T, A16V, S17P, G76D, R97L, H124L, I132S, S143I, G152S, A157T, H165L, T211N, G414A variant) amino acid sequence

<400> SEQUENCE: 64

Met Val Val Ala Ala Thr Ala Ser Ser Ala Phe Phe Pro Val Pro Val
1 5 10 15

Pro Gly Thr Ser Pro Lys Pro Gly Lys Phe Gly Thr Trp Leu Ser Ser
20 25 30

Ser Ser Pro Ser Tyr Lys Pro Lys Ser Asn Pro Ser Gly Gly Phe Gln
35 40 45

Val Lys Ala Asn Ala Ser Ala His Pro Lys Ala Asn Gly Ser Ala Val
50 55 60

Ser Leu Lys Ser Gly Ser Leu Asn Thr Gln Glu Asp Thr Ser Ser Ser
65 70 75 80

Pro Pro Pro Arg Thr Phe Leu Asn Gln Leu Pro Asp Trp Ser Arg Leu
85 90 95

Leu Thr Ala Ile Ser Thr Val Phe Val Ala Ala Glu Lys Gln Leu Thr
100 105 110

Met Leu Asp Arg Lys Ser Lys Arg Pro Asp Met Leu Val Asp Trp Phe
115 120 125

Gly Leu Glu Ser Ile Val Gln Asp Gly Leu Val Phe Arg Glu Ile Tyr
130 135 140

Ser Ile Arg Ser Tyr Glu Ile Ser Ala Asp Arg Thr Thr Ser Ile Glu
145 150 155 160

Thr Val Met Asn Leu Leu Gln Glu Thr Ser Leu Asn His Cys Lys Ser
165 170 175

Met Gly Ile Leu Asn Asp Gly Phe Gly Arg Thr Pro Glu Met Cys Lys
180 185 190

Arg Asp Leu Ile Trp Val Leu Thr Lys Met Gln Ile Leu Val Asn Arg
195 200 205

Tyr Pro Asn Trp Gly Asp Thr Val Glu Ile Asn Ser Trp Phe Ser Gln
210 215 220

Ser Gly Lys Ile Gly Met Gly Arg Asn Trp Leu Ile Ser Asp Cys Asn
225 230 235 240

Thr Gly Glu Ile Leu Ile Arg Ala Thr Ser Ile Trp Ala Met Met Asn
245 250 255

Gln Lys Thr Arg Arg Phe Ser Lys Leu Pro Asn Glu Val Arg Gln Glu
260 265 270

Ile Ala Pro His Phe Val Asp Ala Pro Pro Val Ile Glu Asp Asn Asp
275 280 285

Arg Lys Leu His Lys Phe Asp Val Lys Thr Gly Asp Ser Ile Cys Lys
290 295 300

Gly Leu Thr Pro Glu Trp Asn Asp Leu Asp Val Asn Gln His Val Ser
305 310 315 320

Asn Val Lys Tyr Ile Gly Trp Ile Leu Glu Ser Met Pro Lys Glu Val
325 330 335

Leu Asp Thr Gln Glu Leu Cys Ser Leu Thr Leu Glu Tyr Arg Arg Glu
340 345 350

Cys Gly Arg Asp Ser Val Leu Glu Ser Val Thr Ala Met Asp Pro Ser
355 360 365

Lys Val Gly Asp Arg Ser Gln Tyr Gln His Leu Leu Arg Leu Glu Asp
370 375 380

Gly Thr Asp Ile Met Lys Gly Arg Thr Glu Trp Arg Pro Lys Asn Ala
385 390 395 400

Gly Thr Asn Gly Ala Ile Ser Thr Gly Lys Thr Ser Asn Ala Asn Ser
405 410 415

Val Ser

<210> SEQ ID NO 65
<211> LENGTH: 1257
<212> TYPE: DNA

<213> ORGANISM: Cuphea heterophylla
<220> FEATURE:
<223> OTHER INFORMATION: Cuphea heterophylla (Cht) FATB2g (A6T, A16V, S17P, G76D, R97L, H124L, I132S, S143I, G152S, A157T, H165L, T211N, G414A variant) coding DNA sequence

<400> SEQUENCE: 65

```
atggtggtgg ctgctacagc aagttctgca ttcttccctg ttcctgtacc tggaacctcc     60

cctaaacccg gaaagttcgg gacttggcta tcgagctcga gcccttccta caagcccaag    120

tcaaacccca gtggtggatt tcaggttaag gcaaatgcca gtgctcatcc taaggctaac    180

ggttctgcag taagtctaaa gtctggcagc ctcaacactc aggaggacac ttcgtcgtcc    240

cctcctcctc ggacattcct taaccagttg cctgattgga gtaggcttct gactgcaatc    300

tcgaccgtct tcgtggcggc agagaagcag ttgactatgc tcgatcgaaa atctaagagg    360

cctgacatgc tcgtggactg gtttgggttg gagagtattg ttcaggatgg gctcgtgttc    420

agagagattt attcgatcag gtcttacgaa ataagcgctg atcgaacaac ctctatagag    480

acggtgatga acctcttgca ggaaacatct ctcaatcatt gtaagagtat gggtattctc    540

aatgacggct ttggtcgtac ccccggagatg tgcaaaaggg acctcatttg ggtgcttaca    600

aaaatgcaga tcttggtgaa tcgctatcca aattggggtg atactgtcga gatcaatagc    660

tggttctccc agtccgggaa aatcggtatg ggtcgcaatt ggctaataag tgattgcaac    720

acaggagaaa ttcttataag agcaacgagc atttgggcca tgatgaatca aaagacgaga    780

agattctcaa aacttccaaa cgaggttcgc caggagatag cgcctcattt tgtggacgcc    840

cctcctgtca ttgaagacaa tgatcgaaaa ttgcataagt ttgatgtgaa gactggtgat    900

tccatttgca agggtctaac accggagtgg aatgacttgg atgtcaatca gcacgtaagc    960

aacgtgaagt acattgggtg gattctcgag agtatgccaa aagaagtttt ggacacccag   1020

gagctatgct ctctcaccct tgaatatagg cgggaatgcg gaagggacag tgtgctggag   1080

tctgtgaccg ctatggatcc ctcaaaagtt ggagaccgat ctcagtacca gcaccttctg   1140

cggcttgaag atgggactga tatcatgaag ggcagaactg agtggcgacc aaagaatgca   1200

ggaaccaacg gggcgatatc aacaggaaag acttcaaatg caaactcggt ctcttag      1257
```

<210> SEQ ID NO 66
<211> LENGTH: 1257
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea heterophylla (Cht) FATB2g (A6T, A16V, S17P, G76D, R97L, H124L, I132S, S143I, G152S, A157T, H165L, T211N, G414A variant) coding DNA sequence codon optimized for Prototheca moriformis

<400> SEQUENCE: 66

```
atggtggtgg ccgccaccgc ctcctccgcc ttcttccccg tgcccgtgcc cggcacctcc     60

cccaagcccg gcaagttcgg cacctggctg tcctcctcct cccccctccta caagcccaag    120

tccaacccct ccggcggctt ccaggtgaag gccaacgcct ccgcccaccc caaggccaac    180

ggctccgccg tgtccctgaa gtccggctcc ctgaacaccc aggaggacac ctcctcctcc    240

cccccccccc gcaccttcct gaaccagctg cccgactggt cccgcctgct gaccgccatc    300

tccaccgtgt tcgtggccgc cgagaagcag ctgaccatgc tggaccgcaa gtccaagcgc    360

cccgacatgc tggtggactg gttcggcctg gagtccatcg tgcaggacgg cctggtgttc    420
```

-continued

```
cgcgagatct actccatccg ctcctacgag atctccgccg accgcaccac ctccatcgag    480

accgtgatga acctgctgca ggagacctcc ctgaaccact gcaagtccat gggcatcctg    540

aacgacggct tcggccgcac ccccgagatg tgcaagcgcg acctgatctg ggtgctgacc    600

aagatgcaga tcctggtgaa ccgctacccc aactggggcg acaccgtgga gatcaactcc    660

tggttctccc agtccggcaa gatcggcatg ggccgcaact ggctgatctc cgactgcaac    720

accggcgaga tcctgatccg cgccacctcc atctgggcca tgatgaacca gaagacccgc    780

cgcttctcca agctgcccaa cgaggtgcgc caggagatcg ccccccactt cgtggacgcc    840

ccccccgtga tcgaggacaa cgaccgcaag ctgcacaagt tcgacgtgaa gaccggcgac    900

tccatctgca agggcctgac ccccgagtgg aacgacctgg acgtgaacca gcacgtgtcc    960

aacgtgaagt acatcggctg gatcctggag tccatgccca aggaggtgct ggacacccag   1020

gagctgtgct ccctgaccct ggagtaccgc cgcgagtgcg gccgcgactc cgtgctggag   1080

tccgtgaccg ccatggaccc ctccaaggtg ggcgaccgct cccagtacca gcacctgctg   1140

cgcctggagg acggcaccga catcatgaag ggccgcaccg agtggcgccc caagaacgcc   1200

ggcaccaacg gcgccatctc caccggcaag acctccaacg ccaactccgt gtcctga      1257


<210> SEQ ID NO 67
<211> LENGTH: 414
<212> TYPE: PRT
<213> ORGANISM: Cuphea heterophylla
<220> FEATURE:
<223> OTHER INFORMATION: Cuphea heterophylla (Cht) FATB3aamino acid
      sequence

<400> SEQUENCE: 67

Met Val Ala Thr Ala Ala Ser Ser Ala Phe Phe Pro Val Pro Ser Pro
1               5                   10                  15

Asp Thr Ser Ser Arg Pro Gly Lys Leu Gly Asn Gly Ser Ser Ser Leu
            20                  25                  30

Arg Pro Leu Lys Pro Lys Phe Val Ala Asn Ala Gly Leu Gln Val Lys
        35                  40                  45

Ala Asn Ala Ser Ala Pro Pro Lys Ile Asn Gly Ser Ser Val Ser Leu
    50                  55                  60

Lys Ser Cys Ser Leu Lys Thr His Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Glu Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205
```

-continued

```
Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Trp Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Phe Gly Pro Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Thr Ile Ala Ser Gly Glu Thr Ser Pro Gly Asn Ser
                405                 410
```

<210> SEQ ID NO 68
<211> LENGTH: 1245
<212> TYPE: DNA
<213> ORGANISM: Cuphea heterophylla
<220> FEATURE:
<223> OTHER INFORMATION: Cuphea heterophylla (Cht) FATB3a coding DNA
      sequence

<400> SEQUENCE: 68

```
atggtggcca ccgctgcaag ttctgcattc ttcccggtgc cgtccccgga cacctcctct     60

agaccgggaa agctcggaaa tgggtcatca agcttgaggc cctcaagccc caaatttgtt    120

gccaatgctg ggctgcaggt taaggcaaac gccagtgccc ctcctaagat caatggttcc    180

tcggtcagtc taaagtcttg cagtctcaag actcatgaag acactccttc agctcctcct    240

ccgcggactt ttatcaacca gttgcctgat tggagcatgc ttcttgctgc aatcactact    300

gtcttcttgg cagcagagaa gcagtggatg atgcttgatt ggaaaccaaa gaggcctgac    360

atgcttgtgg acccgttcgg attgggaagg attgttcagg atgggcttgt gttcaggcag    420

aatttttcga ttaggtccta tgaaataggc gctgatcgca ctgcatccat agagacggtg    480

atgaaccact tgcaggaaac ggctctcaat catgttaaga gtgcggggct tcttaatgaa    540

ggctttggtc gtactcctga gatgtataaa agggacctta tttgggttgt cgcgaaaatg    600

caggtcatgg ttaaccgcta tcctacttgg ggtgacacgg ttgaagtgaa tacttgggtt    660

gccaagtcag ggaaaaatgg tatgcgtcgt gattggctca taagtgattg caatacagga    720

gaaattctta caagggcatc aagtgtgtgg gtcatgatga atcaaaagac aagaaaattg    780

tcaaagattc cagatgaggt tcggcatgag atagagcctc attttgtgga ctctgctccc    840

gtcattgaag acgatgactg gaaacttccc aagctggatg agaaaactgc tgactccatc    900
```

-continued

```
cgcaagggtc taactccgaa gtggaatgac ttggatgtca atcagcacgt caacaacgtg    960

aagtacattg ggtggattct tgagagtact ccaccagaag ttctggagac ccaggagtta   1020

tgttccctta ccctggaata caggcgggaa tgcggaaggg agagtgtgct ggagtccctc   1080

actgctgtgg acccctctgg aaagggcttt gggccccagt ttcagcacct tctgaggctt   1140

gaggatggag gtgagatcgt aaaggggaga actgagtggc gacccaagac tgcaggtatc   1200

aatgggacga ttgcatctgg ggagacctca cctggaaact cttag                   1245
```

<210> SEQ ID NO 69
<211> LENGTH: 1245
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea heterophylla (Cht) FATB3a coding DNA sequence codon optimized for Prototheca moriformis

<400> SEQUENCE: 69

```
atggtggcca ccgccgcctc ctccgccttc ttccccgtgc cctcccccga cacctcctcc     60

cgccccggca agctgggcaa cggctcctcc tccctgcgcc ccctgaagcc caagttcgtg    120

gccaacgccg gcctgcaggt gaaggccaac gcctccgccc cccccaagat caacggctcc    180

tccgtgtccc tgaagtcctg ctccctgaag acccacgagg acacccccctc cgcccccccc    240

ccccgcacct tcatcaacca gctgcccgac tggtccatgc tgctggccgc catcaccacc    300

gtgttcctgg ccgccgagaa gcagtggatg atgctggact ggaagcccaa gcgccccgac    360

atgctggtgg acccccttcgg cctgggccgc atcgtgcagg acggcctggt gttccgccag    420

aacttctcca tccgctccta cgagatcggc gccgaccgca ccgcctccat cgagaccgtg    480

atgaaccacc tgcaggagac cgccctgaac cacgtgaagt ccgccggcct gctgaacgag    540

ggcttcggcc gcacccccga gatgtacaag cgcgacctga tctgggtggt ggccaagatg    600

caggtgatgg tgaaccgcta ccccacctgg ggcgacaccg tggaggtgaa cacctgggtg    660

gccaagtccg gcaagaacgg catgcgccgc gactggctga tctccgactg caacaccggc    720

gagatcctga cccgcgcctc ctccgtgtgg gtgatgatga accagaagac ccgcaagctg    780

tccaagatcc ccgacgaggt gcgccacgag atcgagcccc acttcgtgga ctccgccccc    840

gtgatcgagg acgacgactg gaagctgccc aagctggacg agaagaccgc cgactccatc    900

cgcaagggcc tgacccccaa gtggaacgac ctggacgtga accagcacgt gaacaacgtg    960

aagtacatcg gctggatcct ggagtccacc ccccccgagg tgctggagac ccaggagctg   1020

tgctccctga ccctggagta ccgccgcgag tgcggccgcg agtccgtgct ggagtccctg   1080

accgccgtgg acccctccgg caagggcttc ggcccccagt tccagcacct gctgcgcctg   1140

gaggacggcg gcgagatcgt gaagggccgc accgagtggc gccccaagac cgccggcatc   1200

aacggcacca tcgcctccgg cgagacctcc cccggcaact cctga                   1245
```

<210> SEQ ID NO 70
<211> LENGTH: 414
<212> TYPE: PRT
<213> ORGANISM: Cuphea heterophylla
<220> FEATURE:
<223> OTHER INFORMATION: Cuphea heterophylla (Cht) FATB3b (C67G, H72Q, L128F, N179I variant) amino acid sequence

<400> SEQUENCE: 70

```
Met Val Ala Thr Ala Ala Ser Ser Ala Phe Phe Pro Val Pro Ser Pro
1               5                   10                  15

Asp Thr Ser Ser Arg Pro Gly Lys Leu Gly Asn Gly Ser Ser Ser Leu
            20                  25                  30

Arg Pro Leu Lys Pro Lys Phe Val Ala Asn Ala Gly Leu Gln Val Lys
        35                  40                  45

Ala Asn Ala Ser Ala Pro Pro Lys Ile Asn Gly Ser Ser Val Ser Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Phe
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Ile Glu Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Trp Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Phe Gly Pro Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Thr Ile Ala Ser Gly Glu Thr Ser Pro Gly Asn Ser
                405                 410
```

<210> SEQ ID NO 71
<211> LENGTH: 1245
<212> TYPE: DNA
<213> ORGANISM: Cuphea heterophylla
<220> FEATURE:
<223> OTHER INFORMATION: Cuphea heterophylla (Cht) FATB3b (C67G, H72Q, L128F, N179I variant) coding DNA sequence

<400> SEQUENCE: 71

```
atggtggcca ccgctgcaag ttctgcattc ttcccggtgc catccccgga cacctcctct     60

agaccgggaa agctcggaaa tgggtcatca agcttgaggc ccctcaagcc caaatttgtt    120

gccaatgctg ggctgcaggt taaggcaaac gccagtgccc ctcctaagat caatggttcc    180

tcggtcagtc taaagtctgg cagtctcaag actcaggaag acactccttc ggctcctcct    240

ccgcggactt ttatcaacca gttgcctgat tggagcatgc ttcttgctgc aatcactact    300

gtcttcttgg cagcagagaa gcagtggatg atgcttgatt ggaaaccaaa gaggcctgac    360

atgcttgtgg acccgttcgg atttggaagg attgttcagg atgggcttgt gttcaggcag    420

aatttttcga ttaggtccta tgaaataggc gctgatcgca ctgcatctat agagacggtg    480

atgaaccact tgcaggaaac ggctctcaat catgttaaga gtgcggggct tcttattgaa    540

ggctttggtc gtactcctga gatgtataaa agggacctta tttgggttgt cgcgaaaatg    600

caggtcatgg ttaaccgcta tcctacttgg ggtgacacgg ttgaagtgaa tacttgggtt    660

gccaagtcag ggaaaaatgg tatgcgtcgt gattggctca taagtgattg caatacagga    720

gaaattctta ctagagcatc aagtgtgtgg gtcatgatga atcaaaagac aagaaaattg    780

tcaaagattc cagatgaggt tcggcatgag atagagcctc attttgtgga ctctgctccc    840

gtcattgaag acgatgactg gaaacttccc aagctggatg agaaaactgc tgactccatc    900

cgcaagggtc taactccgaa gtggaatgac ttggatgtca atcagcacgt caacaacgtg    960

aagtacattg ggtggattct tgagagtact ccaccagaag ttctggagac ccaggagtta   1020

tgttccctta ccctggaata caggcgggaa tgcggaaggg agagtgtgct ggagtccctc   1080

actgctgtgg acccctctgg aaagggcttt gggccccagt ttcagcacct tctgaggctt   1140

gaggatggag gtgagatcgt aaaggggaga actgagtggc gacccaagac tgcaggtatc   1200

aatgggacga ttgcatctgg ggagacctca cctggaaact cttag                   1245
```

<210> SEQ ID NO 72
<211> LENGTH: 1245
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea heterophylla (Cht) FATB3b (C67G, H72Q, L128F, N179I variant) coding DNA sequence codon optimized for Prototheca moriformis

<400> SEQUENCE: 72

```
atggtggcca ccgccgcctc ctccgccttc ttccccgtgc cctcccccga cacctcctcc     60

cgccccggca agctgggcaa cggctcctcc tccctgcgcc ccctgaagcc caagttcgtg    120

gccaacgccg gcctgcaggt gaaggccaac gcctccgccc cccccaagat caacggctcc    180

tccgtgtccc tgaagtccgg ctccctgaag acccaggagg acacccccte cgcccccccc    240

ccccgcacct tcatcaacca gctgcccgac tggtccatgc tgctggccgc catcaccacc    300

gtgttcctgg ccgccgagaa gcagtggatg atgctggact ggaagcccaa gcgccccgac    360
```

```
atgctggtgg accccttcgg cttcggccgc atcgtgcagg acggcctggt gttccgccag    420

aacttctcca tccgctccta cgagatcggc gccgaccgca ccgcctccat cgagaccgtg    480

atgaaccacc tgcaggagac cgccctgaac cacgtgaagt ccgccggcct gctgatcgag    540

ggcttcggcc gcacccccga gatgtacaag cgcgacctga tctgggtggt ggccaagatg    600

caggtgatgg tgaaccgcta ccccacctgg ggcgacaccg tggaggtgaa cacctgggtg    660

gccaagtccg gcaagaacgg catgcgccgc gactggctga tctccgactg caacaccggc    720

gagatcctga cccgcgcctc ctccgtgtgg gtgatgatga accagaagac ccgcaagctg    780

tccaagatcc ccgacgaggt gcgccacgag atcgagcccc acttcgtgga ctccgccccc    840

gtgatcgagg acgacgactg gaagctgccc aagctggacg agaagaccgc cgactccatc    900

cgcaagggcc tgacccccaa gtggaacgac ctggacgtga accagcacgt gaacaacgtg    960

aagtacatcg gctggatcct ggagtccacc ccccccgagg tgctggagac ccaggagctg   1020

tgctccctga ccctggagta ccgccgcgag tgcggccgcg agtccgtgct ggagtccctg   1080

accgccgtgg acccctccgg caagggcttc ggcccccagt tccagcacct gctgcgcctg   1140

gaggacggcg gcgagatcgt gaagggccgc accgagtggc gccccaagac cgccggcatc   1200

aacggcacca tcgcctccgg cgagacctcc cccggcaact cctga                   1245
```

<210> SEQ ID NO 73
<211> LENGTH: 419
<212> TYPE: PRT
<213> ORGANISM: Cuphea viscosissima
<220> FEATURE:
<223> OTHER INFORMATION: Cuphea viscosissima (Cvis) FATB1 amino acid sequence

<400> SEQUENCE: 73

```
Met Val Ala Ala Ala Ala Thr Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Thr Phe Lys Pro Lys Ser Ile Pro Asn Gly Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Ser Ile Val Arg Asp Gly Leu Val Ser Arg His Ser Phe Ser
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Thr Ile Asn His Cys Lys Ser Leu
                165                 170                 175

Gly Leu His Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
```

-continued

```
        195                 200                 205

Pro Thr Trp Gly Asp Thr Val Glu Ile Asn Thr Trp Phe Ser Gln Ser
    210                 215                 220

Gly Lys Ile Gly Met Ala Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Gln
        275                 280                 285

Lys Leu Arg Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Val Asp Pro Ser Glu
        355                 360                 365

Asn Gly Gly Arg Ser Gln Tyr Lys His Leu Leu Arg Leu Glu Asp Gly
    370                 375                 380

Thr Asp Ile Val Lys Ser Arg Thr Glu Trp Arg Pro Lys Asn Ala Gly
385                 390                 395                 400

Thr Asn Gly Ala Ile Ser Thr Ser Thr Ala Lys Thr Ser Asn Gly Asn
                405                 410                 415

Ser Val Ser


<210> SEQ ID NO 74
<211> LENGTH: 1260
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cuphea viscosissima (Cvis) FATB1 coding DNA
      sequence codon optimized for Prototheca moriformis

<400> SEQUENCE: 74

atggtggccg ccgccgccac ctccgccttc ttccccgtgc ccgcccccgg cacctccccc     60

aagcccggca agtccggcaa ctggccctcc tccctgtccc ccaccttcaa gcccaagtcc    120

atccccaacg gcggcttcca ggtgaaggcc aacgcctccg cccaccccaa ggccaacggc    180

tccgccgtga acctgaagtc cggctccctg aacacccagg aggacacctc ctcctccccc    240

ccccccgcg ccttcctgaa ccagctgccc gactggtcca tgctgctgac cgccatcacc    300

accgtgttcg tggccgccga gaagcagtgg accatgctgg accgcaagtc caagcgcccc    360

gacatgctgg tggactccgt gggcctgaag tccatcgtgc gcgacggcct ggtgtcccgc    420

cactccttct ccatccgctc ctacgagatc ggcgccgacc gcaccgcctc catcgagacc    480

ctgatgaacc acctgcagga gaccaccatc aaccactgca agtccctggg cctgcacaac    540

gacggcttcg gccgcacccc cggcatgtgc aagaacgacc tgatctgggt gctgaccaag    600

atgcagatca tggtgaaccg ctaccccacc tggggcgaca ccgtggagat caacacctgg    660
```

-continued

```
ttctcccagt ccggcaagat cggcatggcc tccgactggc tgatctccga ctgcaacacc    720

ggcgagatcc tgatccgcgc cacctccgtg tgggccatga tgaaccagaa gacccgccgc    780

ttctcccgcc tgccctacga ggtgcgccag gagctgaccc cccacttcgt ggactccccc    840

cacgtgatcg aggacaacga ccagaagctg cgcaagttcg acgtgaagac cggcgactcc    900

atccgcaagg gcctgacccc ccgctggaac gacctggacg tgaaccagca cgtgtccaac    960

gtgaagtaca tcggctggat cctggagtcc atgcccatcg aggtgctgga gacccaggag   1020

ctgtgctccc tgaccgtgga gtaccgccgc gagtgcggca tggactccgt gctggagtcc   1080

gtgaccgccg tggacccctc cgagaacggc ggccgctccc agtacaagca cctgctgcgc   1140

ctggaggacg gcaccgacat cgtgaagtcc cgcaccgagt ggcgccccaa gaacgccggc   1200

accaacggcg ccatctccac ctccaccgcc aagacctcca acggcaactc cgtgtcctga   1260


<210> SEQ ID NO 75
<211> LENGTH: 415
<212> TYPE: PRT
<213> ORGANISM: Cuphea viscosissima
<220> FEATURE:
<223> OTHER INFORMATION: Cuphea viscosissima (Cvis) FATB2 amino acid
      sequence

<400> SEQUENCE: 75

Met Val Ala Thr Ala Ala Ser Ser Ala Phe Phe Pro Val Pro Ser Ala
1               5                   10                  15

Asp Thr Ser Ser Arg Pro Gly Lys Leu Gly Asn Gly Pro Ser Ser Phe
            20                  25                  30

Ser Pro Leu Lys Pro Lys Ser Ile Pro Asn Gly Gly Leu Gln Val Lys
        35                  40                  45

Ala Ser Ala Ser Ala Pro Pro Lys Ile Asn Gly Ser Ser Val Gly Leu
    50                  55                  60

Lys Ser Gly Gly Leu Lys Thr His Asp Asp Ala Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Ala Phe Leu Ala Ala Glu Lys Gln Trp Met Met Leu
            100                 105                 110

Asp Arg Lys Pro Lys Arg Leu Asp Met Leu Glu Asp Pro Phe Gly Leu
        115                 120                 125

Gly Arg Val Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Thr Ala Gly
                165                 170                 175

Leu Ser Asn Asp Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255
```

-continued

```
Thr Arg Lys Leu Ser Lys Ile Pro Asp Glu Val Arg Arg Glu Ile Glu
            260                 265                 270

Pro His Phe Val Asp Ser Ala Pro Val Ile Glu Asp Asp Asp Arg Lys
        275                 280                 285

Leu Pro Lys Leu Asp Glu Lys Ser Ala Asp Ser Ile Arg Lys Gly Leu
    290                 295                 300

Thr Pro Arg Trp Asn Asp Leu Asp Val Asn Gln His Val Asn Asn Ala
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Glu
        355                 360                 365

Gly Tyr Gly Ser Gln Phe Gln His Leu Leu Arg Leu Glu Asp Gly Gly
    370                 375                 380

Glu Ile Val Lys Gly Arg Thr Glu Trp Arg Pro Lys Asn Ala Gly Ile
385                 390                 395                 400

Asn Gly Val Val Pro Ser Glu Glu Ser Ser Pro Gly Asp Tyr Ser
                405                 410                 415
```

<210> SEQ ID NO 76
<211> LENGTH: 1248
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea viscosissima (Cvis) FATB2 coding DNA sequence codon optimized for Prototheca moriformis

<400> SEQUENCE: 76

```
atggtggcca ccgccgcctc ctccgccttc ttccccgtgc cctccgccga cacctcctcc     60

cgccccggca agctgggcaa cggcccctcc tccttctccc ccctgaagcc caagtccatc    120

cccaacggcg gcctgcaggt gaaggcctcc gcctccgccc cccccaagat caacggctcc    180

tccgtgggcc tgaagtccgg cggcctgaag acccacgacg acgccccctc cgcccccccc    240

ccccgcacct tcatcaacca gctgcccgac tggtccatgc tgctggccgc catcaccacc    300

gccttcctgg ccgccgagaa gcagtggatg atgctggacc gcaagcccaa gcgcctggac    360

atgctggagg acccccttcgg cctgggccgc gtggtgcagg acggcctggt gttccgccag    420

aacttctcca tccgctccta cgagatcggc gccgaccgca ccgcctccat cgagaccgtg    480

atgaaccacc tgcaggagac cgccctgaac cacgtgaaga ccgccggcct gtccaacgac    540

ggcttcggcc gcacccccga gatgtacaag cgcgacctga tctgggtggt ggccaagatg    600

caggtgatgg tgaaccgcta ccccacctgg ggcgacaccg tggaggtgaa cacctgggtg    660

gccaagtccg gcaagaacgg catgcgccgc gactggctga tctccgactg caacaccggc    720

gagatcctga cccgcgcctc ctccgtgtgg gtgatgatga accagaagac ccgcaagctg    780

tccaagatcc ccgacgaggt gcgccgcgag atcgagcccc acttcgtgga ctccgccccc    840

gtgatcgagg acgacgaccg caagctgccc aagctggacg agaagtccgc cgactccatc    900

cgcaagggcc tgaccccccg ctggaacgac ctggacgtga accagcacgt gaacaacgcc    960

aagtacatcg gctggatcct ggagtccacc ccccccgagg tgctggagac ccaggagctg   1020

tgctccctga ccctggagta ccgccgcgag tgcggccgcg agtccgtgct ggagtccctg   1080
```

```
accgccgtgg accccctccgg cgagggctac ggctcccagt tccagcacct gctgcgcctg   1140

gaggacggcg gcgagatcgt gaagggccgc accgagtggc gccccaagaa cgccggcatc   1200

aacggcgtgg tgccctccga ggagtcctcc cccggcgact actcctga                1248


<210> SEQ ID NO 77
<211> LENGTH: 412
<212> TYPE: PRT
<213> ORGANISM: Cuphea viscosissima
<220> FEATURE:
<223> OTHER INFORMATION: Cuphea viscosissima (Cvis) FATB3 amino acid
      sequence

<400> SEQUENCE: 77

Met Val Ala Ala Ala Ala Ser Ser Ala Phe Phe Ser Phe Pro Thr Pro
1               5                   10                  15

Gly Thr Ser Pro Lys Pro Gly Lys Phe Gly Asn Trp Pro Ser Ser Leu
            20                  25                  30

Ser Ile Pro Phe Asn Pro Lys Ser Asn His Asn Gly Gly Ile Gln Val
        35                  40                  45

Lys Ala Asn Ala Ser Ala His Pro Lys Ala Asn Gly Ser Ala Val Ser
    50                  55                  60

Leu Lys Ala Gly Ser Leu Glu Thr Gln Glu Asp Thr Ser Ser Pro Ser
65                  70                  75                  80

Pro Pro Pro Arg Thr Phe Ile Ser Gln Leu Pro Asp Trp Ser Met Leu
                85                  90                  95

Val Ser Ala Ile Thr Thr Val Phe Val Ala Ala Glu Lys Gln Trp Thr
            100                 105                 110

Met Leu Asp Arg Lys Ser Lys Arg Pro Asp Val Leu Val Glu Pro Phe
        115                 120                 125

Val Gln Asp Gly Val Ser Phe Arg Gln Ser Phe Ser Ile Arg Ser Tyr
    130                 135                 140

Glu Ile Gly Val Asp Arg Thr Ala Ser Ile Glu Thr Leu Met Asn Ile
145                 150                 155                 160

Phe Gln Glu Thr Ser Leu Asn His Cys Lys Ser Leu Gly Leu Leu Asn
                165                 170                 175

Asp Gly Phe Gly Arg Thr Pro Glu Met Cys Lys Arg Asp Leu Ile Trp
            180                 185                 190

Val Val Thr Lys Met Gln Ile Glu Val Asn Arg Tyr Pro Thr Trp Gly
        195                 200                 205

Asp Thr Ile Glu Val Thr Thr Trp Val Ser Glu Ser Gly Lys Asn Gly
    210                 215                 220

Met Ser Arg Asp Trp Leu Ile Ser Asp Cys His Ser Gly Glu Ile Leu
225                 230                 235                 240

Ile Arg Ala Thr Ser Val Trp Ala Met Met Asn Gln Lys Thr Arg Arg
                245                 250                 255

Leu Ser Lys Ile Pro Asp Glu Val Arg Gln Glu Ile Val Pro Tyr Phe
            260                 265                 270

Val Asp Ser Ala Pro Val Ile Glu Asp Asp Arg Lys Leu His Lys Leu
        275                 280                 285

Asp Val Lys Thr Gly Asp Ser Ile Arg Asn Gly Leu Thr Pro Arg Trp
    290                 295                 300

Asn Asp Phe Asp Val Asn Gln His Val Asn Asn Val Lys Tyr Ile Ala
305                 310                 315                 320

Trp Leu Leu Lys Ser Val Pro Thr Glu Val Phe Glu Thr Gln Glu Leu
```

-continued

```
            325                 330                 335

Cys Gly Leu Thr Leu Glu Tyr Arg Arg Glu Cys Arg Arg Asp Ser Val
            340                 345                 350

Leu Glu Ser Val Thr Ala Met Asp Pro Ser Lys Glu Gly Asp Arg Ser
        355                 360                 365

Leu Tyr Gln His Leu Leu Arg Leu Glu Asn Gly Ala Asp Ile Ala Leu
    370                 375                 380

Gly Arg Thr Glu Trp Arg Pro Lys Asn Ala Gly Ala Thr Gly Ala Val
385                 390                 395                 400

Ser Thr Gly Lys Thr Ser Asn Gly Asn Ser Val Ser
                405                 410
```

```
<210> SEQ ID NO 78
<211> LENGTH: 1239
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cuphea viscosissima (Cvis) FATB3 coding DNA
      sequence codon optimized for Prototheca moriformis

<400> SEQUENCE: 78

atggtggccg ccgccgcctc ctccgccttc ttctccttcc ccacccccgg cacctccccc      60

aagcccggca agttcggcaa ctggccctcc tccctgtcca tcccctcaa ccccaagtcc      120

aaccacaacg gcggcatcca ggtgaaggcc aacgcctccg cccaccccaa ggccaacggc     180

tccgccgtgt ccctgaaggc cggctccctg gagacccagg aggacacctc ctcccctcc      240

cccccccccc gcaccttcat ctcccagctg cccgactggt ccatgctggt gtccgccatc     300

accaccgtgt tcgtggccgc cgagaagcag tggaccatgc tggaccgcaa gtccaagcgc     360

cccgacgtgc tggtggagcc cttcgtgcag gacggcgtgt ccttccgcca gtccttctcc     420

atccgctcct acgagatcgg cgtggaccgc accgcctcca tcgagaccct gatgaacatc     480

ttccaggaga cctccctgaa ccactgcaag tccctgggcc tgctgaacga cggcttcggc     540

cgcacccccg agatgtgcaa gcgcgacctg atctgggtgg tgaccaagat gcagatcgag     600

gtgaaccgct accccacctg gggcgacacc atcgaggtga ccacctgggt gtccgagtcc     660

ggcaagaacg gcatgtcccg cgactggctg atctccgact gccactccgg cgagatcctg     720

atccgcgcca cctccgtgtg ggccatgatg aaccagaaga cccgccgcct gtccaagatc     780

cccgacgagg tgcgccagga gatcgtgccc tacttcgtgg actccgcccc cgtgatcgag     840

gacgaccgca agctgcacaa gctggacgtg aagaccggcg actccatccg caacggcctg     900

accccccgct ggaacgactt cgacgtgaac cagcacgtga acaacgtgaa gtacatcgcc     960

tggctgctga agtccgtgcc caccgaggtg ttcgagaccc aggagctgtg cggcctgacc    1020

ctggagtacc gccgcgagtg ccgccgcgac tccgtgctgg agtccgtgac cgccatggac    1080

ccctccaagg agggcgaccg ctccctgtac cagcacctgc tgcgcctgga gaacggcgcc    1140

gacatcgccc tgggccgcac cgagtggcgc cccaagaacg ccggcgccac cggcgccgtg    1200

tccaccggca agacctccaa cggcaactcc gtgtcctga                           1239
```

```
<210> SEQ ID NO 79
<211> LENGTH: 417
<212> TYPE: PRT
<213> ORGANISM: Cuphea calcarata
<220> FEATURE:
```

-continued

<223> OTHER INFORMATION: Cuphea calcarata (Ccalc) FATB1 amino acid
      sequence

<400> SEQUENCE: 79

```
Met Val Ala Ala Ser Ala Ser Ser Ala Phe Phe Ser Val Pro Thr Pro
1               5                   10                  15

Gly Thr Ser Pro Lys Pro Gly Lys Phe Gly Asn Trp Pro Ser Ser Leu
            20                  25                  30

Ser Val Pro Phe Lys Pro Arg Ser Asn Asn Ser Gly Gly Phe Gln Val
        35                  40                  45

Lys Ala Asn Ala Ser Ala His Pro Lys Ala Asn Gly Ser Ala Val Ser
    50                  55                  60

Leu Lys Ser Gly Ser Leu Glu Thr Gln Glu Asp Asn Ser Ser Ser Ser
65                  70                  75                  80

Arg Pro Pro Arg Thr Phe Ile Lys Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Phe Asp Arg Lys Ser Lys Arg Ser Asp Met Leu Val Asp Pro Phe
        115                 120                 125

Val Val Asp Arg Ile Val Gln Asp Gly Val Leu Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Met Gly Leu Leu Tyr Glu Gly Phe Gly Arg Thr Pro Glu Met Cys Lys
            180                 185                 190

Arg Asp Leu Ile Trp Val Val Thr Lys Ile His Ile Lys Val Asn Arg
        195                 200                 205

Tyr Pro Thr Trp Gly Asp Thr Ile Glu Val Thr Thr Trp Val Ser Glu
    210                 215                 220

Ser Gly Lys Asn Gly Met Gly Arg Asp Trp Leu Ile Ser Asp Cys His
225                 230                 235                 240

Thr Gly Glu Ile Leu Ile Arg Ala Thr Ser Val Trp Ala Met Met Asn
                245                 250                 255

Gln Thr Thr Arg Arg Leu Ser Lys Phe Pro Tyr Glu Leu Arg Gln Glu
            260                 265                 270

Ile Ala Pro His Phe Val Asp Ser Asp Pro Val Ile Glu Asp Asn Arg
        275                 280                 285

Arg Leu Leu Asn Phe Asp Val Lys Thr Gly Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Asp Thr Arg Glu Leu Cys Gly Leu Thr Leu Glu Tyr Arg Gln Glu Cys
            340                 345                 350

Gly Arg Gly Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Thr Asp Ile Val Lys Gly Arg Thr Glu Trp Arg Pro Lys Asn Ala Gly
385                 390                 395                 400
```

Thr Asn Gly Pro Val Ser Thr Arg Lys Thr Thr Asn Gly Ser Ser Val
405 410 415

Ser

<210> SEQ ID NO 80
<211> LENGTH: 1254
<212> TYPE: DNA
<213> ORGANISM: Cuphea calcarata
<220> FEATURE:
<223> OTHER INFORMATION: Cuphea calcarata (Ccalc) FATB1 coding DNA sequence

<400> SEQUENCE: 80
atggtggctg cttcagcaag ttctgcattc ttctccgtcc caacccccggg aacctctcct 60 aaacccggga agttcggcaa ttggccatcg agcttgagcg tcccattcaa gcccagatca 120
aacaacagtg gcggctttca ggttaaggca aacgccagtg ctcatcctaa ggctaacggt 180
tctgcagtaa gtctaaagtc tgggagcctc gagactcagg aggacaattc gtcgtcgtct 240
cgtcctcctc ggactttcat taaacagttg ccggactgga gtatgcttct ttccgcgatc 300
acaaccgtct tcgtggcggc tgagaagcag tggacgatgt ttgatcggaa atctaagagg 360
tctgacatgc tcgtggaccc gtttgtggtt gacaggattg ttcaggatgg ggttctgttc 420
agacagagtt tttcgattag gtcttacgaa ataggcgctg atcgaacagc ctctattgag 480
acgctgatga acatcttcca ggaaacatct ctcaatcatt gtaagagtat gggtcttctc 540
tatgaaggct ttggtcgtac tcctgagatg tgtaagaggg acctcatttg ggtggttacg 600
aaaatacata tcaaggtgaa tcgctatccg acttggggtg atactatcga ggtcactact 660
tgggtctccg agtcgggcaa aaacggtatg ggtcgcgatt ggctgataag tgattgccat 720
acaggagaaa ttcttataag agcaacgagt gtgtgggcta tgatgaatca aacgacgaga 780
agattgtcga aatttccata tgagcttcga caggagatag cgccacattt tgtggactcg 840
gatcctgtca ttgaagacaa tcgaagattg ctcaactttg atgtgaagac gggtgattcc 900
attcgcaagg gtctaactcc aaggtggaat gacttggatg tcaatcagca cgttaacaat 960
gtgaagtaca ttgggtggat tctcgagagt gttccaacag aagttttcga tacccgggag 1020
ctatgcggcc tcacccttga gtataggcag gaatgcggaa gaggaagtgt gctggagtcc 1080
gtgaccgcta tggatccctc aaaagaggga gaccggtctc tgtaccagca ccttcttcgg 1140
cttgaggatg ggactgatat cgtgaagggc agaaccgagt ggcggccaaa gaatgcagga 1200
accaatgggc cagtatcaac aagaaagact acaaatggaa gctcagtctc ttag 1254

<210> SEQ ID NO 81
<211> LENGTH: 1254
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea calcarata (Ccalc) FATB1 coding DNA sequence codon optimized for Prototheca moriformis

<400> SEQUENCE: 81
atggtggccg cctccgcctc ctccgccttc ttctccgtgc ccaccccccgg cacctccccc 60 aagcccggca agttcggcaa ctggccctcc tccctgtccg tgcccttcaa gccccgctcc 120
aacaactccg gcggcttcca ggtgaaggcc aacgcctccg cccaccccaa ggccaacggc 180

-continued

```
tccgccgtgt ccctgaagtc cggctccctg gagacccagg aggacaactc ctcctcctcc    240

cgcccccccc gcaccttcat caagcagctg cccgactggt ccatgctgct gtccgccatc    300

accaccgtgt tcgtggccgc cgagaagcag tggaccatgt tcgaccgcaa gtccaagcgc    360

tccgacatgc tggtggaccc cttcgtggtg gaccgcatcg tgcaggacgg cgtgctgttc    420

cgccagtcct tctccatccg ctcctacgag atcggcgccg accgcaccgc ctccatcgag    480

accctgatga acatcttcca ggagacctcc ctgaaccact gcaagtccat gggcctgctg    540

tacgagggct tcggccgcac ccccgagatg tgcaagcgcg acctgatctg ggtggtgacc    600

aagatccaca tcaaggtgaa ccgctacccc acctggggcg acaccatcga ggtgaccacc    660

tgggtgtccg agtccggcaa gaacggcatg ggccgcgact ggctgatctc cgactgccac    720

accggcgaga tcctgatccg cgccacctcc gtgtgggcca tgatgaacca gaccacccgc    780

cgcctgtcca agttccccta cgagctgcgc caggagatcg ccccccactt cgtggactcc    840

gaccccgtga tcgaggacaa ccgccgcctg ctgaacttcg acgtgaagac cggcgactcc    900

atccgcaagg gcctgacccc ccgctggaac gacctggacg tgaaccagca cgtgaacaac    960

gtgaagtaca tcggctggat cctggagtcc gtgcccaccg aggtgttcga cacccgcgag   1020

ctgtgcggcc tgaccctgga gtaccgccag gagtgcggcc gcggctccgt gctggagtcc   1080

gtgaccgcca tggacccctc caaggagggc gaccgctccc tgtaccagca cctgctgcgc   1140

ctggaggacg gcaccgacat cgtgaagggc cgcaccgagt ggcgccccaa gaacgccggc   1200

accaacggcc ccgtgtccac ccgcaagacc accaacggct cctccgtgtc ctga         1254
```

<210> SEQ ID NO 82
<211> LENGTH: 415
<212> TYPE: PRT
<213> ORGANISM: Cuphea painteri
<220> FEATURE:
<223> OTHER INFORMATION: Cuphea painteri (Cpai) FATB1 amino acid sequence

<400> SEQUENCE: 82

```
Met Val Ala Ala Ala Ala Thr Ser Ala Phe Phe Pro Val Pro Ala Pro
1               5                   10                  15

Gly Thr Ser Pro Asn Pro Arg Lys Phe Gly Ser Trp Pro Ser Ser Leu
            20                  25                  30

Ser Pro Ser Leu Pro Lys Ser Ile Pro Asn Gly Gly Phe Gln Val Lys
        35                  40                  45

Ala Asn Ala Ser Ala His Pro Lys Ala Asn Gly Ser Ala Val Ser Leu
    50                  55                  60

Lys Ser Gly Ser Leu Asn Thr Gln Glu Asn Thr Ser Ser Ser Pro Pro
65                  70                  75                  80

Pro Arg Thr Phe Leu His Gln Leu Pro Asp Trp Ser Arg Leu Leu Thr
                85                  90                  95

Ala Ile Thr Thr Val Phe Val Lys Ser Lys Arg Pro Asp Met His Asp
            100                 105                 110

Arg Lys Ser Lys Arg Pro Asp Met Leu Val Asp Leu Phe Gly Leu Glu
        115                 120                 125

Ser Ser Val Gln Asp Ala Leu Val Phe Arg Gln Ser Phe Ser Ile Arg
    130                 135                 140

Ser Tyr Glu Ile Gly Thr Asp Arg Thr Ala Ser Ile Glu Thr Leu Met
145                 150                 155                 160

Asn His Leu Gln Glu Thr Ser Leu Asn His Cys Lys Ser Thr Gly Ile
                165                 170                 175
```

-continued

```
Leu Leu Asp Gly Phe Gly Arg Thr Leu Glu Met Cys Lys Arg Glu Leu
            180                 185                 190

Ile Trp Val Val Ile Lys Met Gln Ile Gln Val Asn Arg Tyr Pro Ala
        195                 200                 205

Trp Gly Asp Thr Val Glu Ile Asn Thr Arg Phe Ser Arg Leu Gly Lys
    210                 215                 220

Ile Gly Met Gly Arg Asp Trp Leu Ile Ser Asp Cys Asn Thr Gly Glu
225                 230                 235                 240

Ile Leu Ile Arg Ala Thr Ser Glu Tyr Ala Met Met Asn Gln Lys Thr
                245                 250                 255

Arg Arg Leu Ser Lys Leu Pro Tyr Glu Val His Gln Glu Ile Ala Pro
            260                 265                 270

Leu Phe Val Asp Ser Pro Pro Val Ile Glu Asp Asn Asp Leu Lys Val
        275                 280                 285

His Lys Phe Glu Val Lys Thr Gly Asp Ser Ile Gln Lys Gly Leu Ser
    290                 295                 300

Pro Gly Trp Asn Asp Leu Asp Val Asn Gln His Val Ser Asn Val Lys
305                 310                 315                 320

Tyr Ile Gly Trp Ile Leu Glu Ser Met Pro Thr Glu Val Leu Glu Thr
                325                 330                 335

Gln Glu Leu Cys Ser Leu Ala Leu Glu Tyr Arg Arg Glu Cys Gly Arg
            340                 345                 350

Asp Ser Val Leu Glu Ser Val Thr Ala Met Asp Pro Ser Lys Val Gly
        355                 360                 365

Gly Arg Ser Gln Tyr Gln His Leu Leu Arg Leu Glu Asp Gly Thr Ala
    370                 375                 380

Ile Val Asn Gly Ile Thr Glu Trp Arg Pro Lys Asn Ala Gly Ala Asn
385                 390                 395                 400

Gly Ala Ile Ser Thr Gly Lys Thr Ser Asn Gly Asn Ser Val Ser
                405                 410                 415
```

<210> SEQ ID NO 83
<211> LENGTH: 1248
<212> TYPE: DNA
<213> ORGANISM: Cuphea painteri
<220> FEATURE:
<223> OTHER INFORMATION: Cuphea painteri (Cpai) FATB1 coding DNA sequence

<400> SEQUENCE: 83

```
atggtggctg ctgcagcaac ttctgcattc ttccctgttc cagccccggg aacctcccca      60

aatcccagga aattcggaag ttggccatcg agcttgagcc cttccttgcc caagtcaatc     120

cccaatggcg gatttcaggt aaaggcaaat gccagtgccc atccgaaggc taacggttct     180

gcagttagtc taaagtctgg cagcctcaac actcaggaga acacttcgtc gtcccctcct     240

cctcggactt tccttcacca gttgcctgat tggagtaggc ttctgactgc aatcacgacc     300

gtgttcgtga aatctaagag gcctgacatg catgatcgga aatctaagag gcctgacatg     360

ctggtggact tgtttgggtt ggaaagtagt gttcaggatg cgctcgtgtt cagacagagt     420

ttttcgatta ggtcttatga aataggcact gatcgaacag cctctataga gacgctgatg     480

aaccacttgc aggaaacatc tctcaatcat tgtaaaagta ccggtattct ccttgacggc     540

ttcggtcgta ctcttgagat gtgtaaaagg gaactcattt gggtggtaat aaaaatgcaa     600

attcaggtga atcgctatcc agcatggggc gatactgtcg agatcaatac ccggttctcc     660
```

-continued cggttgggga aaattggtat gggtcgcgat tggctaataa gtgattgcaa cacaggagaa 720
attctaataa gagcaacgag cgagtatgcc atgatgaatc aaaagacgag aagactctca 780
aaacttccat acgaggttca ccaggagata gcgcctcttt ttgtcgactc tcctcctgtg 840
attgaagaca atgatctgaa agtgcataaa tttgaagtga agactggtga ttccattcaa 900
aagggtctat ccccggggtg gaatgacttg gatgtcaatc agcacgtaag caacgtgaag 960
tacattgggt ggattctcga gagtatgcca acagaagttt tggagaccca ggagctatgc 1020
tctctcgccc ttgaatatag gcgggaatgc ggaagggaca gtgtgctgga gtccgtgacc 1080
gcaatggatc cctcaaaagt tggaggccgt tctcagtacc agcaccttct gcggcttgag 1140
gatgggactg ctatcgtgaa cggcataact gagtggcggc cgaagaatgc aggagctaat 1200
ggggcgatat caacgggaaa gacttcaaat ggaaactcgg tctcttag 1248

<210> SEQ ID NO 84
<211> LENGTH: 1248
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea painteri (Cpai) FATB1 coding DNA sequence codon optimized for Prototheca moriformis

<400> SEQUENCE: 84
atggtggccg ccgccgccac ctccgccttc ttccccgtgc ccgcccccgg cacctccccc 60
aacccccgca agttcggctc ctggccctcc tccctgtccc cctccctgcc caagtccatc 120
cccaacggcg gcttccaggt gaaggccaac gcctccgccc accccaaggc caacggctcc 180
gccgtgtccc tgaagtccgg ctccctgaac acccaggaga acacctcctc ctcccccccc 240
ccccgcacct tcctgcacca gctgcccgac tggtcccgcc tgctgaccgc catcaccacc 300
gtgttcgtga agtccaagcg ccccgacatg cacgaccgca agtccaagcg ccccgacatg 360
ctggtggacc tgttcggcct ggagtcctcc gtgcaggacg ccctggtgtt ccgccagtcc 420
ttctccatcc gctcctacga gatcggcacc gaccgcaccg cctccatcga gaccctgatg 480
aaccacctgc aggagacctc cctgaaccac tgcaagtcca ccggcatcct gctggacggc 540
ttcggccgca ccctggagat gtgcaagcgc gagctgatct gggtggtgat caagatgcag 600
atccaggtga accgctaccc cgcctggggc gacaccgtgg agatcaacac ccgcttctcc 660
cgcctgggca agatcggcat gggccgcgac tggctgatct ccgactgcaa caccggcgag 720
atcctgatcc gcgccacctc cgagtacgcc atgatgaacc agaagacccg ccgcctgtcc 780
aagctgccct acgaggtgca ccaggagatc gccccccctgt tcgtggactc ccccccgtg 840 atcgaggaca acgacctgaa ggtgcacaag ttcgaggtga agaccggcga ctccatccag 900
aagggcctgt cccccggctg gaacgacctg gacgtgaacc agcacgtgtc caacgtgaag 960
tacatcggct ggatcctgga gtccatgccc accgaggtgc tggagaccca ggagctgtgc 1020
tccctggccc tggagtaccg ccgcgagtgc ggccgcgact ccgtgctgga gtccgtgacc 1080
gccatggacc cctccaaggt gggcggccgc tcccagtacc agcacctgct gcgcctggag 1140
gacggcaccg ccatcgtgaa cggcatcacc gagtggcgcc ccaagaacgc cggcgccaac 1200
ggcgccatct ccaccggcaa gacctccaac ggcaactccg tgtcctga 1248

<210> SEQ ID NO 85
<211> LENGTH: 414

```
<212> TYPE: PRT
<213> ORGANISM: Cuphea hookeriana
<220> FEATURE:
<223> OTHER INFORMATION: Cuphea hookeriana (Chook) FATB4 amino acid
      sequence

<400> SEQUENCE: 85

Met Val Ala Ala Ala Ala Thr Ser Ala Phe Phe Pro Val Pro Ala Pro
1               5                   10                  15

Gly Thr Ser Pro Asn Pro Arg Lys Phe Gly Ser Trp Pro Ser Ser Leu
            20                  25                  30

Ser Pro Ser Leu Pro Asn Ser Ile Pro Asn Gly Gly Phe Gln Val Lys
        35                  40                  45

Ala Asn Ala Ser Ala His Pro Lys Ala Asn Gly Ser Ala Val Ser Leu
    50                  55                  60

Lys Ser Gly Ser Leu Asn Thr Gln Glu Asn Thr Ser Ser Ser Pro Pro
65                  70                  75                  80

Pro Arg Thr Phe Leu His Gln Leu Pro Asp Trp Ser Arg Leu Leu Thr
                85                  90                  95

Ala Ile Thr Thr Val Phe Val Lys Ser Lys Arg Pro Asp Met His Asp
            100                 105                 110

Arg Lys Ser Lys Arg Pro Asp Met Leu Val Asp Leu Phe Gly Leu Glu
        115                 120                 125

Ser Ser Val Gln Asp Ala Leu Val Phe Arg Gln Arg Phe Ser Ile Arg
    130                 135                 140

Ser Tyr Glu Ile Gly Thr Asp Arg Thr Ala Ser Met Glu Thr Leu Met
145                 150                 155                 160

Asn His Leu Gln Glu Thr Ser Leu Asn His Cys Lys Ser Thr Gly Ile
                165                 170                 175

Leu Leu Asp Gly Phe Gly Arg Thr Leu Glu Met Cys Lys Arg Glu Leu
            180                 185                 190

Ile Trp Val Val Ile Lys Met Gln Ile Gln Val Asn Arg Tyr Pro Ala
        195                 200                 205

Trp Gly Asp Thr Val Glu Ile Asn Thr Arg Phe Ser Arg Leu Gly Lys
    210                 215                 220

Ile Gly Met Gly Arg Asp Trp Leu Ile Ser Asp Cys Asn Thr Gly Glu
225                 230                 235                 240

Ile Leu Ile Arg Ala Thr Ser Glu Tyr Ala Met Met Asn Gln Lys Thr
                245                 250                 255

Arg Arg Leu Ser Lys Leu Pro Tyr Glu Val Arg Gln Glu Ile Ala Pro
            260                 265                 270

Leu Phe Val Asp Ser Pro Pro Val Ile Glu Asp Asn Asp Leu Lys Val
        275                 280                 285

His Lys Phe Glu Val Lys Thr Gly Asp Ser Ile His Lys Gly Leu Thr
    290                 295                 300

Pro Gly Trp Asn Asp Leu Asp Val Asn Gln His Val Asn Asn Val Lys
305                 310                 315                 320

Tyr Ile Gly Trp Ile Leu Glu Ser Thr Pro Pro Glu Val Leu Glu Thr
                325                 330                 335

Gln Glu Leu Cys Ser Leu Thr Leu Glu Tyr Arg Arg Glu Cys Gly Arg
            340                 345                 350

Glu Ser Val Leu Glu Ser Leu Thr Ala Met Asp Pro Ser Gly Gly Gly
        355                 360                 365

Tyr Gly Ser Gln Phe Gln His Leu Leu Arg Leu Glu Asp Gly Gly Glu
    370                 375                 380
```

Ile Val Lys Gly Arg Thr Glu Trp Arg Pro Lys Asn Gly Val Ile Asn
385 390 395 400

Gly Val Val Pro Thr Gly Glu Ser Ser Pro Gly Asp Tyr Ser
405 410

<210> SEQ ID NO 86
<211> LENGTH: 1245
<212> TYPE: DNA
<213> ORGANISM: Cuphea hookeriana
<220> FEATURE:
<223> OTHER INFORMATION: Cuphea hookeriana (Chook) FATB4 coding DNA sequence

<400> SEQUENCE: 86
atggtggctg ctgcagcaac ttctgcattc ttccctgttc cagccccggg aacctcccct 60
aatcccagga aattcggaag ttggccatcg agcttgagcc cttccttgcc caactcaatc 120
cccaatggcg gatttcaggt aaaggcaaat gccagtgccc atccgaaggc taacggttct 180
gcagttagtc taaagtctgg cagcctcaac actcaggaga acacttcgtc gtcccctcct 240
cctcggactt tccttcacca gttgcctgat tggagtaggc ttctgactgc aatcacgacc 300
gtgttcgtga aatctaagag gcctgacatg catgatcgga aatctaagag gcctgacatg 360
ctggtggact tgtttgggtt ggagagtagt gttcaggatg cgctcgtgtt cagacagaga 420
ttttcgatta ggtcttatga aataggcact gatcgaacag cctctatgga gacgctgatg 480
aaccacttgc aggaaacatc tctcaatcat tgtaaaagta ccggtattct ccttgacggc 540
ttcggtcgta ctcttgagat gtgtaaaagg gaactcattt gggtggtaat aaaaatgcag 600
attcaggtga atcgctatcc agcatggggc gatactgtcg agatcaatac ccggttctcc 660
cggttgggga aaattggtat gggtcgcgat tggctaataa gtgattgcaa cacaggagaa 720
attcttataa gagcaacgag cgagtatgcc atgatgaatc aaaagacgag aagactctca 780
aaacttccat acgaggttcg ccaggagata gcgcctcttt ttgtcgactc tcctcctgtg 840
attgaagaca atgatctgaa agtgcataaa tttgaagtga agactggtga ttccattcac 900
aagggtctaa ctccggggtg gaatgacttg gatgtcaatc agcacgtcaa caacgtgaag 960
tacatcgggt ggattcttga gagtactcca ccagaagttc tggagaccca ggagttatgt 1020
tcccttactc tggaatacag gcgggaatgt ggaagggaga gcgtgctgga gtccctcact 1080
gctatggatc cctctggagg gggttatggg tcccagtttc agcaccttct gcggcttgag 1140
gatggaggtg agatcgtgaa ggggagaacc gagtggcgac ccaagaatgg tgtaatcaat 1200
ggggtggtac caaccgggga gtcctcacct ggagactact cttag 1245

<210> SEQ ID NO 87
<211> LENGTH: 1245
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea hookeriana (Chook) FATB4 coding DNA sequence codon optimized for Prototheca moriformis

<400> SEQUENCE: 87
atggtggccg ccgccgccac ctccgccttc ttccccgtgc ccgcccccgg cacctccccc 60
aacccccgca agttcggctc ctggccctcc tccctgtccc cctccctgcc caactccatc 120
cccaacggcg gcttccaggt gaaggccaac gcctccgccc accccaaggc caacggctcc 180

-continued

```
gccgtgtccc tgaagtccgg ctccctgaac acccaggaga acacctcctc ctcccccccc    240

ccccgcacct tcctgcacca gctgcccgac tggtcccgcc tgctgaccgc catcaccacc    300

gtgttcgtga agtccaagcg ccccgacatg cacgaccgca agtccaagcg ccccgacatg    360

ctggtggacc tgttcggcct ggagtcctcc gtgcaggacg ccctggtgtt ccgccagcgc    420

ttctccatcc gctcctacga gatcggcacc gaccgcaccg cctccatgga gaccctgatg    480

aaccacctgc aggagacctc cctgaaccac tgcaagtcca ccggcatcct gctggacggc    540

ttcggccgca ccctggagat gtgcaagcgc gagctgatct gggtggtgat caagatgcag    600

atccaggtga accgctaccc cgcctggggc gacaccgtgg agatcaacac ccgcttctcc    660

cgcctgggca agatcggcat gggccgcgac tggctgatct ccgactgcaa caccggcgag    720

atcctgatcc gcgccacctc cgagtacgcc atgatgaacc agaagacccg ccgcctgtcc    780

aagctgccct acgaggtgcg ccaggagatc gcccccctgt tcgtggactc cccccccgtg    840

atcgaggaca acgacctgaa ggtgcacaag ttcgaggtga agaccggcga ctccatccac    900

aagggcctga cccccggctg gaacgacctg gacgtgaacc agcacgtgaa caacgtgaag    960

tacatcggct ggatcctgga gtccaccccc cccgaggtgc tggagaccca ggagctgtgc   1020

tccctgaccc tggagtaccg ccgcgagtgc ggccgcgagt ccgtgctgga gtccctgacc   1080

gccatggacc cctccggcgg cggctacggc tcccagttcc agcacctgct gcgcctggag   1140

gacggcggcg agatcgtgaa gggccgcacc gagtggcgcc ccaagaacgg cgtgatcaac   1200

ggcgtggtgc ccaccggcga gtcctccccc ggcgactact cctga                   1245
```

<210> SEQ ID NO 88
<211> LENGTH: 416
<212> TYPE: PRT
<213> ORGANISM: Cuphea avigera
<220> FEATURE:
<223> OTHER INFORMATION: Cuphea avigera var. pulcherrima (Ca) FATB1
      amino acid sequence

<400> SEQUENCE: 88

```
Met Val Ala Ala Ala Ala Ser Ser Ala Phe Phe Ser Val Pro Val Pro
1               5                   10                  15

Gly Thr Ser Pro Lys Pro Gly Lys Phe Arg Ile Trp Pro Ser Ser Leu
            20                  25                  30

Ser Pro Ser Phe Lys Pro Lys Pro Ile Pro Asn Gly Gly Leu Gln Val
        35                  40                  45

Lys Ala Asn Ser Arg Ala His Pro Lys Ala Asn Gly Ser Ala Val Ser
    50                  55                  60

Leu Lys Ser Gly Ser Leu Asn Thr Gln Glu Asp Thr Ser Ser Ser Pro
65                  70                  75                  80

Pro Pro Arg Thr Phe Leu His Gln Leu Pro Asp Trp Ser Arg Leu Leu
                85                  90                  95

Thr Ala Ile Thr Thr Val Phe Val Lys Ser Lys Arg Pro Asp Met His
            100                 105                 110

Asp Arg Lys Ser Lys Arg Pro Asp Met Leu Met Asp Ser Phe Gly Leu
        115                 120                 125

Glu Ser Ile Val Gln Glu Gly Leu Glu Phe Arg Gln Ser Phe Ser Ile
    130                 135                 140

Arg Ser Tyr Glu Ile Gly Thr Asp Arg Thr Ala Ser Ile Glu Thr Leu
145                 150                 155                 160

Met Asn Tyr Leu Gln Glu Thr Ser Leu Asn His Cys Lys Ser Thr Gly
```

```
                165                 170                 175

Ile Leu Leu Asp Gly Phe Gly Arg Thr Pro Glu Met Cys Lys Arg Asp
            180                 185                 190

Leu Ile Trp Val Val Thr Lys Met Lys Ile Lys Val Asn Arg Tyr Pro
        195                 200                 205

Ala Trp Gly Asp Thr Val Glu Ile Asn Thr Trp Phe Ser Arg Leu Gly
    210                 215                 220

Lys Ile Gly Lys Gly Arg Asp Trp Leu Ile Ser Asp Cys Asn Thr Gly
225                 230                 235                 240

Glu Ile Leu Ile Arg Ala Thr Ser Ala Tyr Ala Thr Met Asn Gln Lys
                245                 250                 255

Thr Arg Arg Leu Ser Lys Leu Pro Tyr Glu Val His Gln Glu Ile Ala
            260                 265                 270

Pro Leu Phe Val Asp Ser Pro Pro Val Ile Glu Asp Asn Asp Leu Lys
        275                 280                 285

Leu His Lys Phe Glu Val Lys Thr Gly Asp Ser Ile His Lys Gly Leu
    290                 295                 300

Thr Pro Gly Trp Asn Asp Leu Asp Val Asn Gln His Val Ser Asn Val
305                 310                 315                 320

Lys Tyr Ile Gly Trp Ile Leu Glu Ser Met Pro Thr Glu Val Leu Glu
                325                 330                 335

Thr Gln Glu Leu Cys Ser Leu Ala Leu Glu Tyr Arg Arg Glu Cys Gly
            340                 345                 350

Arg Asp Ser Val Leu Glu Ser Val Thr Ala Met Asp Pro Thr Lys Val
        355                 360                 365

Gly Gly Arg Ser Gln Tyr Gln His Leu Leu Arg Leu Glu Asp Gly Thr
    370                 375                 380

Asp Ile Val Lys Cys Arg Thr Glu Trp Arg Pro Lys Asn Pro Gly Ala
385                 390                 395                 400

Asn Gly Ala Ile Ser Thr Gly Lys Thr Ser Asn Gly Asn Ser Val Ser
                405                 410                 415
```

<210> SEQ ID NO 89
<211> LENGTH: 1251
<212> TYPE: DNA
<213> ORGANISM: Cuphea avigera
<220> FEATURE:
<223> OTHER INFORMATION: Cuphea avigera var. pulcherrima (Ca) FATB1
coding DNA sequence

<400> SEQUENCE: 89

```
atggtggctg ctgcagcaag ttctgcattc ttctctgttc cagtcccggg aacctctcct     60

aaacccggga agttcagaat ttggccatcg agcttgagcc cttccttcaa gcccaagccg    120

atccccaatg gtggattgca ggttaaggca aattccaggg cacatccgaa ggctaacggt    180

tctgcagtta gtctaaagtc tggcagcctc aacactcagg aggacacttc gtcgtcccct    240

cctcctcgga ctttccttca ccagttgcct gattggagta ggcttctgac tgcaatcacg    300

accgtgttcg tgaaatctaa gaggcctgac atgcatgatc ggaaatctaa gaggcctgac    360

atgctgatgg actcgtttgg gttggagagt attgttcaag aagggctcga gttcagacag    420

agtttttcga ttaggtctta tgaaataggc actgatcgaa cagcctctat agagacgctg    480

atgaactact tgcaggaaac atctctcaat cattgtaaga gtaccggtat tctccttgac    540

ggctttggtc gtactcctga gatgtgtaaa agggacctca tttgggtggt aacaaaaatg    600

aagatcaagg tgaatcgcta tccagcttgg ggcgatactg tcgagatcaa tacctggttc    660
```

tcccggttgg ggaaaatcgg aaagggtcgc gattggctaa taagtgattg caacacagga 720
gaaattctta taagagcaac gagcgcgtat gccacgatga atcaaaagac gagaagactc 780
tcaaaacttc catacgaggt tcaccaggag atagcgcctc tctttgtcga ctctcctcct 840
gtcattgaag acaatgatct gaaattgcat aagtttgaag tgaagactgg tgattccatt 900
cacaagggtc taactccggg gtggaatgac ttggatgtca atcagcacgt aagcaacgtg 960
aagtacattg ggtggattct cgagagtatg ccaacagaag ttttggagac ccaggagcta 1020
tgctctctcg cccttgaata taggcgggaa tgcggaaggg acagtgtgct agagtccgtg 1080
acagctatgg atcccacaaa agttggaggc cggtctcagt accagcacct tctgcgactt 1140
gaggatggga ctgatatcgt gaagtgcaga actgagtggc ggccgaagaa tccaggagct 1200
aatggggcaa tatcaacggg aaagacttca aatggaaact cggtctctta g 1251

<210> SEQ ID NO 90
<211> LENGTH: 1248
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea avigera var. pulcherrima (Ca) FATB1 coding DNA sequence codon optimized for Prototheca moriformis

<400> SEQUENCE: 90
atggtggccg ccgccgcctc ctccgccttc ttctccgtgc ccgtgcccgg cacctccccc 60
aagcccggca agttccgcat ctggccctcc tccctgtccc cctccttcaa gcccaagccc 120
atccccaacg gcggcctgca ggtgaaggcc aactcccgcg cccaccccaa ggccaacggc 180
tccgccgtgt ccctgaagtc cggctccctg aacacccagg aggacacctc ctcctccccc 240 ccccccgca ccttcctgca ccagctgccc gactggtccc gcctgctgac cgccatcacc 300
accgtgttcg tgaagtccaa gcgccccgac atgcacgacc gcaagtccaa gcgccccgac 360
atgctgatgg actccttcgg cctggagtcc atcgtgcagg agggcctgga gttccgccag 420
tccttctcca tccgctccta cgagatcggc accgaccgca ccgcctccat cgagaccctg 480
atgaactacc tgcaggagac ctccctgaac cactgcaagt ccaccggcat cctgctggac 540
ggcttcggcc gcacccccga gatgtgcaag cgcgacctga tctgggtggt gaccaagatg 600
aagatcaagg tgaaccgcta ccccgcctgg ggcgacaccg tggagatcaa cacctggttc 660
tcccgcctgg gcaagatcgg caagggccgc gactggctga tctccgactg caacaccggc 720
gagatcctga tccgcgccac ctccgcctac gccaccatga accagaagac ccgccgcctg 780
tccaagctgc cctacgaggt gcaccaggag atcgcccccc tgttcgtgga ctcccccccc 840
gtgatcgagg acaacgacct gaagctgcac aagttcgagg tgaagaccgg cgactccatc 900
cacaagggcc tgacccccgg ctggaacgac ctggacgtga accagcacgt gtccaacgtg 960
aagtacatcg gctggatcct ggagtccatg cccaccgagg tgctggagac ccaggagctg 1020
tgctccctgg ccctggagta ccgccgcgag tgcggccgcg actccgtgct ggagtccgtg 1080
accgccatgg accccaccaa ggtgggcggc cgctcccagt accagcacct gctgcgcctg 1140
gaggacggca ccgacatcgt gaagtgccgc accgagtggc gccccaagaa ccccggcgcc 1200
aacggcgcca tctccaccgg caagacctcc aacggcaact ccgtgtcc 1248

<210> SEQ ID NO 91

```
<211> LENGTH: 417
<212> TYPE: PRT
<213> ORGANISM: Cuphea paucipetala
<220> FEATURE:
<223> OTHER INFORMATION: Cuphea paucipetala (Cpau) FATB1 amino acid
      sequence

<400> SEQUENCE: 91

Met Val Ala Ala Ala Ala Ser Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Ser Ile Lys Pro Met Ser Ile Pro Asn Gly Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Arg Asp Arg Lys Ser Lys Arg Pro Asp Met Leu Val Asp Ser Val Gly
        115                 120                 125

Leu Lys Ser Val Val Leu Asp Gly Leu Val Ser Arg Gln Ile Phe Ser
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Ile Asn Thr Trp Phe Ser His Ser
    210                 215                 220

Gly Lys Ile Gly Met Ala Ser Asp Trp Leu Ile Thr Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Tyr Val Asp Ser Pro His Val Ile Glu Asp Asn Asp Arg
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Met Asp Pro Ser Glu
        355                 360                 365

Asp Glu Gly Arg Ser Gln Tyr Lys His Leu Leu Arg Leu Glu Asp Gly
```

```
    370                 375                 380

Thr Asp Ile Val Lys Gly Arg Thr Glu Trp Arg Pro Lys Asn Ala Gly
385                 390                 395                 400

Thr Asn Gly Ala Ile Ser Thr Ala Lys Pro Ser Asn Gly Asn Ser Val
                405                 410                 415

Ser


<210> SEQ ID NO 92
<211> LENGTH: 1254
<212> TYPE: DNA
<213> ORGANISM: Cuphea paucipetala
<220> FEATURE:
<223> OTHER INFORMATION: Cuphea paucipetala (Cpau) FATB1 coding DNA
      sequence

<400> SEQUENCE: 92

atggtggctg ctgcagcaag ttctgcattc ttccctgttc cagcccccgg aacctcccct     60

aaacccggga agtccggcaa ctggccatca agcttgagcc cttccatcaa gcccatgtca    120

atccccaatg gcggatttca ggttaaggca aatgccagtg cccatcctaa ggctaacggt    180

tctgcagtaa atctaaagtc tggcagcctc aacactcagg aggacacttc gtcgtcccct    240

cctcctcggg ctttccttaa ccagttgcct gattggagta tgcttctgac tgcaatcacg    300

accgtcttcg tggcggcaga gaagcagtgg actatgcgtg atcggaaatc taagaggcct    360

gacatgctcg tggactcggt tgggttgaag agtgttgttc tggatgggct cgtgtccaga    420

cagatttttt cgattaggtc ttatgaaata ggcgctgatc gaactgcctc tatagagacg    480

ctgatgaacc acttgcagga aacatctatc aatcattgta agagtttggg tcttctcaat    540

gacggctttg gtcgtactcc tgggatgtgt aaaaatgacc tcatttgggt gcttacaaaa    600

atgcagatca tggtgaatcg ctacccaact tggggcgata ctgttgagat caatacctgg    660

ttctcccatt cggggaaaat tggtatggct agcgattggc taataactga ttgcaacaca    720

ggagaaattc ttataagagc aacgagcgtg tgggccatga tgaatcaaaa gacgagaaga    780

ttctcaagac ttccatacga ggttcgccag gagttaacgc ctcattatgt ggactctcct    840

catgtcattg aagataatga tcggaaattg cataagtttg atgtgaagac tggtgattcc    900

attcgtaagg gtctaactcc gaggtggaat gacttggatg tcaatcagca cgtaagcaac    960

gtgaagtaca ttgggtggat tctcgagagt atgccaatag aagttttgga gacccaggag   1020

ctatgctctc tcaccgttga atataggcgg gaatgcggaa tggacagtgt gctggagtcc   1080

gtgactgcta tggatccctc agaagatgaa ggccggtctc agtacaagca ccttctgcgg   1140

cttgaggatg ggactgacat cgtgaagggc agaactgagt ggcgaccgaa gaatgcagga   1200

actaacgggg cgatatcaac agcaaagcct tcaaatggaa actcggtctc ttag         1254


<210> SEQ ID NO 93
<211> LENGTH: 1254
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cuphea paucipetala (Cpau) FATB1 coding DNA
      sequence codon optimized for Prototheca moriformis

<400> SEQUENCE: 93

atggtggccg ccgccgcctc ctccgccttc ttccccgtgc ccgcccccgg cacctccccc     60
```

-continued

```
aagcccggca agtccggcaa ctggccctcc tccctgtccc cctccatcaa gcccatgtcc    120

atccccaacg gcggcttcca ggtgaaggcc aacgcctccg cccaccccaa ggccaacggc    180

tccgccgtga acctgaagtc cggctccctg aacacccagg aggacacctc ctcctccccc    240

ccccccgcg ccttcctgaa ccagctgccc gactggtcca tgctgctgac cgccatcacc    300

accgtgttcg tggccgccga gaagcagtgg accatgcgcg accgcaagtc caagcgcccc    360

gacatgctgg tggactccgt gggcctgaag tccgtggtgc tggacggcct ggtgtcccgc    420

cagatcttct ccatccgctc ctacgagatc ggcgccgacc gcaccgcctc catcgagacc    480

ctgatgaacc acctgcagga gacctccatc aaccactgca agtccctggg cctgctgaac    540

gacggcttcg gccgcacccc cggcatgtgc aagaacgacc tgatctgggt gctgaccaag    600

atgcagatca tggtgaaccg ctaccccacc tggggcgaca ccgtggagat caacacctgg    660

ttctcccact ccggcaagat cggcatggcc tccgactggc tgatcaccga ctgcaacacc    720

ggcgagatcc tgatccgcgc cacctccgtg tgggccatga tgaaccagaa gacccgccgc    780

ttctcccgcc tgccctacga ggtgcgccag gagctgaccc cccactacgt ggactccccc    840

cacgtgatcg aggacaacga ccgcaagctg cacaagttcg acgtgaagac cggcgactcc    900

atccgcaagg gcctgacccc ccgctggaac gacctggacg tgaaccagca cgtgtccaac    960

gtgaagtaca tcggctggat cctggagtcc atgcccatcg aggtgctgga gacccaggag   1020

ctgtgctccc tgaccgtgga gtaccgccgc gagtgcggca tggactccgt gctggagtcc   1080

gtgaccgcca tggacccctc cgaggacgag ggccgctccc agtacaagca cctgctgcgc   1140

ctggaggacg gcaccgacat cgtgaagggc cgcaccgagt ggcgccccaa gaacgccggc   1200

accaacggcg ccatctccac cgccaagccc tccaacggca actccgtgtc ctga         1254
```

<210> SEQ ID NO 94
<211> LENGTH: 417
<212> TYPE: PRT
<213> ORGANISM: Cuphea procumbens
<220> FEATURE:
<223> OTHER INFORMATION: Cuphea procumbens (Cproc) FATB1 amino acid sequence

<400> SEQUENCE: 94

```
Met Val Ala Ala Ala Ala Ser Ser Ala Phe Phe Pro Ala Pro Ala Pro
1               5                   10                  15

Gly Ser Ser Pro Lys Pro Gly Lys Ser Gly Asn Trp Pro Ser Ser Leu
            20                  25                  30

Ser Pro Ser Phe Lys Ser Lys Ser Ile Pro Tyr Gly Arg Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Ser Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Asn Ile Val Arg Asp Gly Leu Val Ser Arg Gln Ser Phe Leu
    130                 135                 140

Ile Arg Ser Tyr Glu Ile Gly Ala Asp Arg Thr Ala Ser Ile Glu Thr
```

```
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Ala Trp Gly Asp Thr Val Glu Ile Asn Thr Trp Phe Ser Gln Ser
    210                 215                 220

Gly Lys Ile Gly Met Gly Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Arg
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Ala Gln Glu Leu Cys Ser Leu Thr Val Glu Tyr Arg Arg Glu Cys
            340                 345                 350

Gly Met Asp Ser Val Leu Glu Ser Val Thr Ala Val Asp Pro Ser Glu
        355                 360                 365

Asp Gly Gly Arg Ser Gln Tyr Asn His Leu Leu Arg Leu Glu Asp Gly
    370                 375                 380

Thr Asp Val Val Lys Gly Arg Thr Glu Trp Arg Pro Lys Asn Ala Glu
385                 390                 395                 400

Thr Asn Gly Ala Ile Ser Pro Gly Asn Thr Ser Asn Gly Asn Ser Ile
                405                 410                 415

Ser


<210> SEQ ID NO 95
<211> LENGTH: 1254
<212> TYPE: DNA
<213> ORGANISM: Cuphea procumbens
<220> FEATURE:
<223> OTHER INFORMATION: Cuphea procumbens (Cproc) FATB1 coding DNA
      sequence

<400> SEQUENCE: 95

atggtggctg ctgcagcaag ttctgcattc ttccctgctc cagccccggg atcctcacct      60

aaacccggga agtccggtaa ttggccatcg agcttgagcc cttccttcaa gtccaagtca     120

atcccctatg gccgatttca ggttaaggca aatgccagtg cccatcctaa ggctaacggt     180

tctgcagtaa atctaaagtc tggcagcctc aacactcagg aggacacttc gtcgtcccct     240

cctcctcggg ctttccttaa ccagttgcct gattggagta tgcttctgtc tgcaatcacg     300

actgtattcg tggcggcaga gaagcagtgg actatgcttg atcggaaatc taagaggcct     360

gacatgcttg tggactcggt tgggttgaag aatattgttc gggatgggct cgtgtccaga     420

cagagttttt tgattagatc ttatgaaata ggcgctgatc gaacagcttc tatagagaca     480
```

-continued

```
ctgatgaacc acttgcagga aacatctatc aatcattgta agagtttggg tcttctcaat    540

gacggctttg gtcgtactcc tgggatgtgt aaaaacgacc tcatttgggt gcttactaaa    600

atgcagatca tggtgaatcg ctacccagct tggggcgata ctgttgagat caatacctgg    660

ttctcccagt cggggaaaat cggtatgggt agcgattggc taataagtga ttgcaacaca    720

ggagaaattc ttataagagc aacgagcgtg tgggccatga tgaatcaaaa aacgagaaga    780

ttctcaagac ttccatacga ggttcgccag gagttaacgc ctcattttgt ggactctcct    840

catgtcattg aagacaatga tcggaaattg cataagttcg atgtgaagac tggtgattct    900

attcgcaagg gtctaactcc gaggtggaat gacttggatg tcaatcagca cgtgagcaac    960

gtgaagtaca ttgggtggat tctcgagagt atgccaatag aagttttgga ggcccaggaa   1020

ctatgctctc tcaccgttga atataggcgg gaatgcggaa tggacagtgt gctggagtcc   1080

gtgactgctg tagatccctc agaagatgga ggccggtctc agtacaatca ccttctgcgg   1140

cttgaggatg ggactgatgt cgtgaagggc agaactgagt ggcgaccgaa gaatgcagaa   1200

actaacgggg cgatatcacc aggaaacact tcaaatggaa actcgatctc ctag         1254
```

```
<210> SEQ ID NO 96
<211> LENGTH: 1254
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cuphea procumbens (Cproc) FATB1 coding DNA
      sequence codon optimized for Prototheca moriformis

<400> SEQUENCE: 96
```

```
atggtggccg ccgccgcctc ctccgccttc ttccccgccc ccgcccccgg ctcctccccc     60

aagcccggca agtccggcaa ctggccctcc tccctgtccc cctccttcaa gtccaagtcc    120

atcccctacg gccgcttcca ggtgaaggcc aacgcctccg cccaccccaa ggccaacggc    180

tccgccgtga acctgaagtc cggctccctg aacacccagg aggacacctc ctcctccccc    240

cccccccgcg ccttcctgaa ccagctgccc gactggtcca tgctgctgtc cgccatcacc    300

accgtgttcg tggccgccga gaagcagtgg accatgctgg accgcaagtc caagcgcccc    360

gacatgctgg tggactccgt gggcctgaag aacatcgtgc gcgacggcct ggtgtcccgc    420

cagtccttcc tgatccgctc ctacgagatc ggcgccgacc gcaccgcctc catcgagacc    480

ctgatgaacc acctgcagga gacctccatc aaccactgca agtccctggg cctgctgaac    540

gacggcttcg gccgcacccc cggcatgtgc aagaacgacc tgatctgggt gctgaccaag    600

atgcagatca tggtgaaccg ctaccccgcc tggggcgaca ccgtggagat caacacctgg    660

ttctcccagt ccggcaagat cggcatgggc tccgactggc tgatctccga ctgcaacacc    720

ggcgagatcc tgatccgcgc cacctccgtg tgggccatga tgaaccagaa gacccgccgc    780

ttctcccgcc tgccctacga ggtgcgccag gagctgaccc cccacttcgt ggactccccc    840

cacgtgatcg aggacaacga ccgcaagctg cacaagttcg acgtgaagac cggcgactcc    900

atccgcaagg gcctgacccc ccgctggaac gacctggacg tgaaccagca cgtgtccaac    960

gtgaagtaca tcggctggat cctggagtcc atgcccatcg aggtgctgga ggcccaggag   1020

ctgtgctccc tgaccgtgga gtaccgccgc gagtgcggca tggactccgt gctggagtcc   1080

gtgaccgccg tggacccctc cgaggacggc ggccgctccc agtacaacca cctgctgcgc   1140

ctggaggacg gcaccgacgt ggtgaagggc cgcaccgagt ggcgccccaa gaacgccgag   1200
```

accaacggcg ccatctcccc cggcaacacc tccaacggca actccatctc ctga 1254

<210> SEQ ID NO 97
<211> LENGTH: 415
<212> TYPE: PRT
<213> ORGANISM: Cuphea procumbens
<220> FEATURE:
<223> OTHER INFORMATION: Cuphea procumbens (Cproc) FATB2 amino acid
sequence

<400> SEQUENCE: 97

Met Val Ala Ala Ala Ala Ser Ser Ala Phe Phe Pro Ala Pro Ala Pro
1 5 10 15

Gly Ser Ser Pro Lys Pro Gly Lys Ser Gly Asn Trp Pro Ser Ser Leu
20 25 30

Ser Pro Ser Phe Lys Ser Lys Ser Ile Pro Tyr Gly Arg Phe Gln Val
35 40 45

Lys Ala Asn Ala Ser Ala His Pro Lys Ala Asn Gly Ser Ala Val Asn
50 55 60

Leu Lys Ser Gly Ser Leu Asn Thr Gln Glu Asp Thr Ser Ser Ser Pro
65 70 75 80

Pro Pro Arg Ala Phe Leu Asn Gln Leu Pro Asp Trp Ser Met Leu Leu
85 90 95

Ser Ala Ile Thr Thr Val Phe Val Ala Ala Glu Lys Gln Trp Thr Met
100 105 110

Leu Asp Arg Lys Ser Lys Arg Pro Asp Met Leu Val Asp Ser Val Gly
115 120 125

Leu Lys Asn Ile Val Arg Asp Gly Leu Val Ser Arg Gln Ser Phe Leu
130 135 140

Ile Arg Ser Tyr Glu Ile Gly Ala Asp Arg Thr Ala Ser Ile Glu Thr
145 150 155 160

Leu Met Asn His Leu Gln Glu Thr Ser Ile Asn His Cys Lys Ser Leu
165 170 175

Gly Leu Leu Asn Asp Gly Phe Gly Arg Thr Pro Gly Met Cys Lys Asn
180 185 190

Asp Leu Ile Trp Val Leu Thr Lys Met Gln Ile Met Val Asn Arg Tyr
195 200 205

Pro Ala Trp Gly Asp Thr Val Glu Ile Asn Thr Trp Phe Ser Gln Ser
210 215 220

Gly Lys Ile Gly Met Gly Ser Asp Trp Leu Ile Ser Asp Cys Asn Thr
225 230 235 240

Gly Glu Ile Leu Ile Arg Ala Thr Ser Val Trp Ala Met Met Asn Gln
245 250 255

Lys Thr Arg Arg Phe Ser Arg Leu Pro Tyr Glu Val Arg Gln Glu Leu
260 265 270

Thr Pro His Phe Val Asp Ser Pro His Val Ile Glu Asp Asn Asp Arg
275 280 285

Lys Leu His Lys Phe Asp Val Lys Thr Gly Asp Ser Ile Arg Lys Gly
290 295 300

Leu Thr Pro Arg Trp Asn Asp Leu Asp Val Asn Gln His Val Asn Asn
305 310 315 320

Val Lys Tyr Ile Gly Trp Ile Leu Glu Ser Thr Pro Pro Glu Val Leu
325 330 335

Glu Thr Gln Glu Leu Cys Ser Leu Thr Leu Glu Tyr Arg Gln Glu Cys
340 345 350

-continued

```
Gly Arg Glu Ser Val Leu Glu Ser Leu Thr Ala Val Asp Pro Ser Gly
        355                 360                 365

Lys Gly Phe Gly Ser Gln Phe Gln His Leu Leu Arg Leu Glu Asp Gly
    370                 375                 380

Gly Glu Ile Val Lys Gly Arg Thr Glu Trp Arg Pro Lys Thr Ala Gly
385                 390                 395                 400

Ile Asn Gly Ala Ile Ala Ser Gly Glu Thr Ser Pro Gly Asp Phe
                405                 410                 415
```

<210> SEQ ID NO 98
<211> LENGTH: 1248
<212> TYPE: DNA
<213> ORGANISM: Cuphea procumbens
<220> FEATURE:
<223> OTHER INFORMATION: Cuphea procumbens (Cproc) FATB2 coding DNA sequence

<400> SEQUENCE: 98

```
atggtggctg ctgcagcaag ttctgcattc ttccctgctc cagccccggg atcctcacct     60

aaacccggga agtccggtaa ttggccatcg agcttgagcc cttccttcaa gtccaagtca    120

atcccctatg gccgatttca ggttaaggca aatgccagtg cccatcctaa ggctaacggt    180

tctgcagtaa atctaaagtc tggcagcctc aacactcagg aggacacttc gtcgtcccct    240

cctcctcggg ctttccttaa ccagttgcct gattggagta tgcttctgtc tgcaatcacg    300

actgtattcg tggcggcaga gaagcagtgg actatgcttg atcggaaatc taagaggcct    360

gacatgcttg tggactcggt tgggttgaag aatattgttc gggatgggct cgtgtccaga    420

cagagttttt tgattagatc ttatgaaata ggcgctgatc gaacagcttc tatagagaca    480

ctgatgaacc acttgcagga aacatctatc aatcattgta agagtttggg tcttctcaat    540

gacggctttg gtcgtactcc tgggatgtgt aaaaacgacc tcatttgggt gcttactaaa    600

atgcagatca tggtgaatcg ctacccagct tggggcgata ctgttgagat caatacctgg    660

ttctcccagt cggggaaaat cggtatgggt agcgattggc taataagtga ttgcaacaca    720

ggagaaattc ttataagagc aacgagcgtg tgggccatga tgaatcaaaa aacgagaaga    780

ttctcaagac ttccatacga ggttcgccag gagttaacgc ctcattttgt ggactctcct    840

catgtcattg aagacaatga tcggaaattg cataagttcg atgtgaagac tggtgattct    900

attcgcaagg gtctaactcc gaggtggaat gacttggatg tcaatcagca cgtcaacaac    960

gtgaagtaca tcgggtggat tcttgagagt actccaccag aagttctgga gacccaggag   1020

ttatgttccc ttaccctgga atacaggcag gaatgcggaa gggagagcgt gctggagtcc   1080

ctcactgctg tggacccctc tggaaagggc tttgggtccc agttccaaca ccttctgagg   1140

cttgaggatg gaggtgagat cgtgaagggg agaactgagt ggcgacccaa gactgcaggt   1200

atcaatgggg cgatagcatc cggggagacc tcacctggag acttttag                1248
```

<210> SEQ ID NO 99
<211> LENGTH: 1248
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea procumbens (Cproc) FATB2 coding DNA sequence codon optimized for Prototheca moriformis

<400> SEQUENCE: 99

```
atggtggccg ccgccgcctc ctccgccttc ttccccgccc ccgcccccgg ctcctccccc     60

aagcccggca agtccggcaa ctggccctcc tccctgtccc cctccttcaa gtccaagtcc    120

atcccctacg gccgcttcca ggtgaaggcc aacgcctccg cccaccccaa ggccaacggc    180

tccgccgtga acctgaagtc cggctccctg aacacccagg aggacacctc ctcctccccc    240

ccccccgcg ccttcctgaa ccagctgccc gactggtcca tgctgctgtc cgccatcacc    300

accgtgttcg tggccgccga gaagcagtgg accatgctgg accgcaagtc caagcgcccc    360

gacatgctgg tggactccgt gggcctgaag aacatcgtgc gcgacggcct ggtgtcccgc    420

cagtccttcc tgatccgctc ctacgagatc ggcgccgacc gcaccgcctc catcgagacc    480

ctgatgaacc acctgcagga gacctccatc aaccactgca agtccctggg cctgctgaac    540

gacggcttcg gccgcacccc cggcatgtgc aagaacgacc tgatctgggt gctgaccaag    600

atgcagatca tggtgaaccg ctaccccgcc tggggcgaca ccgtggagat caacacctgg    660

ttctcccagt ccggcaagat cggcatgggc tccgactggc tgatctccga ctgcaacacc    720

ggcgagatcc tgatccgcgc cacctccgtg tgggccatga tgaaccagaa gacccgccgc    780

ttctcccgcc tgccctacga ggtgcgccag gagctgaccc cccacttcgt ggactccccc    840

cacgtgatcg aggacaacga ccgcaagctg cacaagttcg acgtgaagac cggcgactcc    900

atccgcaagg gcctgacccc ccgctggaac gacctggacg tgaaccagca cgtgaacaac    960

gtgaagtaca tcggctggat cctggagtcc accccccccg aggtgctgga gacccaggag   1020

ctgtgctccc tgaccctgga gtaccgccag gagtgcggcc gcgagtccgt gctggagtcc   1080

ctgaccgccg tggacccctc cggcaagggc ttcggctccc agttccagca cctgctgcgc   1140

ctggaggacg gcggcgagat cgtgaagggc cgcaccgagt ggcgccccaa gaccgccggc   1200

atcaacggcg ccatcgcctc cggcgagacc tcccccggcg acttctga                1248
```

<210> SEQ ID NO 100
<211> LENGTH: 410
<212> TYPE: PRT
<213> ORGANISM: Cuphea procumbens
<220> FEATURE:
<223> OTHER INFORMATION: Cuphea procumbens (Cproc) FATB3 amino acid sequence

<400> SEQUENCE: 100

```
Met Val Ala Ala Ala Ala Ser Ser Ala Phe Phe Pro Ala Pro Ala Pro
1               5                   10                  15

Gly Ser Ser Pro Lys Pro Gly Lys Ser Gly Asn Trp Pro Ser Ser Leu
            20                  25                  30

Ser Pro Ser Phe Lys Ser Lys Ser Ile Pro Tyr Gly Arg Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Ser Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Asn Ile Val Arg Asp Gly Leu Val Ser Arg Gln Ser Phe Leu
```

```
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Ala Trp Gly Asp Thr Val Glu Ile Asn Thr Trp Phe Ser Gln Ser
    210                 215                 220

Gly Lys Ile Gly Met Gly Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Arg
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Pro Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Gly
        355                 360                 365

Glu Gly Gly Tyr Gly Ser Gln Phe Gln His Leu Leu Arg Leu Glu Asp
    370                 375                 380

Gly Gly Glu Ile Val Lys Gly Arg Thr Glu Trp Arg Pro Lys Asn Ala
385                 390                 395                 400

Gly Ile Asn Gly Val Leu Pro Thr Gly Glu
                405                 410
```

<210> SEQ ID NO 101
<211> LENGTH: 1233
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea procumbens (Cproc) FATB3 coding DNA sequence

<400> SEQUENCE: 101

```
atggtggctg ctgcagcaag ttctgcattc ttccctgctc cagccccggg atcctcacct      60

aaacccggga agtccggtaa ttggccatcg agcttgagcc cttccttcaa gtccaagtca     120

atcccctatg gccgatttca ggttaaggca aatgccagtg cccatcctaa ggctaacggt     180

tctgcagtaa atctaaagtc tggcagcctc aacactcagg aggacacttc gtcgtcccct     240

cctcctcggg ctttccttaa ccagttgcct gattggagta tgcttctgtc tgcaatcacg     300

actgtattcg tggcggcaga gaagcagtgg actatgcttg atcggaaatc taagaggcct     360
```

```
gacatgcttg tggactcggt tgggttgaag aatattgttc gggatgggct cgtgtccaga    420

cagagttttt tgattagatc ttatgaaata ggcgctgatc gaacagcttc tatagagaca    480

ctgatgaacc acttgcagga aacatctatc aatcattgta agagtttggg tcttctcaat    540

gacggctttg gtcgtactcc tgggatgtgt aaaaacgacc tcatttgggt gcttactaaa    600

atgcagatca tggtgaatcg ctacccagct tggggcgata ctgttgagat caatacctgg    660

ttctcccagt cggggaaaat cggtatgggt agcgattggc taataagtga ttgcaacaca    720

ggagaaattc ttataagagc aacgagcgtg tgggccatga tgaatcaaaa aacgagaaga    780

ttctcaagac ttccatacga ggttcgccag gagttaacgc ctcattttgt ggactctcct    840

catgtcattg aagacaatga tcggaaattg cataagttcg atgtgaagac tggtgattct    900

attcgcaagg gtctaactcc gaggtggaat gacttggatg tcaatcagca cgtcaacaac    960

gtgaagtaca tcgggtggat tcttgagagt actccaccag aagttctgga gacccaggag   1020

ttatgttccc ttaccctgga atacaggcgg gaatgtggaa gggagagcgt gctggagtcc   1080

ctcactgctg tggacccctc tggagagggg ggctatggat cccagtttca gcaccttctg   1140

cggcttgagg atggaggtga gatcgtgaag ggagaactg agtggcgacc caagaatgct   1200

ggaatcaatg ggtgttacc aaccggggag tag                                1233
```

```
<210> SEQ ID NO 102
<211> LENGTH: 1233
<212> TYPE: DNA
<213> ORGANISM: Cuphea procumbens
<220> FEATURE:
<223> OTHER INFORMATION: Cuphea procumbens (Cproc) FATB3 coding DNA
      sequence codon optimized for Prototheca moriformis

<400> SEQUENCE: 102

atggtggccg ccgccgcctc ctccgccttc ttccccgccc ccgcccccgg ctcctccccc     60

aagcccggca agtccggcaa ctggccctcc tccctgtccc cctccttcaa gtccaagtcc    120

atcccctacg gccgcttcca ggtgaaggcc aacgcctccg cccaccccaa ggccaacggc    180

tccgccgtga acctgaagtc cggctccctg aacacccagg aggacacctc ctcctccccc    240

ccccccgcg ccttcctgaa ccagctgccc gactggtcca tgctgctgtc cgccatcacc    300

accgtgttcg tggccgccga gaagcagtgg accatgctgg accgcaagtc caagcgcccc    360

gacatgctgg tggactccgt gggcctgaag aacatcgtgc gcgacggcct ggtgtcccgc    420

cagtccttcc tgatccgctc ctacgagatc ggcgccgacc gcaccgcctc catcgagacc    480

ctgatgaacc acctgcagga gacctccatc aaccactgca agtccctggg cctgctgaac    540

gacggcttcg gccgcacccc cggcatgtgc aagaacgacc tgatctgggt gctgaccaag    600

atgcagatca tggtgaaccg ctaccccgcc tggggcgaca ccgtggagat caacacctgg    660

ttctcccagt ccggcaagat cggcatgggc tccgactggc tgatctccga ctgcaacacc    720

ggcgagatcc tgatccgcgc cacctccgtg tgggccatga tgaaccagaa gacccgccgc    780

ttctcccgcc tgccctacga ggtgcgccag gagctgaccc cccacttcgt ggactccccc    840

cacgtgatcg aggacaacga ccgcaagctg cacaagttcg acgtgaagac cggcgactcc    900

atccgcaagg gcctgacccc ccgctggaac gacctggacg tgaaccagca cgtgaacaac    960

gtgaagtaca tcggctggat cctggagtcc acccccccg aggtgctgga gacccaggag   1020

ctgtgctccc tgaccctgga gtaccgccgc gagtgcggcc gcgagtccgt gctggagtcc   1080

ctgaccgccg tggacccctc cggcgagggc ggctacggct cccagttcca gcacctgctg   1140
```

-continued

```
cgcctggagg acggcggcga gatcgtgaag ggccgcaccg agtggcgccc caagaacgcc   1200

ggcatcaacg gcgtgctgcc caccggcgag tga                                1233


<210> SEQ ID NO 103
<211> LENGTH: 395
<212> TYPE: PRT
<213> ORGANISM: Cuphea ignea
<220> FEATURE:
<223> OTHER INFORMATION: Cuphea ignea (Cignea) FATB1 amino acid sequence

<400> SEQUENCE: 103

Pro Gly Thr Ser Arg Lys Thr Gly Lys Phe Gly Asn Trp Pro Ser Ser
1               5                   10                  15

Leu Ser Pro Ser Phe Lys Pro Lys Ser Ile Pro Asn Gly Gly Phe Gln
            20                  25                  30

Val Lys Ala Asn Ala Arg Ala His Pro Lys Ala Asn Gly Ser Ala Val
        35                  40                  45

Ser Leu Lys Ser Val Ser Leu Asn Thr Gln Glu Asp Thr Ser Leu Ser
    50                  55                  60

Pro Pro Pro Arg Ala Phe Leu Asn Gln Leu Pro Asp Trp Arg Met Leu
65                  70                  75                  80

Arg Thr Ala Leu Thr Thr Val Phe Val Ala Ala Glu Lys Gln Trp Thr
                85                  90                  95

Met Leu Asp Arg Lys Ser Lys Arg Pro Asp Met Leu Val Asp Ser Phe
            100                 105                 110

Gly Leu Glu Ser Ile Val Gln Glu Gly Leu Val Phe Arg Gln Ser Phe
        115                 120                 125

Ser Ile Arg Ser Tyr Glu Ile Gly Ile Asp Arg Thr Ala Ser Ile Glu
    130                 135                 140

Thr Leu Met Asn His Leu Gln Glu Thr Ser Leu Asn Gln Cys Lys Ser
145                 150                 155                 160

Ala Gly Ile Leu His Asp Gly Phe Gly Arg Thr Leu Glu Met Cys Lys
                165                 170                 175

Arg Asp Leu Ile Trp Val Val Thr Lys Met Gln Ile Lys Val Asn Arg
            180                 185                 190

Tyr Pro Ala Trp Gly Asp Thr Val Glu Ile Ser Thr Arg Phe Ser Arg
        195                 200                 205

Leu Gly Lys Ile Gly Met Gly Arg Asp Trp Leu Ile Cys Asp Cys Asn
    210                 215                 220

Thr Gly Glu Ile Leu Ile Arg Ala Thr Ser Ala Tyr Ala Met Met Asn
225                 230                 235                 240

Gln Lys Thr Arg Arg Leu Ser Lys Leu Pro Asn Glu Val Arg Gln Glu
                245                 250                 255

Ile Ala Pro Leu Phe Val Asp Ser Asp Pro Val Ile Glu Glu Asn Asp
            260                 265                 270

Met Lys Leu His Lys Phe Glu Val Lys Thr Gly Asp Ser Ile Cys Lys
        275                 280                 285

Gly Leu Thr Pro Arg Trp Ser Asp Leu Asp Val Asn Gln His Val Ser
    290                 295                 300

Asn Val Lys Tyr Ile Gly Trp Ile Leu Glu Ser Met Pro Thr Glu Val
305                 310                 315                 320

Leu Glu Thr Gln Glu Leu Cys Ser Leu Ala Leu Glu Tyr Arg Arg Glu
                325                 330                 335

Cys Gly Arg Asp Ser Val Leu Glu Ser Val Thr Ser Met Asp Pro Ser
            340                 345                 350
```

```
Lys Val Gly Gly Trp Ser Gln Tyr Gln His Leu Leu Arg Leu Glu Asp
        355                 360                 365

Gly Ala Asp Ile Val Lys Gly Arg Thr Glu Trp Arg Pro Lys Asn Ala
    370                 375                 380

Gly Ala Asn Gly Ala Ile Ser Thr Gly Lys Thr
385                 390                 395


<210> SEQ ID NO 104
<211> LENGTH: 1188
<212> TYPE: DNA
<213> ORGANISM: Cuphea ignea
<220> FEATURE:
<223> OTHER INFORMATION: Cuphea ignea (Cignea) FATB1 coding DNA sequence

<400> SEQUENCE: 104

ccgggaacct cacgtaaaac cgggaagttc ggcaattggc catcaagctt gagcccttcc     60

ttcaagccca agtcaatccc caatggcgga tttcaggtta aggctaatgc cagagcccat    120

cctaaggcta acggttctgc agtaagtcta aagtctgtca gcctcaacac tcaggaggac    180

acttcgttgt cccctcctcc tcgtgctttc cttaaccagt tgcctgattg gaggatgctt    240

cggactgcac tcacgaccgt ctttgtggcg gcagagaagc agtggactat gcttgatcgg    300

aaatctaaga ggcctgacat gctcgtggac tcgtttgggt tggagagtat tgttcaagaa    360

gggctcgtgt tcagacagag cttttcgatt aggtcttatg aaataggcat tgatcgaaca    420

gcctctatag agacgctgat gaaccacttg caggaaacat ctctcaatca atgtaagagt    480

gctggtattc tccatgacgg cttcggtcgt actcttgaga tgtgtaaaag ggacctcatt    540

tgggttgtta cgaaaatgca gatcaaggtg aatcgctatc cagcttgggg cgatactgtc    600

gagatcagta cccggttctc ccggttgggg aaaatcggta tgggtcgcga ttggctaata    660

tgtgattgca acacaggaga aattcttata agagcaacga gcgcgtatgc catgatgaat    720

caaaagacga gaagactctc aaaacttcca aacgaggttc gccaggagat agcgcctctt    780

tttgtggact ctgatcctgt cattgaagaa aatgatatga aattgcataa gtttgaagtg    840

aagactggtg attccatttg caagggtcta actccgaggt ggagtgactt ggatgtcaat    900

cagcacgtaa gcaacgtgaa gtacataggg tggattctcg agagtatgcc aacagaagtt    960

ttggagacac aggagctatg ctctctcgcc cttgaatata ggcgggaatg cggaagggac   1020

agtgtgctgg agtctgtgac ctctatggat ccctcaaaag ttggaggctg gtctcagtac   1080

cagcaccttc tgcgacttga ggatggggcg gatatcgtga agggcagaac tgagtggcgg   1140

ccgaagaatg caggagctaa cggggcgata tcaacaggaa agacttga                1188


<210> SEQ ID NO 105
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cuphea ignea (Cignea) FATB1 coding DNA sequence
      codon optimized for Prototheca moriformis

<400> SEQUENCE: 105

cccggcacct cccgcaagac cggcaagttc ggcaactggc cctcctccct gtcccccctcc     60

ttcaagccca agtccatccc caacggcggc ttccaggtga aggccaacgc ccgcgcccac    120

cccaaggcca acggctccgc cgtgtccctg aagtccgtgt ccctgaacac ccaggaggac    180
```

-continued

```
acctccctgt cccccccccc ccgcgccttc ctgaaccagc tgcccgactg gcgcatgctg    240

cgcaccgccc tgaccaccgt gttcgtggcc gccgagaagc agtggaccat gctggaccgc    300

aagtccaagc gccccgacat gctggtggac tccttcggcc tggagtccat cgtgcaggag    360

ggcctggtgt tccgccagtc cttctccatc cgctcctacg agatcggcat cgaccgcacc    420

gcctccatcg agaccctgat gaaccacctg caggagacct ccctgaacca gtgcaagtcc    480

gccggcatcc tgcacgacgg cttcggccgc accctggaga tgtgcaagcg cgacctgatc    540

tgggtggtga ccaagatgca gatcaaggtg aaccgctacc ccgcctgggg cgacaccgtg    600

gagatctcca cccgcttctc ccgcctgggc aagatcggca tgggccgcga ctggctgatc    660

tgcgactgca acaccggcga gatcctgatc cgcgccacct ccgcctacgc catgatgaac    720

cagaagaccc gccgcctgtc caagctgccc aacgaggtgc gccaggagat cgccccccctg    780

ttcgtggact ccgaccccgt gatcgaggag aacgacatga agctgcacaa gttcgaggtg    840

aagaccggcg actccatctg caagggcctg accccccgct ggtccgacct ggacgtgaac    900

cagcacgtgt ccaacgtgaa gtacatcggc tggatcctgg agtccatgcc caccgaggtg    960

ctggagaccc aggagctgtg ctccctggcc ctggagtacc gccgcgagtg cggccgcgac   1020

tccgtgctgg agtccgtgac ctccatggac ccctccaagg tgggcggctg gtcccagtac   1080

cagcacctgc tgcgcctgga ggacggcgcc gacatcgtga agggccgcac cgagtggcgc   1140

cccaagaacg ccggcgccaa cggcgccatc tccaccggca agacctga               1188
```

<210> SEQ ID NO 106
<211> LENGTH: 417
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: JcFatB1 consensus amino acid sequence

<400> SEQUENCE: 106

```
Met Val Ala Ala Ala Ala Ser Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Ser Phe Lys Pro Lys Ser Ile Pro Asn Gly Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Arg Ile Val Gln Asp Gly Leu Val Ser Arg Gln Ser Phe Ser
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
```

-continued

```
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Ile Asn Thr Trp Phe Ser Gln Ser
    210                 215                 220

Gly Lys Ile Gly Met Gly Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Arg
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Met Asp Pro Ser Glu
        355                 360                 365

Asn Gly Gly Arg Ser Gln Tyr Lys His Leu Leu Arg Leu Glu Asp Gly
    370                 375                 380

Thr Asp Ile Val Lys Gly Arg Thr Glu Trp Arg Pro Lys Asn Ala Gly
385                 390                 395                 400

Thr Asn Gly Ala Ile Ser Thr Gly Lys Thr Ser Asn Gly Asn Ser Val
                405                 410                 415

Ser
```

<210> SEQ ID NO 107
<211> LENGTH: 1254
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: JcFatB1 consensus DNA sequence codon optimized
      for Prototheca

<400> SEQUENCE: 107

```
atggtggccg ccgccgcctc ctccgccttc ttccccgtgc ccgcccccgg cacctccccc     60

aagcccggca agtccggcaa ctggccctcc tccctgtccc cctccttcaa gcccaagtcc    120

atccccaacg gcggcttcca ggtgaaggcc aacgcctccg cccaccccaa ggccaacggc    180

tccgccgtga acctgaagtc cggctccctg aacacccagg aggacacctc ctcctccccc    240

ccccccgcg ccttcctgaa ccagctgccc gactggtcca tgctgctgac cgccatcacc    300

accgtgttcg tggccgccga gaagcagtgg accatgctgg accgcaagtc caagcgcccc    360

gacatgctgg tggactccgt gggcctgaag cgcatcgtgc aggacggcct ggtgtcccgc    420

cagtccttct ccatccgctc ctacgagatc ggcgccgacc gcaccgcctc catcgagacc    480
```

```
ctgatgaacc acctgcagga gacctccatc aaccactgca agtccctggg cctgctgaac    540

gacggcttcg gccgcacccc cggcatgtgc aagaacgacc tgatctgggt gctgaccaag    600

atgcagatca tggtgaaccg ctaccccacc tggggcgaca ccgtggagat caacacctgg    660

ttctcccagt ccggcaagat cggcatgggc tccgactggc tgatctccga ctgcaacacc    720

ggcgagatcc tgatccgcgc cacctccgtg tgggccatga tgaaccagaa gacccgccgc    780

ttctcccgcc tgccctacga ggtgcgccag gagctgaccc cccacttcgt ggactccccc    840

cacgtgatcg aggacaacga ccgcaagctg cacaagttcg acgtgaagac cggcgactcc    900

atccgcaagg gcctgacccc ccgctggaac gacctggacg tgaaccagca cgtgtccaac    960

gtgaagtaca tcggctggat cctggagtcc atgcccatcg aggtgctgga gacccaggag   1020

ctgtgctccc tgaccgtgga gtaccgccgc gagtgcggca tggactccgt gctggagtcc   1080

gtgaccgcca tggacccctc cgagaacggc ggccgctccc agtacaagca cctgctgcgc   1140

ctggaggacg gcaccgacat cgtgaagggc cgcaccgagt ggcgccccaa gaacgccggc   1200

accaacggcg ccatctccac cggcaagacc tccaacggca actccgtgtc ctga         1254
```

<210> SEQ ID NO 108
<211> LENGTH: 415
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: JcFatB2 consensus amino acid sequence

<400> SEQUENCE: 108

```
Met Val Ala Thr Ala Ala Ser Ser Ala Phe Phe Pro Val Pro Ser Pro
1               5                   10                  15

Asp Thr Ser Ser Arg Pro Gly Lys Leu Gly Asn Gly Ser Ser Ser Leu
            20                  25                  30

Ser Pro Leu Lys Pro Lys Ser Val Ala Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Asp Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
```

```
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Arg Leu Ser Lys Ile Pro Asp Glu Val Arg His Glu Ile Glu
            260                 265                 270

Pro His Phe Val Asp Ser Ala Pro Val Ile Glu Asp Asp Asp Arg Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Tyr Gly Ser Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Ala Ile Ala Ser Gly Glu Thr Ser Pro Gly Asp Ser Ser
                405                 410                 415
```

<210> SEQ ID NO 109
<211> LENGTH: 1248
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: JcFatB2 consensus DNA sequence codon optimized for Prototheca

<400> SEQUENCE: 109

```
atggtggcca ccgccgcctc ctccgccttc ttccccgtgc cctcccccga cacctcctcc     60

cgccccggca agctgggcaa cggctcctcc tccctgtccc ccctgaagcc caagtccgtg    120

gccaacggcg gcctgcaggt gaaggccaac gcctccgccc cccccaagat caacggctcc    180

tccgtgggcc tgaagtccgg ctccctgaag acccaggagg acacccccctc cgcccccccc    240

ccccgcacct tcatcaacca gctgcccgac tggtccatgc tgctggccgc catcaccacc    300

gtgttcctgg ccgccgagaa gcagtggatg atgctggact ggaagcccaa gcgccccgac    360

atgctggtgg acccccttcgg cctgggccgc atcgtgcagg acggcctggt gttccgccag    420

aacttctcca tccgctccta cgagatcggc gccgaccgca ccgcctccat cgagaccgtg    480

atgaaccacc tgcaggagac cgccctgaac cacgtgaagt ccgccggcct gctgaacgac    540

ggcttcggcc gcacccccga gatgtacaag cgcgacctga tctgggtggt ggccaagatg    600

caggtgatgg tgaaccgcta ccccacctgg ggcgacaccg tggaggtgaa cacctgggtg    660

gccaagtccg gcaagaacgg catgcgccgc gactggctga tctccgactg caacaccggc    720

gagatcctga cccgcgcctc ctccgtgtgg gtgatgatga accagaagac ccgccgcctg    780

tccaagatcc ccgacgaggt gcgccacgag atcgagcccc acttcgtgga ctccgccccc    840
```

```
gtgatcgagg acgacgaccg caagctgccc aagctggacg agaagaccgc cgactccatc    900

cgcaagggcc tgacccccaa gtggaacgac ctggacgtga accagcacgt gaacaacgtg    960

aagtacatcg gctggatcct ggagtccacc ccccccgagg tgctggagac ccaggagctg   1020

tgctccctga ccctggagta ccgccgcgag tgcggccgcg agtccgtgct ggagtccctg   1080

accgccgtgg acccctccgg caagggctac ggctcccagt tccagcacct gctgcgcctg   1140

gaggacggcg gcgagatcgt gaagggccgc accgagtggc gccccaagac cgccggcatc   1200

aacggcgcca tcgcctccgg cgagacctcc cccggcgact cctcctga                1248


<210> SEQ ID NO 110
<211> LENGTH: 419
<212> TYPE: PRT
<213> ORGANISM: Cuphea sp.
<220> FEATURE:
<223> OTHER INFORMATION: CuPSR23 FATB3 amino acid sequence

<400> SEQUENCE: 110

Met Val Val Ala Ala Ala Thr Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Thr Phe Lys Pro Lys Ser Ile Pro Asn Ala Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Cys Ile Val Arg Asp Gly Leu Val Ser Arg Gln Ser Phe Leu
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Ile Asn Thr Trp Phe Ser Gln Ser
    210                 215                 220

Gly Lys Ile Gly Met Ala Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Gln
        275                 280                 285
```

```
Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Val Asp Pro Ser Glu
        355                 360                 365

Asn Gly Gly Arg Ser Gln Tyr Lys His Leu Leu Arg Leu Glu Asp Gly
    370                 375                 380

Thr Asp Ile Val Lys Ser Arg Thr Glu Trp Arg Pro Lys Asn Ala Gly
385                 390                 395                 400

Thr Asn Gly Ala Ile Ser Thr Ser Thr Ala Lys Thr Ser Asn Gly Asn
                405                 410                 415

Ser Val Ser


<210> SEQ ID NO 111
<211> LENGTH: 419
<212> TYPE: PRT
<213> ORGANISM: Cuphea sp.
<220> FEATURE:
<223> OTHER INFORMATION: CuPSR23 FATB3b amino acid sequence

<400> SEQUENCE: 111

Met Val Val Ala Ala Ala Thr Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Thr Phe Lys Pro Lys Ser Ile Pro Asn Ala Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Ser Ile Val Arg Asp Gly Leu Val Ser Arg Gln Ser Phe Leu
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Ile Asn Thr Trp Phe Ser Gln Ser
    210                 215                 220

Gly Lys Ile Gly Met Ala Ser Asp Trp Leu Ile Ser Asp Cys Asn Thr
```

```
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Gln
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Val Asp Pro Ser Glu
        355                 360                 365

Asn Gly Gly Arg Ser Gln Tyr Lys His Leu Leu Arg Leu Glu Asp Gly
    370                 375                 380

Thr Asp Ile Val Lys Ser Arg Thr Glu Trp Arg Pro Lys Asn Ala Gly
385                 390                 395                 400

Thr Asn Gly Ala Ile Ser Thr Ser Thr Ala Lys Thr Ser Asn Gly Asn
                405                 410                 415

Ser Ala Ser


<210> SEQ ID NO 112
<211> LENGTH: 408
<212> TYPE: PRT
<213> ORGANISM: Cuphea wrightii
<220> FEATURE:
<223> OTHER INFORMATION: CwFATB3 amino acid sequence

<400> SEQUENCE: 112

Met Val Val Ala Ala Ala Ala Ser Ser Ala Phe Phe Pro Val Pro Ala
1               5                   10                  15

Pro Arg Thr Thr Pro Lys Pro Gly Lys Phe Gly Asn Trp Pro Ser Ser
            20                  25                  30

Leu Ser Pro Pro Phe Lys Pro Lys Ser Asn Pro Asn Gly Arg Phe Gln
        35                  40                  45

Val Lys Ala Asn Val Ser Pro His Pro Lys Ala Asn Gly Ser Ala Val
    50                  55                  60

Ser Leu Lys Ser Gly Ser Leu Asn Thr Leu Glu Asp Pro Pro Ser Ser
65                  70                  75                  80

Pro Pro Pro Arg Thr Phe Leu Asn Gln Leu Pro Asp Trp Ser Arg Leu
                85                  90                  95

Arg Thr Ala Ile Thr Thr Val Phe Val Ala Ala Glu Lys Gln Phe Thr
            100                 105                 110

Arg Leu Asp Arg Lys Ser Lys Arg Pro Asp Met Leu Val Asp Trp Phe
        115                 120                 125

Gly Ser Glu Thr Ile Val Gln Asp Gly Leu Val Phe Arg Glu Arg Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175
```

```
Val Gly Leu Leu Asn Asp Gly Phe Gly Arg Thr Ser Glu Met Cys Thr
            180                 185                 190

Arg Asp Leu Ile Trp Val Leu Thr Lys Met Gln Ile Val Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asp Trp Leu Ile Ser Asp Cys Asn
225                 230                 235                 240

Thr Gly Glu Ile Leu Val Arg Ala Thr Ser Ala Trp Ala Met Met Asn
                245                 250                 255

Gln Lys Thr Arg Arg Phe Ser Lys Leu Pro Cys Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Gly Trp Asn Asp Leu Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Glu Ser Val Val Glu Ser Val Thr Ser Met Asn Pro Ser
        355                 360                 365

Lys Val Gly Asp Arg Ser Gln Tyr Gln His Leu Leu Arg Leu Glu Asp
    370                 375                 380

Gly Ala Asp Ile Met Lys Gly Arg Thr Glu Trp Arg Pro Lys Asn Ala
385                 390                 395                 400

Gly Thr Asn Arg Ala Ile Ser Thr
                405


<210> SEQ ID NO 113
<211> LENGTH: 408
<212> TYPE: PRT
<213> ORGANISM: Cuphea wrightii
<220> FEATURE:
<223> OTHER INFORMATION: CwFATB3a amino acid sequence

<400> SEQUENCE: 113

Met Val Val Ala Ala Ala Ala Ser Ser Ala Phe Phe Pro Val Pro Ala
1               5                   10                  15

Pro Arg Thr Thr Pro Lys Pro Gly Lys Phe Gly Asn Trp Pro Ser Ser
            20                  25                  30

Leu Ser Pro Pro Phe Lys Pro Lys Ser Asn Pro Asn Gly Arg Phe Gln
        35                  40                  45

Val Lys Ala Asn Val Ser Pro His Pro Lys Ala Asn Gly Ser Ala Val
    50                  55                  60

Ser Leu Lys Ser Gly Ser Leu Asn Thr Leu Glu Asp Pro Pro Ser Ser
65                  70                  75                  80

Pro Pro Pro Arg Thr Phe Leu Asn Gln Leu Pro Asp Trp Ser Arg Leu
                85                  90                  95

Arg Thr Ala Ile Thr Thr Val Phe Val Ala Ala Glu Lys Gln Phe Thr
            100                 105                 110

Arg Leu Asp Arg Lys Ser Lys Arg Pro Asp Met Leu Val Asp Trp Phe
        115                 120                 125
```

Gly Ser Glu Thr Ile Val Gln Asp Gly Leu Val Phe Arg Glu Arg Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Ser Glu Met Cys Thr
            180                 185                 190

Arg Asp Leu Ile Trp Val Leu Thr Lys Met Gln Ile Val Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asp Trp Leu Ile Ser Asp Cys Asn
225                 230                 235                 240

Thr Gly Glu Ile Leu Val Arg Ala Thr Ser Ala Trp Ala Met Met Asn
                245                 250                 255

Gln Lys Thr Arg Arg Phe Ser Lys Leu Pro Cys Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Gly Trp Asn Asp Leu Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Glu Ser Val Val Glu Ser Val Thr Ser Met Asn Pro Ser
        355                 360                 365

Lys Val Gly Asp Arg Ser Gln Tyr Gln His Leu Leu Arg Leu Glu Asp
    370                 375                 380

Gly Ala Asp Ile Met Lys Gly Arg Thr Glu Trp Arg Pro Lys Asn Ala
385                 390                 395                 400

Gly Thr Asn Arg Ala Ile Ser Thr
                405

<210> SEQ ID NO 114
<211> LENGTH: 354
<212> TYPE: PRT
<213> ORGANISM: Cuphea wrightii
<220> FEATURE:
<223> OTHER INFORMATION: CwFATB3b amino acid sequence

<400> SEQUENCE: 114

Met Val Val Ala Ala Ala Ala Ser Ser Ala Phe Phe Pro Val Pro Ala
1               5                   10                  15

Pro Arg Thr Thr Pro Lys Pro Gly Lys Phe Gly Asn Trp Pro Ser Ser
            20                  25                  30

Leu Ser Pro Pro Phe Lys Pro Lys Ser Asn Pro Asn Gly Arg Phe Gln
        35                  40                  45

Val Lys Ala Asn Val Ser Pro His Pro Lys Ala Asn Gly Ser Ala Val
    50                  55                  60

Ser Leu Lys Ser Gly Ser Leu Asn Thr Leu Glu Asp Leu Pro Ser Ser
65                  70                  75                  80

Pro Pro Pro Arg Thr Phe Leu Asn Gln Leu Pro Asp Trp Ser Arg Leu
85 90 95

Arg Thr Ala Ile Thr Thr Val Phe Val Ala Ala Glu Lys Gln Phe Thr
100 105 110

Arg Leu Asp Arg Lys Ser Lys Arg Pro Asp Met Leu Val Asp Trp Phe
115 120 125

Gly Ser Glu Thr Ile Val Gln Asp Gly Leu Val Phe Arg Glu Arg Phe
130 135 140

Ser Ile Arg Ser Tyr Glu Ile Gly Ala Asp Arg Thr Ala Ser Ile Glu
145 150 155 160

Thr Leu Met Asn His Leu Gln Asp Thr Ser Leu Asn His Cys Lys Ser
165 170 175

Val Gly Leu Leu Asn Asp Gly Phe Gly Arg Thr Ser Glu Met Cys Thr
180 185 190

Arg Asp Leu Ile Trp Val Leu Thr Lys Met Gln Ile Val Val Asn Arg
195 200 205

Tyr Pro Thr Trp Gly Asp Thr Val Glu Ile Asn Ser Trp Phe Ser Gln
210 215 220

Ser Gly Lys Ile Gly Met Gly Arg Asp Trp Leu Ile Ser Asp Cys Asn
225 230 235 240

Thr Gly Glu Ile Leu Val Arg Ala Thr Ser Ala Trp Ala Met Met Asn
245 250 255

Gln Lys Thr Arg Arg Phe Ser Lys Leu Pro Cys Glu Val Arg Gln Glu
260 265 270

Ile Ala Pro His Phe Val Asp Ala Pro Pro Val Ile Glu Asp Asn Asp
275 280 285

Arg Lys Leu His Lys Phe Asp Val Lys Thr Gly Asp Ser Ile Cys Lys
290 295 300

Gly Leu Thr Pro Gly Trp Asn Asp Leu Asp Val Asn Gln His Val Ser
305 310 315 320

Asn Val Lys Tyr Ile Gly Trp Ile Leu Glu Lys Phe Trp Arg Pro Arg
325 330 335

Ser Tyr Ala Leu Ser Pro Leu Asn Ile Gly Gly Asn Val Glu Gly Lys
340 345 350

Val Trp

<210> SEQ ID NO 115
<211> LENGTH: 354
<212> TYPE: PRT
<213> ORGANISM: Cuphea wrightii
<220> FEATURE:
<223> OTHER INFORMATION: CwFATB3c amino acid sequence

<400> SEQUENCE: 115

Met Val Val Ala Ala Ala Ala Ser Ser Ala Phe Phe Pro Val Pro Ala
1 5 10 15

Pro Arg Thr Thr Pro Lys Pro Gly Lys Phe Gly Asn Trp Pro Ser Ser
20 25 30

Leu Ser Pro Pro Phe Lys Pro Lys Ser Asn Pro Asn Gly Arg Phe Gln
35 40 45

Val Lys Ala Asn Val Ser Pro His Pro Lys Ala Asn Gly Ser Ala Val
50 55 60

Ser Leu Lys Ser Gly Ser Leu Asn Thr Leu Glu Asp Leu Pro Ser Ser
65 70 75 80

-continued

```
Pro Pro Pro Arg Thr Phe Leu Asn Gln Leu Pro Asp Trp Ser Arg Leu
                85                  90                  95

Arg Thr Ala Ile Thr Thr Val Phe Val Ala Thr Glu Lys Gln Phe Thr
            100                 105                 110

Arg Leu Asp Arg Lys Ser Lys Arg Pro Asp Met Leu Val Asp Trp Phe
        115                 120                 125

Gly Ser Glu Thr Ile Val Gln Asp Gly Leu Val Phe Arg Glu Arg Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Ser Glu Met Cys Thr
            180                 185                 190

Arg Asp Leu Ile Trp Val Leu Thr Lys Met Gln Ile Val Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asp Trp Leu Ile Ser Asp Cys Asn
225                 230                 235                 240

Thr Gly Glu Ile Leu Val Arg Ala Thr Ser Ala Trp Ala Met Met Asn
                245                 250                 255

Gln Lys Thr Arg Arg Phe Ser Lys Leu Pro Cys Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Gly Trp Asn Asp Leu Asp Val Asn Gln His Val Ser
305                 310                 315                 320

Asn Val Lys Tyr Ile Gly Trp Ile Leu Glu Lys Phe Trp Arg Pro Arg
                325                 330                 335

Ser Tyr Ala Leu Ser Pro Leu Asn Ile Gly Gly Asn Val Glu Gly Lys
            340                 345                 350

Val Trp


<210> SEQ ID NO 116
<211> LENGTH: 416
<212> TYPE: PRT
<213> ORGANISM: Cuphea wrightii
<220> FEATURE:
<223> OTHER INFORMATION: CwFATB4a amino acid sequence

<400> SEQUENCE: 116

Met Val Ala Thr Ala Ala Ser Ser Ala Phe Phe Pro Val Pro Ser Ala
1               5                   10                  15

Asp Thr Ser Ser Ser Arg Pro Gly Lys Leu Gly Ser Gly Pro Ser Ser
            20                  25                  30

Leu Ser Pro Leu Lys Pro Lys Ser Ile Pro Asn Gly Gly Leu Gln Val
        35                  40                  45

Lys Ala Asn Ala Ser Ala Pro Pro Lys Ile Asn Gly Ser Ser Val Gly
    50                  55                  60

Leu Lys Ser Gly Gly Phe Lys Thr Gln Glu Asp Ser Pro Ser Ala Pro
65                  70                  75                  80

Pro Pro Arg Thr Phe Ile Asn Gln Leu Pro Asp Trp Ser Met Leu Leu
```

-continued

```
                85                  90                  95

Ala Ala Ile Thr Thr Val Phe Leu Ala Ala Glu Lys Gln Trp Met Met
            100                 105                 110

Leu Asp Trp Lys Pro Lys Arg Pro Asp Met Leu Val Asp Pro Phe Gly
        115                 120                 125

Leu Gly Ser Ile Val Gln Asp Gly Leu Val Phe Arg Gln Asn Phe Ser
    130                 135                 140

Ile Arg Ser Tyr Glu Ile Gly Ala Asp Arg Thr Ala Ser Ile Glu Thr
145                 150                 155                 160

Val Met Asn His Leu Gln Glu Thr Ala Leu Asn His Val Lys Ile Ala
                165                 170                 175

Gly Leu Ser Asn Asp Gly Phe Gly Arg Thr Pro Glu Met Tyr Lys Arg
            180                 185                 190

Asp Leu Ile Trp Val Val Ala Lys Met Gln Val Met Val Asn Arg Tyr
        195                 200                 205

Pro Thr Trp Gly Asp Thr Val Glu Val Asn Thr Trp Val Ala Lys Ser
    210                 215                 220

Gly Lys Asn Gly Met Arg Arg Asp Trp Leu Ile Ser Asp Cys Asn Thr
225                 230                 235                 240

Gly Glu Ile Leu Thr Arg Ala Ser Ser Val Trp Val Met Met Asn Gln
                245                 250                 255

Lys Thr Arg Arg Leu Ser Lys Ile Pro Asp Glu Val Arg Asn Glu Ile
            260                 265                 270

Glu Pro His Phe Val Asp Ser Ala Pro Val Val Glu Asp Asp Asp Arg
        275                 280                 285

Lys Leu Pro Lys Leu Asp Glu Asn Thr Ala Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Pro Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Ala
        355                 360                 365

Glu Gly Tyr Ala Ser Arg Phe Gln His Leu Leu Arg Leu Glu Asp Gly
    370                 375                 380

Gly Glu Ile Val Lys Ala Arg Thr Glu Trp Arg Pro Lys Asn Ala Gly
385                 390                 395                 400

Ile Asn Gly Val Val Pro Ser Glu Glu Ser Ser Pro Gly Asp Phe Phe
                405                 410                 415


<210> SEQ ID NO 117
<211> LENGTH: 416
<212> TYPE: PRT
<213> ORGANISM: Cuphea wrightii
<220> FEATURE:
<223> OTHER INFORMATION: CwFATB4a.1 amino acid sequence

<400> SEQUENCE: 117

Met Val Ala Thr Ala Ala Ser Ser Ala Phe Phe Pro Val Pro Ser Ala
1               5                   10                  15

Asp Thr Ser Ser Ser Arg Pro Gly Lys Leu Gly Ser Gly Pro Ser Ser
            20                  25                  30

Leu Ser Pro Leu Lys Pro Lys Ser Ile Pro Asn Gly Gly Leu Gln Val
```

```
        35                  40                  45

Lys Ala Asn Ala Ser Ala Pro Pro Lys Ile Asn Gly Ser Ser Val Gly
    50                  55                  60

Leu Lys Ser Gly Gly Phe Lys Thr Gln Glu Asp Ser Pro Ser Ala Pro
65                  70                  75                  80

Pro Pro Arg Thr Phe Ile Asn Gln Leu Pro Asp Trp Ser Met Leu Leu
                85                  90                  95

Ala Ala Ile Thr Thr Val Phe Leu Ala Ala Glu Lys Gln Trp Met Met
            100                 105                 110

Leu Asp Trp Lys Pro Lys Arg Pro Asp Met Leu Val Asp Pro Phe Gly
        115                 120                 125

Leu Gly Ser Ile Val Gln Asp Gly Leu Val Phe Arg Gln Asn Phe Ser
    130                 135                 140

Ile Arg Ser Tyr Glu Ile Gly Ala Asp Arg Thr Ala Ser Ile Glu Thr
145                 150                 155                 160

Val Met Asn His Leu Gln Glu Thr Ala Leu Asn His Val Lys Ile Ala
                165                 170                 175

Gly Leu Ser Asn Asp Gly Phe Gly Arg Thr Pro Glu Met Tyr Lys Arg
            180                 185                 190

Asp Leu Ile Trp Val Val Ala Lys Met Gln Val Met Val Asn Arg Tyr
        195                 200                 205

Pro Thr Trp Gly Asp Thr Val Glu Val Asn Thr Trp Val Ala Lys Ser
    210                 215                 220

Gly Lys Asn Gly Met Arg Arg Asp Trp Leu Ile Ser Asp Cys Asn Thr
225                 230                 235                 240

Gly Glu Ile Leu Thr Arg Ala Ser Ser Val Trp Val Met Met Asn Gln
                245                 250                 255

Lys Thr Arg Arg Leu Ser Lys Ile Pro Asp Glu Val Arg Asn Glu Ile
            260                 265                 270

Glu Pro His Phe Val Asp Ser Ala Pro Val Val Glu Asp Asp Asp Arg
        275                 280                 285

Lys Leu Pro Lys Leu Asp Glu Asn Thr Ala Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Pro Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Ala
        355                 360                 365

Glu Gly Tyr Ala Ser Arg Phe Gln His Leu Leu Arg Leu Glu Asp Gly
    370                 375                 380

Gly Glu Ile Val Lys Ala Arg Thr Glu Trp Arg Pro Lys Asn Ala Gly
385                 390                 395                 400

Ile Asn Trp Val Val Pro Ser Glu Glu Ser Ser Pro Gly Asp Phe Phe
                405                 410                 415
```

<210> SEQ ID NO 118
<211> LENGTH: 416
<212> TYPE: PRT
<213> ORGANISM: Cuphea wrightii
<220> FEATURE:
<223> OTHER INFORMATION: CwFATB4a.2 amino acid sequence:

<400> SEQUENCE: 118

Met Val Ala Thr Ala Ala Ser Ser Ala Phe Phe Pro Val Pro Ser Ala
1 5 10 15

Asp Thr Ser Ser Ser Arg Pro Gly Lys Leu Gly Asn Gly Pro Ser Ser
20 25 30

Leu Ser Pro Leu Lys Pro Lys Ser Ile Pro Asn Gly Gly Leu Gln Val
35 40 45

Lys Ala Asn Ala Ser Ala Pro Pro Lys Ile Asn Gly Ser Ser Val Gly
50 55 60

Leu Lys Ser Gly Ser Phe Lys Thr Gln Glu Asp Ala Pro Ser Ala Pro
65 70 75 80

Pro Pro Arg Thr Phe Ile Asn Gln Leu Pro Asp Trp Ser Met Leu Leu
85 90 95

Ala Ala Ile Thr Thr Val Phe Leu Ala Ala Glu Lys Gln Trp Met Met
100 105 110

Leu Asp Trp Lys Pro Lys Arg Pro Asp Met Leu Val Asp Pro Phe Gly
115 120 125

Leu Gly Ser Ile Val Gln Asp Gly Leu Val Phe Arg Gln Asn Phe Ser
130 135 140

Ile Arg Ser Tyr Glu Ile Gly Ala Asp Arg Thr Ala Ser Ile Glu Thr
145 150 155 160

Val Met Asn His Leu Gln Glu Thr Ala Leu Asn His Val Lys Ile Ala
165 170 175

Gly Leu Ser Asn Asp Gly Phe Gly Arg Thr Pro Glu Met Tyr Lys Arg
180 185 190

Asp Leu Ile Trp Val Val Ala Lys Met Gln Val Met Val Asn Arg Tyr
195 200 205

Pro Thr Trp Gly Asp Thr Val Glu Val Asn Thr Trp Val Ala Lys Ser
210 215 220

Gly Lys Asn Gly Met Arg Arg Asp Trp Leu Ile Ser Asp Cys Asn Thr
225 230 235 240

Gly Glu Ile Leu Thr Arg Ala Ser Ser Val Trp Val Met Met Asn Gln
245 250 255

Lys Thr Arg Arg Leu Ser Lys Ile Pro Asp Glu Val Arg Asn Glu Ile
260 265 270

Glu Pro His Phe Val Asp Ser Ala Pro Val Val Glu Asp Asp Asp Arg
275 280 285

Lys Leu Pro Lys Leu Asp Glu Asn Thr Ala Asp Ser Ile Arg Lys Gly
290 295 300

Leu Thr Pro Arg Trp Asn Asp Leu Asp Val Asn Gln His Val Asn Asn
305 310 315 320

Val Lys Tyr Ile Gly Trp Ile Leu Glu Ser Thr Pro Pro Glu Val Leu
325 330 335

Glu Thr Gln Glu Leu Cys Ser Leu Thr Leu Glu Tyr Arg Arg Glu Cys
340 345 350

Gly Arg Glu Ser Val Leu Glu Ser Leu Thr Ala Val Asp Pro Ser Ala
355 360 365

Glu Gly Tyr Ala Ser Arg Phe Gln His Leu Leu Arg Leu Glu Asp Gly
370 375 380

Gly Glu Ile Val Lys Ala Arg Thr Glu Trp Arg Pro Lys Asn Ala Gly
385 390 395 400

Ile Asn Gly Val Val Pro Ser Glu Glu Ser Ser Pro Gly Asp Phe Phe
405 410 415

<210> SEQ ID NO 119
<211> LENGTH: 416
<212> TYPE: PRT
<213> ORGANISM: Cuphea wrightii
<220> FEATURE:
<223> OTHER INFORMATION: CwFATB4a.3 amino acid sequence

<400> SEQUENCE: 119

```
Met Val Ala Thr Ala Ala Ser Ser Ala Phe Phe Pro Val Pro Ser Ala
1               5                   10                  15

Asp Thr Ser Ser Ser Arg Pro Gly Lys Leu Gly Ser Gly Pro Ser Ser
            20                  25                  30

Leu Ser Pro Leu Lys Pro Lys Ser Ile Pro Asn Gly Gly Leu Gln Val
        35                  40                  45

Lys Ala Asn Ala Ser Ala Pro Pro Lys Ile Asn Gly Ser Ser Val Gly
    50                  55                  60

Leu Lys Ser Gly Gly Phe Lys Thr Gln Glu Asp Ser Pro Ser Ala Pro
65                  70                  75                  80

Pro Pro Arg Thr Phe Ile Asn Gln Leu Pro Asp Trp Ser Met Leu Leu
                85                  90                  95

Ala Ala Ile Thr Thr Val Phe Leu Ala Ala Glu Lys Gln Trp Met Met
            100                 105                 110

Leu Asp Trp Lys Pro Lys Arg Pro Asp Met Leu Val Asp Pro Phe Gly
        115                 120                 125

Leu Gly Ser Ile Val Gln Asp Gly Leu Val Phe Arg Gln Asn Phe Ser
    130                 135                 140

Ile Arg Ser Tyr Glu Ile Gly Ala Asp Arg Thr Ala Ser Ile Glu Thr
145                 150                 155                 160

Val Met Asn His Leu Gln Glu Thr Ala Leu Asn His Val Lys Ile Ala
                165                 170                 175

Gly Leu Ser Asn Asp Gly Phe Gly Arg Thr Pro Glu Met Tyr Lys Arg
            180                 185                 190

Asp Leu Ile Trp Val Val Ala Lys Met Gln Val Met Val Asn Arg Tyr
        195                 200                 205

Pro Thr Trp Gly Asp Thr Val Glu Val Asn Thr Trp Val Ala Lys Ser
    210                 215                 220

Gly Lys Asn Gly Met Arg Arg Asp Trp Leu Ile Ser Asp Cys Asn Thr
225                 230                 235                 240

Gly Glu Ile Leu Thr Arg Ala Ser Ser Val Trp Val Met Met Asn Gln
                245                 250                 255

Lys Thr Arg Arg Leu Ser Lys Ile Pro Asp Glu Val Arg Asn Glu Ile
            260                 265                 270

Glu Pro His Phe Val Asp Ser Ala Pro Val Val Glu Asp Asp Asp Arg
        275                 280                 285

Lys Leu Pro Lys Leu Asp Glu Asn Thr Ala Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Pro Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Ala
        355                 360                 365
```

```
Glu Gly Tyr Val Ser Arg Phe Gln His Leu Leu Arg Leu Glu Asp Gly
    370                 375                 380

Gly Glu Ile Val Lys Ala Arg Thr Glu Trp Arg Pro Lys Asn Ala Gly
385                 390                 395                 400

Ile Asn Gly Val Val Pro Ser Glu Glu Ser Ser Pro Gly Asp Phe Phe
                405                 410                 415


<210> SEQ ID NO 120
<211> LENGTH: 417
<212> TYPE: PRT
<213> ORGANISM: Cuphea wrightii
<220> FEATURE:
<223> OTHER INFORMATION: CwFATB4b amino acid sequence

<400> SEQUENCE: 120

Met Val Ala Thr Ala Ala Ser Ser Ala Phe Phe Pro Val Pro Ser Ala
1               5                   10                  15

Asp Thr Ser Ser Ser Arg Pro Gly Lys Leu Gly Asn Gly Pro Ser Ser
            20                  25                  30

Leu Ser Pro Leu Lys Pro Lys Ser Ile Pro Asn Gly Gly Leu Gln Val
        35                  40                  45

Lys Ala Asn Ala Ser Ala Pro Pro Lys Ile Asn Gly Ser Ser Val Gly
    50                  55                  60

Leu Lys Ser Gly Ser Phe Lys Thr Gln Glu Asp Ala Pro Ser Ala Pro
65                  70                  75                  80

Pro Pro Arg Thr Phe Ile Asn Gln Leu Pro Asp Trp Ser Met Leu Leu
                85                  90                  95

Ala Ala Ile Thr Thr Val Phe Leu Ala Ala Glu Lys Gln Trp Met Met
            100                 105                 110

Leu Asp Trp Lys Pro Lys Arg Pro Asp Met Leu Val Asp Pro Phe Gly
        115                 120                 125

Leu Gly Ser Ile Val Gln Asp Gly Leu Val Phe Arg Gln Asn Phe Ser
    130                 135                 140

Ile Arg Ser Tyr Glu Ile Gly Ala Asp Arg Thr Ala Ser Ile Glu Thr
145                 150                 155                 160

Val Met Asn His Leu Gln Glu Thr Ala Leu Asn His Val Lys Ile Ala
                165                 170                 175

Gly Leu Ser Ser Asp Gly Phe Gly Arg Thr Pro Ala Met Ser Lys Arg
            180                 185                 190

Asp Leu Ile Trp Val Val Ala Lys Met Gln Val Met Val Asn Arg Tyr
        195                 200                 205

Pro Ala Trp Gly Asp Thr Val Glu Val Asn Thr Trp Val Ala Lys Ser
    210                 215                 220

Gly Lys Asn Gly Met Arg Arg Asp Trp Leu Ile Ser Asp Cys Asn Thr
225                 230                 235                 240

Gly Glu Ile Leu Thr Arg Ala Ser Ser Val Trp Val Met Met Asn Gln
                245                 250                 255

Lys Thr Arg Arg Leu Ser Lys Ile Pro Asp Glu Val Arg Asn Glu Ile
            260                 265                 270

Glu Pro His Phe Val Asp Ser Ala Pro Val Val Glu Asp Asp Asp Arg
        275                 280                 285

Lys Leu Pro Lys Leu Asp Glu Asn Thr Ala Asp Ser Ile Arg Lys Gly
    290                 295                 300

Leu Thr Pro Arg Trp Asn Asp Leu Asp Val Asn Gln His Val Asn Asn
305                 310                 315                 320
```

```
Val Lys Tyr Ile Gly Trp Ile Leu Glu Ser Thr Pro Ala Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Gly
        355                 360                 365

Glu Gly Asp Gly Ser Lys Phe Gln His Leu Leu Arg Leu Glu Asp Gly
    370                 375                 380

Gly Glu Ile Val Lys Ala Arg Thr Glu Trp Arg Pro Lys Asn Ala Gly
385                 390                 395                 400

Ile Asn Gly Val Val Pro Ser Glu Glu Ser Ser Pro Gly Gly Asp Phe
                405                 410                 415

Phe


<210> SEQ ID NO 121
<211> LENGTH: 417
<212> TYPE: PRT
<213> ORGANISM: Cuphea wrightii
<220> FEATURE:
<223> OTHER INFORMATION: CwFATB4b.1 amino acid sequence

<400> SEQUENCE: 121

Met Val Ala Thr Ala Ala Ser Ser Ala Phe Phe Pro Val Pro Ser Ala
1               5                   10                  15

Asp Thr Ser Ser Ser Arg Pro Gly Lys Leu Gly Ser Gly Pro Ser Ser
            20                  25                  30

Leu Ser Pro Leu Lys Pro Lys Ser Ile Pro Asn Gly Gly Leu Gln Val
        35                  40                  45

Lys Ala Asn Ala Ser Ala Pro Pro Lys Ile Asn Gly Ser Ser Val Gly
    50                  55                  60

Leu Lys Ser Gly Ser Phe Lys Thr Gln Glu Asp Ala Pro Ser Ala Pro
65                  70                  75                  80

Pro Pro Arg Thr Phe Ile Asn Gln Leu Pro Asp Trp Ser Met Leu Leu
                85                  90                  95

Ala Ala Ile Thr Thr Val Phe Leu Ala Ala Glu Lys Gln Trp Met Met
            100                 105                 110

Leu Asp Trp Lys Pro Lys Arg Pro Asp Met Leu Val Asp Pro Phe Gly
        115                 120                 125

Leu Gly Ser Ile Val Gln Asp Gly Leu Val Phe Arg Gln Asn Phe Ser
    130                 135                 140

Ile Arg Ser Tyr Glu Ile Gly Ala Asp Arg Thr Ala Ser Ile Glu Thr
145                 150                 155                 160

Val Met Asn His Leu Gln Glu Thr Ala Leu Asn His Val Lys Ile Ala
                165                 170                 175

Gly Leu Ser Ser Asp Gly Phe Gly Arg Thr Pro Ala Met Ser Lys Arg
            180                 185                 190

Asp Leu Ile Trp Val Val Ala Lys Met Gln Val Met Val Asn Arg Tyr
        195                 200                 205

Pro Ala Trp Gly Asp Thr Val Glu Val Asn Thr Trp Val Ala Lys Ser
    210                 215                 220

Gly Lys Asn Gly Met Arg Arg Asp Trp Leu Ile Ser Asp Cys Asn Thr
225                 230                 235                 240

Gly Glu Ile Leu Thr Arg Ala Ser Ser Val Trp Val Met Met Asn Gln
                245                 250                 255
```

-continued

```
Lys Thr Arg Arg Leu Ser Lys Ile Pro Asp Glu Val Arg Asn Glu Ile
            260                 265                 270

Glu Pro His Phe Val Asp Ser Ala Pro Val Val Glu Asp Asp Asp Arg
        275                 280                 285

Lys Leu Pro Lys Leu Asp Glu Asn Thr Ala Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Ala Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Gly
        355                 360                 365

Glu Gly Asp Gly Ser Lys Phe Gln His Leu Leu Arg Leu Glu Asp Gly
    370                 375                 380

Gly Glu Ile Val Lys Ala Arg Thr Glu Trp Arg Pro Lys Asn Ala Gly
385                 390                 395                 400

Ile Asn Gly Val Val Pro Ser Glu Glu Ser Ser Pro Gly Gly Asp Phe
                405                 410                 415

Phe


<210> SEQ ID NO 122
<211> LENGTH: 413
<212> TYPE: PRT
<213> ORGANISM: Cuphea wrightii
<220> FEATURE:
<223> OTHER INFORMATION: CwFATB5 amino acid sequence

<400> SEQUENCE: 122

Met Val Ala Ala Ala Ala Ser Ser Ala Phe Phe Ser Val Pro Thr Pro
1               5                   10                  15

Gly Thr Pro Pro Lys Pro Gly Lys Phe Gly Asn Trp Pro Ser Ser Leu
            20                  25                  30

Ser Val Pro Phe Lys Pro Asp Asn Gly Gly Phe His Val Lys Ala Asn
        35                  40                  45

Ala Ser Ala His Pro Lys Ala Asn Gly Ser Ala Val Asn Leu Lys Ser
    50                  55                  60

Gly Ser Leu Glu Thr Pro Pro Arg Ser Phe Ile Asn Gln Leu Pro Asp
65                  70                  75                  80

Leu Ser Val Leu Leu Ser Lys Ile Thr Thr Val Phe Gly Ala Ala Glu
                85                  90                  95

Lys Gln Trp Lys Arg Pro Gly Met Leu Val Glu Pro Phe Gly Val Asp
            100                 105                 110

Arg Ile Phe Gln Asp Gly Val Phe Phe Arg Gln Ser Phe Ser Ile Arg
        115                 120                 125

Ser Tyr Glu Ile Gly Val Asp Arg Thr Ala Ser Ile Glu Thr Leu Met
    130                 135                 140

Asn Ile Phe Gln Glu Thr Ser Leu Asn His Cys Lys Ser Ile Gly Leu
145                 150                 155                 160

Leu Asn Asp Gly Phe Gly Arg Thr Pro Glu Met Cys Lys Arg Asp Leu
                165                 170                 175

Ile Trp Val Val Thr Lys Ile Gln Val Glu Val Asn Arg Tyr Pro Thr
            180                 185                 190

Trp Gly Asp Thr Ile Glu Val Asn Thr Trp Val Ser Glu Ser Gly Lys
```

```
        195                 200                 205

Asn Gly Met Gly Arg Asp Trp Leu Ile Ser Asp Cys Arg Thr Gly Glu
    210                 215                 220

Ile Leu Ile Arg Ala Thr Ser Val Trp Ala Met Met Asn Gln Asn Thr
225                 230                 235                 240

Arg Arg Leu Ser Lys Phe Pro Tyr Glu Val Arg Gln Glu Ile Ala Pro
                245                 250                 255

His Phe Val Asp Ser Ala Pro Val Ile Glu Asp Asp Gln Lys Leu Gln
            260                 265                 270

Lys Leu Asp Val Lys Thr Gly Asp Ser Ile Arg Asp Gly Leu Thr Pro
        275                 280                 285

Arg Trp Asn Asp Leu Asp Val Asn Gln His Val Asn Asn Val Lys Tyr
    290                 295                 300

Ile Gly Trp Ile Leu Lys Ser Val Pro Ile Glu Val Phe Glu Thr Gln
305                 310                 315                 320

Glu Leu Cys Gly Val Thr Leu Glu Tyr Arg Arg Glu Cys Gly Arg Asp
                325                 330                 335

Ser Val Leu Glu Ser Val Thr Ala Met Asp Pro Ala Lys Glu Gly Asp
            340                 345                 350

Arg Cys Val Tyr Gln His Leu Leu Arg Leu Glu Asp Gly Ala Asp Ile
        355                 360                 365

Thr Ile Gly Arg Thr Glu Trp Arg Pro Lys Asn Ala Gly Ala Asn Gly
    370                 375                 380

Ala Met Ser Ser Gly Lys Thr Ser Asn Gly Asn Cys Leu Ile Glu Gly
385                 390                 395                 400

Arg Gly Trp Gln Pro Phe Arg Val Val Arg Leu Ile Phe
                405                 410


<210> SEQ ID NO 123
<211> LENGTH: 413
<212> TYPE: PRT
<213> ORGANISM: Cuphea wrightii
<220> FEATURE:
<223> OTHER INFORMATION: CwFATB5a amino acid sequence

<400> SEQUENCE: 123

Met Val Ala Ala Ala Ala Ser Ser Ala Phe Phe Ser Val Pro Thr Pro
1               5                   10                  15

Gly Thr Pro Pro Lys Pro Gly Lys Phe Gly Asn Trp Pro Ser Ser Leu
            20                  25                  30

Ser Val Pro Phe Lys Pro Asp Asn Gly Gly Phe His Val Lys Ala Asn
        35                  40                  45

Ala Ser Ala His Pro Lys Ala Asn Gly Ser Ala Val Asn Leu Lys Ser
    50                  55                  60

Gly Ser Leu Glu Thr Pro Pro Arg Ser Phe Ile Asn Gln Leu Pro Asp
65                  70                  75                  80

Leu Ser Val Leu Leu Ser Lys Ile Thr Thr Val Phe Gly Ala Ala Glu
                85                  90                  95

Lys Gln Trp Lys Arg Pro Gly Met Leu Val Glu Pro Phe Gly Val Asp
            100                 105                 110

Arg Ile Phe Gln Asp Gly Phe Phe Phe Arg Gln Ser Phe Ser Ile Arg
        115                 120                 125

Ser Tyr Glu Ile Gly Val Asp Arg Thr Ala Ser Ile Glu Thr Leu Met
    130                 135                 140

Asn Ile Phe Gln Glu Thr Ser Leu Asn His Cys Lys Ser Ile Gly Leu
```

```
145                 150                 155                 160

Leu Asn Asp Gly Phe Gly Arg Thr Pro Glu Met Cys Lys Arg Asp Leu
                165                 170                 175

Ile Trp Val Val Thr Lys Ile Gln Val Glu Val Asn Arg Tyr Pro Thr
            180                 185                 190

Trp Gly Asp Thr Ile Glu Val Asn Thr Trp Val Ser Glu Ser Gly Lys
        195                 200                 205

Asn Gly Met Gly Arg Asp Trp Leu Ile Ser Asp Cys Arg Thr Gly Glu
    210                 215                 220

Ile Leu Ile Arg Ala Thr Ser Val Trp Ala Met Met Asn Gln Asn Thr
225                 230                 235                 240

Arg Arg Leu Ser Lys Phe Pro Tyr Glu Val Arg Gln Glu Ile Ala Pro
                245                 250                 255

His Phe Val Asp Ser Ala Pro Val Ile Glu Asp Asp Gln Lys Leu Gln
            260                 265                 270

Lys Leu Asp Val Lys Thr Gly Asp Ser Ile Arg Asp Gly Leu Thr Pro
        275                 280                 285

Arg Trp Asn Asp Leu Asp Val Asn Gln His Val Asn Asn Val Lys Tyr
    290                 295                 300

Ile Gly Trp Ile Leu Lys Ser Val Pro Ile Glu Val Phe Glu Thr Gln
305                 310                 315                 320

Glu Leu Cys Gly Val Thr Leu Glu Tyr Arg Arg Glu Cys Gly Arg Asp
                325                 330                 335

Ser Val Leu Glu Ser Val Thr Ala Met Asp Pro Ala Lys Glu Gly Asp
            340                 345                 350

Arg Cys Val Tyr Gln His Leu Leu Arg Leu Glu Asp Gly Ala Asp Ile
        355                 360                 365

Thr Ile Gly Arg Thr Glu Trp Arg Pro Lys Asn Ala Gly Ala Asn Gly
    370                 375                 380

Ala Met Ser Ser Gly Lys Thr Ser Asn Gly Asn Cys Leu Ile Glu Gly
385                 390                 395                 400

Arg Gly Trp Gln Pro Phe Arg Val Val Arg Leu Ile Phe
                405                 410


<210> SEQ ID NO 124
<211> LENGTH: 413
<212> TYPE: PRT
<213> ORGANISM: Cuphea wrightii
<220> FEATURE:
<223> OTHER INFORMATION: CwFATB5b amino acid sequence

<400> SEQUENCE: 124

Met Val Ala Ala Ala Ala Ser Ser Ala Phe Phe Ser Val Pro Thr Pro
1               5                   10                  15

Gly Thr Pro Pro Lys Pro Gly Lys Phe Gly Asn Trp Pro Ser Ser Leu
            20                  25                  30

Ser Val Pro Phe Lys Pro Asp Asn Gly Gly Phe His Val Lys Ala Asn
        35                  40                  45

Ala Ser Ala His Pro Lys Ala Asn Gly Ser Ala Val Asn Leu Lys Ser
    50                  55                  60

Gly Ser Leu Glu Thr Pro Pro Arg Ser Phe Ile Asn Gln Leu Pro Asp
65                  70                  75                  80

Leu Ser Val Leu Leu Ser Lys Ile Thr Thr Val Phe Gly Ala Ala Glu
                85                  90                  95

Lys Gln Trp Lys Arg Pro Gly Met Leu Val Glu Pro Phe Gly Val Asp
```

```
            100                 105                 110

Arg Ile Phe Gln Asp Gly Val Phe Phe Arg Gln Ser Phe Ser Ile Arg
        115                 120                 125

Ser Tyr Glu Ile Gly Val Asp Arg Thr Ala Ser Ile Glu Thr Leu Met
    130                 135                 140

Asn Ile Phe Gln Glu Thr Ser Leu Asn His Cys Lys Ser Ile Gly Leu
145                 150                 155                 160

Leu Asn Asp Gly Phe Gly Arg Thr Pro Glu Met Cys Lys Arg Asp Leu
                165                 170                 175

Ile Trp Val Val Thr Lys Ile Gln Val Glu Val Asn Arg Tyr Pro Thr
            180                 185                 190

Trp Gly Asp Thr Ile Glu Val Asn Thr Trp Val Ser Glu Ser Gly Lys
        195                 200                 205

Asn Gly Met Gly Arg Asp Trp Leu Ile Ser Asp Cys Arg Thr Gly Glu
    210                 215                 220

Ile Leu Ile Arg Ala Thr Ser Val Trp Ala Met Met Asn Gln Asn Thr
225                 230                 235                 240

Arg Arg Leu Ser Lys Phe Pro Tyr Glu Val Arg Gln Glu Ile Ala Pro
                245                 250                 255

His Phe Val Asp Ser Ala Pro Val Ile Glu Asp Asp Gln Lys Leu Gln
            260                 265                 270

Lys Leu Asp Val Lys Thr Gly Asp Ser Ile Arg Asp Gly Leu Thr Pro
        275                 280                 285

Arg Trp Asn Asp Leu Asp Val Asn Gln His Val Asn Asn Val Lys Tyr
    290                 295                 300

Ile Gly Trp Ile Leu Lys Ser Val Pro Ile Glu Val Phe Glu Thr Gln
305                 310                 315                 320

Glu Leu Cys Gly Val Thr Leu Glu Tyr Arg Arg Glu Cys Gly Arg Asp
                325                 330                 335

Ser Val Leu Glu Ser Val Thr Ala Met Asp Pro Ala Lys Glu Gly Asp
            340                 345                 350

Arg Cys Val Tyr Gln His Leu Leu Trp Leu Glu Asp Gly Ala Asp Ile
        355                 360                 365

Thr Ile Gly Arg Thr Glu Trp Arg Pro Lys Asn Ala Gly Ala Asn Gly
    370                 375                 380

Ala Met Ser Ser Gly Lys Thr Ser Asn Gly Asn Cys Leu Ile Glu Gly
385                 390                 395                 400

Arg Gly Trp Gln Pro Phe Arg Val Val Arg Leu Ile Phe
                405                 410
```

<210> SEQ ID NO 125
<211> LENGTH: 413
<212> TYPE: PRT
<213> ORGANISM: Cuphea wrightii
<220> FEATURE:
<223> OTHER INFORMATION: CwFATB5c amino acid sequence

<400> SEQUENCE: 125

```
Met Val Ala Ala Ala Ala Ser Ser Ala Phe Phe Ser Val Pro Thr Pro
1               5                   10                  15

Gly Thr Pro Pro Lys Pro Gly Lys Phe Gly Asn Trp Pro Ser Ser Leu
            20                  25                  30

Ser Val Pro Phe Lys Pro Asp Asn Gly Gly Phe His Val Lys Ala Asn
        35                  40                  45

Ala Ser Ala His Pro Lys Ala Asn Gly Ser Ala Val Asn Leu Lys Ser
```

```
    50                  55                  60

Gly Ser Leu Glu Thr Pro Pro Arg Ser Phe Ile Asn Gln Leu Pro Asp
65                  70                  75                  80

Leu Ser Val Leu Leu Ser Lys Ile Thr Thr Val Phe Gly Ala Ala Glu
                85                  90                  95

Lys Gln Trp Lys Arg Pro Gly Met Leu Val Glu Pro Phe Gly Val Asp
            100                 105                 110

Arg Ile Phe Gln Asp Gly Val Phe Phe Arg Gln Ser Phe Ser Ile Arg
        115                 120                 125

Ser Tyr Glu Ile Gly Val Asp Arg Thr Ala Ser Ile Glu Thr Leu Met
    130                 135                 140

Asn Ile Phe Gln Glu Thr Ser Leu Asn His Cys Lys Ser Ile Gly Leu
145                 150                 155                 160

Leu Asn Asp Gly Phe Gly Arg Thr Pro Glu Met Cys Lys Arg Asp Leu
                165                 170                 175

Ile Trp Val Val Thr Lys Ile Gln Val Glu Val Asn Arg Tyr Pro Ile
            180                 185                 190

Trp Gly Asp Thr Ile Glu Val Asn Thr Trp Val Ser Glu Ser Gly Lys
        195                 200                 205

Asn Gly Met Gly Arg Asp Trp Leu Ile Ser Asp Cys Arg Thr Gly Glu
    210                 215                 220

Ile Leu Ile Arg Ala Thr Ser Val Trp Ala Met Met Asn Gln Asn Thr
225                 230                 235                 240

Arg Arg Leu Ser Lys Phe Pro Tyr Glu Val Arg Gln Glu Ile Ala Pro
                245                 250                 255

His Phe Val Asp Ser Ala Pro Val Ile Glu Asp Asp Gln Lys Leu Gln
            260                 265                 270

Lys Leu Asp Val Lys Thr Gly Asp Ser Ile Arg Asp Gly Leu Thr Pro
        275                 280                 285

Arg Trp Asn Asp Leu Asp Val Asn Gln His Val Asn Asn Val Lys Tyr
    290                 295                 300

Ile Gly Trp Ile Leu Lys Ser Val Pro Ile Glu Val Phe Glu Thr Gln
305                 310                 315                 320

Glu Leu Cys Gly Val Thr Leu Glu Tyr Arg Arg Glu Cys Gly Arg Asp
                325                 330                 335

Ser Val Leu Glu Ser Val Thr Ala Met Asp Pro Ala Lys Glu Gly Asp
            340                 345                 350

Arg Cys Val Tyr Gln His Leu Leu Arg Leu Glu Asp Gly Ala Asp Ile
        355                 360                 365

Thr Ile Gly Arg Thr Glu Trp Arg Pro Lys Asn Ala Gly Ala Asn Gly
    370                 375                 380

Ala Met Ser Ser Gly Lys Thr Ser Asn Gly Asn Cys Leu Ile Glu Gly
385                 390                 395                 400

Met Gly Trp Gln Pro Phe Arg Val Val Arg Leu Ile Phe
                405                 410


<210> SEQ ID NO 126
<211> LENGTH: 409
<212> TYPE: PRT
<213> ORGANISM: Cuphea wrightii
<220> FEATURE:
<223> OTHER INFORMATION: CwFATB5.1 amino acid sequence

<400> SEQUENCE: 126

Met Val Ala Ala Ala Ala Ser Ser Ala Phe Phe Ser Val Pro Thr Pro
```

-continued

```
1               5                   10                  15

Gly Thr Ser Pro Lys Pro Gly Lys Phe Arg Asn Trp Pro Ser Ser Leu
            20                  25                  30

Ser Val Pro Phe Lys Pro Glu Thr Asn His Asn Gly Gly Phe His Ile
        35                  40                  45

Lys Ala Asn Ala Ser Ala His Pro Lys Ala Asn Gly Ser Ala Leu Asn
    50                  55                  60

Leu Lys Ser Gly Ser Leu Glu Thr Gln Glu Asp Thr Ser Leu Ser Ser
65                  70                  75                  80

Pro Pro Arg Thr Phe Ile Lys Gln Leu Pro Asp Trp Ser Met Leu Leu
                85                  90                  95

Ser Lys Ile Thr Thr Val Phe Gly Ala Ala Glu Lys Gln Leu Lys Arg
            100                 105                 110

Pro Gly Met Leu Val Glu Pro Phe Gly Val Asp Arg Ile Phe Gln Asp
        115                 120                 125

Gly Val Phe Phe Arg Gln Ser Phe Ser Ile Arg Ser Tyr Glu Ile Gly
    130                 135                 140

Ala Asp Arg Thr Ala Ser Ile Glu Thr Leu Met Asn Ile Phe Gln Glu
145                 150                 155                 160

Thr Ser Leu Asn His Cys Lys Ser Ile Gly Leu Leu Asn Asp Gly Phe
                165                 170                 175

Gly Arg Thr Pro Glu Met Cys Lys Arg Asp Leu Ile Trp Val Val Thr
            180                 185                 190

Lys Ile Gln Val Glu Val Asn Arg Tyr Pro Thr Trp Gly Asp Thr Ile
        195                 200                 205

Glu Val Asn Thr Trp Val Ser Glu Ser Gly Lys Asn Gly Met Gly Arg
    210                 215                 220

Asp Trp Leu Ile Ser Asp Cys Arg Thr Gly Glu Ile Leu Ile Arg Ala
225                 230                 235                 240

Thr Ser Val Trp Ala Met Met Asn Gln Asn Thr Arg Arg Leu Ser Lys
                245                 250                 255

Phe Pro Tyr Glu Val Arg Gln Glu Ile Ala Pro His Phe Val Asp Ser
            260                 265                 270

Ala Pro Val Ile Glu Asp Asp Arg Lys Leu Tyr Lys Leu Asn Val Lys
        275                 280                 285

Thr Gly Asp Ser Ile Arg Asp Gly Leu Thr Pro Arg Trp Asn Asp Leu
    290                 295                 300

Asp Val Asn Gln His Val Asn Asn Val Lys Phe Ile Gly Trp Ile Leu
305                 310                 315                 320

Lys Ser Val Pro Thr Lys Val Phe Glu Thr Gln Glu Leu Cys Gly Val
                325                 330                 335

Thr Leu Glu Tyr Arg Arg Glu Cys Gly Lys Asp Ser Val Leu Glu Ser
            340                 345                 350

Val Thr Ala Met Asp Pro Ala Lys Glu Gly Asp Arg Ser Val Tyr Gln
        355                 360                 365

His Leu Leu Arg Leu Glu Asp Gly Ala Asp Ile Thr Ile Gly Arg Thr
    370                 375                 380

Glu Trp Arg Pro Lys Asn Ala Gly Ala Asn Glu Ala Ile Ser Ser Gly
385                 390                 395                 400

Lys Thr Ser Asn Gly Asn Ser Ala Ser
                405
```

<210> SEQ ID NO 127

```
<211> LENGTH: 409
<212> TYPE: PRT
<213> ORGANISM: Cuphea wrightii
<220> FEATURE:
<223> OTHER INFORMATION: CwFATB5.1a amino acid sequence

<400> SEQUENCE: 127

Met Val Ala Ala Ala Ala Ser Ser Ala Phe Phe Ser Val Pro Thr Pro
1               5                   10                  15

Gly Thr Ser Pro Lys Pro Gly Lys Phe Arg Asn Trp Pro Leu Ser Leu
            20                  25                  30

Ser Val Pro Phe Lys Pro Glu Thr Asn His Asn Gly Gly Phe His Ile
        35                  40                  45

Lys Ala Asn Ala Ser Ala His Pro Lys Ala Asn Gly Ser Ala Leu Asn
    50                  55                  60

Leu Lys Ser Gly Ser Leu Glu Thr Gln Glu Asp Thr Ser Leu Ser Ser
65                  70                  75                  80

Pro Pro Arg Thr Phe Ile Lys Gln Leu Pro Asp Trp Ser Met Leu Leu
                85                  90                  95

Ser Lys Ile Thr Thr Val Phe Gly Ala Ala Glu Lys Gln Leu Lys Arg
            100                 105                 110

Pro Gly Met Leu Val Glu Pro Phe Gly Val Asp Arg Ile Phe Gln Asp
        115                 120                 125

Gly Val Phe Phe Arg Gln Ser Phe Ser Ile Arg Ser Tyr Glu Ile Gly
    130                 135                 140

Ala Asp Arg Thr Ala Ser Ile Glu Thr Leu Met Asn Ile Phe Gln Glu
145                 150                 155                 160

Thr Ser Leu Asn His Cys Lys Ser Ile Gly Leu Leu Asn Asp Gly Phe
                165                 170                 175

Gly Arg Thr Pro Glu Met Cys Lys Arg Asp Leu Ile Trp Val Val Thr
            180                 185                 190

Lys Ile Gln Val Glu Val Asn Arg Tyr Pro Thr Trp Gly Asp Thr Ile
        195                 200                 205

Glu Val Asn Thr Trp Val Ser Glu Ser Gly Lys Asn Gly Met Gly Arg
    210                 215                 220

Asp Trp Leu Ile Ser Asp Cys Arg Thr Gly Glu Ile Leu Ile Arg Ala
225                 230                 235                 240

Thr Ser Val Trp Ala Met Met Asn Gln Asn Thr Arg Arg Leu Ser Lys
                245                 250                 255

Phe Pro Tyr Glu Val Arg Gln Glu Ile Ala Pro His Phe Val Asp Ser
            260                 265                 270

Ala Pro Val Ile Glu Asp Asp Arg Lys Leu Tyr Lys Leu Asn Val Lys
        275                 280                 285

Thr Gly Asp Ser Ile Arg Asp Gly Leu Thr Pro Arg Trp Asn Asp Leu
    290                 295                 300

Asp Val Asn Gln His Val Asn Asn Val Lys Phe Ile Gly Trp Ile Leu
305                 310                 315                 320

Lys Ser Val Pro Thr Lys Val Phe Glu Thr Gln Glu Leu Cys Gly Val
                325                 330                 335

Thr Leu Glu Tyr Arg Arg Glu Cys Gly Lys Asp Ser Val Leu Glu Ser
            340                 345                 350

Val Thr Ala Met Asp Pro Ala Lys Glu Gly Asp Arg Ser Val Tyr Gln
        355                 360                 365

His Leu Leu Arg Leu Glu Asp Gly Ala Asp Ile Thr Ile Gly Arg Thr
    370                 375                 380
```

```
Glu Trp Arg Pro Lys Asn Ala Gly Ala Asn Glu Ala Ile Ser Ser Gly
385                 390                 395                 400

Lys Thr Ser Asn Gly Asn Ser Ala Ser
                405


<210> SEQ ID NO 128
<211> LENGTH: 357
<212> TYPE: PRT
<213> ORGANISM: Cinnamomum camphora
<220> FEATURE:
<223> OTHER INFORMATION: CcFATB2b amino acid sequence

<400> SEQUENCE: 128

Met Val Thr Thr Ser Leu Ala Ser Ala Tyr Phe Ser Met Lys Ala Val
1               5                   10                  15

Met Leu Ala Pro Asp Gly Arg Gly Ile Lys Pro Arg Ser Ser Gly Leu
            20                  25                  30

Gln Val Arg Ala Gly Asn Glu Arg Asn Ser Cys Lys Val Ile Asn Gly
        35                  40                  45

Thr Lys Val Lys Asp Thr Glu Gly Leu Lys Gly Cys Ser Thr Leu Gln
    50                  55                  60

Gly Gln Ser Met Leu Asp Asp His Phe Gly Leu His Gly Leu Val Phe
65                  70                  75                  80

Arg Arg Thr Phe Ala Ile Arg Cys Tyr Glu Val Gly Pro Asp Arg Ser
                85                  90                  95

Thr Ser Ile Met Ala Val Met Asn His Leu Gln Glu Ala Ala Arg Asn
            100                 105                 110

His Ala Glu Ser Leu Gly Leu Leu Gly Asp Gly Phe Gly Glu Thr Leu
        115                 120                 125

Glu Met Ser Lys Arg Asp Leu Ile Trp Val Val Arg Arg Thr His Val
    130                 135                 140

Ala Val Glu Arg Tyr Pro Ala Trp Gly Asp Thr Val Glu Val Glu Ala
145                 150                 155                 160

Trp Val Gly Ala Ser Gly Asn Thr Gly Met Arg Arg Asp Phe Leu Val
                165                 170                 175

Arg Asp Cys Lys Thr Gly His Ile Leu Thr Arg Cys Thr Ser Val Ser
            180                 185                 190

Val Met Met Asn Met Arg Thr Arg Arg Leu Ser Lys Ile Pro Gln Glu
        195                 200                 205

Val Arg Ala Glu Ile Asp Pro Leu Phe Ile Glu Lys Val Ala Val Lys
    210                 215                 220

Glu Gly Glu Ile Lys Lys Leu Gln Lys Leu Asn Asp Ser Thr Ala Asp
225                 230                 235                 240

Tyr Ile Gln Gly Gly Trp Thr Pro Arg Trp Asn Asp Leu Asp Val Asn
                245                 250                 255

Gln His Val Asn Asn Ile Ile Tyr Val Gly Trp Ile Phe Lys Ser Val
            260                 265                 270

Pro Asp Ser Ile Ser Glu Asn His His Leu Ser Ser Ile Thr Leu Glu
        275                 280                 285

Tyr Arg Arg Glu Cys Ile Arg Gly Asn Lys Leu Gln Ser Leu Thr Thr
    290                 295                 300

Val Cys Gly Gly Ser Ser Glu Ala Gly Ile Ile Cys Glu His Leu Leu
305                 310                 315                 320

Gln Leu Glu Asp Gly Ser Glu Val Leu Arg Ala Arg Thr Glu Trp Arg
                325                 330                 335
```

```
Pro Lys His Thr Asp Ser Phe Gln Gly Ile Ser Glu Arg Phe Pro Gln
            340                 345                 350

Gln Glu Pro His Lys
        355


<210> SEQ ID NO 129
<211> LENGTH: 419
<212> TYPE: PRT
<213> ORGANISM: Cinnamomum camphora
<220> FEATURE:
<223> OTHER INFORMATION: CcFATB3 amino acid sequence

<400> SEQUENCE: 129

Met Val Ala Thr Ala Ala Ala Ser Ala Phe Phe Pro Val Gly Ala Pro
1               5                   10                  15

Ala Thr Ser Ser Ala Thr Ser Ala Lys Ala Ser Met Met Pro Asp Asn
            20                  25                  30

Leu Asp Ala Arg Gly Ile Lys Pro Lys Pro Ala Ser Ser Ser Gly Leu
        35                  40                  45

Gln Val Lys Ala Asn Ala His Ala Ser Pro Lys Ile Asn Gly Ser Lys
    50                  55                  60

Val Ser Thr Asp Thr Leu Lys Gly Glu Asp Thr Leu Thr Ser Ser Pro
65                  70                  75                  80

Ala Pro Arg Thr Phe Ile Asn Gln Leu Pro Asp Trp Ser Met Phe Leu
                85                  90                  95

Ala Ala Ile Thr Thr Ile Phe Leu Ala Ala Glu Lys Gln Trp Thr Asn
            100                 105                 110

Leu Asp Trp Lys Pro Arg Arg Pro Asp Met Leu Ala Asp Pro Phe Gly
        115                 120                 125

Ile Gly Arg Phe Met Gln Asp Gly Leu Ile Phe Arg Gln His Phe Ala
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ala Leu Asn His Val Arg Ser Ala
                165                 170                 175

Gly Leu Leu Gly Asp Gly Phe Gly Ala Thr Pro Glu Met Ser Arg Arg
            180                 185                 190

Asp Leu Ile Trp Val Val Thr Arg Met Gln Val Leu Val Asp Arg Tyr
        195                 200                 205

Pro Ala Trp Gly Asp Ile Val Glu Val Glu Thr Trp Val Gly Ala Ser
    210                 215                 220

Gly Lys Asn Gly Met Arg Arg Asp Trp Leu Val Arg Asp Ser Gln Thr
225                 230                 235                 240

Gly Glu Ile Leu Thr Arg Ala Thr Ser Val Trp Val Met Met Asn Lys
                245                 250                 255

Arg Thr Arg Arg Leu Ser Lys Leu Pro Glu Glu Val Arg Gly Glu Ile
            260                 265                 270

Gly Pro Tyr Phe Ile Glu Asp Val Ala Ile Ile Glu Glu Asp Asn Arg
        275                 280                 285

Lys Leu Gln Lys Leu Asn Glu Asn Thr Ala Asp Asn Val Arg Arg Gly
    290                 295                 300

Leu Thr Pro Arg Trp Ser Asp Leu Asp Val Asn Gln His Val Asn Asn
305                 310                 315                 320

Val Lys Tyr Ile Gly Trp Ile Leu Glu Ser Ala Pro Gly Ser Ile Leu
                325                 330                 335
```

```
Glu Ser His Glu Leu Ser Cys Met Thr Leu Glu Tyr Arg Arg Glu Cys
            340                 345                 350

Gly Lys Asp Ser Val Leu Gln Ser Met Thr Ala Val Ser Gly Gly Gly
        355                 360                 365

Ser Ala Ala Gly Gly Ser Pro Glu Ser Ser Val Glu Cys Asp His Leu
    370                 375                 380

Leu Gln Leu Glu Ser Gly Pro Glu Val Val Arg Gly Arg Thr Glu Trp
385                 390                 395                 400

Arg Pro Lys Ser Ala Asn Asn Ser Arg Ser Ile Leu Glu Met Pro Ala
                405                 410                 415

Glu Ser Leu


<210> SEQ ID NO 130
<211> LENGTH: 419
<212> TYPE: PRT
<213> ORGANISM: Cinnamomum camphora
<220> FEATURE:
<223> OTHER INFORMATION: CcFATB3b amino acid sequence

<400> SEQUENCE: 130

Met Val Ala Thr Ala Ala Ala Ser Ala Phe Phe Pro Val Gly Ala Pro
1               5                   10                  15

Ala Thr Ser Ser Ala Thr Ser Ala Lys Ala Ser Met Met Pro Asp Asn
            20                  25                  30

Leu Asp Ala Arg Gly Ile Lys Pro Lys Leu Ala Ser Ser Ser Gly Leu
        35                  40                  45

Gln Val Lys Ala Asn Ala His Ala Ser Pro Lys Ile Asn Gly Ser Lys
    50                  55                  60

Val Ser Thr Asp Thr Leu Lys Gly Glu Asp Thr Leu Thr Ser Ser Pro
65                  70                  75                  80

Ala Pro Arg Thr Phe Ile Asn Gln Leu Pro Asp Trp Ser Met Phe Leu
                85                  90                  95

Ala Ala Ile Thr Thr Ile Phe Leu Ala Ala Glu Lys Gln Trp Thr Asn
            100                 105                 110

Leu Asp Trp Lys Pro Arg Arg Pro Asp Met Leu Ala Asp Pro Phe Gly
        115                 120                 125

Ile Gly Arg Phe Met Gln Asp Gly Leu Ile Phe Arg Gln His Phe Ala
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ala Leu Asn His Val Arg Ser Ala
                165                 170                 175

Gly Leu Leu Gly Asp Gly Phe Gly Ala Thr Pro Glu Met Ser Arg Arg
            180                 185                 190

Asp Leu Ile Trp Val Val Thr Arg Met Gln Val Leu Val Asp Arg Tyr
        195                 200                 205

Pro Ala Trp Gly Asp Ile Val Glu Val Glu Thr Trp Val Gly Ala Ser
    210                 215                 220

Gly Lys Asn Gly Met Arg Arg Asp Trp Leu Val Arg Asp Ser Gln Thr
225                 230                 235                 240

Gly Glu Ile Leu Thr Arg Ala Thr Ser Val Trp Val Met Met Asn Lys
                245                 250                 255

Arg Thr Arg Arg Leu Ser Lys Leu Pro Glu Glu Val Arg Gly Glu Ile
            260                 265                 270
```

```
Gly Pro Tyr Phe Ile Glu Asp Val Ala Ile Ile Glu Glu Asp Asn Arg
        275                 280                 285

Lys Leu Gln Lys Leu Asn Glu Asn Thr Ala Asp Asn Val Arg Arg Gly
    290                 295                 300

Leu Thr Pro Arg Trp Ser Asp Leu Asp Val Asn Gln His Val Asn Asn
305                 310                 315                 320

Val Lys Tyr Ile Gly Trp Ile Leu Glu Ser Ala Pro Gly Ser Ile Leu
                325                 330                 335

Glu Ser His Glu Leu Ser Cys Met Thr Leu Glu Tyr Arg Arg Glu Cys
            340                 345                 350

Gly Lys Asp Ser Val Leu Gln Ser Met Thr Ala Val Ser Gly Gly Gly
        355                 360                 365

Ser Ala Ala Gly Gly Ser Pro Glu Ser Ser Val Glu Cys Asp His Leu
    370                 375                 380

Leu Gln Leu Glu Ser Gly Pro Glu Val Val Arg Gly Arg Thr Glu Trp
385                 390                 395                 400

Arg Pro Lys Ser Ala Asn Asn Ser Arg Ser Ile Leu Glu Met Pro Ala
                405                 410                 415

Glu Ser Leu


<210> SEQ ID NO 131
<211> LENGTH: 419
<212> TYPE: PRT
<213> ORGANISM: Cinnamomum camphora
<220> FEATURE:
<223> OTHER INFORMATION: CcFATB3c amino acid sequence

<400> SEQUENCE: 131

Met Val Ala Thr Ala Ala Ala Ser Ala Phe Phe Pro Val Gly Ala Pro
1               5                   10                  15

Ala Thr Ser Ser Ala Thr Ser Ala Lys Ala Ser Met Met Pro Asp Asn
            20                  25                  30

Leu Asp Ala Arg Gly Ile Lys Pro Lys Pro Ala Ser Ser Ser Gly Leu
        35                  40                  45

Gln Val Lys Ala Asn Ala His Ala Ser Pro Lys Ile Asn Gly Ser Lys
    50                  55                  60

Val Ser Thr Asp Thr Leu Lys Gly Glu Asp Thr Leu Thr Ser Ser Pro
65                  70                  75                  80

Ala Pro Arg Thr Phe Ile Asn Gln Leu Pro Asp Trp Ser Met Phe Leu
                85                  90                  95

Ala Ala Ile Thr Thr Ile Phe Leu Ala Ala Glu Lys Gln Trp Thr Asn
            100                 105                 110

Leu Asp Trp Lys Pro Arg Arg Pro Asp Met Leu Ala Asp Pro Phe Gly
        115                 120                 125

Ile Gly Arg Phe Met Gln Asp Gly Leu Ile Phe Arg Gln His Phe Ala
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ala Leu Asn His Val Arg Ser Ala
                165                 170                 175

Gly Leu Leu Gly Asp Gly Phe Gly Ala Thr Pro Glu Met Ser Arg Arg
            180                 185                 190

Asp Leu Ile Trp Val Val Thr Arg Met Gln Val Leu Val Asp Arg Tyr
        195                 200                 205

Pro Ala Trp Gly Asp Ile Val Glu Val Glu Thr Trp Val Gly Ala Ser
```

```
    210                 215                 220

Gly Lys Asn Gly Met Arg Arg Asp Trp Leu Val Arg Asp Ser Gln Thr
225                 230                 235                 240

Gly Glu Ile Leu Thr Arg Ala Thr Ser Val Trp Val Met Met Asn Lys
                245                 250                 255

Arg Thr Arg Arg Leu Ser Lys Leu Pro Glu Glu Val Arg Gly Glu Ile
            260                 265                 270

Gly Pro Tyr Phe Ile Glu Asp Val Ala Ile Ile Glu Glu Asp Asn Arg
        275                 280                 285

Lys Leu Gln Lys Leu Asn Glu Asn Thr Ala Asp Asn Val Arg Arg Gly
    290                 295                 300

Leu Thr Pro Arg Trp Ser Asp Leu Asp Val Asn Gln His Val Asn Asn
305                 310                 315                 320

Ala Lys Tyr Ile Gly Trp Ile Leu Glu Ser Ala Pro Gly Ser Ile Leu
                325                 330                 335

Glu Ser His Glu Leu Ser Cys Met Thr Leu Glu Tyr Arg Arg Glu Cys
            340                 345                 350

Gly Lys Asp Ser Val Leu Gln Ser Met Thr Ala Val Ser Gly Gly Gly
        355                 360                 365

Ser Ala Ala Gly Gly Ser Pro Glu Ser Ser Val Glu Cys Asp His Leu
    370                 375                 380

Leu Gln Leu Glu Ser Gly Pro Glu Val Val Arg Gly Arg Thr Glu Trp
385                 390                 395                 400

Arg Pro Lys Ser Ala Asn Asn Ser Arg Ser Ile Leu Glu Met Pro Ala
                405                 410                 415

Glu Ser Leu


<210> SEQ ID NO 132
<211> LENGTH: 410
<212> TYPE: PRT
<213> ORGANISM: Cuphea heterophylla
<220> FEATURE:
<223> OTHER INFORMATION: ChtFATB1a amino acid sequence

<400> SEQUENCE: 132

Met Val Ala Ala Ala Ala Ser Ser Ala Phe Phe Ser Val Pro Thr Pro
1               5                   10                  15

Gly Thr Ser Thr Lys Pro Gly Asn Phe Gly Asn Trp Pro Ser Ser Leu
            20                  25                  30

Ser Val Pro Phe Lys Pro Glu Ser Asn His Asn Gly Gly Phe Arg Val
        35                  40                  45

Lys Ala Asn Ala Ser Ala His Pro Lys Ala Asn Gly Ser Ala Val Asn
    50                  55                  60

Leu Lys Ser Gly Ser Leu Glu Thr Gln Glu Asp Thr Ser Ser Ser Ser
65                  70                  75                  80

Pro Pro Pro Arg Thr Phe Ile Lys Gln Leu Pro Asp Trp Gly Met Leu
                85                  90                  95

Leu Ser Lys Ile Thr Thr Val Phe Gly Ala Ala Glu Arg Gln Trp Lys
            100                 105                 110

Arg Pro Gly Met Leu Val Glu Pro Phe Gly Val Asp Arg Ile Phe Gln
        115                 120                 125

Asp Gly Val Phe Phe Arg Gln Ser Phe Ser Ile Arg Ser Tyr Glu Ile
    130                 135                 140

Gly Ala Asp Arg Thr Ala Ser Ile Glu Thr Leu Met Asn Ile Phe Gln
145                 150                 155                 160
```

```
Glu Thr Ser Leu Asn His Cys Lys Ser Ile Gly Leu Leu Asn Asp Gly
                165                 170                 175

Phe Gly Arg Thr Pro Glu Met Cys Lys Arg Asp Leu Ile Trp Val Val
            180                 185                 190

Thr Lys Ile Gln Val Glu Val Asn Arg Tyr Pro Thr Trp Gly Asp Thr
        195                 200                 205

Ile Glu Val Asn Thr Trp Val Ser Glu Ser Gly Lys Asn Gly Met Gly
    210                 215                 220

Arg Asp Trp Leu Ile Ser Asp Cys Arg Thr Gly Glu Ile Leu Ile Arg
225                 230                 235                 240

Ala Thr Ser Val Trp Ala Met Met Asn Arg Lys Thr Arg Arg Leu Ser
                245                 250                 255

Lys Phe Pro Tyr Glu Val Arg Gln Glu Ile Ala Pro His Phe Val Asp
            260                 265                 270

Ser Ala Pro Val Ile Glu Asp Asp Lys Lys Leu His Lys Leu Asp Val
        275                 280                 285

Lys Thr Gly Asp Ser Ile Arg Lys Gly Leu Thr Pro Arg Trp Asn Asp
    290                 295                 300

Leu Asp Val Asn Gln His Val Asn Asn Val Lys Tyr Ile Gly Trp Ile
305                 310                 315                 320

Leu Lys Ser Val Pro Ala Glu Val Phe Glu Thr Gln Glu Leu Cys Gly
                325                 330                 335

Val Thr Leu Glu Tyr Arg Arg Glu Cys Gly Arg Asp Ser Val Leu Glu
            340                 345                 350

Ser Val Thr Ala Met Asp Thr Ala Lys Glu Gly Asp Arg Ser Leu Tyr
        355                 360                 365

Gln His Leu Leu Arg Leu Glu Asp Gly Ala Asp Ile Thr Ile Gly Arg
    370                 375                 380

Thr Glu Trp Arg Pro Lys Asn Ala Gly Ala Asn Gly Ala Ile Ser Thr
385                 390                 395                 400

Gly Lys Thr Ser Asn Glu Asn Ser Val Ser
                405                 410
```

<210> SEQ ID NO 133
<211> LENGTH: 410
<212> TYPE: PRT
<213> ORGANISM: Cuphea heterophylla
<220> FEATURE:
<223> OTHER INFORMATION: ChtFATB1a.1 amino acid sequence

<400> SEQUENCE: 133

```
Met Val Ala Ala Ala Ala Ser Ser Ala Phe Phe Ser Val Pro Thr Pro
1               5                   10                  15

Gly Thr Ser Pro Lys Pro Gly Asn Phe Gly Asn Trp Pro Ser Ser Leu
            20                  25                  30

Ser Val Pro Phe Lys Pro Glu Ser Asn His Asn Gly Gly Phe Arg Val
        35                  40                  45

Lys Ala Asn Ala Ser Ala His Pro Lys Ala Asn Gly Ser Ala Val Asn
    50                  55                  60

Leu Lys Ser Gly Ser Leu Glu Thr Gln Glu Asp Thr Ser Ser Ser Ser
65                  70                  75                  80

Pro Pro Pro Arg Thr Phe Ile Lys Gln Leu Pro Asp Trp Gly Met Leu
                85                  90                  95

Leu Ser Lys Ile Thr Thr Val Phe Gly Ala Ala Glu Arg Gln Trp Lys
            100                 105                 110
```

Arg Pro Gly Met Leu Val Glu Pro Phe Gly Val Asp Arg Ile Phe Gln
115 120 125

Asp Gly Val Phe Phe Arg His Ser Phe Ser Ile Arg Ser Tyr Glu Ile
130 135 140

Gly Ala Asp Arg Thr Ala Ser Ile Glu Thr Leu Met Asn Ile Phe Gln
145 150 155 160

Glu Thr Ser Leu Asn His Cys Lys Ser Ile Gly Leu Leu Asn Asp Gly
165 170 175

Phe Gly Arg Thr Pro Glu Met Cys Lys Arg Asp Leu Ile Trp Val Val
180 185 190

Thr Lys Ile Gln Val Glu Val Asn Arg Tyr Pro Thr Trp Gly Asp Thr
195 200 205

Ile Glu Val Asn Thr Trp Val Ser Glu Ser Gly Lys Asn Gly Met Gly
210 215 220

Arg Asp Trp Leu Ile Gly Asp Cys Arg Thr Gly Glu Ile Leu Ile Arg
225 230 235 240

Ala Thr Ser Val Trp Ala Met Met Asn Arg Lys Thr Arg Arg Leu Ser
245 250 255

Lys Phe Pro Tyr Glu Val Arg Gln Glu Ile Ala Pro His Phe Val Asp
260 265 270

Ser Ala Pro Val Ile Glu Asp Asp Lys Lys Leu His Lys Leu Asp Val
275 280 285

Lys Thr Gly Asp Ser Ile Arg Lys Gly Leu Thr Pro Arg Trp Asn Asp
290 295 300

Leu Asp Val Asn Gln His Val Asn Asn Val Lys Tyr Ile Gly Trp Ile
305 310 315 320

Leu Lys Ser Val Pro Ala Glu Val Phe Glu Thr Gln Glu Leu Cys Gly
325 330 335

Val Thr Leu Glu Tyr Arg Arg Glu Cys Gly Arg Asp Ser Val Leu Glu
340 345 350

Ser Val Thr Ala Met Asp Thr Ala Lys Glu Gly Asp Arg Ser Leu Tyr
355 360 365

Gln His Leu Leu Arg Leu Glu Asp Gly Ala Asp Ile Thr Ile Gly Arg
370 375 380

Thr Glu Trp Arg Pro Lys Asn Ala Gly Ala Asn Gly Ala Leu Ser Thr
385 390 395 400

Gly Lys Thr Ser Asn Gly Asn Ser Val Ser
405 410

<210> SEQ ID NO 134
<211> LENGTH: 410
<212> TYPE: PRT
<213> ORGANISM: Cuphea heterophylla
<220> FEATURE:
<223> OTHER INFORMATION: ChtFATB1a.2 amino acid sequence

<400> SEQUENCE: 134

Met Val Ala Ala Ala Ala Ser Ser Ala Phe Phe Ser Val Pro Thr Pro
1 5 10 15

Gly Thr Ser Pro Lys Pro Gly Asn Phe Gly Asn Trp Pro Ser Asn Leu
20 25 30

Ser Val Pro Phe Lys Pro Glu Ser Asn His Asn Gly Gly Phe Arg Val
35 40 45

Lys Ala Asn Ala Ser Ala His Pro Lys Ala Asn Gly Ser Ala Val Asn
50 55 60

```
Leu Lys Ser Gly Ser Leu Glu Thr Gln Glu Asp Thr Ser Ser Ser Ser
65                  70                  75                  80

Pro Pro Pro Arg Thr Phe Ile Lys Gln Leu Pro Asp Trp Gly Met Leu
                85                  90                  95

Leu Ser Lys Ile Thr Thr Val Phe Gly Ala Ala Glu Arg Gln Trp Lys
            100                 105                 110

Arg Pro Gly Met Leu Val Glu Pro Phe Gly Val Asp Arg Ile Phe Gln
        115                 120                 125

Asp Gly Val Phe Phe Arg Gln Ser Phe Ser Ile Arg Ser Tyr Glu Ile
    130                 135                 140

Gly Ala Asp Arg Thr Ala Ser Ile Glu Thr Leu Met Asn Ile Phe Gln
145                 150                 155                 160

Glu Thr Ser Leu Asn His Cys Lys Ser Ile Gly Leu Leu Asn Asp Gly
                165                 170                 175

Phe Gly Arg Thr Pro Glu Met Cys Lys Arg Asp Leu Ile Trp Val Val
            180                 185                 190

Thr Lys Ile Gln Val Glu Val Asn Arg Tyr Pro Thr Trp Gly Asp Thr
        195                 200                 205

Ile Glu Val Asn Thr Trp Val Ser Glu Ser Gly Lys Asn Gly Met Gly
    210                 215                 220

Arg Asp Trp Leu Ile Ser Asp Cys Arg Thr Gly Glu Ile Leu Ile Arg
225                 230                 235                 240

Ala Thr Ser Val Trp Ala Met Met Asn Arg Lys Thr Arg Arg Leu Ser
                245                 250                 255

Lys Phe Pro Tyr Glu Val Arg Gln Glu Ile Ala Pro His Phe Val Asp
            260                 265                 270

Ser Ala Pro Val Ile Glu Asp Asp Lys Lys Leu His Lys Leu Asp Val
        275                 280                 285

Lys Thr Gly Asp Ser Ile Arg Lys Gly Leu Thr Pro Arg Trp Asn Asp
    290                 295                 300

Phe Asp Val Asn Gln His Val Asn Asn Val Lys Tyr Ile Gly Trp Ile
305                 310                 315                 320

Leu Lys Ser Val Pro Ala Glu Val Phe Glu Thr Gln Glu Leu Cys Gly
                325                 330                 335

Val Thr Leu Glu Tyr Arg Arg Glu Cys Gly Arg Asp Ser Val Leu Glu
            340                 345                 350

Ser Val Thr Ala Met Asp Thr Ala Lys Glu Gly Asp Arg Ser Leu Tyr
        355                 360                 365

Gln His Leu Leu Arg Leu Glu Asp Gly Ala Asp Ile Thr Ile Gly Arg
    370                 375                 380

Thr Glu Trp Arg Pro Lys Asn Ala Gly Ala Asn Gly Ala Ile Ser Thr
385                 390                 395                 400

Gly Lys Thr Ser Asn Glu Asn Ser Val Ser
                405                 410
```

<210> SEQ ID NO 135
<211> LENGTH: 410
<212> TYPE: PRT
<213> ORGANISM: Cuphea heterophylla
<220> FEATURE:
<223> OTHER INFORMATION: ChtFATB1a.3 amino acid sequence

<400> SEQUENCE: 135

```
Met Val Ala Ala Ala Ala Ser Ser Ala Phe Phe Ser Val Pro Thr Pro
1               5                   10                  15
```

```
Gly Thr Ser Pro Lys Pro Gly Asn Phe Gly Asn Trp Pro Ser Ser Leu
            20                  25                  30

Ser Val Pro Phe Lys Pro Glu Ser Asn His Asn Gly Gly Phe Arg Val
        35                  40                  45

Lys Ala Asn Ala Ser Ala His Pro Lys Ala Asn Gly Ser Ala Val Asn
    50                  55                  60

Leu Lys Ser Gly Ser Leu Glu Thr Gln Glu Asp Thr Ser Ser Ser Ser
65                  70                  75                  80

Pro Pro Pro Arg Thr Phe Ile Lys Gln Leu Pro Asp Trp Gly Met Leu
                85                  90                  95

Leu Ser Lys Ile Thr Thr Val Phe Gly Ala Ala Glu Arg Gln Trp Lys
            100                 105                 110

Arg Pro Gly Met Leu Val Glu Pro Phe Gly Val Asp Arg Ile Phe Gln
        115                 120                 125

Asp Gly Val Phe Phe Arg Gln Ser Phe Ser Ile Arg Ser Tyr Glu Ile
    130                 135                 140

Gly Ala Asp Arg Thr Ala Ser Ile Glu Thr Leu Met Asn Ile Phe Gln
145                 150                 155                 160

Glu Thr Ser Leu Asn His Cys Lys Ser Ile Gly Leu Leu Asn Asp Gly
                165                 170                 175

Phe Gly Arg Thr Pro Glu Met Cys Lys Arg Asp Leu Ile Trp Val Val
            180                 185                 190

Thr Lys Ile Gln Val Glu Val Asn Arg Tyr Pro Thr Trp Gly Asp Thr
        195                 200                 205

Ile Glu Val Asn Thr Trp Val Ser Glu Ser Gly Lys Asn Gly Met Gly
    210                 215                 220

Arg Asp Trp Leu Ile Ser Asp Cys Arg Thr Gly Glu Ile Leu Ile Arg
225                 230                 235                 240

Ala Thr Ser Val Trp Ala Met Met Asn Arg Lys Thr Arg Arg Leu Ser
                245                 250                 255

Lys Phe Pro Tyr Glu Val Arg Gln Glu Ile Ala Pro His Phe Val Asp
            260                 265                 270

Ser Ala Pro Val Ile Glu Asp Asp Lys Lys Leu His Lys Leu Asp Val
        275                 280                 285

Lys Thr Gly Asp Ser Ile Arg Lys Gly Leu Thr Pro Arg Trp Asn Asp
    290                 295                 300

Phe Asp Val Asn Gln His Val Asn Asn Val Lys Tyr Ile Gly Trp Ile
305                 310                 315                 320

Leu Lys Ser Val Pro Ala Glu Val Phe Glu Thr Gln Glu Leu Cys Gly
                325                 330                 335

Val Thr Leu Glu Tyr Arg Arg Glu Cys Gly Arg Asp Ser Val Leu Glu
            340                 345                 350

Ser Val Thr Ala Met Asp Thr Ala Lys Glu Gly Asp Arg Ser Leu Tyr
        355                 360                 365

Gln His Leu Leu Arg Leu Glu Asp Gly Ala Asp Ile Thr Ile Gly Arg
    370                 375                 380

Thr Glu Trp Arg Pro Lys Asn Ala Gly Val Asn Gly Ala Ile Ser Thr
385                 390                 395                 400

Gly Lys Thr Ser Asn Glu Asn Ser Val Ser
                405                 410
```

<210> SEQ ID NO 136
<211> LENGTH: 410

```
<212> TYPE: PRT
<213> ORGANISM: Cuphea heterophylla
<220> FEATURE:
<223> OTHER INFORMATION: ChtFATB1a.4 amino acid sequence

<400> SEQUENCE: 136

Met Val Ala Ala Ala Ala Ser Ser Ala Phe Phe Ser Val Pro Thr Pro
1               5                   10                  15

Gly Thr Ser Pro Lys Pro Gly Asn Phe Gly Asn Trp Pro Ser Ser Leu
            20                  25                  30

Ser Val Pro Phe Lys Pro Glu Ser Asn His Asn Gly Gly Phe Arg Val
        35                  40                  45

Lys Ala Asn Ala Ser Ala His Pro Lys Ala Asn Gly Ser Ala Val Asn
    50                  55                  60

Leu Lys Ser Gly Ser Leu Glu Thr Gln Glu Asp Thr Ser Ser Ser Ser
65                  70                  75                  80

Pro Pro Pro Arg Thr Phe Ile Lys Gln Leu Pro Asp Trp Ser Met Leu
                85                  90                  95

Leu Ser Lys Ile Thr Thr Val Phe Gly Ala Ala Glu Arg Gln Trp Lys
            100                 105                 110

Arg Pro Gly Met Leu Val Glu Pro Phe Gly Val Asp Arg Ile Phe Gln
        115                 120                 125

Asp Gly Val Phe Phe Arg Gln Ser Phe Ser Ile Arg Ser Tyr Glu Ile
    130                 135                 140

Gly Ala Asp Arg Thr Ala Ser Ile Glu Thr Leu Met Asn Ile Phe Gln
145                 150                 155                 160

Glu Thr Ser Leu Asn His Cys Lys Ser Ile Gly Leu Leu Asn Asp Gly
                165                 170                 175

Phe Gly Arg Thr Pro Glu Met Cys Lys Arg Asp Leu Ile Trp Val Val
            180                 185                 190

Thr Lys Ile Gln Val Glu Val Asn Arg Tyr Pro Thr Trp Gly Asp Thr
        195                 200                 205

Ile Glu Val Asn Thr Trp Val Ser Glu Ser Gly Lys Asn Gly Met Gly
    210                 215                 220

Arg Asp Trp Leu Ile Ser Asp Cys Arg Thr Gly Glu Ile Leu Ile Arg
225                 230                 235                 240

Ala Thr Ser Val Trp Ala Met Met Asn Arg Lys Thr Arg Arg Leu Ser
                245                 250                 255

Lys Phe Pro Tyr Glu Val Arg Gln Glu Ile Ala Pro His Phe Val Asp
            260                 265                 270

Ser Ala Pro Val Ile Glu Asp Asp Lys Lys Leu His Lys Leu Asp Val
        275                 280                 285

Lys Thr Gly Asp Ser Ile Arg Lys Gly Leu Thr Pro Arg Trp Asn Asp
    290                 295                 300

Phe Asp Val Asn Gln His Val Asn Asn Val Lys Tyr Ile Gly Trp Ile
305                 310                 315                 320

Leu Lys Ser Val Pro Ala Glu Val Phe Glu Thr Gln Glu Leu Cys Gly
                325                 330                 335

Val Thr Leu Glu Tyr Arg Arg Glu Cys Gly Arg Asp Ser Val Leu Glu
            340                 345                 350

Ser Val Thr Ala Met Asp Thr Ala Lys Glu Gly Asp Arg Ser Leu Tyr
        355                 360                 365

Gln His Leu Leu Arg Leu Glu Asp Gly Ala Asp Ile Thr Ile Gly Arg
    370                 375                 380
```

```
Thr Glu Trp Arg Pro Lys Asn Ala Gly Ala Asn Gly Ala Ile Ser Thr
385                 390                 395                 400

Gly Lys Thr Ser Asn Glu Asn Ser Val Ser
                405                 410


<210> SEQ ID NO 137
<211> LENGTH: 410
<212> TYPE: PRT
<213> ORGANISM: Cuphea heterophylla
<220> FEATURE:
<223> OTHER INFORMATION: ChtFATB1b amino acid sequence

<400> SEQUENCE: 137

Met Val Ala Ala Ala Ala Ser Ser Ala Phe Phe Ser Val Pro Thr Ser
1               5                   10                  15

Gly Thr Ser Pro Lys Pro Gly Asn Phe Gly Asn Trp Pro Ser Ser Leu
            20                  25                  30

Ser Val Pro Phe Lys Pro Glu Ser Ser His Asn Gly Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Glu Thr Gln Glu Asp Thr Ser Ser Ser Ser
65                  70                  75                  80

Pro Pro Pro Arg Thr Phe Ile Lys Gln Leu Pro Asp Trp Ser Met Leu
                85                  90                  95

Leu Ser Lys Ile Thr Thr Val Phe Trp Ala Ala Glu Arg Gln Trp Lys
            100                 105                 110

Arg Pro Gly Met Leu Val Glu Pro Phe Gly Val Asp Arg Ile Phe Gln
        115                 120                 125

Asp Gly Val Phe Phe Arg Gln Ser Phe Ser Ile Arg Ser Tyr Glu Ile
    130                 135                 140

Gly Ala Asp Arg Thr Ala Ser Ile Glu Thr Leu Met Asn Ile Phe Gln
145                 150                 155                 160

Glu Thr Ser Leu Asn His Cys Lys Ser Ile Gly Leu Leu Asn Asp Gly
                165                 170                 175

Phe Gly Arg Thr Pro Glu Met Cys Lys Arg Asp Leu Ile Trp Val Val
            180                 185                 190

Thr Lys Ile Gln Val Glu Val Asn Arg Tyr Pro Thr Trp Gly Asp Thr
        195                 200                 205

Ile Glu Val Asn Thr Trp Val Ser Glu Ser Gly Lys Asn Gly Met Gly
    210                 215                 220

Arg Asp Trp Leu Ile Ser Asp Cys Arg Thr Gly Glu Ile Leu Ile Arg
225                 230                 235                 240

Ala Thr Ser Val Trp Ala Met Met Asn Arg Lys Thr Arg Arg Leu Ser
                245                 250                 255

Lys Phe Pro Tyr Glu Val Arg Gln Glu Ile Ala Pro His Phe Val Asp
            260                 265                 270

Ser Ala Pro Val Ile Glu Asp Asp Lys Lys Leu His Lys Leu Asp Val
        275                 280                 285

Lys Thr Gly Asp Phe Ile Arg Lys Gly Leu Thr Pro Arg Trp Asn Asp
    290                 295                 300

Phe Asp Val Asn Gln His Val Asn Asn Val Lys Tyr Ile Gly Trp Ile
305                 310                 315                 320

Leu Lys Ser Val Pro Ala Glu Val Phe Glu Thr Gln Glu Leu Cys Gly
                325                 330                 335
```

-continued

```
Val Thr Leu Glu Tyr Arg Arg Glu Cys Gly Arg Asp Ser Val Leu Glu
            340                 345                 350

Ser Val Thr Ala Met Asp Thr Ala Lys Glu Gly Asp Arg Ser Leu Tyr
        355                 360                 365

Gln His Leu Leu Arg Leu Glu Asp Gly Ala Asp Ile Thr Ile Gly Arg
    370                 375                 380

Thr Glu Trp Arg Pro Lys Asn Ala Gly Ala Asn Gly Ala Ile Ser Thr
385                 390                 395                 400

Gly Lys Thr Ser Asn Glu Asn Ser Val Ser
                405                 410


<210> SEQ ID NO 138
<211> LENGTH: 418
<212> TYPE: PRT
<213> ORGANISM: Cuphea heterophylla
<220> FEATURE:
<223> OTHER INFORMATION: ChtFATB2b amino acid sequence

<400> SEQUENCE: 138

Met Val Val Ala Ala Ala Ala Ser Ser Ala Phe Phe Pro Val Pro Ala
1               5                   10                  15

Ser Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Gln Glu Gly Thr Ser Ser Ser
65                  70                  75                  80

Pro Pro Pro Arg Thr Phe Leu Asn Gln Leu Pro Asp Trp Ser Arg Leu
                85                  90                  95

Arg Thr Ala Ile Thr Thr Val Phe Val Ala Ala Glu Lys Gln Leu Thr
            100                 105                 110

Met Leu Asp Arg Lys Ser Lys Lys Pro Asp Met His Val Asp Trp Phe
        115                 120                 125

Gly Leu Glu Ile Ile Val Gln Asp Gly Leu Val Phe Arg Glu Ser Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Pro Glu Met Cys Lys
            180                 185                 190

Arg Asp Leu Ile Trp Val Leu Thr Lys Met Gln Ile Met Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Lys Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285
```

-continued

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
305                 310                 315                 320

Asn Val Lys Tyr Ile Gly Trp Ile Leu Glu Ser Met Pro Lys Glu Val
                325                 330                 335

Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser

<210> SEQ ID NO 139
<211> LENGTH: 418
<212> TYPE: PRT
<213> ORGANISM: Cuphea heterophylla
<220> FEATURE:
<223> OTHER INFORMATION: ChtFATB2a amino acid sequence

<400> SEQUENCE: 139

Met Val Val Ala Ala Ala Ala Ser Ser Ala Phe Phe Pro Val Pro Ala
1               5                   10                  15

Pro Gly Thr Thr Ser Lys Pro Gly Lys Phe Gly Asn Trp Pro Ser Ser
            20                  25                  30

Leu Ser Pro Ser Phe Lys Pro Lys Ser Asn Pro Asn Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Lys Glu Asp Thr Pro Ser Ser
65                  70                  75                  80

Pro Pro Pro Arg Thr Phe Leu Asn Gln Leu Pro Asp Trp Ser Arg Leu
                85                  90                  95

Arg Thr Ala Ile Thr Thr Val Phe Val Ala Ala Glu Lys Gln Leu Thr
            100                 105                 110

Met Leu Asp Arg Lys Ser Lys Lys Pro Asp Met His Val Asp Trp Phe
        115                 120                 125

Gly Leu Glu Ile Ile Val Gln Asp Trp Leu Val Phe Arg Glu Ser Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Pro Glu Met Cys Lys
            180                 185                 190

Arg Asp Leu Ile Trp Val Leu Thr Lys Met Gln Ile Met Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn

```
225                 230                 235                 240

Thr Gly Glu Ile Leu Ile Arg Ala Thr Ser Ile Trp Ala Met Met Asn
                245                 250                 255

Gln Lys Thr Arg Arg Phe Ser Lys Leu Pro Asn Glu Val Arg Gln Glu
            260                 265                 270

Ile Ala Pro His Phe Val Asp Ala Pro Pro Leu Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
305                 310                 315                 320

Asn Val Lys Tyr Ile Gly Trp Ile Leu Glu Ser Met Pro Lys Glu Val
                325                 330                 335

Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser


<210> SEQ ID NO 140
<211> LENGTH: 418
<212> TYPE: PRT
<213> ORGANISM: Cuphea heterophylla
<220> FEATURE:
<223> OTHER INFORMATION: ChtFATB2c amino acid sequence

<400> SEQUENCE: 140

Met Val Val Ala Ala Ala Ala Ser Ser Ala Phe Phe Pro Val Pro Ala
1               5                   10                  15

Ser Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Lys Glu Asp Thr Pro Ser Ser
65                  70                  75                  80

Pro Pro Pro Arg Thr Phe Leu Asn Gln Leu Pro Asp Trp Asn Arg Leu
                85                  90                  95

Arg Thr Ala Ile Thr Thr Val Phe Val Ala Ala Glu Lys Gln Leu Thr
            100                 105                 110

Met Leu Asp Arg Lys Ser Lys Lys Pro Asp Met His Val Asp Trp Phe
        115                 120                 125

Gly Leu Glu Ile Ile Val Gln Asp Gly Leu Val Phe Arg Glu Ser Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175
```

Val Gly Leu Leu Asn Asp Gly Phe Gly Arg Thr Pro Glu Met Cys Lys
180 185 190

Arg Asp Leu Ile Trp Val Leu Thr Lys Met Gln Ile Met Val Asn Arg
195 200 205

Tyr Pro Thr Trp Gly Asp Thr Val Glu Ile Asn Ser Trp Phe Ser Gln
210 215 220

Ser Gly Lys Ile Gly Met Gly Arg Asn Trp Leu Ile Ser Asp Cys Asn
225 230 235 240

Thr Gly Glu Ile Leu Ile Arg Ala Thr Ser Ile Trp Ala Met Met Asn
245 250 255

Gln Lys Thr Arg Arg Phe Ser Lys Leu Pro Asn Glu Val Arg Gln Glu
260 265 270

Ile Ala Pro His Phe Val Asp Ala Pro Pro Val Ile Glu Asp Asn Asp
275 280 285

Arg Lys Leu His Lys Phe Asp Val Lys Thr Gly Asp Ser Ile Cys Lys
290 295 300

Gly Leu Thr Pro Glu Trp Asn Asp Leu Asp Val Asn Gln His Val Ser
305 310 315 320

Asn Val Lys Tyr Ile Gly Trp Ile Leu Glu Ser Met Pro Lys Glu Val
325 330 335

Leu Asp Thr Gln Glu Leu Cys Ser Leu Thr Leu Glu Tyr Arg Arg Glu
340 345 350

Cys Gly Arg Asp Ser Val Leu Glu Ser Val Thr Ala Met Asp Pro Ser
355 360 365

Lys Val Gly Asp Arg Ser Gln Tyr Gln His Leu Leu Arg Leu Glu Asp
370 375 380

Gly Thr Asp Ile Met Lys Gly Arg Thr Glu Trp Arg Pro Lys Asn Ala
385 390 395 400

Gly Thr Asn Gly Ala Ile Ser Thr Gly Lys Thr Ser Asn Gly Asn Ser
405 410 415

Val Ser

<210> SEQ ID NO 141
<211> LENGTH: 418
<212> TYPE: PRT
<213> ORGANISM: Cuphea heterophylla
<220> FEATURE:
<223> OTHER INFORMATION: ChtFATB2d amino acid sequence

<400> SEQUENCE: 141

Met Val Val Ala Ala Ala Ala Ser Ser Ala Phe Phe Pro Val Pro Ala
1 5 10 15

Pro Gly Thr Thr Ser Lys Pro Gly Lys Phe Gly Asn Trp Pro Ser Ser
20 25 30

Leu Ser Pro Ser Phe Lys Pro Lys Ser Asn Pro Asn Gly Gly Phe Gln
35 40 45

Val Lys Ala Asn Ala Ser Ala His Pro Lys Ala Asn Gly Ser Ala Val
50 55 60

Ser Leu Lys Ser Gly Ser Leu Asn Thr Gln Glu Asp Thr Ser Ser Ser
65 70 75 80

Pro Pro Pro Arg Thr Phe Leu Asn Gln Leu Pro Asp Trp Ser Arg Leu
85 90 95

Leu Thr Ala Ile Ser Thr Val Phe Val Ala Ala Glu Lys Gln Leu Thr
100 105 110

```
Met Leu Asp Arg Lys Ser Lys Arg Pro Asp Met Leu Val Asp Leu Phe
        115                 120                 125

Gly Leu Glu Ser Ile Val Gln Asp Gly Leu Val Phe Arg Glu Ser Tyr
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Pro Glu Met Cys Lys
            180                 185                 190

Arg Asp Leu Ile Trp Val Leu Thr Lys Met Gln Ile Met Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Asn Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Arg Lys
    290                 295                 300

Gly Leu Thr Pro Gly Trp Asn Asp Leu Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Glu Ser Val Leu Glu Ser Val Thr Ala Met Asn Pro Ser
        355                 360                 365

Lys Val Gly Asp Arg Ser Gln Tyr Gln His Leu Leu Arg Leu Glu Asp
    370                 375                 380

Gly Ala Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser
```

<210> SEQ ID NO 142
<211> LENGTH: 418
<212> TYPE: PRT
<213> ORGANISM: Cuphea heterophylla
<220> FEATURE:
<223> OTHER INFORMATION: ChtFATB2e amino acid sequence

<400> SEQUENCE: 142

```
Met Val Val Ala Ala Ala Ala Ser Ser Ala Phe Phe Pro Val Pro Ala
1               5                   10                  15

Ser Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45

Val Lys Ala Asn Ala Ser Ala His Pro Lys Ala Asn Gly Ser Ala Val
```

```
    50                  55                  60

Ser Leu Lys Ser Gly Ser Leu Asn Thr Gln Glu Asp Thr Ser Ser Ser
65                  70                  75                  80

Pro Pro Pro Gln Thr Phe Leu Asn Gln Leu Pro Asp Trp Ser Arg Leu
                85                  90                  95

Leu Thr Ala Ile Ser Thr Val Phe Val Ala Ala Glu Lys Gln Leu Thr
            100                 105                 110

Met Leu Asp Arg Lys Ser Lys Arg Pro Asp Met Leu Val Asp Trp Phe
        115                 120                 125

Gly Leu Glu Ser Ile Val Gln Asp Gly Leu Val Phe Arg Glu Ser Tyr
    130                 135                 140

Ser Ile Arg Ser Tyr Glu Ile Ser Ala Asp Arg Thr Ala Ser Ile Glu
145                 150                 155                 160

Thr Val Met Asn Leu Leu Gln Glu Thr Ser Leu Asn His Cys Lys Ser
                165                 170                 175

Met Gly Ile Leu Asn Asp Gly Phe Gly Arg Thr Pro Glu Met Cys Lys
            180                 185                 190

Arg Asp Leu Ile Trp Val Leu Thr Lys Met Gln Ile Leu Val Asn Arg
        195                 200                 205

Tyr Pro Asn Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Asn Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Arg Lys
    290                 295                 300

Gly Leu Thr Pro Gly Trp Asn Asp Leu Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asn Pro Ser
        355                 360                 365

Lys Val Gly Asp Arg Ser Gln Tyr Gln His Leu Leu Arg Leu Glu Asp
    370                 375                 380

Gly Ala Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser
```

<210> SEQ ID NO 143
<211> LENGTH: 418
<212> TYPE: PRT
<213> ORGANISM: Cuphea heterophylla
<220> FEATURE:
<223> OTHER INFORMATION: ChtFATB2f amino acid sequence

<400> SEQUENCE: 143

```
Met Val Val Ala Ala Ala Ala Ser Ser Ala Phe Phe Pro Val Pro Ala
1               5                   10                  15

Ser Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Gln Glu Gly Thr Ser Ser Ser
65                  70                  75                  80

Pro Pro Pro Arg Thr Phe Leu Asn Gln Leu Pro Asp Trp Ser Arg Leu
                85                  90                  95

Leu Thr Ala Ile Ser Thr Val Phe Val Ala Ala Glu Lys Gln Leu Thr
            100                 105                 110

Met Leu Asp Arg Lys Ser Lys Arg Pro Asp Met Leu Val Asp Trp Phe
        115                 120                 125

Gly Leu Glu Ser Ile Val Gln Asp Gly Leu Val Phe Arg Glu Ser Tyr
    130                 135                 140

Ser Ile Arg Ser Tyr Glu Ile Ser Ala Asp Arg Thr Ala Ser Ile Glu
145                 150                 155                 160

Thr Val Met Asn Leu Leu Gln Glu Thr Ser Leu Asn His Cys Lys Ser
                165                 170                 175

Met Gly Ile Leu Asn Asp Gly Phe Gly Arg Thr Pro Glu Met Cys Lys
            180                 185                 190

Arg Asp Leu Ile Trp Val Leu Thr Lys Met Gln Ile Leu Val Asn Arg
        195                 200                 205

Tyr Pro Asn Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Lys Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
305                 310                 315                 320

Asn Val Lys Tyr Ile Gly Trp Ile Leu Glu Ser Met Pro Lys Glu Val
                325                 330                 335

Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415
```

Val Ser

<210> SEQ ID NO 144
<211> LENGTH: 418
<212> TYPE: PRT
<213> ORGANISM: Cuphea heterophylla
<220> FEATURE:
<223> OTHER INFORMATION: ChtFATB2g amino acid sequence

<400> SEQUENCE: 144

```
Met Val Val Ala Ala Thr Ala Ser Ser Ala Phe Phe Pro Val Pro Val
1               5                   10                  15

Pro Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Gln Glu Asp Thr Ser Ser Ser
65                  70                  75                  80

Pro Pro Pro Arg Thr Phe Leu Asn Gln Leu Pro Asp Trp Ser Arg Leu
                85                  90                  95

Leu Thr Ala Ile Ser Thr Val Phe Val Ala Ala Glu Lys Gln Leu Thr
            100                 105                 110

Met Leu Asp Arg Lys Ser Lys Arg Pro Asp Met Leu Val Asp Trp Phe
        115                 120                 125

Gly Leu Glu Ser Ile Val Gln Asp Gly Leu Val Phe Arg Glu Ile Tyr
    130                 135                 140

Ser Ile Arg Ser Tyr Glu Ile Ser Ala Asp Arg Thr Thr Ser Ile Glu
145                 150                 155                 160

Thr Val Met Asn Leu Leu Gln Glu Thr Ser Leu Asn His Cys Lys Ser
                165                 170                 175

Met Gly Ile Leu Asn Asp Gly Phe Gly Arg Thr Pro Glu Met Cys Lys
            180                 185                 190

Arg Asp Leu Ile Trp Val Leu Thr Lys Met Gln Ile Leu Val Asn Arg
        195                 200                 205

Tyr Pro Asn Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Lys Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
305                 310                 315                 320

Asn Val Lys Tyr Ile Gly Trp Ile Leu Glu Ser Met Pro Lys Glu Val
                325                 330                 335

Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
```

```
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Ala Asn Ser
                405                 410                 415

Val Ser
```

<210> SEQ ID NO 145
<211> LENGTH: 418
<212> TYPE: PRT
<213> ORGANISM: Cuphea heterophylla
<220> FEATURE:
<223> OTHER INFORMATION: ChtFATB2h amino acid sequence

<400> SEQUENCE: 145

```
Met Val Val Ala Ala Ala Ala Ser Ser Ala Phe Phe Pro Val Pro Ala
1               5                   10                  15

Ser Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Gln Glu Gly Thr Ser Ser Ser
65                  70                  75                  80

Pro Pro Pro Arg Thr Phe Leu Asn Gln Leu Pro Asp Trp Ser Arg Leu
                85                  90                  95

Leu Thr Ala Ile Ser Thr Val Phe Val Ala Ala Glu Lys Gln Leu Thr
            100                 105                 110

Met Leu Asp Arg Lys Ser Lys Arg Pro Asp Met Leu Val Asp Trp Phe
        115                 120                 125

Gly Leu Glu Ser Ile Val Gln Asp Gly Leu Val Phe Arg Glu Ser Tyr
    130                 135                 140

Ser Ile Arg Ser Tyr Glu Ile Ser Ala Asp Arg Thr Ala Ser Ile Glu
145                 150                 155                 160

Thr Val Met Asn Leu Leu Gln Glu Thr Ser Leu Asn His Cys Lys Ser
                165                 170                 175

Met Gly Ile Leu Asn Asp Gly Phe Gly Arg Thr Pro Glu Met Cys Lys
            180                 185                 190

Arg Asp Leu Ile Trp Val Leu Thr Lys Met Gln Ile Leu Val Asn Arg
        195                 200                 205

Tyr Pro Asn Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Asn Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Arg Lys
    290                 295                 300
```

```
Gly Leu Thr Pro Gly Trp Asn Asp Leu Asp Val Asn Gln His Val Ser
305                 310                 315                 320

Asn Val Lys Tyr Ile Gly Trp Ile Leu Glu Ser Ile Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Glu Ser Val Leu Glu Ser Val Thr Ala Met Asn Pro Ser
        355                 360                 365

Lys Val Gly Asp Arg Ser Gln Tyr Gln His Leu Leu Arg Leu Glu Asp
    370                 375                 380

Gly Ala Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser


<210> SEQ ID NO 146
<211> LENGTH: 414
<212> TYPE: PRT
<213> ORGANISM: Cuphea heterophylla
<220> FEATURE:
<223> OTHER INFORMATION: ChtFATB3a amino acid sequence

<400> SEQUENCE: 146

Met Val Ala Thr Ala Ala Ser Ser Ala Phe Phe Pro Val Pro Ser Pro
1               5                   10                  15

Asp Thr Ser Ser Arg Pro Gly Lys Leu Gly Asn Gly Ser Ser Ser Leu
            20                  25                  30

Arg Pro Leu Lys Pro Lys Phe Val Ala Asn Ala Gly Leu Gln Val Lys
        35                  40                  45

Ala Asn Ala Ser Ala Pro Pro Lys Ile Asn Gly Ser Ser Val Ser Leu
    50                  55                  60

Lys Ser Cys Ser Leu Lys Thr His Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Glu Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240
```

-continued

```
Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Trp Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Phe Gly Pro Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Thr Ile Ala Ser Gly Glu Thr Ser Pro Gly Asn Ser
                405                 410
```

```
<210> SEQ ID NO 147
<211> LENGTH: 414
<212> TYPE: PRT
<213> ORGANISM: Cuphea heterophylla
<220> FEATURE:
<223> OTHER INFORMATION: ChtFATB3b amino acid sequence

<400> SEQUENCE: 147

Met Val Ala Thr Ala Ala Ser Ser Ala Phe Phe Pro Val Pro Ser Pro
1               5                   10                  15

Asp Thr Ser Ser Arg Pro Gly Lys Leu Gly Asn Gly Ser Ser Ser Leu
            20                  25                  30

Arg Pro Leu Lys Pro Lys Phe Val Ala Asn Ala Gly Leu Gln Val Lys
        35                  40                  45

Ala Asn Ala Ser Ala Pro Pro Lys Ile Asn Gly Ser Ser Val Ser Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Phe
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Ile Glu Gly Phe Gly Arg Thr Pro Glu Met Tyr Lys Arg Asp
            180                 185                 190
```

```
Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Trp Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Phe Gly Pro Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Thr Ile Ala Ser Gly Glu Thr Ser Pro Gly Asn Ser
                405                 410


<210> SEQ ID NO 148
<211> LENGTH: 414
<212> TYPE: PRT
<213> ORGANISM: Cuphea heterophylla
<220> FEATURE:
<223> OTHER INFORMATION: ChtFATB3c amino acid sequence

<400> SEQUENCE: 148

Met Val Ala Thr Ala Ala Ser Ser Ala Phe Phe Pro Val Pro Ser Pro
1               5                   10                  15

Asp Thr Ser Ser Arg Pro Gly Lys Leu Gly Asn Gly Ser Ser Ser Leu
            20                  25                  30

Arg Pro Leu Lys Pro Lys Phe Val Ala Asn Ala Gly Leu Gln Val Lys
        35                  40                  45

Ala Asn Ala Ser Ala Pro Pro Lys Ile Asn Gly Ser Ser Val Ser Leu
    50                  55                  60

Lys Ser Cys Ser Leu Lys Thr His Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140
```

-continued

Arg Ser Tyr Glu Ile Gly Ala Asp Arg Thr Ala Ser Ile Glu Thr Val
145 150 155 160

Met Asn His Leu Gln Glu Thr Ala Leu Asn His Val Lys Ser Ala Gly
165 170 175

Leu Leu Asn Glu Gly Phe Gly Arg Thr Pro Glu Met Tyr Lys Arg Asp
180 185 190

Leu Ile Trp Val Val Ala Lys Met Gln Val Met Val Asn Arg Tyr Pro
195 200 205

Thr Trp Gly Asp Thr Val Glu Val Asn Thr Trp Val Ala Lys Ser Gly
210 215 220

Lys Asn Gly Met Arg Arg Asp Trp Leu Ile Ser Asp Cys Asn Thr Gly
225 230 235 240

Glu Ile Leu Thr Arg Ala Ser Ser Val Trp Val Met Met Asn Gln Lys
245 250 255

Thr Arg Lys Leu Ser Lys Ile Pro Asp Glu Val Arg His Glu Ile Glu
260 265 270

Pro His Phe Val Asp Ser Ala Pro Val Ile Glu Asp Asp Asp Arg Lys
275 280 285

Leu Pro Lys Leu Asp Glu Lys Thr Ala Asp Ser Ile Arg Lys Gly Leu
290 295 300

Thr Pro Lys Trp Asn Asp Leu Asp Val Asn Gln His Val Asn Asn Val
305 310 315 320

Lys Tyr Ile Gly Trp Ile Leu Glu Ser Thr Pro Pro Glu Val Leu Glu
325 330 335

Thr Gln Glu Leu Cys Ser Leu Thr Leu Glu Tyr Arg Arg Glu Cys Gly
340 345 350

Arg Glu Ser Val Leu Glu Ser Leu Thr Ala Val Asp Pro Ser Glu Lys
355 360 365

Gly Phe Gly Pro Gln Phe Gln His Leu Leu Arg Leu Glu Asp Gly Gly
370 375 380

Glu Ile Val Lys Gly Arg Thr Glu Trp Arg Pro Lys Thr Ala Gly Ile
385 390 395 400

Asn Gly Ala Ile Ala Phe Gly Glu Thr Ser Pro Gly Asp Ser
405 410

<210> SEQ ID NO 149
<211> LENGTH: 414
<212> TYPE: PRT
<213> ORGANISM: Cuphea heterophylla
<220> FEATURE:
<223> OTHER INFORMATION: ChtFATB3d amino acid sequence

<400> SEQUENCE: 149

Met Val Ala Thr Ala Ala Ser Ser Ala Phe Phe Pro Val Pro Ser Pro
1 5 10 15

Asp Thr Ser Ser Arg Pro Gly Lys Leu Gly Asn Gly Ser Ser Ser Leu
20 25 30

Arg Pro Leu Lys Pro Lys Phe Val Ala Asn Ala Gly Leu Gln Val Lys
35 40 45

Ala Asn Ala Ser Ala Pro Pro Lys Ile Asn Gly Ser Ser Val Ser Leu
50 55 60

Lys Ser Cys Ser Leu Lys Thr His Glu Asp Thr Pro Ser Ala Pro Pro
65 70 75 80

Pro Arg Thr Phe Ile Asn Gln Leu Pro Asp Trp Ser Met Leu Leu Ala
85 90 95

-continued

Ala Ile Thr Thr Val Phe Leu Ala Ala Glu Lys Gln Trp Met Met Leu
100 105 110

Asp Trp Lys Pro Lys Arg Pro Asp Met Leu Val Asp Pro Phe Gly Leu
115 120 125

Gly Arg Ile Val Gln Asp Gly Leu Val Phe Arg Gln Asn Phe Ser Ile
130 135 140

Arg Ser Tyr Glu Ile Gly Ala Asp Arg Thr Ala Ser Ile Lys Thr Val
145 150 155 160

Met Asn His Leu Gln Glu Thr Ala Leu Asn His Val Lys Ser Ala Gly
165 170 175

Leu Leu Asn Glu Gly Phe Gly Arg Thr Pro Glu Met Tyr Lys Arg Asp
180 185 190

Leu Ile Trp Val Val Ala Lys Met Gln Val Met Val Asn Arg Tyr Pro
195 200 205

Thr Trp Gly Asp Thr Val Glu Val Asn Thr Trp Val Ala Lys Ser Gly
210 215 220

Lys Asn Gly Met Arg Arg Asp Trp Leu Ile Ser Asp Cys Asn Thr Gly
225 230 235 240

Glu Ile Leu Thr Arg Ala Ser Ser Val Trp Val Met Met Asn Gln Lys
245 250 255

Thr Arg Lys Leu Ser Lys Ile Pro Asp Glu Val Arg His Glu Ile Glu
260 265 270

Pro His Phe Val Asp Ser Ala Pro Val Ile Glu Asp Asp Asp Trp Lys
275 280 285

Leu Pro Lys Leu Asp Glu Lys Thr Ala Asp Ser Ile Arg Lys Gly Leu
290 295 300

Thr Pro Lys Trp Asn Asp Leu Asp Val Asn Gln His Val Asn Asn Val
305 310 315 320

Lys Tyr Ile Gly Trp Ile Leu Glu Ser Thr Pro Pro Glu Val Leu Glu
325 330 335

Thr Gln Glu Leu Cys Ser Leu Thr Leu Glu Tyr Arg Arg Glu Cys Gly
340 345 350

Arg Glu Ser Val Leu Glu Ser Leu Thr Ala Val Asp Pro Ser Gly Lys
355 360 365

Gly Phe Gly Pro Gln Phe Gln His Leu Leu Arg Leu Glu Asp Gly Gly
370 375 380

Glu Ile Val Lys Gly Arg Thr Glu Trp Arg Pro Lys Thr Ala Gly Ile
385 390 395 400

Asn Gly Thr Ile Ala Ser Gly Glu Thr Ser Pro Gly Asn Ser
405 410

<210> SEQ ID NO 150
<211> LENGTH: 414
<212> TYPE: PRT
<213> ORGANISM: Cuphea heterophylla
<220> FEATURE:
<223> OTHER INFORMATION: ChtFATB3e amino acid sequence

<400> SEQUENCE: 150

Met Val Ala Thr Ala Ala Ser Ser Ala Phe Phe Pro Val Pro Ser Pro
1 5 10 15

Asp Thr Ser Ser Arg Pro Gly Lys Leu Gly Asn Gly Ser Ser Ser Leu
20 25 30

Arg Pro Leu Lys Pro Lys Phe Val Ala Asn Ala Gly Leu Gln Val Lys
35 40 45

```
Ala Asn Ala Ser Ala Pro Pro Lys Ile Asn Gly Ser Ser Val Ser Leu
    50                  55                  60

Lys Ser Gly Ser Leu Lys Thr His Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Glu Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Trp Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Phe Gly Pro Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Thr Ile Ala Ser Gly Glu Thr Ser Pro Gly Asn Ser
                405                 410
```

<210> SEQ ID NO 151
<211> LENGTH: 414
<212> TYPE: PRT
<213> ORGANISM: Cuphea heterophylla
<220> FEATURE:
<223> OTHER INFORMATION: ChtFATB3f amino acid sequence

<400> SEQUENCE: 151

-continued

```
Met Val Ala Thr Ala Ala Ser Ser Ala Phe Phe Pro Val Pro Ser Pro
1               5                   10                  15

Asp Thr Ser Ser Arg Leu Gly Lys Leu Gly Asn Gly Ser Ser Ser Leu
            20                  25                  30

Arg Pro Leu Lys Pro Lys Phe Val Ala Asn Ala Gly Leu Gln Val Lys
        35                  40                  45

Ala Asn Ala Ser Ala Pro Pro Lys Ile Asn Gly Ser Ser Val Ser Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Pro Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Glu Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Trp Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Glu Lys
        355                 360                 365

Gly Phe Gly Pro Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Thr Ile Ala Ser Gly Glu Thr Ser Pro Gly Asn Ser
                405                 410
```

```
<210> SEQ ID NO 152
<211> LENGTH: 414
<212> TYPE: PRT
<213> ORGANISM: Cuphea heterophylla
<220> FEATURE:
<223> OTHER INFORMATION: ChtFATB3g amino acid sequence

<400> SEQUENCE: 152

Met Val Ala Thr Ala Ala Ser Ser Ala Phe Phe Pro Val Pro Ser Pro
1               5                   10                  15

Asp Thr Ser Ser Arg Ala Gly Lys Leu Gly Asn Gly Ser Ser Ser Leu
            20                  25                  30

Arg Pro Leu Lys Pro Lys Phe Val Ala Asn Ala Gly Leu Gln Val Lys
        35                  40                  45

Ala Asn Ala Ser Ala Pro Pro Lys Ile Asn Gly Ser Ser Val Ser Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Glu Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Trp Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Phe Gly Pro Gln Phe Gln His Leu Leu Arg Leu Glu Asp Gly Gly
```

```
    370                 375                 380

Glu Ile Val Lys Gly Arg Thr Glu Trp Arg Pro Lys Thr Ala Gly Ile
385                 390                 395                 400

Asn Gly Thr Ile Ala Ser Gly Glu Thr Ser Pro Gly Asn Ser
                405                 410


<210> SEQ ID NO 153
<211> LENGTH: 361
<212> TYPE: PRT
<213> ORGANISM: Cuphea hyssopifolia
<220> FEATURE:
<223> OTHER INFORMATION: ChsFATB1 amino acid sequence

<400> SEQUENCE: 153

Met Val Ala Thr Asn Ala Ala Ala Phe Ser Ala Tyr Thr Phe Phe Leu
1               5                   10                  15

Thr Ser Pro Thr His Gly Tyr Ser Ser Lys Arg Leu Ala Asp Thr Gln
            20                  25                  30

Asn Gly Tyr Pro Gly Thr Ser Leu Lys Ser Lys Ser Thr Pro Pro Pro
        35                  40                  45

Ala Ala Ala Ala Ala Arg Asn Gly Ala Leu Pro Leu Leu Ala Ser Ile
    50                  55                  60

Cys Lys Cys Pro Lys Lys Ala Asp Gly Ser Met Gln Leu Asp Ser Ser
65                  70                  75                  80

Leu Val Phe Gly Phe Gln Phe Tyr Ile Arg Ser Tyr Glu Val Gly Ala
                85                  90                  95

Asp Gln Thr Val Ser Ile Gln Thr Val Leu Asn Tyr Leu Gln Glu Ala
            100                 105                 110

Ala Ile Asn His Val Gln Ser Ala Gly Tyr Phe Gly Asp Ser Phe Gly
        115                 120                 125

Ala Thr Pro Glu Met Thr Lys Arg Asn Leu Ile Trp Val Ile Thr Lys
    130                 135                 140

Met Gln Val Leu Val Asp Arg Tyr Pro Ala Trp Gly Asp Val Val Gln
145                 150                 155                 160

Val Asp Thr Trp Thr Cys Ser Ser Gly Lys Asn Ser Met Gln Arg Asp
                165                 170                 175

Trp Phe Val Arg Asp Leu Lys Thr Gly Asp Ile Ile Thr Arg Ala Ser
            180                 185                 190

Ser Val Trp Val Leu Met Asn Arg Leu Thr Arg Lys Leu Ser Lys Ile
        195                 200                 205

Pro Glu Ala Val Leu Glu Glu Ala Lys Leu Phe Val Met Asn Thr Ala
    210                 215                 220

Pro Thr Val Asp Asp Asn Arg Lys Leu Pro Lys Leu Asp Gly Ser Ser
225                 230                 235                 240

Ala Asp Tyr Val Leu Ser Gly Leu Thr Pro Arg Trp Ser Asp Leu Asp
                245                 250                 255

Met Asn Gln His Val Asn Asn Val Lys Tyr Ile Ala Trp Ile Leu Glu
            260                 265                 270

Ser Val Pro Gln Ser Ile Pro Glu Thr His Lys Leu Ser Ala Ile Thr
        275                 280                 285

Val Glu Tyr Arg Arg Glu Cys Gly Lys Asn Ser Val Leu Gln Ser Leu
    290                 295                 300

Thr Asn Val Ser Gly Asp Gly Ile Thr Cys Gly Asn Ser Ile Ile Glu
305                 310                 315                 320

Cys His His Leu Leu Gln Leu Glu Thr Gly Pro Glu Ile Leu Leu Ala
```

```
                325                 330                 335

Arg Thr Glu Trp Ile Ser Lys Glu Pro Gly Phe Arg Gly Ala Pro Ile
            340                 345                 350

Gln Ala Glu Lys Val Tyr Asn Asn Lys
        355                 360


<210> SEQ ID NO 154
<211> LENGTH: 415
<212> TYPE: PRT
<213> ORGANISM: Cuphea hyssopifolia
<220> FEATURE:
<223> OTHER INFORMATION: ChsFATB2 amino acid sequence

<400> SEQUENCE: 154

Met Val Ala Thr Ala Ala Ser Ser Ala Phe Phe Pro Val Pro Ser Pro
1               5                   10                  15

Asp Ala Ser Ser Arg Pro Gly Lys Leu Gly Asn Gly Ser Ser Ser Leu
            20                  25                  30

Ser Pro Leu Lys Pro Lys Leu Met Ala Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Asp Gly Phe Gly Arg Thr Leu Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Arg Leu Ser Lys Ile Pro Asp Glu Val Arg His Glu Ile Glu
            260                 265                 270

Pro His Phe Val Asp Ser Ala Pro Val Ile Glu Asp Asp Asp Arg Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
```

```
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Ser Gly Ser Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Pro Ile Ala Ser Gly Glu Thr Ser Pro Gly Asp Ser Ser
                405                 410                 415


<210> SEQ ID NO 155
<211> LENGTH: 427
<212> TYPE: PRT
<213> ORGANISM: Cuphea hyssopifolia
<220> FEATURE:
<223> OTHER INFORMATION: ChsFatB2b amino acid sequence

<400> SEQUENCE: 155

Met Val Ala Thr Ala Ala Ser Ser Ala Phe Phe Pro Val Pro Ser Pro
1               5                   10                  15

Asp Ala Ser Ser Arg Pro Gly Lys Leu Gly Asn Gly Ser Ser Ser Leu
            20                  25                  30

Ser Pro Leu Lys Pro Lys Leu Met Ala Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Asp Gly Phe Gly Arg Thr Leu Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Lys Ser Gln Ile Met Leu Pro Leu
                245                 250                 255

His Tyr Cys Ser Val Trp Val Met Met Asn Gln Lys Thr Arg Arg Leu
            260                 265                 270

Ser Lys Ile Pro Asp Glu Val Arg His Glu Ile Glu Pro His Phe Val
```

```
        275                 280                 285

Asp Ser Ala Pro Val Ile Glu Asp Asp Asp Arg Lys Leu Pro Lys Leu
    290                 295                 300

Asp Glu Lys Thr Ala Asp Ser Ile Arg Lys Gly Leu Thr Pro Lys Trp
305                 310                 315                 320

Asn Asp Leu Asp Val Asn Gln His Val Asn Asn Val Lys Tyr Ile Gly
                325                 330                 335

Trp Ile Leu Glu Ser Thr Pro Pro Glu Val Leu Glu Thr Gln Glu Leu
            340                 345                 350

Cys Ser Leu Thr Leu Glu Tyr Arg Arg Glu Cys Gly Arg Glu Ser Val
        355                 360                 365

Leu Glu Ser Leu Thr Ala Val Asp Pro Ser Gly Lys Gly Ser Gly Ser
    370                 375                 380

Gln Phe Gln His Leu Leu Arg Leu Glu Asp Gly Gly Glu Ile Val Lys
385                 390                 395                 400

Gly Arg Thr Glu Trp Arg Pro Lys Thr Ala Gly Ile Asn Gly Pro Ile
                405                 410                 415

Ala Ser Gly Glu Thr Ser Pro Gly Asp Ser Ser
            420                 425


<210> SEQ ID NO 156
<211> LENGTH: 415
<212> TYPE: PRT
<213> ORGANISM: Cuphea hyssopifolia
<220> FEATURE:
<223> OTHER INFORMATION: ChsFatB2c amino acid sequence

<400> SEQUENCE: 156

Met Val Ala Thr Ala Ala Ser Ser Ala Phe Phe Pro Val Pro Ser Pro
1               5                   10                  15

Asp Ala Ser Ser Arg Pro Gly Lys Leu Gly Asn Gly Ser Ser Ser Leu
            20                  25                  30

Ser Pro Leu Lys Pro Lys Leu Met Ala Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Asp Gly Phe Gly Arg Thr Leu Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
```

```
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Arg Leu Ser Lys Ile Pro Asp Glu Val Arg His Glu Ile Glu
            260                 265                 270

Pro His Phe Val Asp Ser Ala Pro Val Ile Glu Asp Asp Asp Arg Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Ser Gly Ser Gln Phe Gln His Leu Met Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Pro Ile Ala Ser Gly Glu Thr Ser Pro Gly Asp Ser Ser
                405                 410                 415


<210> SEQ ID NO 157
<211> LENGTH: 415
<212> TYPE: PRT
<213> ORGANISM: Cuphea hyssopifolia
<220> FEATURE:
<223> OTHER INFORMATION: ChsFatB2d amino acid sequence

<400> SEQUENCE: 157

Met Val Ala Thr Ala Ala Ser Ser Ala Phe Phe Pro Val Pro Ser Pro
1               5                   10                  15

Asp Ala Ser Ser Arg Pro Gly Lys Leu Gly Asn Gly Ser Ser Ser Leu
            20                  25                  30

Ser Pro Leu Lys Pro Lys Leu Met Ala Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
```

```
                165                 170                 175

Leu Leu Asn Asp Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Arg Leu Ser Lys Ile Pro Asp Glu Val Arg His Glu Ile Glu
            260                 265                 270

Pro His Phe Val Asp Ser Ala Pro Val Ile Glu Asp Asp Asp Arg Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Ser Gly Ser Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Pro Ile Ala Ser Gly Glu Thr Ser Pro Gly Asp Ser Ser
                405                 410                 415


<210> SEQ ID NO 158
<211> LENGTH: 417
<212> TYPE: PRT
<213> ORGANISM: Cuphea hyssopifolia
<220> FEATURE:
<223> OTHER INFORMATION: Chs FATB3 amino acid sequence

<400> SEQUENCE: 158

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Thr Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Thr Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Pro Asp Met Leu Met Asp Pro Phe
```

```
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Val Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Cys His
225                 230                 235                 240

Thr Gly Glu Ile Leu Ile Arg Ala Thr Ser Met Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Arg Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Ala Asp Ile Ala Lys Gly Arg Thr Lys Trp Arg Pro Lys Asn Ala Gly
385                 390                 395                 400

Thr Asn Gly Ala Ile Ser Thr Gly Lys Thr Ser Asn Gly Asn Ser Ile
                405                 410                 415

Ser


<210> SEQ ID NO 159
<211> LENGTH: 417
<212> TYPE: PRT
<213> ORGANISM: Cuphea hyssopifolia
<220> FEATURE:
<223> OTHER INFORMATION: ChsFatb3b amino acid sequence

<400> SEQUENCE: 159

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Thr Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60
```

Leu Lys Ser Gly Ser Leu Asp Thr Gln Glu Asp Thr Ser Ser Ser Ser
65 70 75 80

Ser Pro Pro Arg Thr Phe Ile Asn Gln Leu Pro Asp Trp Ser Met Leu
85 90 95

Leu Ser Ala Ile Thr Thr Val Phe Val Ala Ala Glu Lys Gln Trp Thr
100 105 110

Met Leu Asp Arg Lys Ser Lys Arg Pro Asp Met Leu Met Asp Pro Phe
115 120 125

Gly Val Asp Arg Val Val Gln Asp Gly Ala Val Phe Arg Gln Ser Phe
130 135 140

Ser Ile Arg Ser Tyr Glu Ile Gly Ala Asp Arg Thr Ala Ser Ile Glu
145 150 155 160

Thr Leu Met Asn Ile Phe Gln Glu Thr Ser Leu Asn His Cys Lys Ser
165 170 175

Ile Gly Leu Leu Asn Asp Gly Phe Gly Arg Thr Pro Glu Met Cys Lys
180 185 190

Arg Asp Leu Ile Trp Val Val Thr Lys Met His Ile Glu Val Asn Arg
195 200 205

Tyr Pro Thr Trp Gly Asp Thr Ile Glu Val Asn Thr Trp Val Ser Glu
210 215 220

Ser Gly Lys Thr Gly Met Gly Arg Asp Trp Leu Ile Ser Asp Phe His
225 230 235 240

Thr Gly Asp Ile Leu Ile Arg Ala Thr Ser Val Cys Ala Met Met Asn
245 250 255

Gln Lys Thr Arg Arg Phe Ser Lys Phe Pro Tyr Glu Val Arg Gln Glu
260 265 270

Leu Ala Pro His Phe Val Asp Ser Ala Pro Val Ile Glu Asp Tyr Gln
275 280 285

Lys Leu His Lys Leu Asp Val Lys Thr Gly Asp Ser Ile Cys Asn Gly
290 295 300

Leu Thr Pro Arg Trp Asn Asp Leu Asp Val Asn Gln His Val Asn Asn
305 310 315 320

Val Lys Tyr Ile Gly Trp Ile Leu Glu Ser Val Pro Thr Glu Val Phe
325 330 335

Glu Thr Gln Glu Leu Cys Gly Leu Thr Leu Glu Tyr Arg Arg Glu Cys
340 345 350

Gly Arg Asp Ser Val Leu Glu Ser Val Thr Ala Met Asp Pro Ser Lys
355 360 365

Glu Gly Asp Arg Ser Leu Tyr Gln His Leu Leu Arg Leu Glu Asp Gly
370 375 380

Ala Asp Ile Ala Lys Gly Arg Thr Lys Trp Arg Pro Lys Asn Ala Gly
385 390 395 400

Thr Asn Gly Ala Ile Ser Thr Gly Lys Thr Ser Asn Gly Asn Ser Ile
405 410 415

Ser

<210> SEQ ID NO 160
<211> LENGTH: 409
<212> TYPE: PRT
<213> ORGANISM: Cuphea hyssopifolia
<220> FEATURE:
<223> OTHER INFORMATION: ChsFatB3c amino acid sequence

<400> SEQUENCE: 160

-continued

```
Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Thr Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Thr Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Pro Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Val Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Cys His
225                 230                 235                 240

Thr Gly Glu Ile Leu Ile Arg Ala Thr Ser Met Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Gln Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Thr Asp Ile Ala Lys Gly Arg Thr Lys Trp Arg Pro Lys Asn Ala Gly
385                 390                 395                 400

Lys Thr Ser Asn Gly Asn Ser Ile Ser
                405
```

```
<210> SEQ ID NO 161
<211> LENGTH: 417
<212> TYPE: PRT
<213> ORGANISM: Cuphea hyssopifolia
<220> FEATURE:
<223> OTHER INFORMATION: ChsFATB3d amino acid sequence

<400> SEQUENCE: 161

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Ser Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Ala Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Ser Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Val Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Cys His
225                 230                 235                 240

Thr Gly Glu Ile Leu Ile Arg Ala Thr Ser Met Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Arg Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
```

```
    370                 375                 380

Ala Asp Ile Ala Lys Gly Arg Thr Lys Trp Arg Pro Lys Asn Ala Gly
385                 390                 395                 400

Thr Asn Gly Ala Ile Ser Thr Gly Lys Thr Ser Asn Gly Asn Ser Ile
                405                 410                 415

Ser


<210> SEQ ID NO 162
<211> LENGTH: 417
<212> TYPE: PRT
<213> ORGANISM: Cuphea hyssopifolia
<220> FEATURE:
<223> OTHER INFORMATION: ChsFATB3e amino acid sequence

<400> SEQUENCE: 162

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Ser Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Ala Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Ser Asp Met Leu Met Asp Pro Phe
        115                 120                 125

Gly Val Asp Arg Val Val Gln Asp Gly Val Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Val Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Cys His
225                 230                 235                 240

Thr Gly Glu Ile Leu Ile Arg Ala Thr Ser Met Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320
```

Val Lys Tyr Ile Gly Trp Ile Leu Glu Ser Val Pro Thr Glu Val Phe
325 330 335

Glu Thr Gln Glu Leu Cys Gly Leu Thr Leu Glu Tyr Arg Arg Glu Cys
340 345 350

Gly Arg Asp Ser Val Leu Glu Ser Val Thr Ala Met Asp Pro Ser Lys
355 360 365

Glu Gly Asp Arg Ser Leu Tyr Gln His Leu Leu Arg Leu Glu Asp Gly
370 375 380

Ala Asp Ile Ala Lys Gly Arg Thr Lys Trp Arg Pro Lys Asn Ala Gly
385 390 395 400

Thr Asn Gly Ala Ile Ser Thr Gly Lys Thr Ser Asn Gly Asn Ser Ile
405 410 415

Ser

<210> SEQ ID NO 163
<211> LENGTH: 417
<212> TYPE: PRT
<213> ORGANISM: Cuphea hyssopifolia
<220> FEATURE:
<223> OTHER INFORMATION: ChsFATB3f amino acid sequence

<400> SEQUENCE: 163

Met Val Ala Ala Glu Ala Ser Ser Ala Leu Phe Ser Val Arg Thr Pro
1 5 10 15

Gly Thr Ser Pro Lys Pro Gly Lys Phe Gly Asn Trp Pro Ser Ser Leu
20 25 30

Ser Val Pro Phe Lys Ser Lys Ser Asn His Asn Gly Gly Phe Gln Val
35 40 45

Lys Ala Asn Ala Ser Ala Arg Pro Lys Ala Asn Gly Ser Ala Val Ser
50 55 60

Leu Lys Ser Gly Ser Leu Asp Thr Gln Glu Asp Thr Ser Ser Ser Ser
65 70 75 80

Ser Pro Pro Arg Thr Phe Ile Asn Gln Leu Pro Asp Trp Ser Met Leu
85 90 95

Leu Ser Ala Ile Thr Thr Val Phe Val Ala Ala Glu Lys Gln Trp Thr
100 105 110

Met Leu Asp Arg Lys Ser Lys Arg Pro Asp Met Leu Met Asp Pro Phe
115 120 125

Gly Val Asp Arg Val Val Gln Asp Gly Ala Val Phe Arg Gln Ser Phe
130 135 140

Ser Ile Arg Ser Tyr Glu Ile Gly Ala Asp Arg Thr Ala Ser Ile Glu
145 150 155 160

Thr Leu Met Asn Ile Phe Gln Glu Thr Ser Leu Asn His Cys Lys Ser
165 170 175

Ile Gly Leu Leu Asn Asp Gly Phe Gly Arg Thr Pro Glu Met Cys Lys
180 185 190

Arg Asp Leu Ile Trp Val Val Thr Lys Met His Val Glu Val Asn Arg
195 200 205

Tyr Pro Thr Trp Gly Asp Thr Ile Glu Val Asn Thr Trp Val Ser Glu
210 215 220

Ser Gly Lys Thr Gly Met Gly Arg Asp Trp Leu Ile Ser Asp Cys His
225 230 235 240

Thr Gly Glu Ile Leu Ile Arg Ala Thr Ser Met Cys Ala Met Met Asn
245 250 255

-continued

```
Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Arg Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Ala Asp Ile Ala Lys Gly Arg Thr Lys Trp Arg Pro Lys Asn Ala Gly
385                 390                 395                 400

Thr Asn Gly Ala Ile Ser Thr Gly Lys Thr Ser Asn Gly Asn Ser Ile
                405                 410                 415

Ser


<210> SEQ ID NO 164
<211> LENGTH: 409
<212> TYPE: PRT
<213> ORGANISM: Cuphea hyssopifolia
<220> FEATURE:
<223> OTHER INFORMATION: ChsFATB3g amino acid sequence

<400> SEQUENCE: 164

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Thr Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Thr Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Pro Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Ile Glu Val Asn Arg
```

```
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Phe His
225                 230                 235                 240

Thr Gly Asp Ile Leu Ile Arg Ala Thr Ser Val Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Gln Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Thr Asp Ile Ala Lys Gly Arg Thr Lys Trp Arg Pro Lys Asn Ala Gly
385                 390                 395                 400

Lys Thr Ser Asn Gly Asn Ser Ile Ser
                405


<210> SEQ ID NO 165
<211> LENGTH: 409
<212> TYPE: PRT
<213> ORGANISM: Cuphea hyssopifolia
<220> FEATURE:
<223> OTHER INFORMATION: ChsFATB3h amino acid sequence

<400> SEQUENCE: 165

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Ser Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Ala Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Ser Asp Met Leu Met Asp Pro Phe
        115                 120                 125

Gly Val Asp Arg Val Val Gln Asp Gly Val Val Phe Arg Gln Ser Phe
    130                 135                 140

Ser Ile Arg Ser Tyr Glu Ile Gly Ala Asp Arg Thr Ala Ser Ile Glu
```

-continued

```
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Ile Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Phe His
225                 230                 235                 240

Thr Gly Asp Ile Leu Ile Arg Ala Thr Ser Val Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Gln Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Thr Asp Ile Ala Lys Gly Arg Thr Lys Trp Arg Pro Lys Asn Ala Gly
385                 390                 395                 400

Lys Thr Ser Asn Gly Asn Ser Ile Ser
                405


<210> SEQ ID NO 166
<211> LENGTH: 417
<212> TYPE: PRT
<213> ORGANISM: Cuphea hyssopifolia
<220> FEATURE:
<223> OTHER INFORMATION: ChsFATB3i amino acid sequence

<400> SEQUENCE: 166

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Thr Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Thr Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
```

```
            100                 105                 110

Met Leu Asp Arg Lys Ser Lys Arg Pro Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Val Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Cys His
225                 230                 235                 240

Thr Gly Glu Ile Leu Ile Arg Ala Thr Ser Met Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Arg Glu Cys
            340                 345                 350

Gly Gly Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Ala Asp Ile Ala Lys Gly Arg Thr Lys Trp Arg Pro Lys Asn Ala Gly
385                 390                 395                 400

Thr Asn Gly Ala Ile Ser Thr Gly Lys Thr Ser Asn Gly Asn Ser Ile
                405                 410                 415

Ser


<210> SEQ ID NO 167
<211> LENGTH: 409
<212> TYPE: PRT
<213> ORGANISM: Cuphea hyssopifolia
<220> FEATURE:
<223> OTHER INFORMATION: ChsFATB3j amino acid sequence

<400> SEQUENCE: 167

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Thr Ser Leu
            20                  25                  30

Ser Val Pro Phe Lys Ser Lys Ser Asn His Asn Gly Gly Phe Gln Val
        35                  40                  45
```

-continued

```
Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Thr Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Pro Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Ile Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Phe His
225                 230                 235                 240

Thr Gly Asp Ile Leu Ile Arg Ala Thr Ser Val Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Gln Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Thr Asp Ile Ala Lys Gly Arg Thr Lys Trp Arg Pro Lys Asn Ala Gly
385                 390                 395                 400

Lys Thr Ser Asn Gly Asn Ser Ile Ser
                405
```

<210> SEQ ID NO 168
<211> LENGTH: 415
<212> TYPE: PRT
<213> ORGANISM: Cuphea calcarata
<220> FEATURE:
<223> OTHER INFORMATION: CcalcFATB1 (Cuphea calcarata FATB1)

<400> SEQUENCE: 168

-continued

```
Met Val Ala Ala Ala Ala Thr Ser Ala Phe Phe Pro Val Pro Ala Pro
1               5                   10                  15

Gly Thr Ser Pro Asn Pro Arg Lys Phe Gly Ser Trp Pro Ser Ser Leu
            20                  25                  30

Ser Pro Ser Leu Pro Lys Ser Ile Pro Asn Gly Gly Phe Gln Val Lys
        35                  40                  45

Ala Asn Ala Ser Ala His Pro Lys Ala Asn Gly Ser Ala Val Ser Leu
    50                  55                  60

Lys Ser Gly Ser Leu Asn Thr Gln Glu Asn Thr Ser Ser Ser Pro Pro
65                  70                  75                  80

Pro Arg Thr Phe Leu His Gln Leu Pro Asp Trp Ser Arg Leu Leu Thr
                85                  90                  95

Ala Ile Thr Thr Val Phe Val Lys Ser Lys Arg Pro Asp Met His Asp
            100                 105                 110

Arg Lys Ser Lys Arg Pro Asp Met Leu Val Asp Leu Phe Gly Leu Glu
        115                 120                 125

Ser Ser Val Gln Asp Ala Leu Val Phe Arg Gln Ser Phe Ser Ile Arg
    130                 135                 140

Ser Tyr Glu Ile Gly Thr Asp Arg Thr Ala Ser Ile Glu Thr Leu Met
145                 150                 155                 160

Asn His Leu Gln Glu Thr Ser Leu Asn His Cys Lys Ser Thr Gly Ile
                165                 170                 175

Leu Leu Asp Gly Phe Gly Arg Thr Leu Glu Met Cys Lys Arg Glu Leu
            180                 185                 190

Ile Trp Val Val Ile Lys Met Gln Ile Gln Val Asn Arg Tyr Pro Ala
        195                 200                 205

Trp Gly Asp Thr Val Glu Ile Asn Thr Arg Phe Ser Arg Leu Gly Lys
    210                 215                 220

Ile Gly Met Gly Arg Asp Trp Leu Ile Ser Asp Cys Asn Thr Gly Glu
225                 230                 235                 240

Ile Leu Ile Arg Ala Thr Ser Glu Tyr Ala Met Met Asn Gln Lys Thr
                245                 250                 255

Arg Arg Leu Ser Lys Leu Pro Tyr Glu Val His Gln Glu Ile Ala Pro
            260                 265                 270

Leu Phe Val Asp Ser Pro Pro Val Ile Glu Asp Asn Asp Leu Lys Val
        275                 280                 285

His Lys Phe Glu Val Lys Thr Gly Asp Ser Ile Gln Lys Gly Leu Ser
    290                 295                 300

Pro Gly Trp Asn Asp Leu Asp Val Asn Gln His Val Ser Asn Val Lys
305                 310                 315                 320

Tyr Ile Gly Trp Ile Leu Glu Ser Met Pro Thr Glu Val Leu Glu Thr
                325                 330                 335

Gln Glu Leu Cys Ser Leu Ala Leu Glu Tyr Arg Arg Glu Cys Gly Arg
            340                 345                 350

Asp Ser Val Leu Glu Ser Val Thr Ala Met Asp Pro Ser Lys Val Gly
        355                 360                 365

Gly Arg Ser Gln Tyr Gln His Leu Leu Arg Leu Glu Asp Gly Thr Ala
    370                 375                 380

Ile Val Asn Gly Ile Thr Glu Trp Arg Pro Lys Asn Ala Gly Ala Asn
385                 390                 395                 400

Gly Ala Ile Ser Thr Gly Lys Thr Ser Asn Gly Asn Ser Val Ser
                405                 410                 415
```

```
<210> SEQ ID NO 169
<211> LENGTH: 414
<212> TYPE: PRT
<213> ORGANISM: Cuphea hookeriana
<220> FEATURE:
<223> OTHER INFORMATION: ChookFATB4 (Cuphea hookeriana FATB4)

<400> SEQUENCE: 169

Met Val Ala Ala Ala Ala Thr Ser Ala Phe Phe Pro Val Pro Ala Pro
1               5                   10                  15

Gly Thr Ser Pro Asn Pro Arg Lys Phe Gly Ser Trp Pro Ser Ser Leu
            20                  25                  30

Ser Pro Ser Leu Pro Asn Ser Ile Pro Asn Gly Gly Phe Gln Val Lys
        35                  40                  45

Ala Asn Ala Ser Ala His Pro Lys Ala Asn Gly Ser Ala Val Ser Leu
    50                  55                  60

Lys Ser Gly Ser Leu Asn Thr Gln Glu Asn Thr Ser Ser Ser Pro Pro
65                  70                  75                  80

Pro Arg Thr Phe Leu His Gln Leu Pro Asp Trp Ser Arg Leu Leu Thr
                85                  90                  95

Ala Ile Thr Thr Val Phe Val Lys Ser Lys Arg Pro Asp Met His Asp
            100                 105                 110

Arg Lys Ser Lys Arg Pro Asp Met Leu Val Asp Leu Phe Gly Leu Glu
        115                 120                 125

Ser Ser Val Gln Asp Ala Leu Val Phe Arg Gln Arg Phe Ser Ile Arg
    130                 135                 140

Ser Tyr Glu Ile Gly Thr Asp Arg Thr Ala Ser Met Glu Thr Leu Met
145                 150                 155                 160

Asn His Leu Gln Glu Thr Ser Leu Asn His Cys Lys Ser Thr Gly Ile
                165                 170                 175

Leu Leu Asp Gly Phe Gly Arg Thr Leu Glu Met Cys Lys Arg Glu Leu
            180                 185                 190

Ile Trp Val Val Ile Lys Met Gln Ile Gln Val Asn Arg Tyr Pro Ala
        195                 200                 205

Trp Gly Asp Thr Val Glu Ile Asn Thr Arg Phe Ser Arg Leu Gly Lys
    210                 215                 220

Ile Gly Met Gly Arg Asp Trp Leu Ile Ser Asp Cys Asn Thr Gly Glu
225                 230                 235                 240

Ile Leu Ile Arg Ala Thr Ser Glu Tyr Ala Met Met Asn Gln Lys Thr
                245                 250                 255

Arg Arg Leu Ser Lys Leu Pro Tyr Glu Val Arg Gln Glu Ile Ala Pro
            260                 265                 270

Leu Phe Val Asp Ser Pro Pro Val Ile Glu Asp Asn Asp Leu Lys Val
        275                 280                 285

His Lys Phe Glu Val Lys Thr Gly Asp Ser Ile His Lys Gly Leu Thr
    290                 295                 300

Pro Gly Trp Asn Asp Leu Asp Val Asn Gln His Val Asn Asn Val Lys
305                 310                 315                 320

Tyr Ile Gly Trp Ile Leu Glu Ser Thr Pro Pro Glu Val Leu Glu Thr
                325                 330                 335

Gln Glu Leu Cys Ser Leu Thr Leu Glu Tyr Arg Arg Glu Cys Gly Arg
            340                 345                 350

Glu Ser Val Leu Glu Ser Leu Thr Ala Met Asp Pro Ser Gly Gly Gly
        355                 360                 365
```

```
Tyr Gly Ser Gln Phe Gln His Leu Leu Arg Leu Glu Asp Gly Gly Glu
    370                 375                 380

Ile Val Lys Gly Arg Thr Glu Trp Arg Pro Lys Asn Gly Val Ile Asn
385                 390                 395                 400

Gly Val Val Pro Thr Gly Glu Ser Ser Pro Gly Asp Tyr Ser
                405                 410


<210> SEQ ID NO 170
<211> LENGTH: 416
<212> TYPE: PRT
<213> ORGANISM: Cuphea avigera
<220> FEATURE:
<223> OTHER INFORMATION: CaFATB1 (Cuphea avigera var. pulcherrima FATB1)

<400> SEQUENCE: 170

Met Val Ala Ala Ala Ala Ser Ser Ala Phe Phe Ser Val Pro Val Pro
1               5                   10                  15

Gly Thr Ser Pro Lys Pro Gly Lys Phe Arg Ile Trp Pro Ser Ser Leu
            20                  25                  30

Ser Pro Ser Phe Lys Pro Lys Pro Ile Pro Asn Gly Gly Leu Gln Val
        35                  40                  45

Lys Ala Asn Ser Arg Ala His Pro Lys Ala Asn Gly Ser Ala Val Ser
    50                  55                  60

Leu Lys Ser Gly Ser Leu Asn Thr Gln Glu Asp Thr Ser Ser Ser Pro
65                  70                  75                  80

Pro Pro Arg Thr Phe Leu His Gln Leu Pro Asp Trp Ser Arg Leu Leu
                85                  90                  95

Thr Ala Ile Thr Thr Val Phe Val Lys Ser Lys Arg Pro Asp Met His
            100                 105                 110

Asp Arg Lys Ser Lys Arg Pro Asp Met Leu Met Asp Ser Phe Gly Leu
        115                 120                 125

Glu Ser Ile Val Gln Glu Gly Leu Glu Phe Arg Gln Ser Phe Ser Ile
    130                 135                 140

Arg Ser Tyr Glu Ile Gly Thr Asp Arg Thr Ala Ser Ile Glu Thr Leu
145                 150                 155                 160

Met Asn Tyr Leu Gln Glu Thr Ser Leu Asn His Cys Lys Ser Thr Gly
                165                 170                 175

Ile Leu Leu Asp Gly Phe Gly Arg Thr Pro Glu Met Cys Lys Arg Asp
            180                 185                 190

Leu Ile Trp Val Val Thr Lys Met Lys Ile Lys Val Asn Arg Tyr Pro
        195                 200                 205

Ala Trp Gly Asp Thr Val Glu Ile Asn Thr Trp Phe Ser Arg Leu Gly
    210                 215                 220

Lys Ile Gly Lys Gly Arg Asp Trp Leu Ile Ser Asp Cys Asn Thr Gly
225                 230                 235                 240

Glu Ile Leu Ile Arg Ala Thr Ser Ala Tyr Ala Thr Met Asn Gln Lys
                245                 250                 255

Thr Arg Arg Leu Ser Lys Leu Pro Tyr Glu Val His Gln Glu Ile Ala
            260                 265                 270

Pro Leu Phe Val Asp Ser Pro Pro Val Ile Glu Asp Asn Asp Leu Lys
        275                 280                 285

Leu His Lys Phe Glu Val Lys Thr Gly Asp Ser Ile His Lys Gly Leu
    290                 295                 300

Thr Pro Gly Trp Asn Asp Leu Asp Val Asn Gln His Val Ser Asn Val
305                 310                 315                 320
```

-continued

```
Lys Tyr Ile Gly Trp Ile Leu Glu Ser Met Pro Thr Glu Val Leu Glu
                325                 330                 335

Thr Gln Glu Leu Cys Ser Leu Ala Leu Glu Tyr Arg Arg Glu Cys Gly
            340                 345                 350

Arg Asp Ser Val Leu Glu Ser Val Thr Ala Met Asp Pro Thr Lys Val
        355                 360                 365

Gly Gly Arg Ser Gln Tyr Gln His Leu Leu Arg Leu Glu Asp Gly Thr
    370                 375                 380

Asp Ile Val Lys Cys Arg Thr Glu Trp Arg Pro Lys Asn Pro Gly Ala
385                 390                 395                 400

Asn Gly Ala Ile Ser Thr Gly Lys Thr Ser Asn Gly Asn Ser Val Ser
                405                 410                 415


<210> SEQ ID NO 171
<211> LENGTH: 417
<212> TYPE: PRT
<213> ORGANISM: Cuphea paucipetala
<220> FEATURE:
<223> OTHER INFORMATION: CpauFATB1 (Cuphea paucipetala FATB1)

<400> SEQUENCE: 171

Met Val Ala Ala Ala Ala Ser Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Ser Ile Lys Pro Met Ser Ile Pro Asn Gly Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Arg Asp Arg Lys Ser Lys Arg Pro Asp Met Leu Val Asp Ser Val Gly
        115                 120                 125

Leu Lys Ser Val Val Leu Asp Gly Leu Val Ser Arg Gln Ile Phe Ser
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Ile Asn Thr Trp Phe Ser His Ser
    210                 215                 220

Gly Lys Ile Gly Met Ala Ser Asp Trp Leu Ile Thr Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270
```

```
Thr Pro His Tyr Val Asp Ser Pro His Val Ile Glu Asp Asn Asp Arg
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Met Asp Pro Ser Glu
        355                 360                 365

Asp Glu Gly Arg Ser Gln Tyr Lys His Leu Leu Arg Leu Glu Asp Gly
    370                 375                 380

Thr Asp Ile Val Lys Gly Arg Thr Glu Trp Arg Pro Lys Asn Ala Gly
385                 390                 395                 400

Thr Asn Gly Ala Ile Ser Thr Ala Lys Pro Ser Asn Gly Asn Ser Val
                405                 410                 415

Ser


<210> SEQ ID NO 172
<211> LENGTH: 417
<212> TYPE: PRT
<213> ORGANISM: Cuphea procumbens
<220> FEATURE:
<223> OTHER INFORMATION: CprocFATB1 (Cuphea procumbens FATB1)

<400> SEQUENCE: 172

Met Val Ala Ala Ala Ala Ser Ser Ala Phe Phe Pro Ala Pro Ala Pro
1               5                   10                  15

Gly Ser Ser Pro Lys Pro Gly Lys Ser Gly Asn Trp Pro Ser Ser Leu
            20                  25                  30

Ser Pro Ser Phe Lys Ser Lys Ser Ile Pro Tyr Gly Arg Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Ser Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Asn Ile Val Arg Asp Gly Leu Val Ser Arg Gln Ser Phe Leu
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Ala Trp Gly Asp Thr Val Glu Ile Asn Thr Trp Phe Ser Gln Ser
```

```
    210                 215                 220

Gly Lys Ile Gly Met Gly Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Arg
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Ala Gln Glu Leu Cys Ser Leu Thr Val Glu Tyr Arg Arg Glu Cys
            340                 345                 350

Gly Met Asp Ser Val Leu Glu Ser Val Thr Ala Val Asp Pro Ser Glu
        355                 360                 365

Asp Gly Gly Arg Ser Gln Tyr Asn His Leu Leu Arg Leu Glu Asp Gly
    370                 375                 380

Thr Asp Val Val Lys Gly Arg Thr Glu Trp Arg Pro Lys Asn Ala Glu
385                 390                 395                 400

Thr Asn Gly Ala Ile Ser Pro Gly Asn Thr Ser Asn Gly Asn Ser Ile
                405                 410                 415

Ser


<210> SEQ ID NO 173
<211> LENGTH: 415
<212> TYPE: PRT
<213> ORGANISM: Cuphea procumbens
<220> FEATURE:
<223> OTHER INFORMATION: CprocFATB2 (Cuphea procumbens FATB2)

<400> SEQUENCE: 173

Met Val Ala Ala Ala Ala Ser Ser Ala Phe Phe Pro Ala Pro Ala Pro
1               5                   10                  15

Gly Ser Ser Pro Lys Pro Gly Lys Ser Gly Asn Trp Pro Ser Ser Leu
            20                  25                  30

Ser Pro Ser Phe Lys Ser Lys Ser Ile Pro Tyr Gly Arg Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Ser Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Asn Ile Val Arg Asp Gly Leu Val Ser Arg Gln Ser Phe Leu
    130                 135                 140

Ile Arg Ser Tyr Glu Ile Gly Ala Asp Arg Thr Ala Ser Ile Glu Thr
145                 150                 155                 160
```

```
Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Ala Trp Gly Asp Thr Val Glu Ile Asn Thr Trp Phe Ser Gln Ser
    210                 215                 220

Gly Lys Ile Gly Met Gly Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Arg
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Pro Glu Val Leu
                325                 330                 335

Glu Thr Gln Glu Leu Cys Ser Leu Thr Leu Glu Tyr Arg Gln Glu Cys
            340                 345                 350

Gly Arg Glu Ser Val Leu Glu Ser Leu Thr Ala Val Asp Pro Ser Gly
        355                 360                 365

Lys Gly Phe Gly Ser Gln Phe Gln His Leu Leu Arg Leu Glu Asp Gly
    370                 375                 380

Gly Glu Ile Val Lys Gly Arg Thr Glu Trp Arg Pro Lys Thr Ala Gly
385                 390                 395                 400

Ile Asn Gly Ala Ile Ala Ser Gly Glu Thr Ser Pro Gly Asp Phe
                405                 410                 415


<210> SEQ ID NO 174
<211> LENGTH: 410
<212> TYPE: PRT
<213> ORGANISM: Cuphea procumbens
<220> FEATURE:
<223> OTHER INFORMATION: CprocFATB3 (Cuphea procumbens FATB3)

<400> SEQUENCE: 174

Met Val Ala Ala Ala Ala Ser Ser Ala Phe Phe Pro Ala Pro Ala Pro
1               5                   10                  15

Gly Ser Ser Pro Lys Pro Gly Lys Ser Gly Asn Trp Pro Ser Ser Leu
            20                  25                  30

Ser Pro Ser Phe Lys Ser Lys Ser Ile Pro Tyr Gly Arg Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Ser Ala Ile Thr Thr Val Phe Val Ala Ala Glu Lys Gln Trp Thr Met
            100                 105                 110
```

Leu Asp Arg Lys Ser Lys Arg Pro Asp Met Leu Val Asp Ser Val Gly
115 120 125

Leu Lys Asn Ile Val Arg Asp Gly Leu Val Ser Arg Gln Ser Phe Leu
130 135 140

Ile Arg Ser Tyr Glu Ile Gly Ala Asp Arg Thr Ala Ser Ile Glu Thr
145 150 155 160

Leu Met Asn His Leu Gln Glu Thr Ser Ile Asn His Cys Lys Ser Leu
165 170 175

Gly Leu Leu Asn Asp Gly Phe Gly Arg Thr Pro Gly Met Cys Lys Asn
180 185 190

Asp Leu Ile Trp Val Leu Thr Lys Met Gln Ile Met Val Asn Arg Tyr
195 200 205

Pro Ala Trp Gly Asp Thr Val Glu Ile Asn Thr Trp Phe Ser Gln Ser
210 215 220

Gly Lys Ile Gly Met Gly Ser Asp Trp Leu Ile Ser Asp Cys Asn Thr
225 230 235 240

Gly Glu Ile Leu Ile Arg Ala Thr Ser Val Trp Ala Met Met Asn Gln
245 250 255

Lys Thr Arg Arg Phe Ser Arg Leu Pro Tyr Glu Val Arg Gln Glu Leu
260 265 270

Thr Pro His Phe Val Asp Ser Pro His Val Ile Glu Asp Asn Asp Arg
275 280 285

Lys Leu His Lys Phe Asp Val Lys Thr Gly Asp Ser Ile Arg Lys Gly
290 295 300

Leu Thr Pro Arg Trp Asn Asp Leu Asp Val Asn Gln His Val Asn Asn
305 310 315 320

Val Lys Tyr Ile Gly Trp Ile Leu Glu Ser Thr Pro Pro Glu Val Leu
325 330 335

Glu Thr Gln Glu Leu Cys Ser Leu Thr Leu Glu Tyr Arg Arg Glu Cys
340 345 350

Gly Arg Glu Ser Val Leu Glu Ser Leu Thr Ala Val Asp Pro Ser Gly
355 360 365

Glu Gly Gly Tyr Gly Ser Gln Phe Gln His Leu Leu Arg Leu Glu Asp
370 375 380

Gly Gly Glu Ile Val Lys Gly Arg Thr Glu Trp Arg Pro Lys Asn Ala
385 390 395 400

Gly Ile Asn Gly Val Leu Pro Thr Gly Glu
405 410

<210> SEQ ID NO 175
<211> LENGTH: 395
<212> TYPE: PRT
<213> ORGANISM: Cuphea ignea
<220> FEATURE:
<223> OTHER INFORMATION: CigneaFATB1 (Cuphea ignea FATB1)

<400> SEQUENCE: 175

Pro Gly Thr Ser Arg Lys Thr Gly Lys Phe Gly Asn Trp Pro Ser Ser
1 5 10 15

Leu Ser Pro Ser Phe Lys Pro Lys Ser Ile Pro Asn Gly Gly Phe Gln
20 25 30

Val Lys Ala Asn Ala Arg Ala His Pro Lys Ala Asn Gly Ser Ala Val
35 40 45

Ser Leu Lys Ser Val Ser Leu Asn Thr Gln Glu Asp Thr Ser Leu Ser
50 55 60

Pro Pro Pro Arg Ala Phe Leu Asn Gln Leu Pro Asp Trp Arg Met Leu
65 70 75 80

Arg Thr Ala Leu Thr Thr Val Phe Val Ala Ala Glu Lys Gln Trp Thr
85 90 95

Met Leu Asp Arg Lys Ser Lys Arg Pro Asp Met Leu Val Asp Ser Phe
100 105 110

Gly Leu Glu Ser Ile Val Gln Glu Gly Leu Val Phe Arg Gln Ser Phe
115 120 125

Ser Ile Arg Ser Tyr Glu Ile Gly Ile Asp Arg Thr Ala Ser Ile Glu
130 135 140

Thr Leu Met Asn His Leu Gln Glu Thr Ser Leu Asn Gln Cys Lys Ser
145 150 155 160

Ala Gly Ile Leu His Asp Gly Phe Gly Arg Thr Leu Glu Met Cys Lys
165 170 175

Arg Asp Leu Ile Trp Val Val Thr Lys Met Gln Ile Lys Val Asn Arg
180 185 190

Tyr Pro Ala Trp Gly Asp Thr Val Glu Ile Ser Thr Arg Phe Ser Arg
195 200 205

Leu Gly Lys Ile Gly Met Gly Arg Asp Trp Leu Ile Cys Asp Cys Asn
210 215 220

Thr Gly Glu Ile Leu Ile Arg Ala Thr Ser Ala Tyr Ala Met Met Asn
225 230 235 240

Gln Lys Thr Arg Arg Leu Ser Lys Leu Pro Asn Glu Val Arg Gln Glu
245 250 255

Ile Ala Pro Leu Phe Val Asp Ser Asp Pro Val Ile Glu Glu Asn Asp
260 265 270

Met Lys Leu His Lys Phe Glu Val Lys Thr Gly Asp Ser Ile Cys Lys
275 280 285

Gly Leu Thr Pro Arg Trp Ser Asp Leu Asp Val Asn Gln His Val Ser
290 295 300

Asn Val Lys Tyr Ile Gly Trp Ile Leu Glu Ser Met Pro Thr Glu Val
305 310 315 320

Leu Glu Thr Gln Glu Leu Cys Ser Leu Ala Leu Glu Tyr Arg Arg Glu
325 330 335

Cys Gly Arg Asp Ser Val Leu Glu Ser Val Thr Ser Met Asp Pro Ser
340 345 350

Lys Val Gly Gly Trp Ser Gln Tyr Gln His Leu Leu Arg Leu Glu Asp
355 360 365

Gly Ala Asp Ile Val Lys Gly Arg Thr Glu Trp Arg Pro Lys Asn Ala
370 375 380

Gly Ala Asn Gly Ala Ile Ser Thr Gly Lys Thr
385 390 395

<210> SEQ ID NO 176
<211> LENGTH: 405
<212> TYPE: PRT
<213> ORGANISM: Cuphea calcarata
<220> FEATURE:
<223> OTHER INFORMATION: CcalcFATB1 (Cuphea calcarata FATB1)

<400> SEQUENCE: 176

Met Ala Thr Ala Ser Thr Phe Ser Ala Phe Asn Ala Arg Cys Gly Asp
1 5 10 15

Leu Arg Arg Ser Ala Gly Ser Gly Pro Arg Arg Pro Ala Arg Pro Leu
20 25 30

```
Pro Val Arg Ala Ala Ile Asn Ala Ser Ala His Pro Lys Ala Asn Gly
        35                  40                  45

Ser Ala Val Ser Leu Lys Ser Gly Ser Leu Glu Thr Gln Glu Asp Asn
    50                  55                  60

Ser Ser Ser Ser Arg Pro Pro Arg Thr Phe Ile Lys Gln Leu Pro Asp
65                  70                  75                  80

Trp Ser Met Leu Leu Ser Ala Ile Thr Thr Val Phe Val Ala Ala Glu
                85                  90                  95

Lys Gln Trp Thr Met Phe Asp Arg Lys Ser Lys Arg Ser Asp Met Leu
            100                 105                 110

Val Asp Pro Phe Val Val Asp Arg Ile Val Gln Asp Gly Val Leu Phe
        115                 120                 125

Arg Gln Ser Phe Ser Ile Arg Ser Tyr Glu Ile Gly Ala Asp Arg Thr
    130                 135                 140

Ala Ser Ile Glu Thr Leu Met Asn Ile Phe Gln Glu Thr Ser Leu Asn
145                 150                 155                 160

His Cys Lys Ser Met Gly Leu Leu Tyr Glu Gly Phe Gly Arg Thr Pro
                165                 170                 175

Glu Met Cys Lys Arg Asp Leu Ile Trp Val Val Thr Lys Ile His Ile
            180                 185                 190

Lys Val Asn Arg Tyr Pro Thr Trp Gly Asp Thr Ile Glu Val Thr Thr
        195                 200                 205

Trp Val Ser Glu Ser Gly Lys Asn Gly Met Gly Arg Asp Trp Leu Ile
    210                 215                 220

Ser Asp Cys His Thr Gly Glu Ile Leu Ile Arg Ala Thr Ser Val Trp
225                 230                 235                 240

Ala Met Met Asn Gln Thr Thr Arg Arg Leu Ser Lys Phe Pro Tyr Glu
                245                 250                 255

Leu Arg Gln Glu Ile Ala Pro His Phe Val Asp Ser Asp Pro Val Ile
            260                 265                 270

Glu Asp Asn Arg Arg Leu Leu Asn Phe Asp Val Lys Thr Gly Asp Ser
        275                 280                 285

Ile Arg Lys Gly Leu Thr Pro Arg Trp Asn Asp Leu Asp Val Asn Gln
    290                 295                 300

His Val Asn Asn Val Lys Tyr Ile Gly Trp Ile Leu Glu Ser Val Pro
305                 310                 315                 320

Thr Glu Val Phe Asp Thr Arg Glu Leu Cys Gly Leu Thr Leu Glu Tyr
                325                 330                 335

Arg Gln Glu Cys Gly Arg Gly Ser Val Leu Glu Ser Val Thr Ala Met
            340                 345                 350

Asp Pro Ser Lys Glu Gly Asp Arg Ser Leu Tyr Gln His Leu Leu Arg
        355                 360                 365

Leu Glu Asp Gly Thr Asp Ile Val Lys Gly Arg Thr Glu Trp Arg Pro
    370                 375                 380

Lys Asn Ala Gly Thr Asn Gly Pro Val Ser Thr Arg Lys Thr Thr Asn
385                 390                 395                 400

Gly Ser Ser Val Ser
                405
```

<210> SEQ ID NO 177
<211> LENGTH: 403
<212> TYPE: PRT
<213> ORGANISM: Cuphea hookeriana
<220> FEATURE:

<223> OTHER INFORMATION: ChookFATB4 (Cuphea hookeriana FATB4)

<400> SEQUENCE: 177

```
Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Ala Ala Ile Asn Ala Ser Ala His Pro Lys Ala Asn Gly
        35                  40                  45

Ser Ala Val Ser Leu Lys Ser Gly Ser Leu Asn Thr Gln Glu Asn Thr
    50                  55                  60

Ser Ser Ser Pro Pro Pro Arg Thr Phe Leu His Gln Leu Pro Asp Trp
65                  70                  75                  80

Ser Arg Leu Leu Thr Ala Ile Thr Thr Val Phe Val Lys Ser Lys Arg
                85                  90                  95

Pro Asp Met His Asp Arg Lys Ser Lys Arg Pro Asp Met Leu Val Asp
            100                 105                 110

Leu Phe Gly Leu Glu Ser Ser Val Gln Asp Ala Leu Val Phe Arg Gln
        115                 120                 125

Arg Phe Ser Ile Arg Ser Tyr Glu Ile Gly Thr Asp Arg Thr Ala Ser
    130                 135                 140

Met Glu Thr Leu Met Asn His Leu Gln Glu Thr Ser Leu Asn His Cys
145                 150                 155                 160

Lys Ser Thr Gly Ile Leu Leu Asp Gly Phe Gly Arg Thr Leu Glu Met
                165                 170                 175

Cys Lys Arg Glu Leu Ile Trp Val Val Ile Lys Met Gln Ile Gln Val
            180                 185                 190

Asn Arg Tyr Pro Ala Trp Gly Asp Thr Val Glu Ile Asn Thr Arg Phe
        195                 200                 205

Ser Arg Leu Gly Lys Ile Gly Met Gly Arg Asp Trp Leu Ile Ser Asp
    210                 215                 220

Cys Asn Thr Gly Glu Ile Leu Ile Arg Ala Thr Ser Glu Tyr Ala Met
225                 230                 235                 240

Met Asn Gln Lys Thr Arg Arg Leu Ser Lys Leu Pro Tyr Glu Val Arg
                245                 250                 255

Gln Glu Ile Ala Pro Leu Phe Val Asp Ser Pro Pro Val Ile Glu Asp
            260                 265                 270

Asn Asp Leu Lys Val His Lys Phe Glu Val Lys Thr Gly Asp Ser Ile
        275                 280                 285

His Lys Gly Leu Thr Pro Gly Trp Asn Asp Leu Asp Val Asn Gln His
    290                 295                 300

Val Asn Asn Val Lys Tyr Ile Gly Trp Ile Leu Glu Ser Thr Pro Pro
305                 310                 315                 320

Glu Val Leu Glu Thr Gln Glu Leu Cys Ser Leu Thr Leu Glu Tyr Arg
                325                 330                 335

Arg Glu Cys Gly Arg Glu Ser Val Leu Glu Ser Leu Thr Ala Met Asp
            340                 345                 350

Pro Ser Gly Gly Gly Tyr Gly Ser Gln Phe Gln His Leu Leu Arg Leu
        355                 360                 365

Glu Asp Gly Gly Glu Ile Val Lys Gly Arg Thr Glu Trp Arg Pro Lys
    370                 375                 380

Asn Gly Val Ile Asn Gly Val Val Pro Thr Gly Glu Ser Ser Pro Gly
385                 390                 395                 400
```

```
Asp Tyr Ser


<210> SEQ ID NO 178
<211> LENGTH: 404
<212> TYPE: PRT
<213> ORGANISM: Cuphea avigera
<220> FEATURE:
<223> OTHER INFORMATION: CaFATB1 (Cuphea avigera var. pulcherrima FATB1)

<400> SEQUENCE: 178

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Ala Ala Ile Asn Ser Arg Ala His Pro Lys Ala Asn Gly
        35                  40                  45

Ser Ala Val Ser Leu Lys Ser Gly Ser Leu Asn Thr Gln Glu Asp Thr
    50                  55                  60

Ser Ser Ser Pro Pro Pro Arg Thr Phe Leu His Gln Leu Pro Asp Trp
65                  70                  75                  80

Ser Arg Leu Leu Thr Ala Ile Thr Thr Val Phe Val Lys Ser Lys Arg
                85                  90                  95

Pro Asp Met His Asp Arg Lys Ser Lys Arg Pro Asp Met Leu Met Asp
            100                 105                 110

Ser Phe Gly Leu Glu Ser Ile Val Gln Glu Gly Leu Glu Phe Arg Gln
        115                 120                 125

Ser Phe Ser Ile Arg Ser Tyr Glu Ile Gly Thr Asp Arg Thr Ala Ser
    130                 135                 140

Ile Glu Thr Leu Met Asn Tyr Leu Gln Glu Thr Ser Leu Asn His Cys
145                 150                 155                 160

Lys Ser Thr Gly Ile Leu Leu Asp Gly Phe Gly Arg Thr Pro Glu Met
                165                 170                 175

Cys Lys Arg Asp Leu Ile Trp Val Val Thr Lys Met Lys Ile Lys Val
            180                 185                 190

Asn Arg Tyr Pro Ala Trp Gly Asp Thr Val Glu Ile Asn Thr Trp Phe
        195                 200                 205

Ser Arg Leu Gly Lys Ile Gly Lys Gly Arg Asp Trp Leu Ile Ser Asp
    210                 215                 220

Cys Asn Thr Gly Glu Ile Leu Ile Arg Ala Thr Ser Ala Tyr Ala Thr
225                 230                 235                 240

Met Asn Gln Lys Thr Arg Arg Leu Ser Lys Leu Pro Tyr Glu Val His
                245                 250                 255

Gln Glu Ile Ala Pro Leu Phe Val Asp Ser Pro Pro Val Ile Glu Asp
            260                 265                 270

Asn Asp Leu Lys Leu His Lys Phe Glu Val Lys Thr Gly Asp Ser Ile
        275                 280                 285

His Lys Gly Leu Thr Pro Gly Trp Asn Asp Leu Asp Val Asn Gln His
    290                 295                 300

Val Ser Asn Val Lys Tyr Ile Gly Trp Ile Leu Glu Ser Met Pro Thr
305                 310                 315                 320

Glu Val Leu Glu Thr Gln Glu Leu Cys Ser Leu Ala Leu Glu Tyr Arg
                325                 330                 335

Arg Glu Cys Gly Arg Asp Ser Val Leu Glu Ser Val Thr Ala Met Asp
            340                 345                 350

Pro Thr Lys Val Gly Gly Arg Ser Gln Tyr Gln His Leu Leu Arg Leu
```

```
        355                 360                 365

Glu Asp Gly Thr Asp Ile Val Lys Cys Arg Thr Glu Trp Arg Pro Lys
    370                 375                 380

Asn Pro Gly Ala Asn Gly Ala Ile Ser Thr Gly Lys Thr Ser Asn Gly
385                 390                 395                 400

Asn Ser Val Ser


<210> SEQ ID NO 179
<211> LENGTH: 405
<212> TYPE: PRT
<213> ORGANISM: Cuphea paucipetala
<220> FEATURE:
<223> OTHER INFORMATION: CpauFATB1 (Cuphea paucipetala FATB1)

<400> SEQUENCE: 179

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Ala Ala Ile Asn Ala Ser Ala His Pro Lys Ala Asn Gly
        35                  40                  45

Ser Ala Val Asn Leu Lys Ser Gly Ser Leu Asn Thr Gln Glu Asp Thr
    50                  55                  60

Ser Ser Ser Pro Pro Pro Arg Ala Phe Leu Asn Gln Leu Pro Asp Trp
65                  70                  75                  80

Ser Met Leu Leu Thr Ala Ile Thr Thr Val Phe Val Ala Ala Glu Lys
                85                  90                  95

Gln Trp Thr Met Arg Asp Arg Lys Ser Lys Arg Pro Asp Met Leu Val
            100                 105                 110

Asp Ser Val Gly Leu Lys Ser Val Val Leu Asp Gly Leu Val Ser Arg
        115                 120                 125

Gln Ile Phe Ser Ile Arg Ser Tyr Glu Ile Gly Ala Asp Arg Thr Ala
    130                 135                 140

Ser Ile Glu Thr Leu Met Asn His Leu Gln Glu Thr Ser Ile Asn His
145                 150                 155                 160

Cys Lys Ser Leu Gly Leu Leu Asn Asp Gly Phe Gly Arg Thr Pro Gly
                165                 170                 175

Met Cys Lys Asn Asp Leu Ile Trp Val Leu Thr Lys Met Gln Ile Met
            180                 185                 190

Val Asn Arg Tyr Pro Thr Trp Gly Asp Thr Val Glu Ile Asn Thr Trp
        195                 200                 205

Phe Ser His Ser Gly Lys Ile Gly Met Ala Ser Asp Trp Leu Ile Thr
    210                 215                 220

Asp Cys Asn Thr Gly Glu Ile Leu Ile Arg Ala Thr Ser Val Trp Ala
225                 230                 235                 240

Met Met Asn Gln Lys Thr Arg Arg Phe Ser Arg Leu Pro Tyr Glu Val
                245                 250                 255

Arg Gln Glu Leu Thr Pro His Tyr Val Asp Ser Pro His Val Ile Glu
            260                 265                 270

Asp Asn Asp Arg Lys Leu His Lys Phe Asp Val Lys Thr Gly Asp Ser
        275                 280                 285

Ile Arg Lys Gly Leu Thr Pro Arg Trp Asn Asp Leu Asp Val Asn Gln
    290                 295                 300

His Val Ser Asn Val Lys Tyr Ile Gly Trp Ile Leu Glu Ser Met Pro
305                 310                 315                 320
```

```
Ile Glu Val Leu Glu Thr Gln Glu Leu Cys Ser Leu Thr Val Glu Tyr
                325                 330                 335

Arg Arg Glu Cys Gly Met Asp Ser Val Leu Glu Ser Val Thr Ala Met
            340                 345                 350

Asp Pro Ser Glu Asp Glu Gly Arg Ser Gln Tyr Lys His Leu Leu Arg
        355                 360                 365

Leu Glu Asp Gly Thr Asp Ile Val Lys Gly Arg Thr Glu Trp Arg Pro
    370                 375                 380

Lys Asn Ala Gly Thr Asn Gly Ala Ile Ser Thr Ala Lys Pro Ser Asn
385                 390                 395                 400

Gly Asn Ser Val Ser
                405


<210> SEQ ID NO 180
<211> LENGTH: 405
<212> TYPE: PRT
<213> ORGANISM: Cuphea procumbens
<220> FEATURE:
<223> OTHER INFORMATION: CprocFATB1 (Cuphea procumbens FATB1)

<400> SEQUENCE: 180

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Ala Ala Ile Asn Ala Ser Ala His Pro Lys Ala Asn Gly
        35                  40                  45

Ser Ala Val Asn Leu Lys Ser Gly Ser Leu Asn Thr Gln Glu Asp Thr
    50                  55                  60

Ser Ser Ser Pro Pro Pro Arg Ala Phe Leu Asn Gln Leu Pro Asp Trp
65                  70                  75                  80

Ser Met Leu Leu Ser Ala Ile Thr Thr Val Phe Val Ala Ala Glu Lys
                85                  90                  95

Gln Trp Thr Met Leu Asp Arg Lys Ser Lys Arg Pro Asp Met Leu Val
            100                 105                 110

Asp Ser Val Gly Leu Lys Asn Ile Val Arg Asp Gly Leu Val Ser Arg
        115                 120                 125

Gln Ser Phe Leu Ile Arg Ser Tyr Glu Ile Gly Ala Asp Arg Thr Ala
    130                 135                 140

Ser Ile Glu Thr Leu Met Asn His Leu Gln Glu Thr Ser Ile Asn His
145                 150                 155                 160

Cys Lys Ser Leu Gly Leu Leu Asn Asp Gly Phe Gly Arg Thr Pro Gly
                165                 170                 175

Met Cys Lys Asn Asp Leu Ile Trp Val Leu Thr Lys Met Gln Ile Met
            180                 185                 190

Val Asn Arg Tyr Pro Ala Trp Gly Asp Thr Val Glu Ile Asn Thr Trp
        195                 200                 205

Phe Ser Gln Ser Gly Lys Ile Gly Met Gly Ser Asp Trp Leu Ile Ser
    210                 215                 220

Asp Cys Asn Thr Gly Glu Ile Leu Ile Arg Ala Thr Ser Val Trp Ala
225                 230                 235                 240

Met Met Asn Gln Lys Thr Arg Arg Phe Ser Arg Leu Pro Tyr Glu Val
                245                 250                 255

Arg Gln Glu Leu Thr Pro His Phe Val Asp Ser Pro His Val Ile Glu
            260                 265                 270
```

Asp Asn Asp Arg Lys Leu His Lys Phe Asp Val Lys Thr Gly Asp Ser
275 280 285

Ile Arg Lys Gly Leu Thr Pro Arg Trp Asn Asp Leu Asp Val Asn Gln
290 295 300

His Val Ser Asn Val Lys Tyr Ile Gly Trp Ile Leu Glu Ser Met Pro
305 310 315 320

Ile Glu Val Leu Glu Ala Gln Glu Leu Cys Ser Leu Thr Val Glu Tyr
325 330 335

Arg Arg Glu Cys Gly Met Asp Ser Val Leu Glu Ser Val Thr Ala Val
340 345 350

Asp Pro Ser Glu Asp Gly Gly Arg Ser Gln Tyr Asn His Leu Leu Arg
355 360 365

Leu Glu Asp Gly Thr Asp Val Val Lys Gly Arg Thr Glu Trp Arg Pro
370 375 380

Lys Asn Ala Glu Thr Asn Gly Ala Ile Ser Pro Gly Asn Thr Ser Asn
385 390 395 400

Gly Asn Ser Ile Ser
405

<210> SEQ ID NO 181
<211> LENGTH: 403
<212> TYPE: PRT
<213> ORGANISM: Cuphea procumbens
<220> FEATURE:
<223> OTHER INFORMATION: CprocFATB2 (Cuphea procumbens FATB2)

<400> SEQUENCE: 181

Met Ala Thr Ala Ser Thr Phe Ser Ala Phe Asn Ala Arg Cys Gly Asp
1 5 10 15

Leu Arg Arg Ser Ala Gly Ser Gly Pro Arg Arg Pro Ala Arg Pro Leu
20 25 30

Pro Val Arg Ala Ala Ile Asn Ala Ser Ala His Pro Lys Ala Asn Gly
35 40 45

Ser Ala Val Asn Leu Lys Ser Gly Ser Leu Asn Thr Gln Glu Asp Thr
50 55 60

Ser Ser Ser Pro Pro Pro Arg Ala Phe Leu Asn Gln Leu Pro Asp Trp
65 70 75 80

Ser Met Leu Leu Ser Ala Ile Thr Thr Val Phe Val Ala Ala Glu Lys
85 90 95

Gln Trp Thr Met Leu Asp Arg Lys Ser Lys Arg Pro Asp Met Leu Val
100 105 110

Asp Ser Val Gly Leu Lys Asn Ile Val Arg Asp Gly Leu Val Ser Arg
115 120 125

Gln Ser Phe Leu Ile Arg Ser Tyr Glu Ile Gly Ala Asp Arg Thr Ala
130 135 140

Ser Ile Glu Thr Leu Met Asn His Leu Gln Glu Thr Ser Ile Asn His
145 150 155 160

Cys Lys Ser Leu Gly Leu Leu Asn Asp Gly Phe Gly Arg Thr Pro Gly
165 170 175

Met Cys Lys Asn Asp Leu Ile Trp Val Leu Thr Lys Met Gln Ile Met
180 185 190

Val Asn Arg Tyr Pro Ala Trp Gly Asp Thr Val Glu Ile Asn Thr Trp
195 200 205

Phe Ser Gln Ser Gly Lys Ile Gly Met Gly Ser Asp Trp Leu Ile Ser
210 215 220

```
Asp Cys Asn Thr Gly Glu Ile Leu Ile Arg Ala Thr Ser Val Trp Ala
225                 230                 235                 240

Met Met Asn Gln Lys Thr Arg Arg Phe Ser Arg Leu Pro Tyr Glu Val
                245                 250                 255

Arg Gln Glu Leu Thr Pro His Phe Val Asp Ser Pro His Val Ile Glu
            260                 265                 270

Asp Asn Asp Arg Lys Leu His Lys Phe Asp Val Lys Thr Gly Asp Ser
        275                 280                 285

Ile Arg Lys Gly Leu Thr Pro Arg Trp Asn Asp Leu Asp Val Asn Gln
    290                 295                 300

His Val Asn Asn Val Lys Tyr Ile Gly Trp Ile Leu Glu Ser Thr Pro
305                 310                 315                 320

Pro Glu Val Leu Glu Thr Gln Glu Leu Cys Ser Leu Thr Leu Glu Tyr
                325                 330                 335

Arg Gln Glu Cys Gly Arg Glu Ser Val Leu Glu Ser Leu Thr Ala Val
            340                 345                 350

Asp Pro Ser Gly Lys Gly Phe Gly Ser Gln Phe Gln His Leu Leu Arg
        355                 360                 365

Leu Glu Asp Gly Gly Glu Ile Val Lys Gly Arg Thr Glu Trp Arg Pro
    370                 375                 380

Lys Thr Ala Gly Ile Asn Gly Ala Ile Ala Ser Gly Glu Thr Ser Pro
385                 390                 395                 400

Gly Asp Phe


<210> SEQ ID NO 182
<211> LENGTH: 398
<212> TYPE: PRT
<213> ORGANISM: Cuphea procumbens
<220> FEATURE:
<223> OTHER INFORMATION: CprocFATB3 (Cuphea procumbens FATB3)

<400> SEQUENCE: 182

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Ala Ala Ile Asn Ala Ser Ala His Pro Lys Ala Asn Gly
        35                  40                  45

Ser Ala Val Asn Leu Lys Ser Gly Ser Leu Asn Thr Gln Glu Asp Thr
    50                  55                  60

Ser Ser Ser Pro Pro Pro Arg Ala Phe Leu Asn Gln Leu Pro Asp Trp
65                  70                  75                  80

Ser Met Leu Leu Ser Ala Ile Thr Thr Val Phe Val Ala Ala Glu Lys
                85                  90                  95

Gln Trp Thr Met Leu Asp Arg Lys Ser Lys Arg Pro Asp Met Leu Val
            100                 105                 110

Asp Ser Val Gly Leu Lys Asn Ile Val Arg Asp Gly Leu Val Ser Arg
        115                 120                 125

Gln Ser Phe Leu Ile Arg Ser Tyr Glu Ile Gly Ala Asp Arg Thr Ala
    130                 135                 140

Ser Ile Glu Thr Leu Met Asn His Leu Gln Glu Thr Ser Ile Asn His
145                 150                 155                 160

Cys Lys Ser Leu Gly Leu Leu Asn Asp Gly Phe Gly Arg Thr Pro Gly
                165                 170                 175
```

Met Cys Lys Asn Asp Leu Ile Trp Val Leu Thr Lys Met Gln Ile Met
180 185 190

Val Asn Arg Tyr Pro Ala Trp Gly Asp Thr Val Glu Ile Asn Thr Trp
195 200 205

Phe Ser Gln Ser Gly Lys Ile Gly Met Gly Ser Asp Trp Leu Ile Ser
210 215 220

Asp Cys Asn Thr Gly Glu Ile Leu Ile Arg Ala Thr Ser Val Trp Ala
225 230 235 240

Met Met Asn Gln Lys Thr Arg Arg Phe Ser Arg Leu Pro Tyr Glu Val
245 250 255

Arg Gln Glu Leu Thr Pro His Phe Val Asp Ser Pro His Val Ile Glu
260 265 270

Asp Asn Asp Arg Lys Leu His Lys Phe Asp Val Lys Thr Gly Asp Ser
275 280 285

Ile Arg Lys Gly Leu Thr Pro Arg Trp Asn Asp Leu Asp Val Asn Gln
290 295 300

His Val Asn Asn Val Lys Tyr Ile Gly Trp Ile Leu Glu Ser Thr Pro
305 310 315 320

Pro Glu Val Leu Glu Thr Gln Glu Leu Cys Ser Leu Thr Leu Glu Tyr
325 330 335

Arg Arg Glu Cys Gly Arg Glu Ser Val Leu Glu Ser Leu Thr Ala Val
340 345 350

Asp Pro Ser Gly Glu Gly Gly Tyr Gly Ser Gln Phe Gln His Leu Leu
355 360 365

Arg Leu Glu Asp Gly Gly Glu Ile Val Lys Gly Arg Thr Glu Trp Arg
370 375 380

Pro Lys Asn Ala Gly Ile Asn Gly Val Leu Pro Thr Gly Glu
385 390 395

<210> SEQ ID NO 183
<211> LENGTH: 398
<212> TYPE: PRT
<213> ORGANISM: Cuphea ignea
<220> FEATURE:
<223> OTHER INFORMATION: CigneaFATB1 (Cuphea ignea FATB1)

<400> SEQUENCE: 183

Met Ala Thr Ala Ser Thr Phe Ser Ala Phe Asn Ala Arg Cys Gly Asp
1 5 10 15

Leu Arg Arg Ser Ala Gly Ser Gly Pro Arg Arg Pro Ala Arg Pro Leu
20 25 30

Pro Val Arg Ala Ala Ile Asn Ala Arg Ala His Pro Lys Ala Asn Gly
35 40 45

Ser Ala Val Ser Leu Lys Ser Val Ser Leu Asn Thr Gln Glu Asp Thr
50 55 60

Ser Leu Ser Pro Pro Pro Arg Ala Phe Leu Asn Gln Leu Pro Asp Trp
65 70 75 80

Arg Met Leu Arg Thr Ala Leu Thr Thr Val Phe Val Ala Ala Glu Lys
85 90 95

Gln Trp Thr Met Leu Asp Arg Lys Ser Lys Arg Pro Asp Met Leu Val
100 105 110

Asp Ser Phe Gly Leu Glu Ser Ile Val Gln Glu Gly Leu Val Phe Arg
115 120 125

Gln Ser Phe Ser Ile Arg Ser Tyr Glu Ile Gly Ile Asp Arg Thr Ala
130 135 140

-continued

Ser Ile Glu Thr Leu Met Asn His Leu Gln Glu Thr Ser Leu Asn Gln
145 150 155 160

Cys Lys Ser Ala Gly Ile Leu His Asp Gly Phe Gly Arg Thr Leu Glu
165 170 175

Met Cys Lys Arg Asp Leu Ile Trp Val Val Thr Lys Met Gln Ile Lys
180 185 190

Val Asn Arg Tyr Pro Ala Trp Gly Asp Thr Val Glu Ile Ser Thr Arg
195 200 205

Phe Ser Arg Leu Gly Lys Ile Gly Met Gly Arg Asp Trp Leu Ile Cys
210 215 220

Asp Cys Asn Thr Gly Glu Ile Leu Ile Arg Ala Thr Ser Ala Tyr Ala
225 230 235 240

Met Met Asn Gln Lys Thr Arg Arg Leu Ser Lys Leu Pro Asn Glu Val
245 250 255

Arg Gln Glu Ile Ala Pro Leu Phe Val Asp Ser Asp Pro Val Ile Glu
260 265 270

Glu Asn Asp Met Lys Leu His Lys Phe Glu Val Lys Thr Gly Asp Ser
275 280 285

Ile Cys Lys Gly Leu Thr Pro Arg Trp Ser Asp Leu Asp Val Asn Gln
290 295 300

His Val Ser Asn Val Lys Tyr Ile Gly Trp Ile Leu Glu Ser Met Pro
305 310 315 320

Thr Glu Val Leu Glu Thr Gln Glu Leu Cys Ser Leu Ala Leu Glu Tyr
325 330 335

Arg Arg Glu Cys Gly Arg Asp Ser Val Leu Glu Ser Val Thr Ser Met
340 345 350

Asp Pro Ser Lys Val Gly Gly Trp Ser Gln Tyr Gln His Leu Leu Arg
355 360 365

Leu Glu Asp Gly Ala Asp Ile Val Lys Gly Arg Thr Glu Trp Arg Pro
370 375 380

Lys Asn Ala Gly Ala Asn Gly Ala Ile Ser Thr Gly Lys Thr
385 390 395

<210> SEQ ID NO 184
<211> LENGTH: 414
<212> TYPE: PRT
<213> ORGANISM: Cuphea glossostoma
<220> FEATURE:
<223> OTHER INFORMATION: CgFATB1 (Cuphea glossostoma FATB1)

<400> SEQUENCE: 184

Met Val Ala Ala Ala Ala Ser Ser Ala Phe Phe Pro Ser Pro Ala Pro
1 5 10 15

Gly Ser Ser Pro Lys Pro Gly Asn Arg Pro Ser Ser Leu Ser Pro Ser
20 25 30

Phe Lys Pro Lys Ser Ile Pro Asn Gly Ala Phe Gln Val Lys Ala Asn
35 40 45

Ala Ser Ala His Pro Lys Ala Asn Gly Ser Ala Val Asn Leu Lys Ser
50 55 60

Gly Ser Leu Asn Thr Gln Glu Asp Ser Ser Ser Ser Pro Ser Pro Arg
65 70 75 80

Ala Phe Leu Asn Gln Leu Pro Asp Trp Ser Val Leu Leu Thr Ala Ile
85 90 95

Thr Thr Val Phe Val Ala Ala Glu Lys Gln Trp Thr Met Leu Asp Arg
100 105 110

```
Lys Ser Lys Arg Pro Asp Val Leu Val Asp Ser Val Gly Leu Lys Ser
        115                 120                 125

Ile Val Gln Asp Gly Leu Val Ser Arg Gln Ser Phe Ser Ile Arg Ser
    130                 135                 140

Tyr Glu Ile Gly Ala Asp Arg Thr Ala Ser Ile Glu Thr Leu Met Asn
145                 150                 155                 160

His Leu Gln Glu Thr Ser Ile Asn His Cys Lys Ser Leu Gly Leu Leu
                165                 170                 175

Asn Asp Gly Phe Gly Arg Thr Pro Gly Met Cys Lys Asn Asp Leu Ile
            180                 185                 190

Trp Val Leu Thr Lys Met Gln Ile Met Val Asn Arg Tyr Pro Ala Trp
        195                 200                 205

Gly Asp Thr Val Glu Ile Asn Thr Trp Phe Ser Gln Ser Gly Lys Ile
    210                 215                 220

Gly Met Gly Ser Asp Trp Leu Ile Ser Asp Cys Asn Thr Gly Glu Ile
225                 230                 235                 240

Leu Ile Arg Ala Thr Ser Val Trp Ala Met Met Asn Gln Lys Thr Arg
                245                 250                 255

Arg Phe Ser Arg Leu Pro Tyr Glu Val Arg Gln Glu Leu Thr Pro His
            260                 265                 270

Phe Val Asp Ser Pro His Val Ile Glu Asp Asn Asp Arg Lys Leu His
        275                 280                 285

Lys Phe Asp Val Lys Thr Gly Asp Ser Ile Arg Lys Gly Leu Thr Pro
    290                 295                 300

Arg Trp Asn Asp Leu Asp Val Asn Gln His Val Ser Asn Val Lys Tyr
305                 310                 315                 320

Ile Gly Trp Ile Leu Glu Ser Met Pro Ile Glu Val Leu Glu Thr Gln
                325                 330                 335

Glu Leu Cys Ser Leu Thr Val Glu Tyr Arg Arg Glu Cys Gly Met Asp
            340                 345                 350

Ser Val Leu Glu Ser Val Thr Ala Met Asp Pro Ser Glu Asp Gly Gly
        355                 360                 365

Arg Ser Gln Tyr Asn His Leu Leu Arg Leu Glu Asp Gly Thr Asp Val
    370                 375                 380

Val Lys Gly Arg Thr Glu Trp Arg Pro Lys Asn Ala Gly Thr Asn Gly
385                 390                 395                 400

Ala Ile Ser Thr Thr Lys Thr Ser Asn Gly Asn Ser Val Ser
                405                 410
```

<210> SEQ ID NO 185
<211> LENGTH: 414
<212> TYPE: PRT
<213> ORGANISM: Cuphea glossostoma
<220> FEATURE:
<223> OTHER INFORMATION: CgFATB1b (Cuphea glossostoma FATB1 C170F,M198T, T374S variant)

<400> SEQUENCE: 185

```
Met Val Ala Ala Ala Ala Ser Ser Ala Phe Phe Pro Ser Pro Ala Pro
1               5                   10                  15

Gly Ser Ser Pro Lys Pro Gly Asn Arg Pro Ser Ser Leu Ser Pro Ser
            20                  25                  30

Phe Lys Pro Lys Ser Ile Pro Asn Gly Ala Phe Gln Val Lys Ala Asn
        35                  40                  45

Ala Ser Ala His Pro Lys Ala Asn Gly Ser Ala Val Asn Leu Lys Ser
    50                  55                  60
```

```
Gly Ser Leu Asn Thr Gln Glu Asp Ser Ser Ser Ser Pro Ser Pro Arg
65                  70                  75                  80

Ala Phe Leu Asn Gln Leu Pro Asp Trp Ser Val Leu Leu Thr Ala Ile
                85                  90                  95

Thr Thr Val Phe Val Ala Ala Glu Lys Gln Trp Thr Met Leu Asp Arg
            100                 105                 110

Lys Ser Lys Arg Pro Asp Val Leu Val Asp Ser Val Gly Leu Lys Ser
        115                 120                 125

Ile Val Gln Asp Gly Leu Val Ser Arg Gln Ser Phe Ser Ile Arg Ser
    130                 135                 140

Tyr Glu Ile Gly Ala Asp Arg Thr Ala Ser Ile Glu Thr Leu Met Asn
145                 150                 155                 160

His Leu Gln Glu Thr Ser Ile Asn His Phe Lys Ser Leu Gly Leu Leu
                165                 170                 175

Asn Asp Gly Phe Gly Arg Thr Pro Gly Met Cys Lys Asn Asp Leu Ile
            180                 185                 190

Trp Val Leu Thr Lys Thr Gln Ile Met Val Asn Arg Tyr Pro Ala Trp
        195                 200                 205

Gly Asp Thr Val Glu Ile Asn Thr Trp Phe Ser Gln Ser Gly Lys Ile
    210                 215                 220

Gly Met Gly Ser Asp Trp Leu Ile Ser Asp Cys Asn Thr Gly Glu Ile
225                 230                 235                 240

Leu Ile Arg Ala Thr Ser Val Trp Ala Met Met Asn Gln Lys Thr Arg
                245                 250                 255

Arg Phe Ser Arg Leu Pro Tyr Glu Val Arg Gln Glu Leu Thr Pro His
            260                 265                 270

Phe Val Asp Ser Pro His Val Ile Glu Asp Asn Asp Arg Lys Leu His
        275                 280                 285

Lys Phe Asp Val Lys Thr Gly Asp Ser Ile Arg Lys Gly Leu Thr Pro
    290                 295                 300

Arg Trp Asn Asp Leu Asp Val Asn Gln His Val Ser Asn Val Lys Tyr
305                 310                 315                 320

Ile Gly Trp Ile Leu Glu Ser Met Pro Ile Glu Val Leu Glu Thr Gln
                325                 330                 335

Glu Leu Cys Ser Leu Thr Val Glu Tyr Arg Arg Glu Cys Gly Met Asp
            340                 345                 350

Ser Val Leu Glu Ser Val Ser Ala Met Asp Pro Ser Glu Asp Gly Gly
        355                 360                 365

Arg Ser Gln Tyr Asn His Leu Leu Arg Leu Glu Asp Gly Thr Asp Val
    370                 375                 380

Val Lys Gly Arg Thr Glu Trp Arg Pro Lys Asn Ala Gly Thr Asn Gly
385                 390                 395                 400

Ala Ile Ser Thr Thr Lys Thr Ser Asn Gly Asn Ser Val Ser
                405                 410
```

<210> SEQ ID NO 186
<211> LENGTH: 434
<212> TYPE: PRT
<213> ORGANISM: Umbellularia californica
<220> FEATURE:
<223> OTHER INFORMATION: Umbellularia californica UcFATB3 amino acid sequence

<400> SEQUENCE: 186

```
Met Val Ala Thr Ala Ala Ala Ser Ala Phe Phe Pro Val Gly Ser Pro
```

-continued

```
1               5                   10                  15

Ala Thr Ser Ser Ala Thr Ser Ala Lys Ala Ser Met Met Pro Asp Asn
            20                  25                  30

Leu Asp Ala Arg Gly Ile Lys Pro Lys Pro Ala Ser Ser Ser Gly Leu
        35                  40                  45

Gln Val Lys Ala Asn Ala His Ala Ser Pro Lys Ile Asn Gly Ser Lys
    50                  55                  60

Val Ser Thr Asp Thr Leu Lys Gly Glu Asp Thr Leu Thr Ser Ser Pro
65                  70                  75                  80

Ala Pro Arg Thr Phe Ile Asn Gln Leu Pro Asp Trp Ser Met Phe Leu
                85                  90                  95

Ala Ala Ile Thr Thr Ile Phe Leu Ala Ala Glu Lys Gln Trp Thr Asn
            100                 105                 110

Leu Asp Trp Lys Pro Arg Arg Pro Asp Met Leu Ala Asp Pro Phe Gly
        115                 120                 125

Ile Gly Arg Phe Met Gln Asp Gly Leu Ile Phe Arg Gln His Phe Ala
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ala Leu Asn His Val Arg Ser Ala
                165                 170                 175

Gly Leu Leu Gly Asp Gly Phe Gly Ala Thr Pro Glu Met Ser Arg Arg
            180                 185                 190

Asp Leu Ile Trp Val Val Thr Arg Met Gln Val Leu Val Asp Arg Tyr
        195                 200                 205

Pro Ala Trp Gly Asp Ile Val Glu Val Glu Thr Trp Val Gly Ala Ser
    210                 215                 220

Gly Lys Asn Gly Met Arg Arg Asp Trp Leu Val Arg Asp Ser Gln Thr
225                 230                 235                 240

Gly Glu Ile Leu Thr Arg Ala Thr Ser Val Trp Val Met Met Asn Lys
                245                 250                 255

Arg Thr Arg Arg Leu Ser Lys Ile Pro Glu Glu Val Arg Gly Glu Ile
            260                 265                 270

Gly Pro Tyr Phe Met Glu Asn Val Ala Ile Ile Glu Glu Asp Ser Arg
        275                 280                 285

Lys Leu Gln Lys Leu Asn Glu Asn Ile Ile Glu Glu Asp Ser Arg Lys
    290                 295                 300

Leu Gln Lys Leu Asn Glu Asn Thr Ala Asp Asn Val Arg Arg Gly Leu
305                 310                 315                 320

Thr Pro Arg Trp Ser Asp Leu Asp Val Asn Gln His Val Asn Asn Val
                325                 330                 335

Lys Tyr Ile Gly Trp Ile Leu Glu Ser Ala Pro Gly Ser Ile Leu Glu
            340                 345                 350

Ser His Glu Leu Ser Cys Met Thr Leu Glu Tyr Arg Arg Glu Cys Gly
        355                 360                 365

Lys Asp Ser Val Leu Gln Ser Met Thr Val Val Ser Gly Gly Gly Ser
    370                 375                 380

Ala Ala Gly Gly Ser Pro Glu Ser Ser Val Glu Cys Asp His Leu Leu
385                 390                 395                 400

Gln Leu Glu Ser Gly Pro Glu Val Val Lys Ala Arg Thr Glu Trp Arg
                405                 410                 415

Pro Lys Ser Ala Asn Asn Pro Arg Ser Ile Leu Glu Met Pro Ala Glu
    420                 425                 430
```

Ser Ser

<210> SEQ ID NO 187
<211> LENGTH: 417
<212> TYPE: PRT
<213> ORGANISM: Cuphea carthagenensis
<220> FEATURE:
<223> OTHER INFORMATION: Cuphea carthagenensis CCrFATB2c (V138L variant
of FATB2)

<400> SEQUENCE: 187

```
Met Val Ala Ala Ala Ala Ser Ser Ala Phe Phe Pro Val Thr Thr Pro
1               5                   10                  15

Gly Thr Ser Arg Lys Pro Gly Lys Phe Gly Asn Trp Leu Ser Ser Leu
            20                  25                  30

Ser Pro Pro Phe Arg Pro Lys Ser Ile Pro Ser Gly Gly Phe Gln Val
        35                  40                  45

Lys Ala Asn Ala Ser Ala His Pro Lys Ala Asn Gly Ser Ala Val Ser
    50                  55                  60

Leu Lys Ser Gly Ser Leu Asn Thr Gln Glu Asp Thr Ser Ser Ser Pro
65                  70                  75                  80

Pro Pro Arg Ala Phe Ile Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Ser Asp Met Leu Val Asp Ser Phe Gly
        115                 120                 125

Met Glu Arg Ile Val Gln Asp Gly Leu Leu Phe Arg Gln Ser Phe Ser
    130                 135                 140

Ile Arg Ser Tyr Glu Ile Gly Ala Asp Arg Arg Ala Ser Ile Glu Thr
145                 150                 155                 160

Leu Met Asn His Leu Gln Glu Thr Ser Leu Asn His Cys Lys Ser Ile
                165                 170                 175

Arg Leu Leu Asn Glu Gly Phe Gly Arg Thr Pro Glu Met Cys Lys Arg
            180                 185                 190

Asp Leu Ile Trp Val Val Thr Arg Met His Ile Met Val Asn Arg Tyr
        195                 200                 205

Pro Thr Trp Gly Asp Thr Val Glu Ile Asn Thr Trp Val Ser Gln Ser
    210                 215                 220

Gly Lys Asn Gly Met Gly Arg Asp Trp Leu Ile Ser Asp Cys Asn Thr
225                 230                 235                 240

Gly Glu Ile Leu Ile Arg Ala Thr Ser Ala Trp Ala Met Met Asn Gln
                245                 250                 255

Lys Thr Arg Arg Leu Ser Lys Leu Pro Tyr Glu Val Ser Gln Glu Ile
            260                 265                 270

Ala Pro His Phe Val Asp Ser Pro Pro Val Ile Glu Asp Gly Asp Arg
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Met Pro Thr Glu Val Leu
                325                 330                 335

Glu Thr His Glu Leu Cys Phe Leu Thr Leu Glu Tyr Arg Arg Glu Cys
            340                 345                 350
```

```
Gly Arg Asp Ser Val Leu Glu Ser Val Thr Ala Met Asp Pro Ser Asn
        355                 360                 365

Glu Gly Gly Arg Ser His Tyr Gln His Leu Leu Arg Leu Glu Asp Gly
    370                 375                 380

Thr Asp Ile Val Lys Gly Arg Thr Glu Trp Arg Pro Lys Asn Ala Arg
385                 390                 395                 400

Asn Ile Gly Ala Ile Ser Thr Gly Lys Thr Ser Asn Gly Asn Pro Ala
                405                 410                 415

Ser


<210> SEQ ID NO 188
<211> LENGTH: 417
<212> TYPE: PRT
<213> ORGANISM: Cuphea carthagenensis
<220> FEATURE:
<223> OTHER INFORMATION: Cuphea carthagenensis CCrFATB2

<400> SEQUENCE: 188

Met Val Ala Ala Ala Ala Ser Ser Ala Phe Phe Pro Val Thr Thr Pro
1               5                   10                  15

Gly Thr Ser Arg Lys Pro Gly Lys Phe Gly Asn Trp Leu Ser Ser Leu
            20                  25                  30

Ser Pro Pro Phe Arg Pro Lys Ser Ile Pro Ser Gly Gly Phe Gln Val
        35                  40                  45

Lys Ala Asn Ala Ser Ala His Pro Lys Ala Asn Gly Ser Ala Val Ser
    50                  55                  60

Leu Lys Ser Gly Ser Leu Asn Thr Gln Glu Asp Thr Ser Ser Ser Pro
65                  70                  75                  80

Pro Pro Arg Ala Phe Ile Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Ser Asp Met Leu Val Asp Ser Phe Gly
        115                 120                 125

Met Glu Arg Ile Val Gln Asp Gly Leu Val Phe Arg Gln Ser Phe Ser
    130                 135                 140

Ile Arg Ser Tyr Glu Ile Gly Ala Asp Arg Arg Ala Ser Ile Glu Thr
145                 150                 155                 160

Leu Met Asn His Leu Gln Glu Thr Ser Leu Asn His Cys Lys Ser Ile
                165                 170                 175

Arg Leu Leu Asn Glu Gly Phe Gly Arg Thr Pro Glu Met Cys Lys Arg
            180                 185                 190

Asp Leu Ile Trp Val Val Thr Arg Met His Ile Met Val Asn Arg Tyr
        195                 200                 205

Pro Thr Trp Gly Asp Thr Val Glu Ile Asn Thr Trp Val Ser Gln Ser
    210                 215                 220

Gly Lys Asn Gly Met Gly Arg Asp Trp Leu Ile Ser Asp Cys Asn Thr
225                 230                 235                 240

Gly Glu Ile Leu Ile Arg Ala Thr Ser Ala Trp Ala Met Met Asn Gln
                245                 250                 255

Lys Thr Arg Arg Leu Ser Lys Leu Pro Tyr Glu Val Ser Gln Glu Ile
            260                 265                 270

Ala Pro His Phe Val Asp Ser Pro Pro Val Ile Glu Asp Gly Asp Arg
        275                 280                 285
```

Lys Leu His Lys Phe Asp Val Lys Thr Gly Asp Ser Ile Arg Lys Gly
290 295 300

Leu Thr Pro Arg Trp Asn Asp Leu Asp Val Asn Gln His Val Asn Asn
305 310 315 320

Val Lys Tyr Ile Gly Trp Ile Leu Glu Ser Met Pro Thr Glu Val Leu
325 330 335

Glu Thr His Glu Leu Cys Phe Leu Thr Leu Glu Tyr Arg Arg Glu Cys
340 345 350

Gly Arg Asp Ser Val Leu Glu Ser Val Thr Ala Met Asp Pro Ser Asn
355 360 365

Glu Gly Gly Arg Ser His Tyr Gln His Leu Leu Arg Leu Glu Asp Gly
370 375 380

Thr Asp Ile Val Lys Gly Arg Thr Glu Trp Arg Pro Lys Asn Ala Arg
385 390 395 400

Asn Ile Gly Ala Ile Ser Thr Gly Lys Thr Ser Asn Gly Asn Pro Ala
405 410 415

Ser

<210> SEQ ID NO 189
<211> LENGTH: 417
<212> TYPE: PRT
<213> ORGANISM: Cuphea carthagenensis
<220> FEATURE:
<223> OTHER INFORMATION: CcrFATB2b

<400> SEQUENCE: 189

Met Val Ala Ala Ala Ala Ser Ser Ala Phe Phe Pro Val Thr Thr Pro
1 5 10 15

Gly Thr Ser Arg Lys Pro Gly Lys Phe Gly Asn Trp Leu Ser Ser Leu
20 25 30

Ser Pro Pro Phe Arg Pro Lys Ser Ile Pro Ser Gly Gly Phe Gln Val
35 40 45

Lys Ala Asn Ala Ser Ala His Pro Lys Ala Asn Gly Ser Ala Val Ser
50 55 60

Leu Lys Ser Gly Ser Leu Asn Thr Gln Glu Asp Thr Ser Ser Ser Pro
65 70 75 80

Pro Pro Arg Ala Phe Ile Asn Gln Leu Pro Asp Trp Ser Met Leu Leu
85 90 95

Thr Ala Ile Thr Thr Val Phe Val Ala Ala Glu Lys Gln Trp Thr Met
100 105 110

Leu Asp Arg Lys Ser Lys Arg Ser Asp Met Leu Val Asp Ser Phe Gly
115 120 125

Met Glu Arg Ile Val Gln Asp Gly Leu Val Phe Arg Gln Ser Phe Ser
130 135 140

Ile Arg Ser Tyr Glu Ile Gly Ala Asp Arg Arg Ala Ser Ile Glu Thr
145 150 155 160

Leu Met Asn His Leu Gln Glu Thr Ser Leu Asn His Cys Lys Ser Ile
165 170 175

Arg Leu Leu Asn Glu Gly Phe Gly Arg Thr Pro Glu Met Cys Lys Arg
180 185 190

Asp Leu Ile Trp Val Phe Thr Arg Met His Ile Met Val Asn Arg Tyr
195 200 205

Pro Thr Trp Gly Asp Thr Val Glu Ile Asn Thr Trp Val Ser Gln Ser
210 215 220

Gly Lys Asn Gly Met Gly Arg Asp Trp Leu Ile Ser Asp Cys Asn Thr 225 230 235 240

Gly Glu Ile Leu Ile Arg Ala Thr Ser Ala Trp Ala Met Met Asn Gln
245 250 255

Lys Thr Arg Arg Leu Ser Lys Leu Pro Tyr Glu Val Ser Gln Glu Ile
260 265 270

Ala Pro His Phe Val Asp Ser Pro Pro Val Ile Glu Asp Gly Asp Arg
275 280 285

Lys Leu His Lys Phe Asp Val Lys Thr Gly Asp Ser Ile Arg Lys Gly
290 295 300

Leu Thr Pro Arg Trp Asn Asp Leu Asp Val Asn Gln His Val Asn Asn
305 310 315 320

Val Lys Tyr Ile Gly Trp Ile Leu Glu Ser Met Pro Thr Glu Val Leu
325 330 335

Glu Thr His Glu Leu Cys Phe Leu Thr Leu Glu Tyr Arg Arg Glu Cys
340 345 350

Gly Arg Asp Ser Val Leu Glu Ser Val Thr Ala Met Asp Pro Ser Asn
355 360 365

Glu Gly Gly Arg Ser His Tyr Gln His Leu Leu Arg Leu Glu Asp Gly
370 375 380

Thr Asp Ile Val Lys Gly Arg Thr Glu Trp Arg Pro Lys Asn Ala Arg
385 390 395 400

Asn Ile Gly Ala Ile Pro Thr Gly Lys Thr Ser Asn Gly Asn Pro Ala
405 410 415

Ser

<210> SEQ ID NO 190
<211> LENGTH: 414
<212> TYPE: PRT
<213> ORGANISM: Cuphea carthagenensis
<220> FEATURE:
<223> OTHER INFORMATION: CcrFATB1

<400> SEQUENCE: 190

Met Val Ala Thr Ala Ala Ser Ser Ala Phe Phe Pro Val Pro Ser Pro
1 5 10 15

Asp Ser Ser Ser Arg Pro Gly Lys Leu Gly Asn Gly Pro Ser Ser Leu
20 25 30

Ser Pro Leu Lys Pro Lys Ser Thr Pro Asn Gly Gly Leu Gln Val Lys
35 40 45

Ala Asn Ala Ser Ala Pro Pro Lys Ile Asn Gly Ser Ser Val Gly Leu
50 55 60

Lys Ser Ser Ser Leu Lys Thr Gln Asp Asp Thr Pro Ser Ala Pro Pro
65 70 75 80

Pro Arg Thr Phe Ile Asn Gln Leu Pro Asp Trp Ser Met Leu Leu Ala
85 90 95

Ala Ile Thr Thr Val Phe Leu Ala Ala Glu Lys Gln Trp Met Met Leu
100 105 110

Asp Trp Lys Pro Lys Arg Pro Asp Met Leu Thr Asp Pro Phe Gly Leu
115 120 125

Gly Arg Ile Val Gln Asp Gly Leu Val Phe Arg Gln Asn Phe Ser Ile
130 135 140

Arg Ser Tyr Glu Ile Gly Ala Asp Arg Thr Ala Ser Ile Glu Thr Val
145 150 155 160

Met Asn His Leu Gln Glu Thr Ala Leu Asn His Val Lys Ser Ala Gly
165 170 175

```
Leu Leu Asn Asp Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Arg Leu Ser Lys Ile Pro Asp Glu Val Arg His Glu Ile Glu
            260                 265                 270

Pro His Phe Val Asp Ser Ala Pro Val Ile Glu Asp Asp Asp Arg Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Lys Glu Ser Val Leu Glu Ser Leu Thr Ala Val Asp Pro Ser Gly Lys
        355                 360                 365

Gly Trp Gly Ser His Phe Gln His Leu Leu Arg Leu Glu Asp Gly Gly
    370                 375                 380

Glu Ile Val Lys Gly Arg Thr Glu Trp Arg Pro Lys Asn Ala Gly Ile
385                 390                 395                 400

Asn Gly Ala Val Ala Phe Glu Glu Thr Ser Pro Gly Asp Ser
                405                 410


<210> SEQ ID NO 191
<211> LENGTH: 414
<212> TYPE: PRT
<213> ORGANISM: Cuphea carthagenensis
<220> FEATURE:
<223> OTHER INFORMATION: CcrFATB1b

<400> SEQUENCE: 191

Met Val Ala Thr Ala Ala Ser Ser Ala Phe Phe Pro Val Pro Ser Pro
1               5                   10                  15

Asp Ser Ser Ser Arg Pro Gly Lys Leu Gly Asn Gly Pro Ser Ser Leu
            20                  25                  30

Ser Pro Leu Lys Pro Lys Ser Thr Pro Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Ser Ser Leu Lys Thr Gln Asp Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Thr Asp Pro Phe Gly Leu
        115                 120                 125
```

```
Gly Arg Ile Ala Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Asp Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Arg Leu Ser Lys Ile Pro Asp Glu Val Arg His Glu Ile Glu
            260                 265                 270

Pro His Phe Val Asp Ser Ala Pro Val Ile Glu Asp Asp Asp Arg Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Lys Glu Ser Val Leu Glu Ser Leu Thr Ala Val Asp Pro Ser Gly Lys
        355                 360                 365

Gly Trp Gly Ser His Phe Gln His Leu Leu Arg Leu Glu Asp Gly Gly
    370                 375                 380

Glu Ile Val Lys Gly Arg Thr Glu Trp Arg Pro Lys Asn Ala Gly Ile
385                 390                 395                 400

Asn Gly Ala Val Ala Phe Glu Glu Thr Ser Pro Gly Asp Ser
                405                 410
```

<210> SEQ ID NO 192
<211> LENGTH: 398
<212> TYPE: PRT
<213> ORGANISM: Cuphea carthagenensis
<220> FEATURE:
<223> OTHER INFORMATION: CCrFATB1c

<400> SEQUENCE: 192

```
Met Val Ala Thr Ala Ala Ser Ser Ala Phe Phe Pro Val Pro Ser Pro
1               5                   10                  15

Asp Ser Ser Ser Arg Pro Gly Lys Leu Gly Asn Gly Pro Ser Ser Leu
            20                  25                  30

Ser Pro Leu Lys Pro Lys Ser Thr Pro Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Ser Ser Leu Lys Thr Gln Asp Asp Thr Pro Ser Ala Pro Pro
65                  70                  75                  80
```

```
Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Thr Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Asp Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Arg Leu Ser Lys Ile Pro Asp Glu Val Arg His Glu Ile Glu
            260                 265                 270

Pro His Phe Val Asp Ser Ala Pro Val Ile Glu Asp Asp Asp Arg Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Lys Glu Ser Val Leu Glu Ser Leu Thr Ala Val Asp Pro Ser Gly Lys
        355                 360                 365

Gly Trp Gly Ser His Phe Gln His Leu Leu Arg Leu Glu Asp Gly Gly
    370                 375                 380

Glu Ile Val Lys Gly Arg Thr Glu Trp Arg Pro Lys Asn Ala
385                 390                 395
```

```
<210> SEQ ID NO 193
<211> LENGTH: 6541
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 193

gctcttcgcc gccgccactc ctgctcgagc gcgcccgcgc gtgcgccgcc agcgccttgg     60

ccttttcgcc gcgctcgtgc gcgtcgctga tgtccatcac caggtccatg aggtctgcct    120

tgcgccggct gagccactgc ttcgtccggg cggccaagag gagcatgagg gaggactcct    180

ggtccagggt cctgacgtgg tcgcggctct gggagcgggc cagcatcatc tggctctgcc    240
```

-continued

```
gcaccgaggc cgcctccaac tggtcctcca gcagccgcag tcgccgccga ccctggcaga    300
ggaagacagg tgaggggggt atgaattgta cagaacaacc acgagccttg tctaggcaga    360
atccctacca gtcatggctt tacctggatg acggcctgcg aacagctgtc cagcgaccct    420
cgctgccgcc gcttctcccg cacgcttctt tccagcaccg tgatggcgcg agccagcgcc    480
gcacgctggc gctgcgcttc gccgatctga ggacagtcgg ggaactctga tcagtctaaa    540
ccccctgcg cgttagtgtt gccatccttt gcagaccggt gagagccgac ttgttgtgcg    600
ccaccccca caccacctcc tcccagacca attctgtcac ctttttggcg aaggcatcgg    660
cctcggcctg cagagaggac agcagtgccc agccgctggg ggttggcgga tgcacgctca    720
ggtacccttt cttgcgctat gacacttcca gcaaaaggta gggcgggctg cgagacggct    780
tcccggcgct gcatgcaaca ccgatgatgc ttcgaccccc cgaagctcct tcggggctgc    840
atgggcgctc cgatgccgct ccagggcgag cgctgtttaa atagccaggc ccccgattgc    900
aaagacatta tagcgagcta ccaaagccat attcaaacac ctagatcact accacttcta    960
cacaggccac tcgagcttgt gatcgcactc cgctaagggg gcgcctcttc ctcttcgttt   1020
cagtcacaac ccgcaaacgg cgcgccatgc tgctgcaggc cttcctgttc ctgctggccg   1080
gcttcgccgc caagatcagc gcctccatga cgaacgagac gtccgaccgc cccctggtgc   1140
acttcacccc caacaagggc tggatgaacg accccaacgg cctgtggtac gacgagaagg   1200
acgccaagtg gcacctgtac ttccagtaca acccgaacga caccgtctgg gggacgccct   1260
tgttctgggg ccacgccacg tccgacgacc tgaccaactg ggaggaccag cccatcgcca   1320
tcgccccgaa gcgcaacgac tccggcgcct tctccggctc catggtggtg gactacaaca   1380
acacctccgg cttcttcaac gacaccatcg acccgcgcca gcgctgcgtg gccatctgga   1440
cctacaacac cccggagtcc gaggagcagt acatctccta cagcctggac ggcggctaca   1500
ccttcaccga gtaccagaag aaccccgtgc tggccgccaa ctccacccag ttccgcgacc   1560
cgaaggtctt ctggtacgag ccctcccaga agtggatcat gaccgcggcc aagtcccagg   1620
actacaagat cgagatctac tcctccgacg acctgaagtc ctggaagctg gagtccgcgt   1680
tcgccaacga gggcttcctc ggctaccagt acgagtgccc cggcctgatc gaggtcccca   1740
ccgagcagga ccccagcaag tcctactggg tgatgttcat ctccatcaac cccggcgccc   1800
cggccggcgg ctccttcaac cagtacttcg tcggcagctt caacggcacc cacttcgagg   1860
ccttcgacaa ccagtcccgc gtggtggact tcggcaagga ctactacgcc ctgcagacct   1920
tcttcaacac cgacccgacc tacgggagcg ccctgggcat cgcgtgggcc tccaactggg   1980
agtactccgc cttcgtgccc accaacccct ggcgctcctc catgtccctc gtgcgcaagt   2040
tctccctcaa caccgagtac caggccaacc cggagacgga gctgatcaac ctgaaggccg   2100
agccgatcct gaacatcagc aacgccggcc cctggagccg gttcgccacc aacaccacgt   2160
tgacgaaggc caacagctac aacgtcgacc tgtccaacag caccggcacc ctggagttcg   2220
agctggtgta cgccgtcaac accacccaga cgatctccaa gtccgtgttc gcggacctct   2280
ccctctggtt caagggcctg gaggaccccg aggagtacct ccgcatgggc ttcgaggtgt   2340
ccgcgtcctc cttcttcctg gaccgcggga acagcaaggt gaagttcgtg aaggagaacc   2400
cctacttcac caaccgcatg agcgtgaaca accagccctt caagagcgag aacgacctgt   2460
cctactacaa ggtgtacggc ttgctggacc agaacatcct ggagctgtac ttcaacgacg   2520
gcgacgtcgt gtccaccaac acctacttca tgaccaccgg gaacgccctg ggctccgtga   2580
```

-continued

```
acatgacgac gggggtggac aacctgttct acatcgacaa gttccaggtg cgcgaggtca   2640
agtgacaatt ggcagcagca gctcggatag tatcgacaca ctctggacgc tggtcgtgtg   2700
atggactgtt gccgccacac ttgctgcctt gacctgtgaa tatccctgcc gcttttatca   2760
aacagcctca gtgtgtttga tcttgtgtgt acgcgctttt gcgagttgct agctgcttgt   2820
gctatttgcg aataccaccc ccagcatccc cttccctcgt ttcatatcgc ttgcatccca   2880
accgcaactt atctacgctg tcctgctatc cctcagcgct gctcctgctc ctgctcactg   2940
cccctcgcac agccttggtt tgggctccgc ctgtattctc ctggtactgc aacctgtaaa   3000
ccagcactgc aatgctgatg cacgggaagt agtgggatgg gaacacaaat ggaaagctgt   3060
atagggataa gaattcggcc gacaggacgc gcgtcaaagg tgctggtcgt gtatgccctg   3120
gccggcaggt cgttgctgct gctggttagt gattccgcaa ccctgatttt ggcgtcttat   3180
tttggcgtgg caaacgctgg cgcccgcgag ccgggccggc ggcgatgcgg tgccccacgg   3240
ctgccggaat ccaagggagg caagagcgcc cgggtcagtt gaagggcttt acgcgcaagg   3300
tacagccgct cctgcaaggc tgcgtggtgg aattggacgt gcaggtcctg ctgaagttcc   3360
tccaccgcct caccagcgga caaagcaccg gtgtatcagg tccgtgtcat ccactctaaa   3420
gaactcgact acgacctact gatggcccta gattcttcat caaaaacgcc tgagacactt   3480
gcccaggatt gaaactccct gaagggacca ccaggggccc tgagttgttc cttcccccg    3540
tggcgagctg ccagccaggc tgtacctgtg atcgaggctg gcgggaaaat aggcttcgtg   3600
tgctcaggtc atgggaggtg caggacagct catgaaacgc caacaatcgc acaattcatg   3660
tcaagctaat cagctatttc ctcttcacga gctgtaattg tcccaaaatt ctggtctacc   3720
gggggtgatc cttcgtgtac gggcccttcc ctcaacccta ggtatgcgcg catgcggtcg   3780
ccgcgcaact cgcgcgaggg ccgagggttt gggacgggcc gtcccgaaat gcagttgcac   3840
ccggatgcgt ggcacctttt ttgcgataat ttatgcaatg gactgctctg caaaattctg   3900
gctctgtcgc caaccctagg atcagcggcg taggatttcg taatcattcg tcctgatggg   3960
gagctaccga ctaccctaat atcagcccga ctgcctgacg ccagcgtcca cttttgtgca   4020
cacattccat tcgtgcccaa gacatttcat tgtggtgcga agcgtcccca gttacgctca   4080
cctgtttccc gacctcctta ctgttctgtc gacagagcgg gcccacaggc cggtcgcagc   4140
cactagtatg gccaccacct ccctggcctc cgccttctgc tccatgaagg ccgtgatgct   4200
ggcccgcgac ggccgcggcc tgaagccccg ctcctccgac ctgcagctgc gcgccggcaa   4260
cgcccagacc tccctgaaga tgatcaacgg caccaagttc tcctacaccg agtccctgaa   4320
gaagctgccc gactggtcca tgctgttcgc cgtgatcacc accatcttct ccgccgccga   4380
gaagcagtgg accaacctgg agtggaagcc caagcccaac ccccccagc tgctggacga    4440
ccacttcggc ccccacggcc tggtgttccg ccgcaccttc gccatccgct cctacgaggt   4500
gggccccgac cgctccacct ccatcgtggc cgtgatgaac cacctgcagg aggccgccct   4560
gaaccacgcc aagtccgtgg gcatcctggg cgacggcttc ggcaccaccc tggagatgtc   4620
caagcgcgac ctgatctggg tggtgaagcg cacccacgtg gccgtggagc gctaccccgc   4680
ctggggcgac accgtggagg tggagtgctg ggtgggcgcc tccggcaaca acggccgccg   4740
ccacgacttc ctggtgcgcg actgcaagac cggcgagatc ctgacccgct gcacctccct   4800
gtccgtgatg atgaacaccc gcacccgccg cctgtccaag atccccgagg aggtgcgcgg   4860
cgagatcggc cccgccttca tcgacaacgt ggccgtgaag gacgaggaga tcaagaagcc   4920
ccagaagctg aacgactcca ccgccgacta catccagggc ggcctgaccc cccgctggaa   4980
```

-continued

```
cgacctggac atcaaccagc acgtgaacaa catcaagtac gtggactgga tcctggagac   5040
cgtgcccgac tccatcttcg agtcccacca catctcctcc ttcaccatcg agtaccgccg   5100
cgagtgcacc cgcgactccg tgctgcagtc cctgaccacc gtgtccggcg gctcctccga   5160
ggccggcctg gtgtgcgagc acctgctgca gctggagggc ggctccgagg tgctgcgcgc   5220
caagaccgag tggcgcccca agctgtcctt ccgcggcatc tccgtgatcc ccgccgagtc   5280
ctccgtgatg gactacaagg accacgacgg cgactacaag gaccacgaca tcgactacaa   5340
ggacgacgac gacaagtgac tcgaggcagc agcagctcgg atagtatcga cacactctgg   5400
acgctggtcg tgtgatggac tgttgccgcc acacttgctg ccttgacctg tgaatatccc   5460
tgccgctttt atcaaacagc ctcagtgtgt ttgatcttgt gtgtacgcgc ttttgcgagt   5520
tgctagctgc ttgtgctatt tgcgaatacc acccccagca tccccttccc tcgtttcata   5580
tcgcttgcat cccaaccgca acttatctac gctgtcctgc tatccctcag cgctgctcct   5640
gctcctgctc actgcccctc gcacagcctt ggtttgggct ccgcctgtat tctcctggta   5700
ctgcaacctg taaaccagca ctgcaatgct gatgcacggg aagtagtggg atgggaacac   5760
aaatggaaag ctgtataggg ataacagggt aatgagctct tgttttccag aaggagttgc   5820
tccttgagcc tttcattctc agcctcgata acctccaaag ccgctctaat tgtggagggg   5880
gttcgaattt aaaagcttgg aatgttggtt cgtgcgtctg gaacaagccc agacttgttg   5940
ctcactggga aaaggaccat cagctccaaa aaacttgccg ctcaaaccgc gtacctctgc   6000
tttcgcgcaa tctgccctgt tgaaatcgcc accacattca tattgtgacg cttgagcagt   6060
ctgtaattgc ctcagaatgt ggaatcatct gccccctgtg cgagcccatg ccaggcatgt   6120
cgcgggcgag gacacccgcc actcgtacag cagaccatta tgctacctca caatagttca   6180
taacagtgac catatttctc gaagctcccc aacgagcacc tccatgctct gagtggccac   6240
cccccggccc tggtgcttgc ggagggcagg tcaaccggca tggggctacc gaaatccccg   6300
accggatccc accacccccg cgatgggaag aatctctccc cgggatgtgg gcccaccacc   6360
agcacaacct gctggcccag gcgagcgtca aaccatacca cacaaatatc cttggcatcg   6420
gccctgaatt ccttctgccg ctctgctacc cggtgcttct gtccgaagca ggggttgcta   6480
gggatcgctc cgagtccgca aacccttgtc gcgtggcggg gcttgttcga gcttgaagag   6540
c                                                                   6541
```